US011884920B2

(12) United States Patent
Li et al.

(10) Patent No.: US 11,884,920 B2
(45) Date of Patent: *Jan. 30, 2024

(54) ALPHA-1 ANTITRYPSIN (AAT) RNAI AGENTS, COMPOSITIONS INCLUDING AAT RNAI AGENTS, AND METHODS OF USE

(71) Applicant: Arrowhead Pharmaceuticals, Inc., Pasadena, CA (US)

(72) Inventors: Zhen Li, Westfield, NJ (US); Rui Zhu, Middleton, WI (US); Christine I. Wooddell, Madison, WI (US); Tao Pei, Middleton, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 121 days.

This patent is subject to a terminal disclaimer.

(21) Appl. No.: 17/523,173

(22) Filed: Nov. 10, 2021

(65) Prior Publication Data

US 2022/0170015 A1    Jun. 2, 2022

Related U.S. Application Data

(62) Division of application No. 16/568,387, filed on Sep. 12, 2019, now Pat. No. 11,203,756, which is a division of application No. 15/867,107, filed on Jan. 10, 2018, now Pat. No. 10,450,565.

(60) Provisional application No. 62/596,232, filed on Dec. 8, 2017, provisional application No. 62/486,720, filed on Apr. 18, 2017, provisional application No. 62/444,452, filed on Jan. 10, 2017.

(51) Int. Cl.
| | |
|---|---|
| C12N 15/113 | (2010.01) |
| A61K 9/00 | (2006.01) |
| A61P 1/16 | (2006.01) |
| G01N 33/68 | (2006.01) |
| C12Q 1/6883 | (2018.01) |
| A61K 31/713 | (2006.01) |

(52) U.S. Cl.
CPC .......... *C12N 15/113* (2013.01); *A61K 9/0019* (2013.01); *A61K 31/713* (2013.01); *A61P 1/16* (2018.01); *C12Q 1/6883* (2013.01); *G01N 33/6893* (2013.01); *C12N 2310/14* (2013.01); *C12N 2310/315* (2013.01); *C12N 2310/317* (2013.01); *C12N 2310/32* (2013.01); *C12N 2310/321* (2013.01); *C12N 2310/322* (2013.01); *C12N 2310/333* (2013.01); *C12N 2310/334* (2013.01); *C12N 2310/335* (2013.01); *C12N 2310/336* (2013.01); *C12N 2310/343* (2013.01); *C12N 2310/346* (2013.01); *C12N 2310/351* (2013.01); *C12N 2320/31* (2013.01); *C12Q 2600/156* (2013.01); *C12Q 2600/158* (2013.01); *G01N 2333/8125* (2013.01); *G01N 2800/085* (2013.01)

(58) Field of Classification Search
CPC .............. C12N 15/113; C12N 2310/14; C12N 2310/315; C12N 2310/317; C12N 2310/32; C12N 2310/321; C12N 2310/322; C12N 2310/333; C12N 2310/334; C12N 2310/335; C12N 2310/336; C12N 2310/343; C12N 2310/346; C12N 2310/351; A61K 9/0019; A61K 31/713; A61P 1/16; G01N 2333/8125
See application file for complete search history.

(56) References Cited

U.S. PATENT DOCUMENTS

| | | |
|---|---|---|
| 3,687,808 A | 8/1972 | Merigan et al. |
| 5,034,506 A | 7/1991 | Summerton et al. |
| 5,134,066 A | 7/1992 | Rogers et al. |
| 5,212,295 A | 5/1993 | Cook |
| 5,359,044 A | 10/1994 | Cook et al. |
| 5,459,255 A | 10/1995 | Cook et al. |
| 5,466,786 A | 11/1995 | Buhr et al. |
| 5,489,677 A | 2/1996 | Sanghvi et al. |
| 5,519,134 A | 5/1996 | Acevedo et al. |
| 5,521,302 A | 5/1996 | Cook |
| 5,539,082 A | 7/1996 | Nielson et al. |
| 5,552,540 A | 9/1996 | Haralambidis |
| 5,587,361 A | 12/1996 | Cook et al. |
| 5,591,722 A | 1/1997 | Montgomery et al. |
| 5,594,121 A | 1/1997 | Froehler et al. |
| 5,596,091 A | 1/1997 | Switzer |

(Continued)

FOREIGN PATENT DOCUMENTS

| | | |
|---|---|---|
| CN | 103547272 A | 1/2014 |
| CN | 106535917 A | 3/2017 |

(Continued)

OTHER PUBLICATIONS

U.S. Appl. No. 17/616,292, filed Dec. 3, 2021, Given et al.

(Continued)

*Primary Examiner* — J. E. Angell
(74) *Attorney, Agent, or Firm* — Wolf, Greenfield & Sacks, P.C.

(57) ABSTRACT

RNAi agents for inhibiting the expression of the alpha-1 antitrypsin (AAT) gene, compositions including AAT RNAi agents, and methods of use are described. Also disclosed are pharmaceutical compositions including one or more AAT RNAi agents together with one or more excipients capable of delivering the RNAi agent(s) to a liver cell in vivo. Delivery of the AAT RNAi agent(s) to liver cells in vivo inhibits AAT gene expression and treats diseases associated with AAT deficiency such as chronic hepatitis, cirrhosis, hepatocellular carcinoma, transaminitis, cholestasis, fibrosis, and fulminant hepatic failure.

21 Claims, 44 Drawing Sheets
Specification includes a Sequence Listing.

(56) References Cited

U.S. PATENT DOCUMENTS

| | | |
|---|---|---|
| 5,597,909 A | 1/1997 | Urdea et al. |
| 5,602,240 A | 2/1997 | De Mesmaeker et al. |
| 5,646,265 A | 7/1997 | McGee |
| 5,700,920 A | 12/1997 | Altmann et al. |
| 5,885,968 A | 3/1999 | Biessen et al. |
| 6,172,209 B1 | 1/2001 | Manoharan et al. |
| 6,268,490 B1 | 7/2001 | Imanishi et al. |
| 6,271,358 B1 | 8/2001 | Manoharan et al. |
| 7,056,704 B2 | 6/2006 | Tuschl et al. |
| 7,335,765 B2 | 2/2008 | Kaneko et al. |
| 7,691,997 B2 | 4/2010 | Khvorova et al. |
| 8,084,599 B2 | 12/2011 | Rossi et al. |
| 8,349,809 B2 | 1/2013 | Brown |
| 8,394,628 B2 | 3/2013 | Tuschl et al. |
| 8,513,207 B2 | 8/2013 | Brown |
| 8,648,185 B2 | 2/2014 | Mcswigen et al. |
| 9,340,784 B2 | 5/2016 | Monia et al. |
| 9,458,457 B2 | 10/2016 | Brown et al. |
| 9,879,261 B2 | 1/2018 | Brown et al. |
| 10,006,025 B2 | 6/2018 | Wooddell et al. |
| 10,450,565 B2 | 10/2019 | Li et al. |
| 11,203,756 B2 | 12/2021 | Li et al. |
| 11,384,355 B2 | 7/2022 | Wooddell et al. |
| 2005/0137153 A1 | 6/2005 | Mcswiggen et al. |
| 2006/0234247 A1 | 10/2006 | Puttaraju et al. |
| 2007/0253936 A1 | 11/2007 | Kay et al. |
| 2009/0029931 A1 | 1/2009 | Tachas et al. |
| 2009/0247608 A1 | 1/2009 | Manoharan et al. |
| 2010/0048680 A1 | 2/2010 | Liu et al. |
| 2010/0056768 A1 | 3/2010 | Wengel |
| 2011/0028531 A1 | 2/2011 | Feinstein et al. |
| 2011/0207799 A1 | 8/2011 | Rozema et al. |
| 2013/0190484 A1 | 7/2013 | Rozema et al. |
| 2013/0281658 A1 | 10/2013 | Rozema et al. |
| 2014/0235693 A1 | 8/2014 | Sehgal et al. |
| 2014/0350071 A1 | 11/2014 | Sehgal et al. |
| 2015/0011607 A1 | 1/2015 | Brown et al. |
| 2015/0361427 A1 | 12/2015 | Wooddell et al. |
| 2016/0244752 A1 | 8/2016 | Sehgal et al. |
| 2017/0035796 A1 | 2/2017 | Wooddell et al. |
| 2017/0130221 A1 | 5/2017 | Brown et al. |
| 2017/0253875 A1 | 9/2017 | Rozema et al. |
| 2018/0064819 A1 | 3/2018 | Li et al. |
| 2018/0195069 A1 | 7/2018 | Li et al. |
| 2018/0258430 A1 | 9/2018 | Wooddell et al. |
| 2019/0071670 A1 | 3/2019 | Wooddell et al. |
| 2019/0284558 A1 | 9/2019 | Wooddell et al. |
| 2020/0208149 A1 | 7/2020 | Li et al. |
| 2022/0305046 A1 | 9/2022 | Given et al. |
| 2023/0002768 A1 | 1/2023 | Wooddell et al. |

FOREIGN PATENT DOCUMENTS

| | | |
|---|---|---|
| JP | 2013-539967 A | 10/2013 |
| JP | 2016-520312 A | 7/2016 |
| WO | WO 1993/007883 A1 | 4/1993 |
| WO | WO 1997/044348 A1 | 11/1997 |
| WO | WO 1999/014226 A2 | 3/1999 |
| WO | WO 1999/038987 A1 | 8/1999 |
| WO | WO 2000/053722 A2 | 9/2000 |
| WO | WO 2004/045543 A2 | 6/2004 |
| WO | WO 2004/083430 A1 | 9/2004 |
| WO | WO 2008/016391 A2 | 2/2008 |
| WO | WO 2008/022309 A2 | 2/2008 |
| WO | WO 2011/104169 A1 | 9/2011 |
| WO | WO 2012/033848 A1 | 3/2012 |
| WO | WO 2012/083185 A2 | 6/2012 |
| WO | WO 2012/178033 A2 | 12/2012 |
| WO | WO 2013/032829 A1 | 3/2013 |
| WO | WO 2013/158141 A1 | 10/2013 |
| WO | WO 2014/190137 A1 | 11/2014 |
| WO | WO 2014/197524 A2 | 12/2014 |
| WO | WO 2015/003113 A2 | 1/2015 |
| WO | WO 2015/188197 A2 | 12/2015 |
| WO | WO 2015/0195628 A2 | 12/2015 |
| WO | WO 2013/142514 A1 | 9/2016 |
| WO | WO 2017/139616 A1 | 8/2017 |
| WO | WO 2017/156012 A1 | 9/2017 |
| WO | WO 2017/214518 A1 | 12/2017 |
| WO | WO 2018/098117 A1 | 5/2018 |
| WO | WO 2018/236273 A1 | 12/2018 |
| WO | WO 2020/0247774 A1 | 12/2020 |

OTHER PUBLICATIONS

U.S. Appl. No. 16/428,431, filed May 31, 2019, Wooddell et al.

EP18739290.1, Nov. 6, 2020, *Supplemental European Search Report.

PCT/US2018/013102, May 3, 2018, *International Search Report and Written Opinion.

PCT/US2018/013102, Jul. 25, 2019, International Preliminary Report on Patentability.

International Search Report and Written Opinion for Application No. PCT/US2018/013102, dated May 3, 2018.

International Preliminary Report on Patentability for Application No. PCT/US2018/013102, dated Jul. 25, 2019.

Supplementary European Search Report and Opinion dated Nov. 6, 2020 in EP Application No. 18739290, EPO, Netherlands, 21 pages.

Akinc et al., Targeted delivery of RNAi therapeutics with endogenous and exogenous ligand-based mechanisms. Mol Ther. Jul. 2010;18(7):1357-64. doi: 10.1038/mt.2010.85. Epub May 11, 2010.

American Thoracic Society, American Thoracic Society/European Respiratory Society statement: standards for the diagnosis and management of individuals with alpha-1 antitrypsin deficiency. Am J Respir Crit Care Med. Oct. 1, 2003;168(7):818-900. doi: 10.1164/rccm.168.7.818.

Baenziger et al., Galactose and N-Acetylgalactosamine-Specific Endocytosis of Glycopeptides by Isolated Rat Hepatocytes. Cell. Nov. 1980;22(2 Pt 2):611-20. doi: 10.1016/0092-8674(80)90371-2.

Bals, Alpha-1-antitrypsin deficiency. Best Pract Res Clin Gastroenterol. Oct. 2010;24(5):629- 33. doi: 10.1016/j.bpg.2010.08.006.

Biessen et al., Synthesis of cluster galactosides with high affinity for the hepatic asialoglycoprotein receptor. J Med Chem. Apr. 28, 1995;38(9):1538-46. doi: 10.1021/jm00009a014.

Bondensgaard et al., Structural studies of LNA:RNA duplexes by NMR: conformations and implications for RNase H activity. Chemistry. Aug. 4, 2000;6(15):2687-95. doi: 10.1002/1521-3765(20000804)6:15<2687::aid-chem2687>3.0.co;2-u.

Braasch et al., Locked nucleic acid (LNA): fine-tuning the recognition of DNA and RNA. Chem Biol. Jan. 2001;8(1):1-7. doi: 10.1016/s1074-5521(00)00058-2.

Carlson et al., Accumulation of PiZ alpha 1-antitrypsin causes liver damage in transgenic mice. J Clin Invest. Apr. 1989;83(4):1183-90. doi: 10.1172/JCI113999.

Carrell et al., Alpha1-antitrypsin deficiency—a model for conformational diseases. N Engl J Med. Jan. 3, 2002;346(1):45-53. doi: 10.1056/NEJMra010772.

Cichy et al., Biosynthesis of alpha1-proteinase inhibitor by human lung-derived epithelial cells. J Biol Chem. Mar. 28, 1997;272(13):8250-5. doi: 10.1074/jbc.272.13.8250.

Cohen, Interrelationships between the human alveolar macrophage and alpha-1-antitrypsin. J Clin Invest. Nov. 1973;52(11):2793-9. doi: 10.1172/JCI107475.

Connolly et al., Binding and endocytosis of cluster glycosides by rabbit hepatocytes. Evidence for a short-circuit pathway that does not lead to degradation. J Biol Chem. Jan. 25, 1982;257(2):939-45.

Cook, Medicinal Chemistry of Antisense Oligonucleotides-Future Opportunities. Anti-Cancer Drug Des. Dec. 1991;6(6):585-607.

Crinelli et al., Design and characterization of decoy oligonucleotides containing locked nucleic acids. Nucleic Acids Res. Jun. 1, 2002;30(11):2435-43. doi: 10.1093/nar/30.11.2435.

Crooke et al., Pharmacokinetic properties of several novel oligonucleotide analogs in mice. J Pharmacol Exp Ther. May 1996;277(2):923-37.

Cruz et al., In vivo post-transcriptional gene silencing of alpha-1 antitrypsin by adeno- associated virus vectors expressing siRNA. Lab Invest. Sep. 2007;87(9):893-902. doi: 10.1038/labinvest.3700629. Epub Jun. 25, 2007.

(56) References Cited

OTHER PUBLICATIONS

Cruz et al., Post-Transcriptional Gene Silencing of Alpha-I Antitrypsin by Small Interfering RNAs (siRNA). Mol Ther. 2006; 13(1):S45-S46.
Czauderna et al., Structural variations and stabilising modifications of synthetic siRNAs in mammalian cells. Nucleic Acids Res. Jun. 1, 2003;31(11):2705-16. doi: 10.1093/nar/gkg393.
De Serres et al., Prevalence of α1-antitrypsin deficiency alleles PI*S and PI*Z worldwide and effective screening for each of the five phenotypic classes PI*MS, PI*MZ, PI*SS, PI*SZ, and PI*ZZ: a comprehensive review. Ther Adv Respir Dis. Oct. 2012;6(5):277-95. doi: 10.1177/1753465812457113. Epub Aug. 29, 2012.
Delgado et al., The Uses and Properties of PEG-Linked Proteins. Crit Rev Ther Drug Carrier Syst. 1992;9(3-4):249-304.
Elmen et al., Locked nucleic acid (LNA) mediated improvements in siRNA stability and functionality. Nucleic Acids Res. Jan. 14, 2005;33(1):439-47. doi: 10.1093/nar/gki193. Print 2005.
Elzouki et al., Risk of hepatobiliary disease in adults with severe alpha 1-antitrypsin deficiency (PiZZ): is chronic viral hepatitis B or C an additional risk factor for cirrhosis and hepatocellular carcinoma? Eur J Gastroenterol Hepatol. Oct. 1996;8(10):989-94. doi: 10.1097/00042737-199610000-00010.
Eriksson, Alpha-1-antitrypsin deficiency: natural course and therapeutic strategies. Falk Symposium 115: Liver cirrhosis and its development. 2001; 307-15.
Feldmann et al., The ultrastructure of hepatocytes in alpha-1-antitrypsin deficiency with the genotype Pi--. Gut. Oct. 1975;16(10):796-9. doi: 10.1136/gut.16.10.796.
Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.
Greene et al., Z α-1 antitrypsin deficiency and the endoplasmic reticulum stress response. World J Gastrointest Pharmacol Ther. Oct. 6, 2010;1(5):94-101. doi: 10.4292/wjgpt.v1.i5.94.
Grimm et al., Fatality in mice due to oversaturation of cellular microRNA/short hairpin RNA Pathways. Nature. May 25, 2006;441(7092):537-41. doi: 10.1038/nature04791.
Guo et al., Antisense oligonucleotide treatment ameliorates alpha-1 antitrypsin-related liver disease in mice. J Clin Invest. Jan. 2014; 124(1):251-61. doi: 10.1172/JCI67968. Epub Dec. 20, 2013.
Guzaev et al., A conformationally preorganized universal solid support for efficient oligonucleotide synthesis. J Am Chem Soc. Mar. 5, 2003;125(9):2380-1. doi: 10.1021/ja0284613.
Hamm et al., Incorporation of 2'-Deoxy-2'-mercaptocytidine into Oligonucleotides via Phosphoramidite Chemistry. J Org Chem. May 16, 1997;62(10):3415-3420. doi: 10.1021/jo970096o.
Hunt et al., Alpha 1 anti-trypsin: one protein, many functions. Curr Mol Med. Aug. 2012;12(7):827-35. doi: 10.2174/156652412801318755.
Iobst et al., Selective sugar binding to the carbohydrate recognition domains of the rat hepatic and macrophage asialoglycoprotein receptors. J Biol Chem. Mar. 22, 1996;271(12):6686-93. doi: 10.1074/jbc.271.12.6686.
Joshi et al., siRNA: novel therapeutics from functional genomics. Biotechnol Genet Eng Rev. Oct. 2014;30(1-2):1-30. doi: 10.1080/02648725.2014.921495.
Kabanov et al., A new class of antivirals; antisense oligonucleotides combined with a hydrophobic substituent effectively inhibit influenza virus reproduction and synthesis of virus- specific proteins in MDCK cells. FEBS Lett. Jan. 1, 1990;259(2):327-30. doi: 10.1016/0014-5793(90)80039-1.
Kamola et al., The siRNA Non-seed Region and Its Target Sequences Are Auxiliary Determinants of Off-Target Effects. PLoS Comput Biol. Dec. 11, 2015;11(12):e1004656. doi: 10.1371/journal.pcbi.1004656. eCollection Dec. 2015.
Kemmer et al., Alpha-1-antitrypsin deficiency: outcomes after liver transplantation. Transplant Proc. Jun. 2008;40(5):1492-4. doi: 10.1016/j.transproceed.2008.02.075.
Kok et al., Prevalence of genetic polymorphisms in the promoter region of the alpha-1 antitrypsin (SERPINA1) gene in chronic liver disease: a case control study. BMC Gastroenterology. Feb. 20, 2010;10:22. doi: 10.1186/1471-230X-10-22.
Kurreck et al., Design of Antisense Oligonucleotides Stabilized by Locked Nucleic Acids. Nucleic Acids Res. May 1, 2002;30(9):1911-8. doi: 10.1093/nar/30.9.1911.
Letsinger et al., Cholesteryl-conjugated oligonucleotides: synthesis, properties, and activity as inhibitors of replication of human immunodeficiency virus in cell culture. Proc Natl Acad Sci USA. Sep. 1989;86(17):6553-6. doi: 10.1073/pnas.86.17.6553.
Li et al., Combination Therapy Utilizing shRNA and Optimize Alpha-I Antitrypsin (AAT) Expression Cassette for Treatment and Correction of AAT Liver Deficiency. Mol Ther. 2009; 17(1):S12.
Lindblad et al., Alpha-1-antitrypsin mutant Z protein content in individual hepatocytes correlates with cell death in a mouse model. Hepatology. Oct. 2007;46(4):1228-35. doi: 10.1002/hep.21822.
Lomas et al., The mechanism of Z alpha 1-antitrypsin accumulation in the liver. Nature. Jun. 18, 1992;357(6379):605-7. doi: 10.1038/357605a0.
Long et al., Complete sequence of the cDNA for human alpha 1-antitrypsin and the gene for the S variant. Biochemistry. Oct. 9, 1984;23(21):4828-37. doi: 10.1021/bi00316a003.
Manoharan et al., Lipidic Nucleic Acids. Tetrahedron Letters. 1995; 36: 3651-4.
McLean et al., Gene targeted therapeutics for liver disease in alpha-I antitrypsin deficiency. Biologics. 2009;3:63-75. Epub Jul. 13, 2009.
Mishra et al., Improved leishmanicidal effect of phosphorothioate antisense oligonucleotides by LDL-mediated delivery. Biochim Biophys Acta. Nov. 7, 1995;1264(2):229-37. doi: 10.1016/0167-4781(95)00145-7.
Mueller et al., Development of Simultaneous Gene Augmentation and Reduction of Mutant Gene Expression with a Single Recombinant AAV for Alpha One Antitrypsin Disease. Mol Ther. 2009; 17(1): S391-S392.
Mueller et al., In Vivo Allele Specific Knockdown of Mutant Alpha One Antitrypsin using Recombinant AAV Delivered shRNA. Mol Ther. 2009; 17(1): S313.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. doi: 10.1038/mt.2011.292. Epub Jan. 17, 2012.
Nelson et al., Diagnosis and management of patients with al-antitrypsin (A1AT) deficiency. Clin Gastroenterol Hepatol. Jun. 2012;10(6):575-80. doi: 10.1016/j.cgh.2011.12.028. Epub Dec. 23, 2011.
Nielsen et al., Incorporation of (R)- and (S)-3',4'-seco-thymidine into oligodeoxynucleotides: hybridization properties and enzymatic stability. Nucleic Acids Res. Mar. 11, 1994;22(5):703-10. doi: 10.1093/nar/22.5.703.
Nielsen et al., Synthesis and evaluation of oligodeoxynucleotides containing acyclic nucleosides: introduction of three novel analogues and a summary. Bioorg Med Chem. Jan. 1995;3(1):19-28. doi: 10.1016/0968-0896(94)00143-q.
Paakko et al., Activated neutrophils secrete stored alpha 1-antitrypsin. Am J Respir Crit Care Med. Dec. 1996;154(6 Pt 1):1829-33. doi: 10.1164/ajrccm.154.6.8970377.
Perlmutter et al., Hepatic fibrosis and carcinogenesis in α1-antitrypsin deficiency: a prototype for chronic tissue damage in gain-of-function disorders. Cold Spring Harb Perspect Biol. Mar. 1, 2011;3(3):a005801. doi: 10.1101/cshperspect.a005801.
Perlmutter, Alpha-1-antitrypsin deficiency: importance of proteasomal and autophagic degradative pathways in disposal of liver disease-associated protein aggregates. Annu Rev Med. 2011;62:333-45. doi: 10.1146/annurev-med-042409-151920.
Propst et al., Prevalence of hepatocellular carcinoma in alpha-1-antitrypsin deficiency. J Hepatol. Dec. 1994;21(6):1006-11. doi: 10.1016/s0168-8278(05)80609-9.
Saison-Behmoaras et al., Short Modified Antisense Oligonucleotides Directed Against Ha-ras Point Mutation Induce Selective Cleavage of the mRNA and Inhibit T24 Cells Proliferation. Embo J. May 1991;10(5):1111-8.
Sehgal et al., Developing an RNAi Therapeutic for Liver Disease Associated With Alpha-1-Antitrypsin Deficiency. AASLD Poster. Nov. 2013.

(56) References Cited

OTHER PUBLICATIONS

Shea et al., Synthesis, hybridization properties and antiviral activity of lipid-oligodeoxynucleotide conjugates. Nucleic Acids Res. Jul. 11, 1990;18(13):3777-83. doi: 10.1093/nar/18.13.3777.

Song et al., Crystal structure of an uncleaved alpha 1-antitrypsin reveals the conformation of its inhibitory reactive loop. FEBS Lett. Dec. 18, 1995;377(2):150-4. doi: 10.1016/0014-5793(95)01331-8.

Stoller et al., A review of α1-antitrypsin deficiency. Am J Respir Crit Care Med. Feb. 1, 2012;185(3):246-59. doi: 10.1164/rccm.201108-1428CI. Epub Sep. 29, 2011.

Sveger, Liver disease in alpha1-antitrypsin deficiency detected by screening of 200,000 infants. N Engl J Med. Jun. 10, 1976;294(24):1316-21. doi: 10.1056/NEJM197606102942404.

Svinarchuk et al., Inhibition of HIV proliferation in MT-4 cells by antisense oligonucleotide conjugated to lipophilic groups. Biochimie. 1993;75(1-2):49-54. doi: 10.1016/0300-9084(93)90024-m.

Teckman et al., Advances in alpha-1-antitrypsin deficiency liver disease. Curr Gastroenterol Rep. Jan. 2014;16(1):367. doi: 10.1007/s11894-013-0367-8.

Teckman et al., Mitochondrial autophagy and injury in the liver in alpha 1-antitrypsin deficiency. Am J Physiol Gastrointest Liver Physiol. May 2004;286(5):G851-62. doi: 10.1152/ajpgi.00175.2003. Epub Dec. 18, 2003.

Teckman, Liver disease in alpha-1 antitrypsin deficiency: current understanding and future therapy. COPD. Mar. 2013; 10 Suppl 1:35-43. doi: 10.3109/15412555.2013.765839.

Thomson et al., Synthesis and Properties of Diuridine Phosphate Analogues Containing Thio and Amino Modifications. J Org Chem. Sep. 6, 1996;61(18):6273-6281. doi: 10.1021/jo9607951.

Venembre et al., Secretion of alpha 1-antitrypsin by alveolar epithelial cells. FEBS Lett. Jun. 13, 1994;346(2-3):171-4. doi: 10.1016/0014-5793(94)80695-0.

Wagner, The state of the art in antisense research. Nat Med. Nov. 1995;1(11):1116-8. doi: 10.1038/nm1195-1116.

Wahlestedt et al., Potent and nontoxic antisense oligonucleotides containing locked nucleic acids. Proc Natl Acad Sci U S A. May 9, 2000;97(10):5633-8. doi: 10.1073/pnas.97.10.5633.

U.S. Appl. No. 18/026,340, filed Mar. 14, 2023, Christianson et al.

SEQUENCE LISTING

<160> NUMBER OF SEQ ID NOS: 1279

<210> SEQ ID NO 1
<211> LENGTH: 3220
<212> TYPE: DNA
<213> ORGANISM: Homo sapiens
<220> FEATURE:
<221> NAME/KEY: misc_feature
<222> LOCATION: (1)..(3220)
<223> OTHER INFORMATION: Serpin family A member 1 (SERPINA1), transcript variant 1, complete gene (NM_000295.4)

<400> SEQUENCE: 1

| | | | | | |
|---|---|---|---|---|---|
| acaatgactc | ctttcggtaa | gtgcagtgga | agctgtacac | tgcccaggca | aagcgtccgg | 60 |
| gcagcgtagg | cgggcgactc | agatcccagc | cagtggactt | agcccctgtt | tgctcctccg | 120 |
| ataactgggg | tgaccttggt | taatattcac | cagcagcctc | ccccgttgcc | cctctggatc | 180 |
| cactgcttaa | atacggacga | ggacagggcc | ctgtctcctc | agcttcaggc | accaccactg | 240 |
| acctgggaca | gtgaatcgac | aatgccgtct | tctgtctcgt | ggggcatcct | cctgctggca | 300 |
| ggcctgtgct | gcctggtccc | tgtctccctg | gctgaggatc | cccagggaga | tgctgcccag | 360 |
| aagacagata | catcccacca | tgatcaggat | cacccaacct | tcaacaagat | cacccccaac | 420 |
| ctggctgagt | tcgccttcag | cctataccgc | cagctggcac | accagtccaa | cagcaccaat | 480 |
| atcttcttct | ccccagtgag | catcgctaca | gcctttgcaa | tgctctccct | ggggaccaag | 540 |
| gctgacactc | acgatgaaat | cctggagggc | ctgaatttca | acctcacgga | gattccggag | 600 |
| gctcagatcc | atgaaggctt | ccaggaactc | ctccgtaccc | tcaaccagcc | agacagccag | 660 |
| ctccagctga | ccaccggcaa | tggcctgttc | ctcagcgagg | gcctgaagct | agtggataag | 720 |
| tttttggagg | atgttaaaaa | gttgtaccac | tcagaagcct | tcactgtcaa | cttcggggac | 780 |
| accgaagagg | ccaagaaaca | gatcaacgat | tacgtggaga | agggtactca | agggaaaatt | 840 |
| gtggatttgg | tcaaggagct | tgacagagac | acagttttg | ctctggtgaa | ttacatcttc | 900 |
| tttaaaggca | aatgggagag | acccttgaa | gtcaaggaca | ccgaggaaga | ggacttccac | 960 |
| gtggaccagg | tgaccaccgt | gaaggtgcct | atgatgaagc | gtttaggcat | gtttaacatc | 1020 |
| cagcactgta | agaagctgtc | cagctgggtg | ctgctgatga | aatacctggg | caatgccacc | 1080 |
| gccatcttct | tcctgcctga | tgaggggaaa | ctacagcacc | tggaaaatga | actcacccac | 1140 |
| gatatcatca | ccaagttcct | ggaaaatgaa | gacagaaggt | ctgccagctt | acatttaccc | 1200 |
| aaactgtcca | ttactggaac | ctatgatctg | aagagcgtcc | tggtcaact | gggcatcact | 1260 |
| aaggtcttca | gcaatggggc | tgacctctcc | ggggtcacag | aggaggcacc | cctgaagctc | 1320 |
| tccaaggccg | tgcataaggc | tgtgctgacc | atcgacgaga | aagggactga | agctgctggg | 1380 |
| gccatgtttt | tagaggccat | acccatgtct | atccccccg | aggtcaagtt | caacaaaccc | 1440 |
| tttgtcttct | taatgattga | acaaaatacc | aagtctcccc | tcttcatggg | aaaagtggtg | 1500 |
| aatcccaccc | aaaaataact | gcctctcgct | cctcaacccc | tccctccat | ccctggcccc | 1560 |
| ctccctggat | gacattaaag | aagggttgag | ctggtccctg | cctgcatgtg | actgtaaatc | 1620 |
| cctcccatgt | tttctctgag | tctccctttg | cctgctgagg | ctgtatgtgg | gctccaggta | 1680 |
| acagtgctgt | cttcgggccc | cctgaactgt | gttcatggag | catctggctg | ggtaggcaca | 1740 |
| tgctgggctt | gaatccaggg | gggactgaat | cctcagctta | cggacctggg | cccatctgtt | 1800 |
| tctggagggc | tccagtcttc | cttgtcctgt | cttggagtcc | caagaagga | atcacagggg | 1860 |
| aggaaccaga | taccagccat | gaccccaggc | tccaccaagc | atcttcatgt | ccccctgctc | 1920 |

-continued

```
atccccact    cccccccacc    cagagttgct    catcctgcca    gggctggctg    tgcccacccc    1980
aaggctgccc    tcctgggggc    cccagaactg    cctgatcgtg    ccgtggccca    gttttgtggc    2040
atctgcagca    acacaagaga    gaggacaatg    tcctcctctt    gacccgctgt    cacctaacca    2100
gactcgggcc    ctgcacctct    caggcacttc    tggaaaatga    ctgaggcaga    ttcttcctga    2160
agcccattct    ccatggggca    acaaggacac    ctattctgtc    cttgtccttc    catcgctgcc    2220
ccagaaagcc    tcacatatct    ccgtttagaa    tcaggtccct    tctccccaga    tgaagaggag    2280
ggtctctgct    ttgttttctc    tatctcctcc    tcagacttga    ccaggcccag    caggcccag     2340
aagaccatta    ccctatatcc    cttctcctcc    ctagtcacat    ggccataggc    ctgctgatgg    2400
ctcaggaagg    ccattgcaag    gactcctcag    ctatgggaga    ggaagcacat    cacccattga    2460
cccccgcaac    ccctcccttt    cctcctctga    gtcccgactg    gggccacatg    cagcctgact    2520
tctttgtgcc    tgttgctgtc    cctgcagtct    tcagagggcc    accgcagctc    cagtgccacg    2580
gcaggaggct    gttcctgaat    agccctgtgt    gtaaggccca    ggagagtcct    tccatcctcc    2640
aagccctgc    taaaggacac    agcagccagg    aagtcccctg    gcccctagc     tgaaggacag    2700
cctgctccct    ccgtctctac    caggaatggc    cttgtcctat    ggaaggcact    gcccatccc     2760
aaactaatct    aggaatcact    gtctaaccac    tcactgtcat    gaatgtgtac    ttaaaggatg    2820
aggttgagtc    ataccaaata    gtgatttcga    tagttcaaaa    tggtgaaatt    agcaattcta    2880
catgattcag    tctaatcaat    ggataccgac    tgtttcccac    acaagtctcc    tgttctctta    2940
agcttactca    ctgacagcct    ttcactctcc    acaaatacat    taaagatatg    gccatcacca    3000
agccccctag    gatgacacca    gacctgagag    tctgaagacc    tggatccaag    ttctgactt     3060
tccccctgac    agctgtgtga    ccttcgtgaa    gtcgccaaac    ctctctgagc    cccagtcatt    3120
gctagtaaga    cctgccttgt    agttggtatg    atgttcaagt    tagataacaa    aatgtttata    3180
cccattagaa    cagagaataa    atagaactac    atttcttgca                               3220
```

<210> SEQ ID NO 2  
<211> LENGTH: 19  
<212> TYPE: RNA  
<213> ORGANISM: Artificial sequence  
<220> FEATURE:  
<223> OTHER INFORMATION: AAT mRNA target sequence

<400> SEQUENCE: 2
cguuuaggca uguuuaaca                                                               19

<210> SEQ ID NO 3  
<211> LENGTH: 19  
<212> TYPE: RNA  
<213> ORGANISM: Artificial sequence  
<220> FEATURE:  
<223> OTHER INFORMATION: AAT mRNA target sequence

<400> SEQUENCE: 3
aacagcacca auaucuucu                                                               19

<210> SEQ ID NO 4  
<211> LENGTH: 19  
<212> TYPE: RNA  
<213> ORGANISM: Artificial sequence  
<220> FEATURE:  
<223> OTHER INFORMATION: AAT mRNA target sequence

<400> SEQUENCE: 4
auaucaucac caaguuccu                                                               19

```
<210> SEQ ID NO 5
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 5
agaugcugcc cagaagaca                                                   19

<210> SEQ ID NO 6
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 6
cuggcacacc aguccaaca                                                   19

<210> SEQ ID NO 7
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 7
uggcacacca guccaacag                                                   19

<210> SEQ ID NO 8
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 8
gcacaccagu ccaacagca                                                   19

<210> SEQ ID NO 9
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 9
caguccaaca gcaccaaua                                                   19

<210> SEQ ID NO 10
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 10
aguccaacag caccaauau                                                   19

<210> SEQ ID NO 11
<211> LENGTH: 19
<212> TYPE: RNA
<213> ORGANISM: Artificial sequence
<220> FEATURE:
```

<223> OTHER INFORMATION: AAT mRNA target sequence

<400> SEQUENCE: 11
guccaacagc accaauauc                                                    19

<210> SEQ ID NO 12
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 12
ccaacagcac caauaucuu                                                    19

<210> SEQ ID NO 13
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 13
ccccagugag caucgcuac                                                    19

<210> SEQ ID NO 14
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 14
gagcaucgcu acagccuuu                                                    19

<210> SEQ ID NO 15
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 15
gcaucgcuac agccuuugc                                                    19

<210> SEQ ID NO 16
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 16
caucgcuaca gccuuugca                                                    19

<210> SEQ ID NO 17
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 17
ucgcuacagc cuuugcaau                                                    19

```
<210> SEQ ID NO 18
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 18
cuacagccuu ugcaaugcu                                                19

<210> SEQ ID NO 19
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 19
acagccuuug caaugcucu                                                19

<210> SEQ ID NO 20
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 20
gaaggcuucc aggaacucc                                                19

<210> SEQ ID NO 21
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 21
uaguggauaa guuuuugga                                                19

<210> SEQ ID NO 22
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 22
uguaccacuc agaagccuu                                                19

<210> SEQ ID NO 23
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 23
guaccacuca gaagccuuc                                                19

<210> SEQ ID NO 24
<211> LENGTH: 19
<212> TYPE: RNA
<213> ORGANISM: Artificial sequence
<220> FEATURE:
<223> OTHER INFORMATION: AAT mRNA target sequence
```

```
<400> SEQUENCE: 24
acaccgaaga ggccaagaa                                              19

<210> SEQ ID NO 25
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 25
accgaagagg ccaagaaac                                              19

<210> SEQ ID NO 26
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 26
aggccaagaa acagaucaa                                              19

<210> SEQ ID NO 27
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 27
ggccaagaaa cagaucaac                                              19

<210> SEQ ID NO 28
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 28
gccaagaaac agaucaacg                                              19

<210> SEQ ID NO 29
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 29
uacucaaggg aaaauugug                                              19

<210> SEQ ID NO 30
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 30
cucaagggaa aauugugga                                              19

<210> SEQ ID NO 31
<211> LENGTH: 19
```

```
<212> TYPE: RNA
<213> ORGANISM: Artificial sequence
<220> FEATURE:
<223> OTHER INFORMATION: AAT mRNA target sequence

<400> SEQUENCE: 31
ucaagggaaa auuguggau                                                 19

<210> SEQ ID NO 32
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 32
uuggucaagg agcuugaca                                                 19

<210> SEQ ID NO 33
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 33
aggagcuuga cagagacac                                                 19

<210> SEQ ID NO 34
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 34
agcuugacag agacacagu                                                 19

<210> SEQ ID NO 35
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 35
uuugcucugg ugaauuaca                                                 19

<210> SEQ ID NO 36
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 36
agcguuuagg cauguuuaa                                                 19

<210> SEQ ID NO 37
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 37
```
gcguuuaggc auguuuaac                                                19

<210> SEQ ID NO 38
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 38
uuaggcaugu uuaacaucc                                                19

<210> SEQ ID NO 39
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 39
ugggugcugc ugaugaaau                                                19

<210> SEQ ID NO 40
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 40
ugccaccgcc aucuucuuc                                                19

<210> SEQ ID NO 41
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 41
ccuggaaaau gaacucacc                                                19

<210> SEQ ID NO 42
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 42
cgauaucauc accaaguuc                                                19

<210> SEQ ID NO 43
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 43
accaaguucc uggaaaaug                                                19

<210> SEQ ID NO 44
<211> LENGTH: 19
<212> TYPE: RNA
<213> ORGANISM: Artificial sequence -continued

```
<220> FEATURE:
<223> OTHER INFORMATION: AAT mRNA target sequence

<400> SEQUENCE: 44
uccauuacug gaaccuaug                                                      19

<210> SEQ ID NO 45
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 45
ccauuacugg aaccauga                                                       19

<210> SEQ ID NO 46
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 46
acuggaaccu augaucuga                                                      19

<210> SEQ ID NO 47
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 47
ggaaccuaug aucugaaga                                                      19

<210> SEQ ID NO 48
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 48
gaaccuauga ucugaagag                                                      19

<210> SEQ ID NO 49
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 49
cagcaauggg gcugaccuc                                                      19

<210> SEQ ID NO 50
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 50
gcaauggggc ugaccucuc                                                      19
```

```
<210> SEQ ID NO 51
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 51
agaggaggca ccccugaag                                                  19

<210> SEQ ID NO 52
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 52 aggcacccu gaagcucuc                                                   19

<210> SEQ ID NO 53
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 53
ucuccaaggc cgugcauaa                                                  19

<210> SEQ ID NO 54
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 54
uccaaggccg ugcauaagg                                                  19

<210> SEQ ID NO 55
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 55
ccaaggccgu gcauaaggc                                                  19

<210> SEQ ID NO 56
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 56
caaggccgug cauaaggcu                                                  19

<210> SEQ ID NO 57
<211> LENGTH: 19
<212> TYPE: RNA
<213> ORGANISM: Artificial sequence
<220> FEATURE:
<223> OTHER INFORMATION: AAT mRNA target sequence
```

```
<400> SEQUENCE: 57
aaggcugugc ugaccaucg                                               19

<210> SEQ ID NO 58
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 58
ggcugugcug accaucgac                                               19

<210> SEQ ID NO 59
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 59
cugcuggggc cauguuuuu                                               19

<210> SEQ ID NO 60
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 60
gcuggggcca uguuuuuag                                               19

<210> SEQ ID NO 61
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 61
cuggggccau guuuuuaga                                               19

<210> SEQ ID NO 62
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 62
ggggccaugu uuuagagg                                                19

<210> SEQ ID NO 63
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 63
gggccauguu uuagaggc                                                19

<210> SEQ ID NO 64
```

```
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 64
gaggccauac ccaugucua                                              19

<210> SEQ ID NO 65
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 65
ggccauaccc augucuauc                                              19

<210> SEQ ID NO 66
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 66
cccgagguca aguucaaca                                              19

<210> SEQ ID NO 67
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 67
aggucaaguu caacaaacc                                              19

<210> SEQ ID NO 68
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 68
caaguucaac aaacccuuu                                              19

<210> SEQ ID NO 69
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 69
aguucaacaa acccuuugu                                              19

<210> SEQ ID NO 70
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 70
```

```
guucaacaaa cccuuuguc                                              19

<210> SEQ ID NO 71
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 71
ucaacaaacc cuuugucuu                                              19

<210> SEQ ID NO 72
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 72
acccuuuguc uucuuaaug                                              19

<210> SEQ ID NO 73
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 73
ccuuugucuu cuuaaugau                                              19

<210> SEQ ID NO 74
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 74
uaccaagucu ccccucuuc                                              19

<210> SEQ ID NO 75
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 75 aaguccccc ucuucaugg                                               19

<210> SEQ ID NO 76
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 76
agucuccccu cuucauggg                                              19

<210> SEQ ID NO 77
<211> LENGTH: 19
<212> TYPE: RNA
```

```
<213> ORGANISM: Artificial sequence
<220> FEATURE:
<223> OTHER INFORMATION: AAT mRNA target sequence

<400> SEQUENCE: 77
ucuccccucu ucaugggaa                                                  19

<210> SEQ ID NO 78
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 78
cuccccucuu caugggaaa                                                  19

<210> SEQ ID NO 79
<211> LENGTH: 19
<212> TYPE: RNA
<213> ORGANISM: Artificial sequence
<220> FEATURE:
<223> OTHER INFORMATION: AAT mRNA target sequence

<400> SEQUENCE: 79
augacauuaa agaaggguu                                                  19

<210> SEQ ID NO 80
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 80
uguuaaacau gccuaaacg                                                  19

<210> SEQ ID NO 81
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 81
aguuaaacau gccuaaacg                                                  19

<210> SEQ ID NO 82
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 82
nguuaaacau gccuaaacg                                                  19
```

```
<210> SEQ ID NO 83
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 83
nguuaaacau gccuaaacn                                               19

<210> SEQ ID NO 84
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 84
agaagauauu ggugcuguu                                               19

<210> SEQ ID NO 85
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 85
ugaagauauu ggugcuguu                                               19

<210> SEQ ID NO 86
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 86
ngaagauauu ggugcuguu                                               19

<210> SEQ ID NO 87
<211> LENGTH: 19
<212> TYPE: RNA
<213> ORGANISM: Artificial sequence
<220> FEATURE:
<223> OTHER INFORMATION: AAT RNAi agent antisense strand core stretch
```

```
     base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 87
ngaagauauu ggugcugun                                            19

<210> SEQ ID NO 88
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 88
aggaacuugg ugaugauau                                            19

<210> SEQ ID NO 89
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 89
uggaacuugg ugaugauau                                            19

<210> SEQ ID NO 90
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 90
nggaacuugg ugaugauau                                            19

<210> SEQ ID NO 91
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
```

<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 91
nggaacuugg ugaugauan                                                19

<210> SEQ ID NO 92
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 92
ugucuucugg gcagcaucu                                                19

<210> SEQ ID NO 93
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 93
agucuucugg gcagcaucu                                                19

<210> SEQ ID NO 94
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 94
ngucuucugg gcagcaucu                                                19

<210> SEQ ID NO 95
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 95
ngucuucugg gcagcaucn                                                    19

<210> SEQ ID NO 96
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 96
uguuggacug gugugccag                                                    19

<210> SEQ ID NO 97
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 97
aguuggacug gugugccag                                                    19

<210> SEQ ID NO 98
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 98
nguuggacug gugugccag                                                    19

<210> SEQ ID NO 99
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 99
nguuggacug gugugccan                                                    19

<210> SEQ ID NO 100
<211> LENGTH: 19

```
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 100
cuguuggacu ggugugcca                                                    19

<210> SEQ ID NO 101
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 101
uuguuggacu ggugugcca                                                    19

<210> SEQ ID NO 102
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 102
auguuggacu ggugugcca                                                    19

<210> SEQ ID NO 103
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 103
nuguuggacu ggugugcca                                                    19

<210> SEQ ID NO 104
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 104
```
nuguuggacu ggugugccn                                                    19

<210> SEQ ID NO 105
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 105
ugcuguugga cuggugugc                                                    19

<210> SEQ ID NO 106
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 106
agcuguugga cuggugugc                                                    19

<210> SEQ ID NO 107
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 107
ngcuguugga cuggugugc                                                    19

<210> SEQ ID NO 108
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 108
ngcuguugga cuggugugn                                                    19

<210> SEQ ID NO 109
<211> LENGTH: 19
<212> TYPE: RNA

```
<213> ORGANISM: Artificial sequence
<220> FEATURE:
<223> OTHER INFORMATION: AAT RNAi agent antisense strand core stretch
      base sequence

<400> SEQUENCE: 109
uauuggugcu guuggacug                                                    19

<210> SEQ ID NO 110
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 110
aauuggugcu guuggacug                                                    19

<210> SEQ ID NO 111
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 111
nauuggugcu guuggacug                                                    19

<210> SEQ ID NO 112
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 112
nauuggugcu guuggacun                                                    19

<210> SEQ ID NO 113
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 113
```
auauuggugc uguuggacu                                              19

<210> SEQ ID NO 114
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 114
uuauuggugc uguuggacu                                              19

<210> SEQ ID NO 115
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 115
nuauuggugc uguuggacu                                              19

<210> SEQ ID NO 116
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 116
nuauuggugc uguuggacn                                              19

<210> SEQ ID NO 117
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 117
gauauuggug cuguuggac                                              19

<210> SEQ ID NO 118
<211> LENGTH: 19
<212> TYPE: RNA
<213> ORGANISM: Artificial sequence

```
<220> FEATURE:
<223> OTHER INFORMATION: AAT RNAi agent antisense strand core stretch
      base sequence

<400> SEQUENCE: 118
uauauuggug cguuggac                                                  19

<210> SEQ ID NO 119
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 119
aauauuggug cguuggac                                                  19

<210> SEQ ID NO 120
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 120
nauauuggug cguuggac                                                  19

<210> SEQ ID NO 121
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 121
nauauuggug cguuggan                                                  19

<210> SEQ ID NO 122
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 122
aagauauugg ugcuguugg                                                 19
```

-continued

```
<210> SEQ ID NO 123
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 123
uagauauugg ugcuguugg                                                     19

<210> SEQ ID NO 124
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 124
nagauauugg ugcuguugg                                                     19

<210> SEQ ID NO 125
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 125
nagauauugg ugcuguugn                                                     19

<210> SEQ ID NO 126
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 126
guagcgaugc ucacuggggg                                                    19

<210> SEQ ID NO 127
<211> LENGTH: 19
<212> TYPE: RNA
<213> ORGANISM: Artificial sequence
<220> FEATURE:
```

```
<223> OTHER INFORMATION: AAT RNAi agent antisense strand core stretch
      base sequence

<400> SEQUENCE: 127
uuagcgaugc ucacugggg                                                  19

<210> SEQ ID NO 128
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 128
auagcgaugc ucacugggg                                                  19

<210> SEQ ID NO 129
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 129
nuagcgaugc ucacugggg                                                  19

<210> SEQ ID NO 130
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 130
nuagcgaugc ucacugggn                                                  19

<210> SEQ ID NO 131
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 131
aaaggcugua gcgaugcuc                                                  19
```

```
<210> SEQ ID NO 132
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 132
uaaggcugua gcgaugcuc                                                     19

<210> SEQ ID NO 133
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 133
naaggcugua gcgaugcuc                                                     19

<210> SEQ ID NO 134
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 134
naaggcugua gcgaugcun                                                     19

<210> SEQ ID NO 135
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 135
gcaaaggcug uagcgaugc                                                     19

<210> SEQ ID NO 136
<211> LENGTH: 19
<212> TYPE: RNA
<213> ORGANISM: Artificial sequence
<220> FEATURE:
<223> OTHER INFORMATION: AAT RNAi agent antisense strand core stretch
```

```
                       base sequence

<400> SEQUENCE: 136
ucaaaggcug uagcgaugc                                              19

<210> SEQ ID NO 137
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 137
acaaaggcug uagcgaugc                                              19

<210> SEQ ID NO 138
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 138
ncaaaggcug uagcgaugc                                              19

<210> SEQ ID NO 139
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 139
ncaaaggcug uagcgaugn                                              19

<210> SEQ ID NO 140
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 140
ugcaaaggcu guagcgaug                                              19
```

```
<210> SEQ ID NO 141
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 141
agcaaaggcu guagcgaug                                                    19

<210> SEQ ID NO 142
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 142
ngcaaaggcu guagcgaug                                                    19

<210> SEQ ID NO 143
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 143
ngcaaaggcu guagcgaun                                                    19

<210> SEQ ID NO 144
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 144
auugcaaagg cuguagcga                                                    19

<210> SEQ ID NO 145
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
```

```
<400> SEQUENCE: 145
uuugcaaagg cuguagcga                                              19

<210> SEQ ID NO 146
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 146
nuugcaaagg cuguagcga                                              19

<210> SEQ ID NO 147
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 147
nuugcaaagg cuguagcgn                                              19

<210> SEQ ID NO 148
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 148
agcauugcaa aggcuguag                                              19

<210> SEQ ID NO 149
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 149
ugcauugcaa aggcuguag                                              19

<210> SEQ ID NO 150
```

```
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 150
ngcauugcaa aggcuguag                                              19

<210> SEQ ID NO 151
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 151
ngcauugcaa aggcuguan                                              19

<210> SEQ ID NO 152
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 152
agagcauugc aaaggcugu                                              19

<210> SEQ ID NO 153
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 153
ugagcauugc aaaggcugu                                              19

<210> SEQ ID NO 154
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
```

```
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 154
ngagcauugc aaaggcugu                                                     19

<210> SEQ ID NO 155
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 155
ngagcauugc aaaggcugu                                                     19

<210> SEQ ID NO 156
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 156
ggaguuccug gaagccuuc                                                     19

<210> SEQ ID NO 157
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 157
ugaguuccug gaagccuuc                                                     19

<210> SEQ ID NO 158
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 158
agaguuccug gaagccuuc                                                     19

<210> SEQ ID NO 159
<211> LENGTH: 19
<212> TYPE: RNA
<213> ORGANISM: Artificial sequence
<220> FEATURE:
<223> OTHER INFORMATION: AAT RNAi agent antisense strand core stretch
```

```
            base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 159
ngaguuccug gaagccuuc                                              19

<210> SEQ ID NO 160
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 160
ngaguuccug gaagccuun                                              19

<210> SEQ ID NO 161
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 161
uccaaaaacu uauccacua                                              19

<210> SEQ ID NO 162
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 162
accaaaaacu uauccacua                                              19

<210> SEQ ID NO 163
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
```

```
<222> LOCATION: (1)..(1)
<223> OTHER INFORMATION: n is a, c, g, or u

<400> SEQUENCE: 163
nccaaaaacu uauccacua                                                19

<210> SEQ ID NO 164
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 164
nccaaaaacu uauccacun                                                19

<210> SEQ ID NO 165
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 165
aaggcuucug agugguaca                                                19

<210> SEQ ID NO 166
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 166
uaggcuucug agugguaca                                                19

<210> SEQ ID NO 167
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 167
naggcuucug agugguaca                                                19
```

```
<210> SEQ ID NO 168
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 168
naggcuucug agugguacn                                                19

<210> SEQ ID NO 169
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 169
gaaggcuucu gagugguac                                                19

<210> SEQ ID NO 170
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 170
uaaggcuucu gagugguac                                                19

<210> SEQ ID NO 171
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 171
aaaggcuucu gagugguac                                                19

<210> SEQ ID NO 172
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
```

<223> OTHER INFORMATION: n is a, c, g, or u

<400> SEQUENCE: 172
naaggcuucu gagugguac                                                    19

<210> SEQ ID NO 173
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 173
naaggcuucu gaguggnan                                                    19

<210> SEQ ID NO 174
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 174
uucuuggccu cuucggugu                                                    19

<210> SEQ ID NO 175
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 175
aucuuggccu cuucggugu                                                    19

<210> SEQ ID NO 176
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 176
nucuuggccu cuucggugu                                                    19

```
<210> SEQ ID NO 177
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 177
nucuuggccu cuucggugn                                              19

<210> SEQ ID NO 178
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 178
guuucuuggc cucuucggu                                              19

<210> SEQ ID NO 179
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 179
uuuucuuggc cucuucggu                                              19

<210> SEQ ID NO 180
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 180
auuucuuggc cucuucggu                                              19

<210> SEQ ID NO 181
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
```

<400> SEQUENCE: 181
nuuucuuggc cucuucggu                                                    19

<210> SEQ ID NO 182
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 182
nuuucuuggc cucuucggn                                                    19

<210> SEQ ID NO 183
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 183
uugaucuguu ucuuggccu                                                    19

<210> SEQ ID NO 184
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 184
augaucuguu ucuuggccu                                                    19

<210> SEQ ID NO 185
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 185
nugaucuguu ucuuggccu                                                    19

<210> SEQ ID NO 186

```
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 186
nugaucuguu ucuuggccn                                                19

<210> SEQ ID NO 187
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 187
guugaucugu uucuuggcc                                                19

<210> SEQ ID NO 188
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 188
uuugaucugu uucuuggcc                                                19

<210> SEQ ID NO 189
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 189
auugaucugu uucuuggcc                                                19

<210> SEQ ID NO 190
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
```

```
<400> SEQUENCE: 190
nuugaucugu uucuuggcc                                               19

<210> SEQ ID NO 191
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 191
nuugaucugu uucuuggcn                                               19

<210> SEQ ID NO 192
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 192
cguugaucug uuucuuggc                                               19

<210> SEQ ID NO 193
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 193
uguugaucug uuucuuggc                                               19

<210> SEQ ID NO 194
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 194
aguugaucug uuucuuggc                                               19

<210> SEQ ID NO 195
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
```

```
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 195
nguugaucug uuucuuggc                                              19

<210> SEQ ID NO 196
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 196
nguugaucug uuucuuggn                                              19

<210> SEQ ID NO 197
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 197
cacaauuuuc ccuugagua                                              19

<210> SEQ ID NO 198
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 198
uacaauuuuc ccuugagua                                              19

<210> SEQ ID NO 199
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 199
aacaauuuuc ccuugagua                                              19

<210> SEQ ID NO 200
<211> LENGTH: 19
<212> TYPE: RNA
<213> ORGANISM: Artificial sequence
```

```
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 200
nacaauuuuc ccuugagua                                                  19

<210> SEQ ID NO 201
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 201
nacaauuuuc ccuugagun                                                  19

<210> SEQ ID NO 202
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 202
uccacaauuu ucccuugag                                                  19

<210> SEQ ID NO 203
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 203
accacaauuu ucccuugag                                                  19

<210> SEQ ID NO 204
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
```

```
<220> FEATURE:
<221> NAME/KEY: misc_feature
<222> LOCATION: (1)..(1)
<223> OTHER INFORMATION: n is a, c, g, or u

<400> SEQUENCE: 204
nccacaauuu ucccuugag                                                        19

<210> SEQ ID NO 205
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 205
nccacaauuu ucccuugan                                                        19

<210> SEQ ID NO 206
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 206
auccacaauu ucccuuga                                                         19

<210> SEQ ID NO 207
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 207
uuccacaauu ucccuuga                                                         19

<210> SEQ ID NO 208
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 208
```
nuccacaauu ucccuuga                                                19

<210> SEQ ID NO 209
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 209
nuccacaauu ucccuugn                                                19

<210> SEQ ID NO 210
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 210
ugucaagcuc cuugaccaa                                               19

<210> SEQ ID NO 211
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 211
agucaagcuc cuugaccaa                                               19

<210> SEQ ID NO 212
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 212
ngucaagcuc cuugaccaa                                               19

<210> SEQ ID NO 213
<211> LENGTH: 19
<212> TYPE: RNA
<213> ORGANISM: Artificial sequence

```
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 213
ngucaagcuc cuugaccaa                                                    19

<210> SEQ ID NO 214
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 214
gugucucugu caagcuccu                                                    19

<210> SEQ ID NO 215
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 215
uugucucugu caagcuccu                                                    19

<210> SEQ ID NO 216
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 216
augucucugu caagcuccu                                                    19

<210> SEQ ID NO 217
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 217
nugucucugu caagcuccu                                                    19

<210> SEQ ID NO 218
<211> LENGTH: 19
```

```
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 218
nugucucugu caagcuccn                                                  19

<210> SEQ ID NO 219
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 219
acugugucuc ugucaagcu                                                  19

<210> SEQ ID NO 220
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 220
ucugugucuc ugucaagcu                                                  19

<210> SEQ ID NO 221
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 221
ncugugucuc ugucaagcu                                                  19

<210> SEQ ID NO 222
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
```

```
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 222
ncugugucuc ugucaagcn                                              19

<210> SEQ ID NO 223
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 223
uguaauucac cagagcaaa                                              19

<210> SEQ ID NO 224
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 224
aguaauucac cagagcaaa                                              19

<210> SEQ ID NO 225
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 225
nguaauucac cagagcaaa                                              19

<210> SEQ ID NO 226
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
```

```
<221> NAME/KEY: misc_feature
<222> LOCATION: (19)..(19)
<223> OTHER INFORMATION: n is a, c, g, or u

<400> SEQUENCE: 226
nguaauucac cagagcaan                                                   19

<210> SEQ ID NO 227
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 227
uuaaacaugc cuaaacgcu                                                   19

<210> SEQ ID NO 228
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 228
auaaacaugc cuaaacgcu                                                   19

<210> SEQ ID NO 229
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 229
nuaaacaugc cuaaacgcu                                                   19

<210> SEQ ID NO 230
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 230
nuaaacaugc cuaaacgcn                                                   19
```

```
<210> SEQ ID NO 231
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 231
guuaaacaug ccuaaacgc                                                19

<210> SEQ ID NO 232
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 232
uuuaaacaug ccuaaacgc                                                19

<210> SEQ ID NO 233
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 233
auuaaacaug ccuaaacgc                                                19

<210> SEQ ID NO 234
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 234
nuuaaacaug ccuaaacgc                                                19

<210> SEQ ID NO 235
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
```

```
<222> LOCATION: (19)..(19)
<223> OTHER INFORMATION: n is a, c, g, or u

<400> SEQUENCE: 235
nuuaaacaug ccuaaacgn                                                  19

<210> SEQ ID NO 236
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 236
ggauguuaaa caugccuaa                                                  19

<210> SEQ ID NO 237
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 237
ugauguuaaa caugccuaa                                                  19

<210> SEQ ID NO 238
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 238
agauguuaaa caugccuaa                                                  19

<210> SEQ ID NO 239
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 239
ngauguuaaa caugccuaa                                                  19

<210> SEQ ID NO 240
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
```

```
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 240
ngauguuaaa caugccuan                                           19

<210> SEQ ID NO 241
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 241
auuucaucag cagcaccca                                           19

<210> SEQ ID NO 242
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 242
uuuucaucag cagcaccca                                           19

<210> SEQ ID NO 243
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 243
nuuucaucag cagcaccca                                           19

<210> SEQ ID NO 244
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
```

<223> OTHER INFORMATION: n is a, c, g, or u

<400> SEQUENCE: 244
nuuucaucag cagcacccn                                              19

<210> SEQ ID NO 245
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 245
gaagaagaug gcgguggca                                              19

<210> SEQ ID NO 246
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 246
uaagaagaug gcgguggca                                              19

<210> SEQ ID NO 247
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 247
aaagaagaug gcgguggca                                              19

<210> SEQ ID NO 248
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 248
naagaagaug gcgguggca                                              19

<210> SEQ ID NO 249
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:

```
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 249
naagaagaug gcgguggcn                                                   19

<210> SEQ ID NO 250
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 250
ggugaguuca uuuccagg                                                    19

<210> SEQ ID NO 251
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 251
ugugaguuca uuuccagg                                                    19

<210> SEQ ID NO 252
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 252
agugaguuca uuuccagg                                                    19

<210> SEQ ID NO 253
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 253
ngugaguuca uuuccagg                                                    19

<210> SEQ ID NO 254
<211> LENGTH: 19
<212> TYPE: RNA
<213> ORGANISM: Artificial sequence
<220> FEATURE:
<223> OTHER INFORMATION: AAT RNAi agent antisense strand core stretch
```

```
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 254
ngugaguuca uuuuccagn                                               19

<210> SEQ ID NO 255
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 255
gaacuuggug augauaucg                                               19

<210> SEQ ID NO 256
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 256
uaacuuggug augauaucg                                               19

<210> SEQ ID NO 257
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 257
aaacuuggug augauaucg                                               19

<210> SEQ ID NO 258
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 258
naacuuggug augauaucg                                               19
```

```
<210> SEQ ID NO 259
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 259
naacuuggug augauaucn                                               19

<210> SEQ ID NO 260
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 260
cauuuuccag gaacuuggu                                               19

<210> SEQ ID NO 261
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 261
uauuuuccag gaacuuggu                                               19

<210> SEQ ID NO 262
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 262
aauuuuccag gaacuuggu                                               19

<210> SEQ ID NO 263
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
```

<400> SEQUENCE: 263
nauuuuccag gaacuuggu					19

<210> SEQ ID NO 264
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 264
nauuuuccag gaacuuggn					19

<210> SEQ ID NO 265
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 265
cauagguucc aguaaugga					19

<210> SEQ ID NO 266
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 266
uauagguucc aguaaugga					19

<210> SEQ ID NO 267
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 267
aauagguucc aguaaugga					19

<210> SEQ ID NO 268
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base

```
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 268
nauagguucc aguaaugga                                                  19

<210> SEQ ID NO 269
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 269
nauagguucc aguaauggn                                                  19

<210> SEQ ID NO 270
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 270
ucauagguuc caguaaugg                                                  19

<210> SEQ ID NO 271
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 271
acauagguuc caguaaugg                                                  19

<210> SEQ ID NO 272
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
```

```
<400> SEQUENCE: 272
ncauagguuc caguaaugg                                                19

<210> SEQ ID NO 273
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 273
ncauagguuc caguaaugn                                                19

<210> SEQ ID NO 274
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 274
ucagaucaua gguuccagu                                                19

<210> SEQ ID NO 275
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 275
acagaucaua gguuccagu                                                19

<210> SEQ ID NO 276
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 276
ncagaucaua gguuccagu                                                19

<210> SEQ ID NO 277
<211> LENGTH: 19
```

```
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 277
ncagaucaua gguuccagn                                                    19

<210> SEQ ID NO 278
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 278
ucuucagauc auagguucc                                                    19

<210> SEQ ID NO 279
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 279
acuucagauc auagguucc                                                    19

<210> SEQ ID NO 280
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 280
ncuucagauc auagguucc                                                    19

<210> SEQ ID NO 281
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
```

```
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 281
ncuucagauc auagguucn                                              19

<210> SEQ ID NO 282
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 282
cucuucagau cauagguuc                                              19

<210> SEQ ID NO 283
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 283
uucuucagau cauagguuc                                              19

<210> SEQ ID NO 284
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 284
aucuucagau cauagguuc                                              19

<210> SEQ ID NO 285
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 285
nucuucagau cauagguuc                                              19

<210> SEQ ID NO 286
<211> LENGTH: 19
<212> TYPE: RNA
```

```
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 286
nucuucagau cauagguun                                              19

<210> SEQ ID NO 287
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 287
gaggucagcc ccauugcug                                              19

<210> SEQ ID NO 288
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 288
uaggucagcc ccauugcug                                              19

<210> SEQ ID NO 289
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 289
aaggucagcc ccauugcug                                              19

<210> SEQ ID NO 290
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 290
```
naggucagcc ccauugcug                                              19

<210> SEQ ID NO 291
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 291
naggucagcc ccauugcun                                              19

<210> SEQ ID NO 292
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 292
gagaggucag ccccauugc                                              19

<210> SEQ ID NO 293
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 293
uagaggucag ccccauugc                                              19

<210> SEQ ID NO 294
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 294
aagaggucag ccccauugc                                              19

<210> SEQ ID NO 295
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:

```
<221> NAME/KEY: misc_feature
<222> LOCATION: (1)..(1)
<223> OTHER INFORMATION: n is a, c, g, or u

<400> SEQUENCE: 295
nagaggucag ccccauugc                                                    19

<210> SEQ ID NO 296
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 296
nagaggucag ccccauugn                                                    19

<210> SEQ ID NO 297
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 297
cuucaggggu gccuccucu                                                    19

<210> SEQ ID NO 298
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 298
uuucaggggu gccuccucu                                                    19

<210> SEQ ID NO 299
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 299
auucaggggu gccuccucu                                                    19

<210> SEQ ID NO 300
<211> LENGTH: 19
<212> TYPE: RNA
<213> ORGANISM: Artificial sequence
<220> FEATURE:
<223> OTHER INFORMATION: AAT RNAi agent antisense strand core stretch
``` base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 300
nuucaggggu gccuccucu                                                    19

<210> SEQ ID NO 301
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 301
nuucaggggu gccuccucn                                                    19

<210> SEQ ID NO 302
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 302
gagagcuuca ggggugccu                                                    19

<210> SEQ ID NO 303
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 303
uagagcuuca ggggugccu                                                    19

<210> SEQ ID NO 304
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 304
aagagcuuca ggggugccu                                                    19

```
<210> SEQ ID NO 305
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 305
nagagcuuca ggggugccu                                                   19

<210> SEQ ID NO 306
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 306
nagagcuuca ggggugccn                                                   19

<210> SEQ ID NO 307
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 307
uuaugcacgg ccuuggaga                                                   19

<210> SEQ ID NO 308
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 308
auaugcacgg ccuuggaga                                                   19

<210> SEQ ID NO 309
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
```

```
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 309
nuaugcacgg ccuuggaga                                               19

<210> SEQ ID NO 310
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 310
nuaugcacgg ccuuggagn                                               19

<210> SEQ ID NO 311
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 311
ccuuaugcac ggccuugga                                               19

<210> SEQ ID NO 312
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 312
ucuuaugcac ggccuugga                                               19

<210> SEQ ID NO 313
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 313
acuuaugcac ggccuugga                                               19

<210> SEQ ID NO 314
```

```
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 314
ncuuaugcac ggccuugga                                                    19

<210> SEQ ID NO 315
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 315
ncuuaugcac ggccuuggn                                                    19

<210> SEQ ID NO 316
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 316
gccuuaugca cggccuugg                                                    19

<210> SEQ ID NO 317
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 317
uccuuaugca cggccuugg                                                    19

<210> SEQ ID NO 318
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
```

```
<400> SEQUENCE: 318
accuuaugca cggccuugg                                              19

<210> SEQ ID NO 319
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 319
nccuuaugca cggccuugg                                              19

<210> SEQ ID NO 320
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 320
nccuuaugca cggccuugn                                              19

<210> SEQ ID NO 321
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 321
agccuuaugc acggccuug                                              19

<210> SEQ ID NO 322
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 322
ugccuuaugc acggccuug                                              19

<210> SEQ ID NO 323
<211> LENGTH: 19
```

```
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 323
ngccuuaugc acggccuug                                                  19

<210> SEQ ID NO 324
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 324
ngccuuaugc acggccuun                                                  19

<210> SEQ ID NO 325
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 325
cgauggucag cacagccuu                                                  19

<210> SEQ ID NO 326
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 326
ugauggucag cacagccuu                                                  19

<210> SEQ ID NO 327
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 327
```
agauggucag cacagccuu                                                        19

<210> SEQ ID NO 328
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 328
ngauggucag cacagccuu                                                        19

<210> SEQ ID NO 329
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 329
ngauggucag cacagccun                                                        19

<210> SEQ ID NO 330
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 330
gucgaugguc agcacagcc                                                        19

<210> SEQ ID NO 331
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 331
uucgaugguc agcacagcc                                                        19

<210> SEQ ID NO 332
<211> LENGTH: 19
<212> TYPE: RNA

```
<213> ORGANISM: Artificial sequence
<220> FEATURE:
<223> OTHER INFORMATION: AAT RNAi agent antisense strand core stretch
      base sequence

<400> SEQUENCE: 332
aucgaugguc agcacagcc                                                 19

<210> SEQ ID NO 333
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 333
nucgaugguc agcacagcc                                                 19

<210> SEQ ID NO 334
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 334
nucgaugguc agcacagcn                                                 19

<210> SEQ ID NO 335
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 335
aaaaacaugg ccccagcag                                                 19

<210> SEQ ID NO 336
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 336
```
uaaaacaugg ccccagcag                                                    19

<210> SEQ ID NO 337
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 337
naaaacaugg ccccagcag                                                    19

<210> SEQ ID NO 338
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 338
naaaacaugg ccccagcan                                                    19

<210> SEQ ID NO 339
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 339
cuaaaaacau ggccccagc                                                    19

<210> SEQ ID NO 340
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 340
uuaaaaacau ggccccagc                                                    19

<210> SEQ ID NO 341
<211> LENGTH: 19
<212> TYPE: RNA
<213> ORGANISM: Artificial sequence

```
<220> FEATURE:
<223> OTHER INFORMATION: AAT RNAi agent antisense strand core stretch
      base sequence

<400> SEQUENCE: 341
auaaaaacau ggccccagc                                                    19

<210> SEQ ID NO 342
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 342
nuaaaaacau ggccccagc                                                    19

<210> SEQ ID NO 343
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 343
nuaaaaacau ggcccagn                                                     19

<210> SEQ ID NO 344
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 344
ucuaaaaaca uggccccag                                                    19

<210> SEQ ID NO 345
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 345
acuaaaaaca uggccccag                                                    19
```

<210> SEQ ID NO 346
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 346
ncuaaaaaca uggccccag                                                19

<210> SEQ ID NO 347
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 347
ncuaaaaaca uggccccan                                                19

<210> SEQ ID NO 348
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 348
ccucuaaaaa cauggcccc                                                19

<210> SEQ ID NO 349
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 349
ucucuaaaaa cauggcccc                                                19

<210> SEQ ID NO 350
<211> LENGTH: 19
<212> TYPE: RNA
<213> ORGANISM: Artificial sequence
<220> FEATURE:

<223> OTHER INFORMATION: AAT RNAi agent antisense strand core stretch
      base sequence

<400> SEQUENCE: 350
acucuaaaaa cauggcccc                                              19

<210> SEQ ID NO 351
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 351
ncucuaaaaa cauggcccc                                              19

<210> SEQ ID NO 352
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 352
ncucuaaaaa cauggcccn                                              19

<210> SEQ ID NO 353
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 353
gccucuaaaa acauggccc                                              19

<210> SEQ ID NO 354
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 354
uccucuaaaa acauggccc                                              19

```
<210> SEQ ID NO 355
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 355
accucuaaaa acauggccc                                              19

<210> SEQ ID NO 356
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 356
nccucuaaaa acauggccc                                              19

<210> SEQ ID NO 357
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 357
nccucuaaaa acauggccn                                              19

<210> SEQ ID NO 358
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 358
uagacauggg uauggccuc                                              19

<210> SEQ ID NO 359
<211> LENGTH: 19
<212> TYPE: RNA
<213> ORGANISM: Artificial sequence
<220> FEATURE:
<223> OTHER INFORMATION: AAT RNAi agent antisense strand core stretch
``` base sequence

<400> SEQUENCE: 359
aagacauggg uauggccuc                                                19

<210> SEQ ID NO 360
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 360
nagacauggg uauggccuc                                                19

<210> SEQ ID NO 361
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 361
nagacauggg uauggccun                                                19

<210> SEQ ID NO 362
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 362
gauagacaug gguauggcc                                                19

<210> SEQ ID NO 363
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 363
uauagacaug gguauggcc                                                19

```
<210> SEQ ID NO 364
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 364
aauagacaug gguauggcc                                                    19

<210> SEQ ID NO 365
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 365
nauagacaug gguauggcc                                                    19

<210> SEQ ID NO 366
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 366
nauagacaug gguauggcn                                                    19

<210> SEQ ID NO 367
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 367
uguugaacuu gaccucggg                                                    19

<210> SEQ ID NO 368
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
```

```
<400> SEQUENCE: 368
aguugaacuu gaccucggg                                                    19

<210> SEQ ID NO 369
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 369
nguugaacuu gaccucggg                                                    19

<210> SEQ ID NO 370
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 370
nguugaacuu gaccucggn                                                    19

<210> SEQ ID NO 371
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 371
gguuuguuga acuugaccu                                                    19

<210> SEQ ID NO 372
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 372
uguuuguuga acuugaccu                                                    19

<210> SEQ ID NO 373
```

```
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 373
aguuuguuga acugaccu                                                   19

<210> SEQ ID NO 374
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 374
nguuuguuga acugaccu                                                   19

<210> SEQ ID NO 375
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 375
nguuuguuga acugaccn                                                   19

<210> SEQ ID NO 376
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 376
aaaggguuug uugaacuug                                                  19

<210> SEQ ID NO 377
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
```

```
<400> SEQUENCE: 377
uaaggguuug uugaacuug                                                     19

<210> SEQ ID NO 378
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 378
naaggguuug uugaacuug                                                     19

<210> SEQ ID NO 379
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 379
naaggguuug uugaacuun                                                     19

<210> SEQ ID NO 380
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 380 acaaagggu uguugaacu                                                      19

<210> SEQ ID NO 381
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 381
ucaaaggguu uguugaacu                                                     19

<210> SEQ ID NO 382
<211> LENGTH: 19
```

```
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 382
ncaaaggguu uguugaacu                                                19

<210> SEQ ID NO 383
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 383
ncaaaggguu uguugaacn                                                19

<210> SEQ ID NO 384
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 384
gacaaagggu uguugaac                                                 19

<210> SEQ ID NO 385
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 385
uacaaagggu uuguugaac                                                19

<210> SEQ ID NO 386
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 386
```
aacaaagggu uuguugaac            19

<210> SEQ ID NO 387
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 387
nacaaagggu uuguugaac            19

<210> SEQ ID NO 388
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 388
nacaaagggu uuguugaan            19

<210> SEQ ID NO 389
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 389
aagacaaagg guuguuga            19

<210> SEQ ID NO 390
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 390
uagacaaagg guuuguuga            19

<210> SEQ ID NO 391
<211> LENGTH: 19
<212> TYPE: RNA

```
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 391
nagacaaagg guuuguuga                                                    19

<210> SEQ ID NO 392
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 392
nagacaaagg guuuguugn                                                    19

<210> SEQ ID NO 393
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 393
cauuaagaag acaaagggu                                                    19

<210> SEQ ID NO 394
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 394
uauuaagaag acaaagggu                                                    19

<210> SEQ ID NO 395
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 395
```
aauuaagaag acaaagggu                                                19

<210> SEQ ID NO 396
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 396
nauuaagaag acaaagggu                                                19

<210> SEQ ID NO 397
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 397
nauuaagaag acaaagggn                                                19

<210> SEQ ID NO 398
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 398
aucauuaaga agacaaagg                                                19

<210> SEQ ID NO 399
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 399
uucauuaaga agacaaagg                                                19

<210> SEQ ID NO 400
<211> LENGTH: 19
<212> TYPE: RNA
<213> ORGANISM: Artificial sequence

```
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 400
nucauuaaga agacaaagg                                                    19

<210> SEQ ID NO 401
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 401
nucauuaaga agacaaagn                                                    19

<210> SEQ ID NO 402
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 402
gaagagggga gacuuggua                                                    19

<210> SEQ ID NO 403
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 403
uaagagggga gacuuggua                                                    19

<210> SEQ ID NO 404
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 404
aaagagggga gacuuggua                                                    19
```

<210> SEQ ID NO 405
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 405
naagagggga gacuuggua                                               19

<210> SEQ ID NO 406
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 406
naagagggga gacuuggun                                               19

<210> SEQ ID NO 407
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 407
ccaugaagag gggagacuu                                               19

<210> SEQ ID NO 408
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 408
ucaugaagag gggagacuu                                               19

<210> SEQ ID NO 409
<211> LENGTH: 19
<212> TYPE: RNA
<213> ORGANISM: Artificial sequence
<220> FEATURE:

```
<223> OTHER INFORMATION: AAT RNAi agent antisense strand core stretch
      base sequence

<400> SEQUENCE: 409
acaugaagag gggagacuu                                                    19

<210> SEQ ID NO 410
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 410
ncaugaagag gggagacuu                                                    19

<210> SEQ ID NO 411
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 411
ncaugaagag gggagacun                                                    19

<210> SEQ ID NO 412
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 412
cccaugaaga ggggagacu                                                    19

<210> SEQ ID NO 413
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 413
uccaugaaga ggggagacu                                                    19
```

<210> SEQ ID NO 414
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 414
accaugaaga ggggagacu                                                    19

<210> SEQ ID NO 415
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 415
nccaugaaga ggggagacu                                                    19

<210> SEQ ID NO 416
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 416
nccaugaaga ggggagacn                                                    19

<210> SEQ ID NO 417
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 417
uucccaugaa gagggaga                                                     19

<210> SEQ ID NO 418
<211> LENGTH: 19
<212> TYPE: RNA
<213> ORGANISM: Artificial sequence
<220> FEATURE:
<223> OTHER INFORMATION: AAT RNAi agent antisense strand core stretch -continued

```
       base sequence

<400> SEQUENCE: 418
aucccaugaa gagggga                                                    19

<210> SEQ ID NO 419
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 419
nucccaugaa gagggga                                                    19

<210> SEQ ID NO 420
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 420
nucccaugaa gaggggagn                                                  19

<210> SEQ ID NO 421
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 421
uuucccauga agaggggag                                                  19

<210> SEQ ID NO 422
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 422
auucccauga agaggggag                                                  19
```

```
<210> SEQ ID NO 423
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 423
nuucccauga agaggggag                                                     19

<210> SEQ ID NO 424
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 424
nuucccauga agaggggan                                                     19

<210> SEQ ID NO 425
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 425
aacccuucuu uaaugcau                                                      19

<210> SEQ ID NO 426
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence

<400> SEQUENCE: 426
uacccuucuu uaaugcau                                                      19

<210> SEQ ID NO 427
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
```

```
<220> FEATURE:
<221> NAME/KEY: modified_base
<222> LOCATION: (1)..(1)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

<400> SEQUENCE: 427
nacccuucuu uaaugucau                                              19

<210> SEQ ID NO 428
<211> LENGTH: 19
<212> TYPE: RNA
<213> ORGANISM: Artificial sequence
<220> FEATURE:
<223> OTHER INFORMATION: AAT RNAi agent antisense strand core stretch
      base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 428
nacccuucuu uaaugucan                                              19

<210> SEQ ID NO 429
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 429
cguuuaggca uguuuaaca                                              19

<210> SEQ ID NO 430
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 430
cguuuaggca uguuuaacu                                              19

<210> SEQ ID NO 431
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
```

<223> OTHER INFORMATION: n is a, c, g, or u

<400> SEQUENCE: 431
cguuuaggca uguuuaacn                                                    19

<210> SEQ ID NO 432
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 432
nguuuaggca uguuuaacn                                                    19

<210> SEQ ID NO 433
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 433
aacagcacca auaucuucu                                                    19

<210> SEQ ID NO 434
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 434
aacagcacca auaucuuca                                                    19

<210> SEQ ID NO 435
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 435
aacagcacca auaucuucn                                                    19

```
<210> SEQ ID NO 436
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 436
nacagcacca auaucuucn                                                    19

<210> SEQ ID NO 437
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 437
auaucaucac caaguuccu                                                    19

<210> SEQ ID NO 438
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 438
auaucaucac caaguucca                                                    19

<210> SEQ ID NO 439
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 439
auaucaucac caaguuccn                                                    19

<210> SEQ ID NO 440
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
```

```
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 440
nuaucaucac caaguuccn                                                  19

<210> SEQ ID NO 441
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 441
agaugcugcc cagaagaca                                                  19

<210> SEQ ID NO 442
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 442
agaugcugcc cagaagacu                                                  19

<210> SEQ ID NO 443
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 443
agaugcugcc cagaagacn                                                  19

<210> SEQ ID NO 444
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
```

```
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 444
ngaugcugcc cagaagacn                                                19

<210> SEQ ID NO 445
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 445
cuggcacacc aguccaaca                                                19

<210> SEQ ID NO 446
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 446
cuggcacacc aguccaacu                                                19

<210> SEQ ID NO 447
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 447
cuggcacacc aguccaacn                                                19

<210> SEQ ID NO 448
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 448
```
nuggcacacc aguccaacn                                                19

<210> SEQ ID NO 449
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 449
uggcacacca guccaacag                                                19

<210> SEQ ID NO 450
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 450
uggcacacca guccaacaa                                                19

<210> SEQ ID NO 451
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 451
uggcacacca guccaacau                                                19

<210> SEQ ID NO 452
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 452
uggcacacca guccaacan                                                19

<210> SEQ ID NO 453
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u

```
<220> FEATURE:
<221> NAME/KEY: misc_feature
<222> LOCATION: (19)..(19)
<223> OTHER INFORMATION: n is a, c, g, or u

<400> SEQUENCE: 453
nggcacacca guccaacan                                                19

<210> SEQ ID NO 454
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 454
gcacaccagu ccaacagca                                                19

<210> SEQ ID NO 455
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 455
gcacaccagu ccaacagcu                                                19

<210> SEQ ID NO 456
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 456
gcacaccagu ccaacagcn                                                19

<210> SEQ ID NO 457
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 457
```
ncacaccagu ccaacagcn                                                19

<210> SEQ ID NO 458
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 458
caguccaaca gcaccaaua                                                19

<210> SEQ ID NO 459
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 459
caguccaaca gcaccaauu                                                19

<210> SEQ ID NO 460
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 460
caguccaaca gcaccaaun                                                19

<210> SEQ ID NO 461
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 461
naguccaaca gcaccaaun                                                19

<210> SEQ ID NO 462
<211> LENGTH: 19
<212> TYPE: RNA
<213> ORGANISM: Artificial sequence

```
<220> FEATURE:
<223> OTHER INFORMATION: AAT RNAi agent sense strand core stretch base
      sequence

<400> SEQUENCE: 462
aguccaacag caccaauau                                                    19

<210> SEQ ID NO 463
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 463
aguccaacag caccaauaa                                                    19

<210> SEQ ID NO 464
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 464
aguccaacag caccaauan                                                    19

<210> SEQ ID NO 465
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 465
nguccaacag caccaauan                                                    19

<210> SEQ ID NO 466
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 466
guccaacagc accaauauc                                                    19
```

<210> SEQ ID NO 467
<211> LENGTH: 19
<212> TYPE: RNA
<213> ORGANISM: Artificial sequence
<220> FEATURE:
<223> OTHER INFORMATION: AAT RNAi agent sense strand core stretch base sequence

<400> SEQUENCE: 467
guccaacagc accaauaua                                              19

<210> SEQ ID NO 468
<211> LENGTH: 19
<212> TYPE: RNA
<213> ORGANISM: Artificial sequence
<220> FEATURE:
<223> OTHER INFORMATION: AAT RNAi agent sense strand core stretch base sequence

<400> SEQUENCE: 468
guccaacagc accaauauu                                              19

<210> SEQ ID NO 469
<211> LENGTH: 19
<212> TYPE: RNA
<213> ORGANISM: Artificial sequence
<220> FEATURE:
<223> OTHER INFORMATION: AAT RNAi agent sense strand core stretch base sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 469
guccaacagc accaauaun                                              19

<210> SEQ ID NO 470
<211> LENGTH: 19
<212> TYPE: RNA
<213> ORGANISM: Artificial sequence
<220> FEATURE:
<223> OTHER INFORMATION: AAT RNAi agent sense strand core stretch base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 470
nuccaacagc accaauaun                                              19

<210> SEQ ID NO 471
<211> LENGTH: 19
<212> TYPE: RNA
<213> ORGANISM: Artificial sequence
<220> FEATURE:

```
<223> OTHER INFORMATION: AAT RNAi agent sense strand core stretch base
      sequence

<400> SEQUENCE: 471
ccaacagcac caauaucuu                                                  19

<210> SEQ ID NO 472
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 472
ccaacagcac caauaucua                                                  19

<210> SEQ ID NO 473
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 473
ccaacagcac caauaucun                                                  19

<210> SEQ ID NO 474
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 474
ncaacagcac caauaucun                                                  19

<210> SEQ ID NO 475
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 475
ccccagugag caucgcuac                                                  19
```

<210> SEQ ID NO 476
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 476
ccccagugag caucgcuaa                                                        19

<210> SEQ ID NO 477
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 477
ccccagugag caucgcuau                                                        19

<210> SEQ ID NO 478
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 478
ccccagugag caucgcuan                                                        19

<210> SEQ ID NO 479
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 479
ncccagugag caucgcuan                                                        19

<210> SEQ ID NO 480
<211> LENGTH: 19
<212> TYPE: RNA
<213> ORGANISM: Artificial sequence
<220> FEATURE:
<223> OTHER INFORMATION: AAT RNAi agent sense strand core stretch base sequence

<400> SEQUENCE: 480
gagcaucgcu acagccuuu                                                    19

<210> SEQ ID NO 481
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 481
gagcaucgcu acagccuua                                                    19

<210> SEQ ID NO 482
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 482
gagcaucgcu acagccuun                                                    19

<210> SEQ ID NO 483
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 483
nagcaucgcu acagccuun                                                    19

<210> SEQ ID NO 484
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 484
gcaucgcuac agccuuugc                                                    19

```
<210> SEQ ID NO 485
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 485
gcaucgcuac agccuuuga                                                19

<210> SEQ ID NO 486
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 486
gcaucgcuac agccuuugu                                                19

<210> SEQ ID NO 487
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 487
gcaucgcuac agccuuugn                                                19

<210> SEQ ID NO 488
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 488
ncaucgcuac agccuuugn                                                19

<210> SEQ ID NO 489
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
```

```
<400> SEQUENCE: 489
caucgcuaca gccuuugca                                                19

<210> SEQ ID NO 490
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 490
caucgcuaca gccuuugcu                                                19

<210> SEQ ID NO 491
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 491
naucgcuaca gccuuugcn                                                19

<210> SEQ ID NO 492
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 492
naucgcuaca gccuuugcn                                                19

<210> SEQ ID NO 493
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 493
```
ucgcuacagc cuuugcaau                                                19

<210> SEQ ID NO 494
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 494
ucgcuacagc cuuugcaaa                                                19

<210> SEQ ID NO 495
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 495
ucgcuacagc cuuugcaan                                                19

<210> SEQ ID NO 496
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 496
ncgcuacagc cuuugcaan                                                19

<210> SEQ ID NO 497
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 497
cuacagccuu ugcaaugcu                                                19

<210> SEQ ID NO 498
<211> LENGTH: 19
<212> TYPE: RNA
<213> ORGANISM: Artificial sequence

```
<220> FEATURE:
<223> OTHER INFORMATION: AAT RNAi agent sense strand core stretch base
      sequence

<400> SEQUENCE: 498
cuacagccuu ugcaaugca                                                    19

<210> SEQ ID NO 499
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 499
cuacagccuu ugcaaugcn                                                    19

<210> SEQ ID NO 500
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 500
nuacagccuu ugcaaugcn                                                    19

<210> SEQ ID NO 501
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 501
acagccuuug caaugcucu                                                    19

<210> SEQ ID NO 502
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 502
acagccuuug caaugcuca                                                    19
```

```
<210> SEQ ID NO 503
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 503
acagccuuug caaugcucn                                                    19

<210> SEQ ID NO 504
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 504
ncagccuuug caaugcucn                                                    19

<210> SEQ ID NO 505
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 505
gaaggcuucc aggaacucc                                                    19

<210> SEQ ID NO 506
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 506
gaaggcuucc aggaacuca                                                    19

<210> SEQ ID NO 507
<211> LENGTH: 19
<212> TYPE: RNA
<213> ORGANISM: Artificial sequence
<220> FEATURE:
```

```
<223> OTHER INFORMATION: AAT RNAi agent sense strand core stretch base
      sequence

<400> SEQUENCE: 507
gaaggcuucc aggaacucu                                                      19

<210> SEQ ID NO 508
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 508
gaaggcuucc aggaacucn                                                      19

<210> SEQ ID NO 509
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 509
naaggcuucc aggaacucn                                                      19

<210> SEQ ID NO 510
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 510
uaguggauaa guuuuugga                                                      19

<210> SEQ ID NO 511
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 511
uaguggauaa guuuuuggu                                                      19
```

```
<210> SEQ ID NO 512
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 512
uaguggauaa guuuuuggn                                                      19

<210> SEQ ID NO 513
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 513
naguggauaa guuuuuggn                                                      19

<210> SEQ ID NO 514
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 514
uguaccacuc agaagccuu                                                      19

<210> SEQ ID NO 515
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 515
uguaccacuc agaagccua                                                      19

<210> SEQ ID NO 516
<211> LENGTH: 19
<212> TYPE: RNA
<213> ORGANISM: Artificial sequence
<220> FEATURE:
<223> OTHER INFORMATION: AAT RNAi agent sense strand core stretch base
```

```
                              sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 516
uguaccacuc agaagccun                                                    19

<210> SEQ ID NO 517
<211> LENGTH: 19
<212> TYPE: RNA
<213> ORGANISM: Artificial sequence
<220> FEATURE:
<223> OTHER INFORMATION: AAT RNAi agent sense strand core stretch base
                              sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 517
nguaccacuc agaagccun                                                    19

<210> SEQ ID NO 518
<211> LENGTH: 19
<212> TYPE: RNA
<213> ORGANISM: Artificial sequence
<220> FEATURE:
<223> OTHER INFORMATION: AAT RNAi agent sense strand core stretch base
                              sequence

<400> SEQUENCE: 518
guaccacuca gaagccuuc                                                    19

<210> SEQ ID NO 519
<211> LENGTH: 19
<212> TYPE: RNA
<213> ORGANISM: Artificial sequence
<220> FEATURE:
<223> OTHER INFORMATION: AAT RNAi agent sense strand core stretch base
                              sequence

<400> SEQUENCE: 519
guaccacuca gaagccuua                                                    19

<210> SEQ ID NO 520
<211> LENGTH: 19
<212> TYPE: RNA
<213> ORGANISM: Artificial sequence
<220> FEATURE:
<223> OTHER INFORMATION: AAT RNAi agent sense strand core stretch base
                              sequence

<400> SEQUENCE: 520
guaccacuca gaagccuuu                                                    19
```

```
<210> SEQ ID NO 521
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 521
guaccacuca gaagccuun                                               19

<210> SEQ ID NO 522
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 522
nuaccacuca gaagccuun                                               19

<210> SEQ ID NO 523
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 523
acaccgaaga ggccaagaa                                               19

<210> SEQ ID NO 524
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 524
acaccgaaga ggccaagau                                               19

<210> SEQ ID NO 525
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
```

```
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 525
acaccgaaga ggccaagan                                              19

<210> SEQ ID NO 526
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 526
ncaccgaaga ggccaagan                                              19

<210> SEQ ID NO 527
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 527
accgaagagg ccaagaaac                                              19

<210> SEQ ID NO 528
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 528
accgaagagg ccaagaaaa                                              19

<210> SEQ ID NO 529
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 529
accgaagagg ccaagaaau                                              19

<210> SEQ ID NO 530
```

```
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 530
accgaagagg ccaagaaan                                                     19

<210> SEQ ID NO 531
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 531
nccgaagagg ccaagaaan                                                     19

<210> SEQ ID NO 532
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 532
aggccaagaa acagaucaa                                                     19

<210> SEQ ID NO 533
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 533
aggccaagaa acagaucau                                                     19

<210> SEQ ID NO 534
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
```

```
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 534
aggccaagaa acagaucan                                            19

<210> SEQ ID NO 535
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 535
nggccaagaa acagaucan                                            19

<210> SEQ ID NO 536
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 536
ggccaagaaa cagaucaac                                            19

<210> SEQ ID NO 537
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 537
ggccaagaaa cagaucaaa                                            19

<210> SEQ ID NO 538
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 538
ggccaagaaa cagaucaau                                            19

<210> SEQ ID NO 539
<211> LENGTH: 19
```

```
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 539
ggccaagaaa cagaucaan                                              19

<210> SEQ ID NO 540
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 540
ngccaagaaa cagaucaan                                              19

<210> SEQ ID NO 541
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 541
gccaagaaac agaucaacg                                              19

<210> SEQ ID NO 542
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 542
gccaagaaac agaucaaca                                              19

<210> SEQ ID NO 543
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 543
```
gccaagaaac agaucaacu                                                19

<210> SEQ ID NO 544
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 544
gccaagaaac agaucaacn                                                19

<210> SEQ ID NO 545
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 545
nccaagaaac agaucaacn                                                19

<210> SEQ ID NO 546
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 546
uacucaaggg aaaauugug                                                19

<210> SEQ ID NO 547
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 547
uacucaaggg aaaauugua                                                19

<210> SEQ ID NO 548
<211> LENGTH: 19
<212> TYPE: RNA

```
<213> ORGANISM: Artificial sequence
<220> FEATURE:
<223> OTHER INFORMATION: AAT RNAi agent sense strand core stretch base
      sequence

<400> SEQUENCE: 548
uacucaaggg aaaauuguu                                                    19

<210> SEQ ID NO 549
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 549
uacucaaggg aaaauugun                                                    19

<210> SEQ ID NO 550
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 550
nacucaaggg aaaauugun                                                    19

<210> SEQ ID NO 551
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 551
cucaagggaa aauugugga                                                    19

<210> SEQ ID NO 552
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 552
```
cucaagggaa aauuguggu                                                          19

<210> SEQ ID NO 553
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 553
cucaagggaa aauuguggn                                                          19

<210> SEQ ID NO 554
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 554
nucaagggaa aauuguggn                                                          19

<210> SEQ ID NO 555
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 555
ucaagggaaa auuguggau                                                          19

<210> SEQ ID NO 556
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 556
ucaagggaaa auuguggaa                                                          19

<210> SEQ ID NO 557
<211> LENGTH: 19
<212> TYPE: RNA
<213> ORGANISM: Artificial sequence

```
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 557
ucaagggaaa auguggan                                                   19

<210> SEQ ID NO 558
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 558
ncaagggaaa auguggan                                                   19

<210> SEQ ID NO 559
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 559
uuggucaagg agcuugaca                                                  19

<210> SEQ ID NO 560
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 560
uuggucaagg agcuugacu                                                  19

<210> SEQ ID NO 561
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(1)
<223> OTHER INFORMATION: n = any nucleotide
```

```
<220> FEATURE:
<221> NAME/KEY: misc_feature
<222> LOCATION: (1)..(1)
<223> OTHER INFORMATION: n is a, c, g, or u

<400> SEQUENCE: 561
nuggucaagg agcuugaca                                                   19

<210> SEQ ID NO 562
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 562
nuggucaagg agcuugacn                                                   19

<210> SEQ ID NO 563
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 563
aggagcuuga cagagacac                                                   19

<210> SEQ ID NO 564
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 564
aggagcuuga cagagacaa                                                   19

<210> SEQ ID NO 565
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 565
aggagcuuga cagagacau                                                   19

<210> SEQ ID NO 566
<211> LENGTH: 19
<212> TYPE: RNA
<213> ORGANISM: Artificial sequence
<220> FEATURE:
```

```
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 566
aggagcuuga cagagacan                                              19

<210> SEQ ID NO 567
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 567
nggagcuuga cagagacan                                              19

<210> SEQ ID NO 568
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 568
agcuugacag agacacagu                                              19

<210> SEQ ID NO 569
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 569
agcuugacag agacacaga                                              19

<210> SEQ ID NO 570
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
```

```
<221> NAME/KEY: misc_feature
<222> LOCATION: (19)..(19)
<223> OTHER INFORMATION: n is a, c, g, or u

<400> SEQUENCE: 570
agcuugacag agacacagn                                              19

<210> SEQ ID NO 571
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 571
ngcuugacag agacacagn                                              19

<210> SEQ ID NO 572
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 572
uuugcucugg ugaauuaca                                              19

<210> SEQ ID NO 573
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 573
uuugcucugg ugaauuacu                                              19

<210> SEQ ID NO 574
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 574
uuugcucugg ugaauuacn                                              19
```

```
<210> SEQ ID NO 575
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 575
nuugcucugg ugaauuacn                                              19

<210> SEQ ID NO 576
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 576
agcguuuagg cauguuuaa                                              19

<210> SEQ ID NO 577
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 577
agcguuuagg cauguuuau                                              19

<210> SEQ ID NO 578
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 578
agcguuuagg cauguuuan                                              19

<210> SEQ ID NO 579
<211> LENGTH: 19
<212> TYPE: RNA
<213> ORGANISM: Artificial sequence
<220> FEATURE:
```

```
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 579
ngcguuuagg cauguuuan                                                  19

<210> SEQ ID NO 580
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 580
gcguuuaggc auguuuaac                                                  19

<210> SEQ ID NO 581
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 581
gcguuuaggc auguuuaaa                                                  19

<210> SEQ ID NO 582
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 582
gcguuuaggc auguuuaau                                                  19

<210> SEQ ID NO 583
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 583
gcguuuaggc auguuuaan                                                  19
```

```
<210> SEQ ID NO 584
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 584
ncguuuaggc auguuuaan                                              19

<210> SEQ ID NO 585
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 585
uuaggcaugu uuaacaucc                                              19

<210> SEQ ID NO 586
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 586
uuaggcaugu uuaacauca                                              19

<210> SEQ ID NO 587
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 587
uuaggcaugu uuaacaucu                                              19

<210> SEQ ID NO 588
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
```

```
<223> OTHER INFORMATION: n is a, c, g, or u

<400> SEQUENCE: 588
uuaggcaugu uuaacaucn                                              19

<210> SEQ ID NO 589
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 589
nuaggcaugu uuaacaucn                                              19

<210> SEQ ID NO 590
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 590
ugggugcugc ugaugaaau                                              19

<210> SEQ ID NO 591
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 591
ugggugcugc ugaugaaaa                                              19

<210> SEQ ID NO 592
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 592
ugggugcugc ugaugaaan                                              19
```

```
<210> SEQ ID NO 593
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 593
ngggugcugc ugaugaaan                                              19

<210> SEQ ID NO 594
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 594
ugccaccgcc aucuucuuc                                              19

<210> SEQ ID NO 595
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 595
ugccaccgcc aucuucuua                                              19

<210> SEQ ID NO 596
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 596
ugccaccgcc aucuucuuu                                              19

<210> SEQ ID NO 597
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u
```

<400> SEQUENCE: 597
ugccaccgcc aucuucuun                                                    19

<210> SEQ ID NO 598
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 598
ngccaccgcc aucuucuun                                                    19

<210> SEQ ID NO 599
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 599
ccuggaaaau gaacucacc                                                    19

<210> SEQ ID NO 600
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 600
ccuggaaaau gaacucaca                                                    19

<210> SEQ ID NO 601
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 601
ccuggaaaau gaacucacu                                                    19

<210> SEQ ID NO 602
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base

```
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 602
ccuggaaaau gaacucacn                                                   19

<210> SEQ ID NO 603
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 603
ncuggaaaau gaacucacn                                                   19

<210> SEQ ID NO 604
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 604
cgauaucauc accaaguuc                                                   19

<210> SEQ ID NO 605
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 605
cgauaucauc accaaguua                                                   19

<210> SEQ ID NO 606
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 606
cgauaucauc accaaguuu                                                   19

<210> SEQ ID NO 607
<211> LENGTH: 19
<212> TYPE: RNA
```

```
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 607
cgauaucauc accaaguun                                                 19

<210> SEQ ID NO 608
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 608
ngauaucauc accaaguun                                                 19

<210> SEQ ID NO 609
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 609
accaaguucc uggaaaaug                                                 19

<210> SEQ ID NO 610
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 610
accaaguucc uggaaaaua                                                 19

<210> SEQ ID NO 611
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 611
```

```
accaaguucc uggaaaauu                                              19

<210> SEQ ID NO 612
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 612
accaaguucc uggaaaaun                                              19

<210> SEQ ID NO 613
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 613
nccaaguucc uggaaaaun                                              19

<210> SEQ ID NO 614
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 614
uccauuacug gaaccuaug                                              19

<210> SEQ ID NO 615
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 615
uccauuacug gaaccuaua                                              19

<210> SEQ ID NO 616
<211> LENGTH: 19
<212> TYPE: RNA
<213> ORGANISM: Artificial sequence
```

```
<220> FEATURE:
<223> OTHER INFORMATION: AAT RNAi agent sense strand core stretch base
      sequence

<400> SEQUENCE: 616
uccauuacug gaaccuauu                                                      19

<210> SEQ ID NO 617
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 617
uccauuacug gaaccuaun                                                      19

<210> SEQ ID NO 618
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 618
nccauuacug gaaccuaun                                                      19

<210> SEQ ID NO 619
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 619
ccauuacugg aaccauga                                                       19

<210> SEQ ID NO 620
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 620
ccauuacugg aaccaugu                                                       19
```

<210> SEQ ID NO 621
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 621
ccauuacugg aaccuaugn                                                    19

<210> SEQ ID NO 622
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 622
ncauuacugg aaccuaugn                                                    19

<210> SEQ ID NO 623
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 623
acuggaaccu augaucuga                                                    19

<210> SEQ ID NO 624
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 624
acuggaaccu augaucugu                                                    19

<210> SEQ ID NO 625
<211> LENGTH: 19
<212> TYPE: RNA
<213> ORGANISM: Artificial sequence
<220> FEATURE:

<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 625
acuggaaccu augaucugn                                                  19

<210> SEQ ID NO 626
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 626
ncuggaaccu augaucugn                                                  19

<210> SEQ ID NO 627
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 627
ggaaccuaug aucugaaga                                                  19

<210> SEQ ID NO 628
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 628
ggaaccuaug aucugaagu                                                  19

<210> SEQ ID NO 629
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:

```
<221> NAME/KEY: misc_feature
<222> LOCATION: (19)..(19)
<223> OTHER INFORMATION: n is a, c, g, or u

<400> SEQUENCE: 629
ggaaccuaug aucugaagn                                               19

<210> SEQ ID NO 630
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 630
ngaaccuaug aucugaagn                                               19

<210> SEQ ID NO 631
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 631
gaaccuauga ucugaagag                                               19

<210> SEQ ID NO 632
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 632
gaaccuauga ucugaagaa                                               19

<210> SEQ ID NO 633
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 633
gaaccuauga ucugaagau                                               19

<210> SEQ ID NO 634
<211> LENGTH: 19
<212> TYPE: RNA
<213> ORGANISM: Artificial sequence
<220> FEATURE:
<223> OTHER INFORMATION: AAT RNAi agent sense strand core stretch base
``` sequence

<400> SEQUENCE: 634 gaaccauga ucugaagag                                                19

<210> SEQ ID NO 635
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 635 naaccauga ucugaagan                                                19

<210> SEQ ID NO 636
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 636
cagcaauggg gcugaccuc                                               19

<210> SEQ ID NO 637
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 637
cagcaauggg gcugaccua                                               19

<210> SEQ ID NO 638
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 638
cagcaauggg gcugaccuu                                               19

<210> SEQ ID NO 639
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:

```
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 639
cagcaauggg gcugaccun                                                  19

<210> SEQ ID NO 640
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 640
nagcaauggg gcugaccun                                                  19

<210> SEQ ID NO 641
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 641
gcaauggggc ugaccucuc                                                  19

<210> SEQ ID NO 642
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 642
gcaauggggc ugaccucua                                                  19

<210> SEQ ID NO 643
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide

<400> SEQUENCE: 643
gcaauggggc ugaccucuu                                                  19
```

<210> SEQ ID NO 644
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 644
gcaauggggc ugaccucun                                                   19

<210> SEQ ID NO 645
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 645
ncaauggggc ugaccucun                                                   19

<210> SEQ ID NO 646
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 646
agaggaggca ccccugaag                                                   19

<210> SEQ ID NO 647
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 647
agaggaggca ccccugaaa                                                   19

<210> SEQ ID NO 648
<211> LENGTH: 19
<212> TYPE: RNA
<213> ORGANISM: Artificial sequence
<220> FEATURE:

```
<223> OTHER INFORMATION: AAT RNAi agent sense strand core stretch base
      sequence

<400> SEQUENCE: 648
agaggaggca ccccugaau                                                  19

<210> SEQ ID NO 649
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 649
agaggaggca ccccugaan                                                  19

<210> SEQ ID NO 650
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 650
ngaggaggca ccccugaan                                                  19

<210> SEQ ID NO 651
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 651
aggcaccccu gaagcucuc                                                  19

<210> SEQ ID NO 652
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 652
aggcaccccu gaagcucua                                                  19
```

<210> SEQ ID NO 653
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 653
aggcaccccu gaagcucuu                                                    19

<210> SEQ ID NO 654
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 654
aggcaccccu gaagcucun                                                    19

<210> SEQ ID NO 655
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 655
nggcaccccu gaagcucun                                                    19

<210> SEQ ID NO 656
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 656
ucuccaaggc cgugcauaa                                                    19

<210> SEQ ID NO 657
<211> LENGTH: 19
<212> TYPE: RNA
<213> ORGANISM: Artificial sequence
<220> FEATURE:
<223> OTHER INFORMATION: AAT RNAi agent sense strand core stretch base sequence

<400> SEQUENCE: 657
ucuccaaggc cgugcauau                                                        19

<210> SEQ ID NO 658
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 658
ucuccaaggc cgugcauan                                                        19

<210> SEQ ID NO 659
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 659
ncuccaaggc cgugcauan                                                        19

<210> SEQ ID NO 660
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 660
uccaaggccg ugcauaagg                                                        19

<210> SEQ ID NO 661
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 661
uccaaggccg ugcauaaga                                                        19

```
<210> SEQ ID NO 662
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 662
uccaaggccg ugcauaagu                                             19

<210> SEQ ID NO 663
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 663
uccaaggccg ugcauaagn                                             19

<210> SEQ ID NO 664
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 664
nccaaggccg ugcauaagn                                             19

<210> SEQ ID NO 665
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 665
ccaaggccgu gcauaaggc                                             19

<210> SEQ ID NO 666
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
```

```
<400> SEQUENCE: 666
ccaaggccgu gcauaagga                                              19

<210> SEQ ID NO 667
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 667
ccaaggccgu gcauaaggu                                              19

<210> SEQ ID NO 668
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 668
ccaaggccgu gcauaaggn                                              19

<210> SEQ ID NO 669
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 669
ncaaggccgu gcauaaggn                                              19

<210> SEQ ID NO 670
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 670
caaggccgug cauaaggcu                                              19

<210> SEQ ID NO 671
```

```
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 671
caaggccgug cauaaggca                                                       19

<210> SEQ ID NO 672
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 672
caaggccgug cauaaggcn                                                       19

<210> SEQ ID NO 673
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 673
naaggccgug cauaaggcn                                                       19

<210> SEQ ID NO 674
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 674
aaggcugugc ugaccaucg                                                       19

<210> SEQ ID NO 675
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
```

```
<400> SEQUENCE: 675
aaggcugugc ugaccauca                                                    19

<210> SEQ ID NO 676
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 676
aaggcugugc ugaccaucu                                                    19

<210> SEQ ID NO 677
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 677
aaggcugugc ugaccaucn                                                    19

<210> SEQ ID NO 678
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 678
naggcugugc ugaccaucn                                                    19

<210> SEQ ID NO 679
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 679
ggcugugcug accaucgac                                                    19

<210> SEQ ID NO 680
<211> LENGTH: 19
```

```
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 680
ggcugugcug accaucgaa                                              19

<210> SEQ ID NO 681
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 681
ggcugugcug accaucgau                                              19

<210> SEQ ID NO 682
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 682
ggcugugcug accaucgan                                              19

<210> SEQ ID NO 683
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 683
ngcugugcug accaucgan                                              19

<210> SEQ ID NO 684
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 684
```
cugcuggggc cauguuuuu                                                  19

<210> SEQ ID NO 685
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 685
cugcuggggc cauguuuua                                                  19

<210> SEQ ID NO 686
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide

<400> SEQUENCE: 686
cugcuggggc cauguuuuu                                                  19

<210> SEQ ID NO 687
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 687
nugcuggggc cauguuuun                                                  19

<210> SEQ ID NO 688
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 688
gcuggggcca uguuuuuag                                                  19

<210> SEQ ID NO 689
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

```
<400> SEQUENCE: 689
gcuggggcca uguuuuuaa                                                    19

<210> SEQ ID NO 690
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 690
gcuggggcca uguuuuuau                                                    19

<210> SEQ ID NO 691
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 691
gcuggggcca uguuuuuan                                                    19

<210> SEQ ID NO 692
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 692
ncuggggcca uguuuuuan                                                    19

<210> SEQ ID NO 693
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 693
cuggggccau guuuuuaga                                                    19

<210> SEQ ID NO 694
```

```
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 694 cugggggccau guuuuuagu                                                    19

<210> SEQ ID NO 695
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 695
cuggggccau guuuuuagn                                                     19

<210> SEQ ID NO 696
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 696
nuggggccau guuuuuagn                                                     19

<210> SEQ ID NO 697
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 697
ggggccaugu uuuagagg                                                      19

<210> SEQ ID NO 698
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
```

-continued

<400> SEQUENCE: 698
ggggccaugu uuuagaga                                                        19

<210> SEQ ID NO 699
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 699
ggggccaugu uuuagagu                                                        19

<210> SEQ ID NO 700
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 700
ggggccaugu uuuagagn                                                        19

<210> SEQ ID NO 701
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 701
ngggccaugu uuuagagn                                                        19

<210> SEQ ID NO 702
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 702
gggccauguu uuagaggc                                                        19

<210> SEQ ID NO 703
<211> LENGTH: 19

```
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 703
gggccauguu uuagagga                                                  19

<210> SEQ ID NO 704
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 704
gggccauguu uuagaggu                                                  19

<210> SEQ ID NO 705
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 705
gggccauguu uuagaggn                                                  19

<210> SEQ ID NO 706
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 706
nggccauguu uuagaggn                                                  19

<210> SEQ ID NO 707
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 707
```
gaggccauac ccaugucua                                              19

<210> SEQ ID NO 708
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 708
gaggccauac ccaugucuu                                              19

<210> SEQ ID NO 709
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 709
gaggccauac ccaugucun                                              19

<210> SEQ ID NO 710
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 710
naggccauac ccaugucun                                              19

<210> SEQ ID NO 711
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 711
ggccauaccc augucuauc                                              19

<210> SEQ ID NO 712
<211> LENGTH: 19
<212> TYPE: RNA

<213> ORGANISM: Artificial sequence
<220> FEATURE:
<223> OTHER INFORMATION: AAT RNAi agent sense strand core stretch base sequence

<400> SEQUENCE: 712
ggccauaccc augucuaua                                                    19

<210> SEQ ID NO 713
<211> LENGTH: 19
<212> TYPE: RNA
<213> ORGANISM: Artificial sequence
<220> FEATURE:
<223> OTHER INFORMATION: AAT RNAi agent sense strand core stretch base sequence

<400> SEQUENCE: 713
ggccauaccc augucuauu                                                    19

<210> SEQ ID NO 714
<211> LENGTH: 19
<212> TYPE: RNA
<213> ORGANISM: Artificial sequence
<220> FEATURE:
<223> OTHER INFORMATION: AAT RNAi agent sense strand core stretch base sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 714
ggccauaccc augucuaun                                                    19

<210> SEQ ID NO 715
<211> LENGTH: 19
<212> TYPE: RNA
<213> ORGANISM: Artificial sequence
<220> FEATURE:
<223> OTHER INFORMATION: AAT RNAi agent sense strand core stretch base sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 715
ngccauaccc augucuaun                                                    19

<210> SEQ ID NO 716
<211> LENGTH: 19
<212> TYPE: RNA
<213> ORGANISM: Artificial sequence
<220> FEATURE:
<223> OTHER INFORMATION: AAT RNAi agent sense strand core stretch base sequence

<400> SEQUENCE: 716
cccgagguca aguucaaca                                          19

<210> SEQ ID NO 717
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 717
cccgagguca aguucaacu                                          19

<210> SEQ ID NO 718
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 718
cccgagguca aguucaacn                                          19

<210> SEQ ID NO 719
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 719
nccgagguca aguucaacn                                          19

<210> SEQ ID NO 720
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 720
aggucaaguu caacaaacc                                          19

<210> SEQ ID NO 721
<211> LENGTH: 19
<212> TYPE: RNA
<213> ORGANISM: Artificial sequence

```
<220> FEATURE:
<223> OTHER INFORMATION: AAT RNAi agent sense strand core stretch base
      sequence

<400> SEQUENCE: 721
aggucaaguu caacaaaca                                                    19

<210> SEQ ID NO 722
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 722
aggucaaguu caacaaacu                                                    19

<210> SEQ ID NO 723
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 723
aggucaaguu caacaaacn                                                    19

<210> SEQ ID NO 724
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 724
nggucaaguu caacaaacn                                                    19

<210> SEQ ID NO 725
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 725
caaguucaac aaacccuuu                                                    19
```

<210> SEQ ID NO 726
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 726
caaguucaac aaacccuua                                                19

<210> SEQ ID NO 727
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 727
caaguucaac aaacccuun                                                19

<210> SEQ ID NO 728
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 728
naaguucaac aaacccuun                                                19

<210> SEQ ID NO 729
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 729
aguucaacaa acccuuugu                                                19

<210> SEQ ID NO 730
<211> LENGTH: 19
<212> TYPE: RNA
<213> ORGANISM: Artificial sequence
<220> FEATURE:

```
<223> OTHER INFORMATION: AAT RNAi agent sense strand core stretch base
      sequence

<400> SEQUENCE: 730
aguucaacaa acccuuuga                                              19

<210> SEQ ID NO 731
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 731
aguucaacaa acccuuugn                                              19

<210> SEQ ID NO 732
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 732
nguucaacaa acccuuugn                                              19

<210> SEQ ID NO 733
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 733
guucaacaaa cccuuuguc                                              19

<210> SEQ ID NO 734
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 734
guucaacaaa cccuuugua                                              19
```

<210> SEQ ID NO 735
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 735
guucaacaaa cccuuuguu                                                       19

<210> SEQ ID NO 736
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 736
guucaacaaa cccuuugun                                                       19

<210> SEQ ID NO 737
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 737
nuucaacaaa cccuuugun                                                       19

<210> SEQ ID NO 738
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 738
ucaacaaacc cuuugucuu                                                       19

<210> SEQ ID NO 739
<211> LENGTH: 19
<212> TYPE: RNA
<213> ORGANISM: Artificial sequence
<220> FEATURE:
<223> OTHER INFORMATION: AAT RNAi agent sense strand core stretch base

```
                          sequence

<400> SEQUENCE: 739
ucaacaaacc cuuugucua                                                19

<210> SEQ ID NO 740
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 740
ucaacaaacc cuuugucun                                                19

<210> SEQ ID NO 741
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 741
ncaacaaacc cuuugucun                                                19

<210> SEQ ID NO 742
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 742
acccuuuguc uucuuaaug                                                19

<210> SEQ ID NO 743
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 743
acccuuuguc uucuuaaua                                                19
```

```
<210> SEQ ID NO 744
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 744 acccuuguc uucuuaauu                                                        19

<210> SEQ ID NO 745
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 745 acccuuguc uucuuaaun                                                        19

<210> SEQ ID NO 746
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 746 ncccuuguc uucuuaaun                                                        19

<210> SEQ ID NO 747
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 747
ccuuugucuu cuuaaugau                                                       19

<210> SEQ ID NO 748
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
```

<400> SEQUENCE: 748
ccuuugucuu cuuaaugaa                                                         19

<210> SEQ ID NO 749
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 749
ccuuugucuu cuuaaugan                                                         19

<210> SEQ ID NO 750
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 750
ncuuugucuu cuuaaugan                                                         19

<210> SEQ ID NO 751
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 751
uaccaagucu ccccucuuc                                                         19

<210> SEQ ID NO 752
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 752
uaccaagucu ccccucuua                                                         19

<210> SEQ ID NO 753

```
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 753
uaccaagucu ccccucuuu                                                    19

<210> SEQ ID NO 754
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 754
uaccaagucu ccccucuun                                                    19

<210> SEQ ID NO 755
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 755
naccaagucu ccccucuun                                                    19

<210> SEQ ID NO 756
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 756
aagucccccc ucuucaugg                                                    19

<210> SEQ ID NO 757
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
```

```
<400> SEQUENCE: 757
aagucucccc ucuucauga                                                    19

<210> SEQ ID NO 758
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 758
aagucucccc ucuucaugu                                                    19

<210> SEQ ID NO 759
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 759
aagucucccc ucuucaugn                                                    19

<210> SEQ ID NO 760
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 760
nagucucccc ucuucaugn                                                    19

<210> SEQ ID NO 761
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 761
agucuccccu cuucaugg                                                     19

<210> SEQ ID NO 762
<211> LENGTH: 19
```

```
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 762
agucuccccu cuucaugga                                              19

<210> SEQ ID NO 763
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 763
agucuccccu cuucauggu                                              19

<210> SEQ ID NO 764
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 764
agucuccccu cuucauggn                                              19

<210> SEQ ID NO 765
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 765
ngucuccccu cuucauggn                                              19

<210> SEQ ID NO 766
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 766
```
ucuccccucu ucauggaa                                                          19

<210> SEQ ID NO 767
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 767
ucuccccucu ucauggau                                                          19

<210> SEQ ID NO 768
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 768
ucuccccucu ucaugggan                                                         19

<210> SEQ ID NO 769
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 769
ncuccccucu ucaugggan                                                         19

<210> SEQ ID NO 770
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 770
cuccccucuu caugggaaa                                                         19

<210> SEQ ID NO 771
<211> LENGTH: 19
<212> TYPE: RNA

```
<213> ORGANISM: Artificial sequence
<220> FEATURE:
<223> OTHER INFORMATION: AAT RNAi agent sense strand core stretch base
      sequence

<400> SEQUENCE: 771
cuccccucuu caugggaau                                                    19

<210> SEQ ID NO 772
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 772
cuccccucuu caugggaan                                                    19

<210> SEQ ID NO 773
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 773
nuccccucuu caugggaan                                                    19

<210> SEQ ID NO 774
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 774
augacauuaa agaagggull                                                   19

<210> SEQ ID NO 775
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence

<400> SEQUENCE: 775
```
augacauuaa agaagggua                                          19

<210> SEQ ID NO 776
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (19)..(19)
<223> OTHER INFORMATION: n = any nucleotide
<220> FEATURE:
<221> NAME/KEY: misc_feature
<222> LOCATION: (19)..(19)
<223> OTHER INFORMATION: n is a, c, g, or u

<400> SEQUENCE: 776
augacauuaa agaagggun                                          19

<210> SEQ ID NO 777
<211> LENGTH: 19
<212> TYPE: RNA
<213> ORGANISM: Artificial sequence
<220> FEATURE:
<223> OTHER INFORMATION: AAT RNAi agent sense strand core stretch base
      sequence
<220> FEATURE:
<221> NAME/KEY: modified_base
<222> LOCATION: (1)..(19)
<223> OTHER INFORMATION: n = any nucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 777
nugacauuaa agaagggun                                          19

<210> SEQ ID NO 778
<211> LENGTH: 18
<212> TYPE: RNA
<213> ORGANISM: Artificial sequence
<220> FEATURE:
<223> OTHER INFORMATION: AAT RNAi agent antisense strand base sequence

<400> SEQUENCE: 778
ggaacuuggu gaugauau                                           18

<210> SEQ ID NO 779
<211> LENGTH: 18
<212> TYPE: RNA
<213> ORGANISM: Artificial sequence
<220> FEATURE:
<223> OTHER INFORMATION: AAT RNAi agent antisense strand base sequence

<400> SEQUENCE: 779
gaucauaggu uccaguaa                                           18

<210> SEQ ID NO 780
<211> LENGTH: 18
<212> TYPE: RNA
<213> ORGANISM: Artificial sequence
<220> FEATURE:
<223> OTHER INFORMATION: AAT RNAi agent antisense strand base sequence -continued

```
<400> SEQUENCE: 780
acagccuuau gcacggcc                                                18

<210> SEQ ID NO 781
<211> LENGTH: 18
<212> TYPE: RNA
<213> ORGANISM: Artificial sequence
<220> FEATURE:
<223> OTHER INFORMATION: AAT RNAi agent antisense strand base sequence

<400> SEQUENCE: 781
ucgaugguca gcacagcc                                                18

<210> SEQ ID NO 782
<211> LENGTH: 18
<212> TYPE: RNA
<213> ORGANISM: Artificial sequence
<220> FEATURE:
<223> OTHER INFORMATION: AAT RNAi agent antisense strand base sequence

<400> SEQUENCE: 782
caaaggguuu guugaacu                                                18

<210> SEQ ID NO 783
<211> LENGTH: 21
<212> TYPE: DNA
<213> ORGANISM: Artificial sequence
<220> FEATURE:
<223> OTHER INFORMATION: AAT RNAi agent antisense strand base sequence

<400> SEQUENCE: 783
tggaacuugg ugaugauaut t                                            21

<210> SEQ ID NO 784
<211> LENGTH: 23
<212> TYPE: DNA
<213> ORGANISM: Artificial sequence
<220> FEATURE:
<223> OTHER INFORMATION: AAT RNAi agent antisense strand base sequence

<400> SEQUENCE: 784
tggaacuugg ugaugauauc gug                                          23

<210> SEQ ID NO 785
<211> LENGTH: 17
<212> TYPE: DNA
<213> ORGANISM: Artificial sequence
<220> FEATURE:
<223> OTHER INFORMATION: AAT RNAi agent antisense strand base sequence

<400> SEQUENCE: 785
acuuggugau gauautt                                                 17

<210> SEQ ID NO 786
<211> LENGTH: 21
<212> TYPE: DNA
<213> ORGANISM: Artificial sequence
<220> FEATURE:
<223> OTHER INFORMATION: AAT RNAi agent antisense strand base sequence

<400> SEQUENCE: 786
tggaacttgg tgatgatatt t                                            21

<210> SEQ ID NO 787
```

```
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 787
uuuaaacaug ccuaaacgcu u                                              21

<210> SEQ ID NO 788
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 788
ugcauugccc agguauuucu u                                              21

<210> SEQ ID NO 789
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 789
uggaacuugg ugaugauauu u                                              21

<210> SEQ ID NO 790
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 790
ugaucauagg uuccaguaau u                                              21

<210> SEQ ID NO 791
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 791
uacagccuua ugcacggccu u                                              21

<210> SEQ ID NO 792
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 792
uucgaugguc agcacagccu u                                              21

<210> SEQ ID NO 793
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 793
``` ucaaagggéuu uguugaacuu u                                    21

<210> SEQ ID NO 794
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 794
uguuaaacau gccuaaacgu u                                    21

<210> SEQ ID NO 795
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 795
uuuaaacgug ccuaaacgcu g                                    21

<210> SEQ ID NO 796
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 796
ugcauugccc agguauuuca g                                    21

<210> SEQ ID NO 797
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 797
uggaacuugg ugaugauauc g                                    21

<210> SEQ ID NO 798
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 798
ugaucauagg uuccaguaau g                                    21

<210> SEQ ID NO 799
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 799 ucaaagggéuu uguugaacuu g                                   21

<210> SEQ ID NO 800
<211> LENGTH: 21
<212> TYPE: RNA

```
<213> ORGANISM: Artificial sequence
<220> FEATURE:
<223> OTHER INFORMATION: AAT RNAi agent antisense strand base sequence

<400> SEQUENCE: 800
uguuaaacau gccuaaacgc g                                              21

<210> SEQ ID NO 801
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 801
uguuaaacau gccuaaacgc u                                              21

<210> SEQ ID NO 802
<211> LENGTH: 23
<212> TYPE: RNA
<213> ORGANISM: Artificial sequence
<220> FEATURE:
<223> OTHER INFORMATION: AAT RNAi agent antisense strand base sequence

<400> SEQUENCE: 802
uguuaaacau gccuaaacgc uuc                                            23

<210> SEQ ID NO 803
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 803
ugcuguugga cuggugugcu u                                              21

<210> SEQ ID NO 804
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 804
ugcuguugga cuggugugcc a                                              21

<210> SEQ ID NO 805
<211> LENGTH: 23
<212> TYPE: RNA
<213> ORGANISM: Artificial sequence
<220> FEATURE:
<223> OTHER INFORMATION: AAT RNAi agent antisense strand base sequence

<400> SEQUENCE: 805
ugcuguugga cuggugugcc auu                                            23

<210> SEQ ID NO 806
<211> LENGTH: 23
<212> TYPE: RNA
<213> ORGANISM: Artificial sequence
<220> FEATURE:
<223> OTHER INFORMATION: AAT RNAi agent antisense strand base sequence

<400> SEQUENCE: 806
ugcuguugga cuggugugcc agc                                            23
```

<210> SEQ ID NO 807
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 807
uaaggcuucu gagugguacu u                                              21

<210> SEQ ID NO 808
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 808
uaaggcuucu gagugguaca a                                              21

<210> SEQ ID NO 809
<211> LENGTH: 23
<212> TYPE: RNA
<213> ORGANISM: Artificial sequence
<220> FEATURE:
<223> OTHER INFORMATION: AAT RNAi agent antisense strand base sequence

<400> SEQUENCE: 809
uaaggcuucu gagugguaca acu                                            23

<210> SEQ ID NO 810
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 810
gaaggcuucu gagugguacu u                                              21

<210> SEQ ID NO 811
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 811
aagacaaagg guuuguugau u                                              21

<210> SEQ ID NO 812
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 812
aagacaaagg guuuguugaa c                                              21

<210> SEQ ID NO 813
<211> LENGTH: 21
<212> TYPE: RNA
<213> ORGANISM: Artificial sequence
<220> FEATURE:

<223> OTHER INFORMATION: AAT RNAi agent antisense strand base sequence

<400> SEQUENCE: 813
uagacaaagg guuguugaa c                                             21

<210> SEQ ID NO 814
<211> LENGTH: 23
<212> TYPE: RNA
<213> ORGANISM: Artificial sequence
<220> FEATURE:
<223> OTHER INFORMATION: AAT RNAi agent antisense strand base sequence

<400> SEQUENCE: 814
aagacaaagg guuguugaa cuu                                           23

<210> SEQ ID NO 815
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 815
uagacauggg uauggccucu u                                            21

<210> SEQ ID NO 816
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 816
uagacauggg uauggccucu a                                            21

<210> SEQ ID NO 817
<211> LENGTH: 23
<212> TYPE: RNA
<213> ORGANISM: Artificial sequence
<220> FEATURE:
<223> OTHER INFORMATION: AAT RNAi agent antisense strand base sequence

<400> SEQUENCE: 817
uagacauggg uauggccucu aaa                                          23

<210> SEQ ID NO 818
<211> LENGTH: 23
<212> TYPE: RNA
<213> ORGANISM: Artificial sequence
<220> FEATURE:
<223> OTHER INFORMATION: AAT RNAi agent antisense strand base sequence

<400> SEQUENCE: 818
uagacauggg uauggccucu auu                                          23

<210> SEQ ID NO 819
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 819
uuugaucugu uucuuggccu u                                            21

```
<210> SEQ ID NO 820
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 820
uuugaucugu uucuuggccu c                                             21

<210> SEQ ID NO 821
<211> LENGTH: 23
<212> TYPE: RNA
<213> ORGANISM: Artificial sequence
<220> FEATURE:
<223> OTHER INFORMATION: AAT RNAi agent antisense strand base sequence

<400> SEQUENCE: 821
uuugaucugu uucuuggccu cuu                                           23

<210> SEQ ID NO 822
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 822
uguuggacug gugugccagu u                                             21

<210> SEQ ID NO 823
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 823
uguuggacug gugugccagc u                                             21

<210> SEQ ID NO 824
<211> LENGTH: 23
<212> TYPE: RNA
<213> ORGANISM: Artificial sequence
<220> FEATURE:
<223> OTHER INFORMATION: AAT RNAi agent antisense strand base sequence

<400> SEQUENCE: 824
uguuggacug gugugccagc ugg                                           23

<210> SEQ ID NO 825
<211> LENGTH: 22
<212> TYPE: RNA
<213> ORGANISM: Artificial sequence
<220> FEATURE:
<223> OTHER INFORMATION: AAT RNAi agent antisense strand base sequence

<400> SEQUENCE: 825
uguuggacug gugugccagc ug                                            22

<210> SEQ ID NO 826
<211> LENGTH: 21
<212> TYPE: RNA
<213> ORGANISM: Artificial sequence
<220> FEATURE:
<223> OTHER INFORMATION: AAT RNAi agent antisense strand base sequence
```

```
<400> SEQUENCE: 826
aaaggguuug uugaacuugu u                                              21

<210> SEQ ID NO 827
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 827
aaaggguuug uugaacuuga c                                              21

<210> SEQ ID NO 828
<211> LENGTH: 23
<212> TYPE: RNA
<213> ORGANISM: Artificial sequence
<220> FEATURE:
<223> OTHER INFORMATION: AAT RNAi agent antisense strand base sequence

<400> SEQUENCE: 828
uaaggguuug uugaacuuga ccu                                            23

<210> SEQ ID NO 829
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 829
uaaggguuug uugaacuuga c                                              21

<210> SEQ ID NO 830
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 830
uauuggugcu guuggacugu u                                              21

<210> SEQ ID NO 831
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 831
uauuggugcu guuggacugg u                                              21

<210> SEQ ID NO 832
<211> LENGTH: 22
<212> TYPE: RNA
<213> ORGANISM: Artificial sequence
<220> FEATURE:
<223> OTHER INFORMATION: AAT RNAi agent antisense strand base sequence

<400> SEQUENCE: 832
uauuggugcu guuggacugg uu                                             22

<210> SEQ ID NO 833
<211> LENGTH: 20
```

```
<212> TYPE: RNA
<213> ORGANISM: Artificial sequence
<220> FEATURE:
<223> OTHER INFORMATION: AAT RNAi agent antisense strand base sequence

<400> SEQUENCE: 833
uuguuggacu ggugugccag                                                  20

<210> SEQ ID NO 834
<211> LENGTH: 22
<212> TYPE: RNA
<213> ORGANISM: Artificial sequence
<220> FEATURE:
<223> OTHER INFORMATION: AAT RNAi agent antisense strand base sequence

<400> SEQUENCE: 834
uuguuggacu ggugugccag cu                                               22

<210> SEQ ID NO 835
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 835
uauagacaug gguauggccu c                                                21

<210> SEQ ID NO 836
<211> LENGTH: 23
<212> TYPE: RNA
<213> ORGANISM: Artificial sequence
<220> FEATURE:
<223> OTHER INFORMATION: AAT RNAi agent antisense strand base sequence

<400> SEQUENCE: 836
ucaaaggguu uguugaacuu gac                                              23

<210> SEQ ID NO 837
<211> LENGTH: 21
<212> TYPE: RNA
<213> ORGANISM: Artificial sequence
<220> FEATURE:
<223> OTHER INFORMATION: AAT RNAi agent antisense strand base sequence

<400> SEQUENCE: 837
uuauuggugc uguuggacug g                                                21

<210> SEQ ID NO 838
<211> LENGTH: 20
<212> TYPE: RNA
<213> ORGANISM: Artificial sequence
<220> FEATURE:
<223> OTHER INFORMATION: AAT RNAi agent antisense strand base sequence

<400> SEQUENCE: 838
uguuaaacau gccuaaacgc                                                  20

<210> SEQ ID NO 839
<211> LENGTH: 22
<212> TYPE: RNA
<213> ORGANISM: Artificial sequence
<220> FEATURE:
<223> OTHER INFORMATION: AAT RNAi agent antisense strand base sequence

<400> SEQUENCE: 839
```

| | |
|---|---|
| uguuaaacau gccuaaacgc uu | 22 |

<210> SEQ ID NO 840
<211> LENGTH: 18
<212> TYPE: RNA
<213> ORGANISM: Artificial sequence
<220> FEATURE:
<223> OTHER INFORMATION: AAT RNAi agent sense strand base sequence

<400> SEQUENCE: 840

| | |
|---|---|
| auaucaucac caaguucc | 18 |

<210> SEQ ID NO 841
<211> LENGTH: 18
<212> TYPE: RNA
<213> ORGANISM: Artificial sequence
<220> FEATURE:
<223> OTHER INFORMATION: AAT RNAi agent sense strand base sequence

<400> SEQUENCE: 841

| | |
|---|---|
| uuacuggaac cuaugauc | 18 |

<210> SEQ ID NO 842
<211> LENGTH: 18
<212> TYPE: RNA
<213> ORGANISM: Artificial sequence
<220> FEATURE:
<223> OTHER INFORMATION: AAT RNAi agent sense strand base sequence

<400> SEQUENCE: 842

| | |
|---|---|
| ggccgugcau aaggcugu | 18 |

<210> SEQ ID NO 843
<211> LENGTH: 18
<212> TYPE: RNA
<213> ORGANISM: Artificial sequence
<220> FEATURE:
<223> OTHER INFORMATION: AAT RNAi agent sense strand base sequence

<400> SEQUENCE: 843

| | |
|---|---|
| ggcugugcug accaucga | 18 |

<210> SEQ ID NO 844
<211> LENGTH: 18
<212> TYPE: RNA
<213> ORGANISM: Artificial sequence
<220> FEATURE:
<223> OTHER INFORMATION: AAT RNAi agent sense strand base sequence

<400> SEQUENCE: 844

| | |
|---|---|
| aguucaacaa acccuuug | 18 |

<210> SEQ ID NO 845
<211> LENGTH: 23
<212> TYPE: DNA
<213> ORGANISM: Artificial sequence
<220> FEATURE:
<223> OTHER INFORMATION: AAT RNAi agent sense strand base sequence

<400> SEQUENCE: 845

| | |
|---|---|
| uauauaucau caccaaguuc cat | 23 |

<210> SEQ ID NO 846
<211> LENGTH: 20
<212> TYPE: DNA
<213> ORGANISM: Artificial sequence

```
<220> FEATURE:
<223> OTHER INFORMATION: AAT RNAi agent sense strand base sequence

<400> SEQUENCE: 846
auaucaucac caaguuccat                                                   20

<210> SEQ ID NO 847
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 847
cgauaucauc accaaguucc a                                                 21

<210> SEQ ID NO 848
<211> LENGTH: 19
<212> TYPE: DNA
<213> ORGANISM: Artificial sequence
<220> FEATURE:
<223> OTHER INFORMATION: AAT RNAi agent sense strand base sequence

<400> SEQUENCE: 848
uaucaucacc aaguuccat                                                    19

<210> SEQ ID NO 849
<211> LENGTH: 23
<212> TYPE: DNA
<213> ORGANISM: Artificial sequence
<220> FEATURE:
<223> OTHER INFORMATION: AAT RNAi agent sense strand base sequence

<400> SEQUENCE: 849
tatatatcat caccaagttc cat                                               23

<210> SEQ ID NO 850
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 850
gcguuuaggc auguuuaaau u                                                 21

<210> SEQ ID NO 851
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 851
gaaauaccug ggcaaugcau u                                                 21

<210> SEQ ID NO 852
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 852
auaucaucac caaguuccau u                                                 21
```

<210> SEQ ID NO 853
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 853
uuacuggaac cuaugaucau u                                              21

<210> SEQ ID NO 854
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 854
ggccgugcau aaggcuguau u                                              21

<210> SEQ ID NO 855
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 855
ggcugugcug accaucgaau u                                              21

<210> SEQ ID NO 856
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 856
aguucaacaa acccuuugau u                                              21

<210> SEQ ID NO 857
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 857
cguuuaggca uguuuaacau u                                              21

<210> SEQ ID NO 858
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 858
cagcguuuag gcauguuuaa a                                              21

<210> SEQ ID NO 859
<211> LENGTH: 21
<212> TYPE: RNA
<213> ORGANISM: Artificial sequence
<220> FEATURE:
<223> OTHER INFORMATION: AAT RNAi agent sense strand base sequence -continued

```
<400> SEQUENCE: 859
cugaaauacc ugggcaaugc a                                              21

<210> SEQ ID NO 860
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 860
cauuacugga accaugauc a                                               21

<210> SEQ ID NO 861
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 861
aaggccgugc auaaggcugu a                                              21

<210> SEQ ID NO 862
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 862
aaggcugugc ugaccaucga a                                              21

<210> SEQ ID NO 863
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 863
caaguucaac aaacccuuug a                                              21

<210> SEQ ID NO 864
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 864
cgcguuuagg cauguuuaac a                                              21

<210> SEQ ID NO 865
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 865
aacguuuagg cauguuuaac a                                              21

<210> SEQ ID NO 866
```

```
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 866
agcguuuagg cauguuuaac a                                              21

<210> SEQ ID NO 867
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 867
uggcacacca guccaacagc a                                              21

<210> SEQ ID NO 868
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 868
aagcacacca guccaacagc a                                              21

<210> SEQ ID NO 869
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 869
uuguaccacu cagaagccuu a                                              21

<210> SEQ ID NO 870
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 870
guucaacaaa cccuuugucu u                                              21

<210> SEQ ID NO 871
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 871
guucaacaaa cccuuugucu a                                              21

<210> SEQ ID NO 872
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 872
```

```
uagaggccau acccaugucu a                                              21

<210> SEQ ID NO 873
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 873
gaggccaaga aacagaucaa a                                              21

<210> SEQ ID NO 874
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 874
agcuggcaca ccaguccaac a                                              21

<210> SEQ ID NO 875
<211> LENGTH: 20
<212> TYPE: RNA
<213> ORGANISM: Artificial sequence
<220> FEATURE:
<223> OTHER INFORMATION: AAT RNAi agent sense strand base sequence

<400> SEQUENCE: 875
gcuggcacac caguccaaca                                                20

<210> SEQ ID NO 876
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 876
gucaaguuca acaaacccuu u                                              21

<210> SEQ ID NO 877
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 877
gucaaguuca acaaacccuu a                                              21

<210> SEQ ID NO 878
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 878
accaguccaa cagcaccaau a                                              21

<210> SEQ ID NO 879
<211> LENGTH: 20
<212> TYPE: RNA
```

```
<213> ORGANISM: Artificial sequence
<220> FEATURE:
<223> OTHER INFORMATION: AAT RNAi agent sense strand base sequence

<400> SEQUENCE: 879
ccaguccaac agcaccaaua                                               20

<210> SEQ ID NO 880
<211> LENGTH: 20
<212> TYPE: RNA
<213> ORGANISM: Artificial sequence
<220> FEATURE:
<223> OTHER INFORMATION: AAT RNAi agent sense strand base sequence

<400> SEQUENCE: 880
cuggcacacc aguccaacaa                                               20

<210> SEQ ID NO 881
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 881
gaggccauac ccaugucuau a                                             21

<210> SEQ ID NO 882
<211> LENGTH: 23
<212> TYPE: RNA
<213> ORGANISM: Artificial sequence
<220> FEATURE:
<223> OTHER INFORMATION: AAT RNAi agent sense strand base sequence

<400> SEQUENCE: 882
gucaaguuca acaaacccuu uga                                           23

<210> SEQ ID NO 883
<211> LENGTH: 21
<212> TYPE: RNA
<213> ORGANISM: Artificial sequence
<220> FEATURE:
<223> OTHER INFORMATION: AAT RNAi agent sense strand base sequence

<400> SEQUENCE: 883
ccaguccaac agcaccaaua a                                             21

<210> SEQ ID NO 884
<211> LENGTH: 20
<212> TYPE: RNA
<213> ORGANISM: Artificial sequence
<220> FEATURE:
<223> OTHER INFORMATION: AAT RNAi agent sense strand base sequence

<400> SEQUENCE: 884
gcguuuaggc auguuuaaca                                               20

<210> SEQ ID NO 885
<211> LENGTH: 22
<212> TYPE: RNA
<213> ORGANISM: Artificial sequence
<220> FEATURE:
<223> OTHER INFORMATION: AAT RNAi agent sense strand base sequence

<400> SEQUENCE: 885
gcguuuaggc auguuuaaca uu                                            22
```

```
<210> SEQ ID NO 886
<211> LENGTH: 23
<212> TYPE: RNA
<213> ORGANISM: Artificial sequence
<220> FEATURE:
<223> OTHER INFORMATION: AAT RNAi agent sense strand base sequence

<400> SEQUENCE: 886
cgcguuuagg cauguuuaac auu                                              23

<210> SEQ ID NO 887
<211> LENGTH: 23
<212> TYPE: RNA
<213> ORGANISM: Artificial sequence
<220> FEATURE:
<223> OTHER INFORMATION: AAT RNAi agent sense strand base sequence

<400> SEQUENCE: 887
agcguuuagg cauguuuaac auu                                              23

<210> SEQ ID NO 888
<211> LENGTH: 21
<212> TYPE: DNA
<213> ORGANISM: Artificial sequence
<220> FEATURE:
<223> OTHER INFORMATION: AAT RNAi agent antisense strand modified
      sequence

<400> SEQUENCE: 888
tggaacuugg ugaugauaut t                                                21

<210> SEQ ID NO 889
<211> LENGTH: 21
<212> TYPE: DNA
<213> ORGANISM: Artificial sequence
<220> FEATURE:
<223> OTHER INFORMATION: AAT RNAi agent antisense strand modified
      sequence

<400> SEQUENCE: 889
tggaacuugg ugaugauaut t                                                21

<210> SEQ ID NO 890
<211> LENGTH: 23
<212> TYPE: DNA
<213> ORGANISM: Artificial sequence
<220> FEATURE:
<223> OTHER INFORMATION: AAT RNAi agent antisense strand modified
      sequence

<400> SEQUENCE: 890
tggaacuugg ugaugauauc gug                                              23

<210> SEQ ID NO 891
<211> LENGTH: 17
<212> TYPE: DNA
<213> ORGANISM: Artificial sequence
<220> FEATURE:
<223> OTHER INFORMATION: AAT RNAi agent antisense strand modified
      sequence

<400> SEQUENCE: 891
acuuggugau gauautt                                                     17

<210> SEQ ID NO 892
```

```
<211> LENGTH: 21
<212> TYPE: DNA
<213> ORGANISM: Artificial sequence
<220> FEATURE:
<223> OTHER INFORMATION: AAT RNAi agent antisense strand modified
      sequence

<400> SEQUENCE: 892
tggaacttgg tgatgatatt t                                              21

<210> SEQ ID NO 893
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 893
uuuaaacaug ccuaaacgcu u                                              21

<210> SEQ ID NO 894
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 894
ugcauugccc agguauuucu u                                              21

<210> SEQ ID NO 895
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 895
uggaacuugg ugaugauauu u                                              21

<210> SEQ ID NO 896
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 896
ugaucauagg uuccaguaau u                                              21

<210> SEQ ID NO 897
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 897
uacagccuua ugcacggccu u                                              21

<210> SEQ ID NO 898
<211> LENGTH: 21
```

```
<212> TYPE: RNA
<213> ORGANISM: Artificial sequence
<220> FEATURE:
<223> OTHER INFORMATION: AAT RNAi agent antisense strand modified
      sequence

<400> SEQUENCE: 898
uucgaugguc agcacagccu u                                           21

<210> SEQ ID NO 899
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 899 ucaaagggu uguugaacuu u                                            21

<210> SEQ ID NO 900
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 900
uguuaaacau gccuaaacgu u                                           21

<210> SEQ ID NO 901
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 901
uuuaaacgug ccuaaacgcu g                                           21

<210> SEQ ID NO 902
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 902
ugcauugccc agguauuuca g                                           21

<210> SEQ ID NO 903
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 903
uggaacuugg ugaugauauc g                                           21

<210> SEQ ID NO 904
<211> LENGTH: 21
<212> TYPE: RNA
```

```
<213> ORGANISM: Artificial sequence
<220> FEATURE:
<223> OTHER INFORMATION: AAT RNAi agent antisense strand modified
      sequence

<400> SEQUENCE: 904
ugaucauagg uuccaguaau g                                              21

<210> SEQ ID NO 905
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 905
uacagccuua ugcacggccu u                                              21

<210> SEQ ID NO 906
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 906
uucgaugguc agcacagccu u                                              21

<210> SEQ ID NO 907
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 907
ucaaaggguu uguugaacuu g                                              21

<210> SEQ ID NO 908
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 908
uguuaaacau gccuaaacgc g                                              21

<210> SEQ ID NO 909
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 909
uuuaaacgug ccuaaacgcu g                                              21

<210> SEQ ID NO 910
<211> LENGTH: 21
<212> TYPE: RNA
<213> ORGANISM: Artificial sequence
```

-continued

<220> FEATURE:
<223> OTHER INFORMATION: AAT RNAi agent antisense strand modified
      sequence

<400> SEQUENCE: 910
uguuaaacau gccuaaacgu u                                         21

<210> SEQ ID NO 911
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 911
uguuaaacau gccuaaacgu u                                         21

<210> SEQ ID NO 912
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 912
uguuaaacau gccuaaacgc u                                         21

<210> SEQ ID NO 913
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 913
uguuaaacau gccuaaacgu u                                         21

<210> SEQ ID NO 914
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 914
uguuaaacau gccuaaacgc u                                         21

<210> SEQ ID NO 915
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 915
uguuaaacau gccuaaacgc u                                         21

<210> SEQ ID NO 916
<211> LENGTH: 23
<212> TYPE: RNA
<213> ORGANISM: Artificial sequence
<220> FEATURE:

```
<223> OTHER INFORMATION: AAT RNAi agent antisense strand modified
      sequence

<400> SEQUENCE: 916
uguuaaacau gccuaaacgc uuc                                              23

<210> SEQ ID NO 917
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 917
uguuaaacau gccuaaacgc u                                                21

<210> SEQ ID NO 918
<211> LENGTH: 23
<212> TYPE: RNA
<213> ORGANISM: Artificial sequence
<220> FEATURE:
<223> OTHER INFORMATION: AAT RNAi agent antisense strand modified
      sequence

<400> SEQUENCE: 918
uguuaaacau gccuaaacgc uuc                                              23

<210> SEQ ID NO 919
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 919
uguuaaacau gccuaaacgc g                                                21

<210> SEQ ID NO 920
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 920
uggaacuugg ugaugauauu u                                                21

<210> SEQ ID NO 921
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 921
ugcuguugga cuggugugcu u                                                21

<210> SEQ ID NO 922
<211> LENGTH: 21
<212> TYPE: RNA
<213> ORGANISM: Artificial sequence
<220> FEATURE:
<223> OTHER INFORMATION: AAT RNAi agent antisense strand modified
```

-continued

<400> SEQUENCE: 922
ugcuguugga cuggugugcc a                                                         21

<210> SEQ ID NO 923
<211> LENGTH: 23
<212> TYPE: RNA
<213> ORGANISM: Artificial sequence
<220> FEATURE:
<223> OTHER INFORMATION: AAT RNAi agent antisense strand modified
      sequence

<400> SEQUENCE: 923
ugcuguugga cuggugugcc auu                                                       23

<210> SEQ ID NO 924
<211> LENGTH: 23
<212> TYPE: RNA
<213> ORGANISM: Artificial sequence
<220> FEATURE:
<223> OTHER INFORMATION: AAT RNAi agent antisense strand modified
      sequence

<400> SEQUENCE: 924
ugcuguugga cuggugugcc agc                                                       23

<210> SEQ ID NO 925
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 925
uaaggcuucu gagugguacu u                                                         21

<210> SEQ ID NO 926
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 926
uaaggcuucu gagugguaca a                                                         21

<210> SEQ ID NO 927
<211> LENGTH: 23
<212> TYPE: RNA
<213> ORGANISM: Artificial sequence
<220> FEATURE:
<223> OTHER INFORMATION: AAT RNAi agent antisense strand modified
      sequence

<400> SEQUENCE: 927
uaaggcuucu gagugguaca acu                                                       23

<210> SEQ ID NO 928
<211> LENGTH: 21
<212> TYPE: RNA
<213> ORGANISM: Artificial sequence
<220> FEATURE:
<223> OTHER INFORMATION: AAT RNAi agent antisense strand modified
      sequence

```
<400> SEQUENCE: 928
gaaggcuucu gagugguacu u                                              21

<210> SEQ ID NO 929
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 929
aagacaaagg guuuguugau u                                              21

<210> SEQ ID NO 930
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 930
aagacaaagg guuuguugaa c                                              21

<210> SEQ ID NO 931
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 931
uagacaaagg guuuguugaa c                                              21

<210> SEQ ID NO 932
<211> LENGTH: 23
<212> TYPE: RNA
<213> ORGANISM: Artificial sequence
<220> FEATURE:
<223> OTHER INFORMATION: AAT RNAi agent antisense strand modified
      sequence

<400> SEQUENCE: 932
aagacaaagg guuuguugaa cuu                                            23

<210> SEQ ID NO 933
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 933
uagacauggg uauggccucu u                                              21

<210> SEQ ID NO 934
<211> LENGTH: 21
<212> TYPE: RNA
<213> ORGANISM: Artificial sequence
<220> FEATURE:
<223> OTHER INFORMATION: AAT RNAi agent antisense strand modified
      sequence
```

-continued

```
<400> SEQUENCE: 934
uagacauggg uauggccucu a                                              21

<210> SEQ ID NO 935
<211> LENGTH: 23
<212> TYPE: RNA
<213> ORGANISM: Artificial sequence
<220> FEATURE:
<223> OTHER INFORMATION: AAT RNAi agent antisense strand modified
      sequence

<400> SEQUENCE: 935
uagacauggg uauggccucu aaa                                            23

<210> SEQ ID NO 936
<211> LENGTH: 23
<212> TYPE: RNA
<213> ORGANISM: Artificial sequence
<220> FEATURE:
<223> OTHER INFORMATION: AAT RNAi agent antisense strand modified
      sequence

<400> SEQUENCE: 936
uagacauggg uauggccucu auu                                            23

<210> SEQ ID NO 937
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 937
uuugaucugu uucuuggccu u                                              21

<210> SEQ ID NO 938
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 938
uuugaucugu uucuuggccu c                                              21

<210> SEQ ID NO 939
<211> LENGTH: 23
<212> TYPE: RNA
<213> ORGANISM: Artificial sequence
<220> FEATURE:
<223> OTHER INFORMATION: AAT RNAi agent antisense strand modified
      sequence

<400> SEQUENCE: 939
uuugaucugu uucuuggccu cuu                                            23

<210> SEQ ID NO 940
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 940
```

-continued

```
uguuggacug gugugccagu u                                            21

<210> SEQ ID NO 941
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 941
uguuggacug gugugccagc u                                            21

<210> SEQ ID NO 942
<211> LENGTH: 23
<212> TYPE: RNA
<213> ORGANISM: Artificial sequence
<220> FEATURE:
<223> OTHER INFORMATION: AAT RNAi agent antisense strand modified
      sequence

<400> SEQUENCE: 942
uguuggacug gugugccagc ugg                                          23

<210> SEQ ID NO 943
<211> LENGTH: 22
<212> TYPE: RNA
<213> ORGANISM: Artificial sequence
<220> FEATURE:
<223> OTHER INFORMATION: AAT RNAi agent antisense strand modified
      sequence

<400> SEQUENCE: 943
uguuggacug gugugccagc ug                                           22

<210> SEQ ID NO 944
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 944
aaaggguuug uugaacuugu u                                            21

<210> SEQ ID NO 945
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 945
aaaggguuug uugaacuuga c                                            21

<210> SEQ ID NO 946
<211> LENGTH: 23
<212> TYPE: RNA
<213> ORGANISM: Artificial sequence
<220> FEATURE:
<223> OTHER INFORMATION: AAT RNAi agent antisense strand modified
      sequence

<400> SEQUENCE: 946
```

| | |
|---|---|
| uaaggguuug uugaacuuga ccu | 23 |

<210> SEQ ID NO 947
<211> LENGTH: 21
<212> TYPE: RNA
<213> ORGANISM: Artificial sequence
<220> FEATURE:
<223> OTHER INFORMATION: AAT RNAi agent antisense strand modified sequence

<400> SEQUENCE: 947

| | |
|---|---|
| uaaggguuug uugaacuuga c | 21 |

<210> SEQ ID NO 948
<211> LENGTH: 21
<212> TYPE: RNA
<213> ORGANISM: Artificial sequence
<220> FEATURE:
<223> OTHER INFORMATION: AAT RNAi agent antisense strand modified sequence

<400> SEQUENCE: 948

| | |
|---|---|
| uauuggugcu guuggacugu u | 21 |

<210> SEQ ID NO 949
<211> LENGTH: 21
<212> TYPE: RNA
<213> ORGANISM: Artificial sequence
<220> FEATURE:
<223> OTHER INFORMATION: AAT RNAi agent antisense strand modified sequence

<400> SEQUENCE: 949

| | |
|---|---|
| uauuggugcu guuggacugg u | 21 |

<210> SEQ ID NO 950
<211> LENGTH: 22
<212> TYPE: RNA
<213> ORGANISM: Artificial sequence
<220> FEATURE:
<223> OTHER INFORMATION: AAT RNAi agent antisense strand modified sequence

<400> SEQUENCE: 950

| | |
|---|---|
| uauuggugcu guuggacugg uu | 22 |

<210> SEQ ID NO 951
<211> LENGTH: 20
<212> TYPE: RNA
<213> ORGANISM: Artificial sequence
<220> FEATURE:
<223> OTHER INFORMATION: AAT RNAi agent antisense strand modified sequence

<400> SEQUENCE: 951

| | |
|---|---|
| uuguuggacu ggugugccag | 20 |

<210> SEQ ID NO 952
<211> LENGTH: 22
<212> TYPE: RNA
<213> ORGANISM: Artificial sequence
<220> FEATURE:
<223> OTHER INFORMATION: AAT RNAi agent antisense strand modified sequence

<400> SEQUENCE: 952

| | |
|---|---|
| uuguuggacu ggugugccag cu | 22 |

<210> SEQ ID NO 953
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 953
uauagacaug gguauggccu c                                              21

<210> SEQ ID NO 954
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 954
uauagacaug gguauggccu c                                              21

<210> SEQ ID NO 955
<211> LENGTH: 23
<212> TYPE: RNA
<213> ORGANISM: Artificial sequence
<220> FEATURE:
<223> OTHER INFORMATION: AAT RNAi agent antisense strand modified
      sequence

<400> SEQUENCE: 955
ucaaaggguu uguugaacuu gac                                            23

<210> SEQ ID NO 956
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 956
uuauuggugc uguuggacug g                                              21

<210> SEQ ID NO 957
<211> LENGTH: 20
<212> TYPE: RNA
<213> ORGANISM: Artificial sequence
<220> FEATURE:
<223> OTHER INFORMATION: AAT RNAi agent antisense strand modified
      sequence

<400> SEQUENCE: 957
uguuaaacau gccuaaacgc                                                20

<210> SEQ ID NO 958
<211> LENGTH: 22
<212> TYPE: RNA
<213> ORGANISM: Artificial sequence
<220> FEATURE:
<223> OTHER INFORMATION: AAT RNAi agent antisense strand modified
      sequence

<400> SEQUENCE: 958
uguuaaacau gccuaaacgc uu                                             22

-continued

<210> SEQ ID NO 959
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 959
uguuaaacau gccuaaacgc g                                              21

<210> SEQ ID NO 960
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 960
uguuaaacau gccuaaacgc u                                              21

<210> SEQ ID NO 961
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 961
uguuaaacau gccuaaacgc g                                              21

<210> SEQ ID NO 962
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 962
uguuaaacau gccuaaacgu u                                              21

<210> SEQ ID NO 963
<211> LENGTH: 21
<212> TYPE: RNA
<213> ORGANISM: Artificial sequence
<220> FEATURE:
<223> OTHER INFORMATION: AAT RNAi agent antisense strand modified
      sequence

<400> SEQUENCE: 963
uguuaaacau gccuaaacgu u                                              21

<210> SEQ ID NO 964
<211> LENGTH: 23
<212> TYPE: DNA
<213> ORGANISM: Artificial sequence
<220> FEATURE:
<223> OTHER INFORMATION: AAT RNAi agent sense strand modified sequence

<400> SEQUENCE: 964
uauauaucau caccaaguuc cat                                            23

<210> SEQ ID NO 965

-continued

<211> LENGTH: 23
<212> TYPE: DNA
<213> ORGANISM: Artificial sequence
<220> FEATURE:
<223> OTHER INFORMATION: AAT RNAi agent sense strand modified sequence

<400> SEQUENCE: 965
uauauaucau caccaaguuc cat                                              23

<210> SEQ ID NO 966
<211> LENGTH: 20
<212> TYPE: DNA
<213> ORGANISM: Artificial sequence
<220> FEATURE:
<223> OTHER INFORMATION: AAT RNAi agent sense strand modified sequence

<400> SEQUENCE: 966
auaucaucac caaguuccat                                                  20

<210> SEQ ID NO 967
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 967
cgauaucauc accaaguucc a                                                21

<210> SEQ ID NO 968
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 968
cgauaucauc accaaguucc a                                                21

<210> SEQ ID NO 969
<211> LENGTH: 19
<212> TYPE: DNA
<213> ORGANISM: Artificial sequence
<220> FEATURE:
<223> OTHER INFORMATION: AAT RNAi agent sense strand modified sequence

<400> SEQUENCE: 969
uaucaucacc aaguuccat                                                   19

<210> SEQ ID NO 970
<211> LENGTH: 23
<212> TYPE: DNA
<213> ORGANISM: Artificial sequence
<220> FEATURE:
<223> OTHER INFORMATION: AAT RNAi agent sense strand modified sequence

<400> SEQUENCE: 970
tatatatcat caccaagttc cat                                              23

<210> SEQ ID NO 971
<211> LENGTH: 23
<212> TYPE: DNA
<213> ORGANISM: Artificial sequence
<220> FEATURE:
<223> OTHER INFORMATION: AAT RNAi agent sense strand modified sequence

<400> SEQUENCE: 971

```
tatatatcat caccaagttc cat                                          23

<210> SEQ ID NO 972
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 972
gcguuuaggc auguuuaaau u                                            21

<210> SEQ ID NO 973
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 973
gaaauaccug ggcaaugcau u                                            21

<210> SEQ ID NO 974
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 974
auaucaucac caaguuccau u                                            21

<210> SEQ ID NO 975
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 975
uuacuggaac cuaugaucau u                                            21

<210> SEQ ID NO 976
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 976
ggccgugcau aaggcuguau u                                            21

<210> SEQ ID NO 977
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 977
ggcugugcug accaucgaau u                                            21

<210> SEQ ID NO 978
<211> LENGTH: 21
<212> TYPE: RNA
```

```
<213> ORGANISM: Artificial sequence
<220> FEATURE:
<223> OTHER INFORMATION: AAT RNAi agent sense strand modified sequence

<400> SEQUENCE: 978
aguucaacaa acccuuugau u                                              21

<210> SEQ ID NO 979
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 979
cguuuaggca uguuuaacau u                                              21

<210> SEQ ID NO 980
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 980
cagcguuuag gcauguuuaa a                                              21

<210> SEQ ID NO 981
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 981
cugaaauacc ugggcaaugc a                                              21

<210> SEQ ID NO 982
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 982
cgauaucauc accaaguucc a                                              21

<210> SEQ ID NO 983
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 983
cauuacugga accuaugauc a                                              21

<210> SEQ ID NO 984
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 984
aaggccgugc auaaggcugu a                                              21
```

<210> SEQ ID NO 985
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 985
aaggcugugc ugaccaucga a                                    21

<210> SEQ ID NO 986
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 986
caaguucaac aaacccuuug a                                    21

<210> SEQ ID NO 987
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 987
cgcguuuagg cauguuuaac a                                    21

<210> SEQ ID NO 988
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 988
cagcguuuag gcauguuuaa a                                    21

<210> SEQ ID NO 989
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 989
cguuuaggca uguuuaacau u                                    21

<210> SEQ ID NO 990
<211> LENGTH: 19
<212> TYPE: RNA
<213> ORGANISM: Artificial sequence
<220> FEATURE:
<223> OTHER INFORMATION: AAT RNAi agent sense strand modified sequence

<400> SEQUENCE: 990
cguuuaggca uguuuaaca                                       19

<210> SEQ ID NO 991
<211> LENGTH: 19
<212> TYPE: RNA
<213> ORGANISM: Artificial sequence
<220> FEATURE:

<223> OTHER INFORMATION: AAT RNAi agent sense strand modified sequence

<400> SEQUENCE: 991
cguuuaggca uguuuaaca                              19

<210> SEQ ID NO 992
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 992
aacguuuagg cauguuuaac a                           21

<210> SEQ ID NO 993
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 993
agcguuuagg cauguuuaac a                           21

<210> SEQ ID NO 994
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 994
aacguuuagg cauguuuaac a                           21

<210> SEQ ID NO 995
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 995
agcguuuagg cauguuuaac a                           21

<210> SEQ ID NO 996
<211> LENGTH: 19
<212> TYPE: RNA
<213> ORGANISM: Artificial sequence
<220> FEATURE:
<223> OTHER INFORMATION: AAT RNAi agent sense strand modified sequence

<400> SEQUENCE: 996
gcacaccagu ccaacagca                              19

<210> SEQ ID NO 997
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 997
uggcacacca guccaacagc a                           21

```
<210> SEQ ID NO 998
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 998
aagcacacca guccaacagc a                                              21

<210> SEQ ID NO 999
<211> LENGTH: 19
<212> TYPE: RNA
<213> ORGANISM: Artificial sequence
<220> FEATURE:
<223> OTHER INFORMATION: AAT RNAi agent sense strand modified sequence

<400> SEQUENCE: 999
guaccacuca gaagccuua                                                 19

<210> SEQ ID NO 1000
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1000
uuguaccacu cagaagccuu a                                              21

<210> SEQ ID NO 1001
<211> LENGTH: 19
<212> TYPE: RNA
<213> ORGANISM: Artificial sequence
<220> FEATURE:
<223> OTHER INFORMATION: AAT RNAi agent sense strand modified sequence

<400> SEQUENCE: 1001
guaccacuca gaagccuuc                                                 19

<210> SEQ ID NO 1002
<211> LENGTH: 19
<212> TYPE: RNA
<213> ORGANISM: Artificial sequence
<220> FEATURE:
<223> OTHER INFORMATION: AAT RNAi agent sense strand modified sequence

<400> SEQUENCE: 1002
ucaacaaacc cuuugucuu                                                 19

<210> SEQ ID NO 1003
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1003
guucaacaaa cccuuugucu u                                              21

<210> SEQ ID NO 1004
<211> LENGTH: 21
<212> TYPE: RNA
<213> ORGANISM: Artificial sequence
<220> FEATURE:
<223> OTHER INFORMATION: AAT RNAi agent sense strand modified sequence
```

<400> SEQUENCE: 1004
guucaacaaa cccuuugucu a					21

<210> SEQ ID NO 1005
<211> LENGTH: 19
<212> TYPE: RNA
<213> ORGANISM: Artificial sequence
<220> FEATURE:
<223> OTHER INFORMATION: AAT RNAi agent sense strand modified sequence

<400> SEQUENCE: 1005
gaggccauac ccaugucua					19

<210> SEQ ID NO 1006
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1006
uagaggccau acccaugucu a					21

<210> SEQ ID NO 1007
<211> LENGTH: 19
<212> TYPE: RNA
<213> ORGANISM: Artificial sequence
<220> FEATURE:
<223> OTHER INFORMATION: AAT RNAi agent sense strand modified sequence

<400> SEQUENCE: 1007
ggccaagaaa cagaucaaa					19

<210> SEQ ID NO 1008
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1008
gaggccaaga aacagaucaa a					21

<210> SEQ ID NO 1009
<211> LENGTH: 19
<212> TYPE: RNA
<213> ORGANISM: Artificial sequence
<220> FEATURE:
<223> OTHER INFORMATION: AAT RNAi agent sense strand modified sequence

<400> SEQUENCE: 1009
cuggcacacc aguccaaca					19

<210> SEQ ID NO 1010
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1010
agcuggcaca ccaguccaac a					21

<210> SEQ ID NO 1011
<211> LENGTH: 20

```
<212> TYPE: RNA
<213> ORGANISM: Artificial sequence
<220> FEATURE:
<223> OTHER INFORMATION: AAT RNAi agent sense strand modified sequence

<400> SEQUENCE: 1011
gcuggcacac caguccaaca                                          20

<210> SEQ ID NO 1012
<211> LENGTH: 19
<212> TYPE: RNA
<213> ORGANISM: Artificial sequence
<220> FEATURE:
<223> OTHER INFORMATION: AAT RNAi agent sense strand modified sequence

<400> SEQUENCE: 1012
caaguucaac aaacccuuu                                           19

<210> SEQ ID NO 1013
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1013
gucaaguuca acaaacccuu u                                        21

<210> SEQ ID NO 1014
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1014
gucaaguuca acaaacccuu a                                        21

<210> SEQ ID NO 1015
<211> LENGTH: 19
<212> TYPE: RNA
<213> ORGANISM: Artificial sequence
<220> FEATURE:
<223> OTHER INFORMATION: AAT RNAi agent sense strand modified sequence

<400> SEQUENCE: 1015
caguccaaca gcaccaaua                                           19

<210> SEQ ID NO 1016
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1016
accaguccaa cagcaccaau a                                        21

<210> SEQ ID NO 1017
<211> LENGTH: 20
<212> TYPE: RNA
<213> ORGANISM: Artificial sequence
<220> FEATURE:
<223> OTHER INFORMATION: AAT RNAi agent sense strand modified sequence

<400> SEQUENCE: 1017
```
ccaguccaac agcaccaaua                                          20

<210> SEQ ID NO 1018
<211> LENGTH: 20
<212> TYPE: RNA
<213> ORGANISM: Artificial sequence
<220> FEATURE:
<223> OTHER INFORMATION: AAT RNAi agent sense strand modified sequence

<400> SEQUENCE: 1018
cuggcacacc aguccaacaa                                          20

<210> SEQ ID NO 1019
<211> LENGTH: 19
<212> TYPE: RNA
<213> ORGANISM: Artificial sequence
<220> FEATURE:
<223> OTHER INFORMATION: AAT RNAi agent sense strand modified sequence

<400> SEQUENCE: 1019
ggccauaccc augucuaua                                           19

<210> SEQ ID NO 1020
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1020
gaggccauac ccaugucuau a                                        21

<210> SEQ ID NO 1021
<211> LENGTH: 23
<212> TYPE: RNA
<213> ORGANISM: Artificial sequence
<220> FEATURE:
<223> OTHER INFORMATION: AAT RNAi agent sense strand modified sequence

<400> SEQUENCE: 1021
gucaaguuca acaaacccuu uga                                      23

<210> SEQ ID NO 1022
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1022
caaguucaac aaacccuuug a                                        21

<210> SEQ ID NO 1023
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1023
ccaguccaac agcaccaaua a                                        21

<210> SEQ ID NO 1024
<211> LENGTH: 21
<212> TYPE: RNA
<213> ORGANISM: Artificial sequence

```
<220> FEATURE:
<223> OTHER INFORMATION: AAT RNAi agent sense strand modified sequence

<400> SEQUENCE: 1024
cgcguuuagg cauguuuaac a                                              21

<210> SEQ ID NO 1025
<211> LENGTH: 19
<212> TYPE: RNA
<213> ORGANISM: Artificial sequence
<220> FEATURE:
<223> OTHER INFORMATION: AAT RNAi agent sense strand modified sequence

<400> SEQUENCE: 1025
cguuuaggca uguuuaaca                                                 19

<210> SEQ ID NO 1026
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1026
cgcguuuagg cauguuuaac a                                              21

<210> SEQ ID NO 1027
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1027
agcguuuagg cauguuuaac a                                              21

<210> SEQ ID NO 1028
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1028
cguuuaggca uguuuaacau u                                              21

<210> SEQ ID NO 1029
<211> LENGTH: 20
<212> TYPE: RNA
<213> ORGANISM: Artificial sequence
<220> FEATURE:
<223> OTHER INFORMATION: AAT RNAi agent sense strand modified sequence

<400> SEQUENCE: 1029
gcguuuaggc auguuuaaca                                                20

<210> SEQ ID NO 1030
<211> LENGTH: 22
<212> TYPE: RNA
<213> ORGANISM: Artificial sequence
<220> FEATURE:
<223> OTHER INFORMATION: AAT RNAi agent sense strand modified sequence

<400> SEQUENCE: 1030
gcguuuaggc auguuuaaca uu                                             22
```

<210> SEQ ID NO 1031
<211> LENGTH: 23
<212> TYPE: RNA
<213> ORGANISM: Artificial sequence
<220> FEATURE:
<223> OTHER INFORMATION: AAT RNAi agent sense strand modified sequence

<400> SEQUENCE: 1031
cgcguuuagg cauguuuaac auu					23

<210> SEQ ID NO 1032
<211> LENGTH: 23
<212> TYPE: RNA
<213> ORGANISM: Artificial sequence
<220> FEATURE:
<223> OTHER INFORMATION: AAT RNAi agent sense strand modified sequence

<400> SEQUENCE: 1032
agcguuuagg cauguuuaac auu					23

<210> SEQ ID NO 1033
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1033
agcguuuagg cauguuuaac a						21

<210> SEQ ID NO 1034
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1034
cgcguuuagg cauguuuaac a						21

<210> SEQ ID NO 1035
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1035
agaagauauu ggugcuguuu u						21

<210> SEQ ID NO 1036
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1036
aggaacuugg ugaugauauu u						21

<210> SEQ ID NO 1037
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1037
ugucuucugg gcagcaucuu u         21

<210> SEQ ID NO 1038
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1038
uguuggacug gugugccagu u         21

<210> SEQ ID NO 1039
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1039
cuguuggacu ggugugccau u         21

<210> SEQ ID NO 1040
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1040
ugcuguugga cuggugugcu u         21

<210> SEQ ID NO 1041
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1041
uauuggugcu guuggacugu u         21

<210> SEQ ID NO 1042
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1042
auauuggugc uguuggacuu u         21

<210> SEQ ID NO 1043
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1043
gauauuggug cuguuggacu u         21

<210> SEQ ID NO 1044

```
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1044
aagauauugg ugcuguuggu u                                              21

<210> SEQ ID NO 1045
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1045
guagcgaugc ucacugggu u                                               21

<210> SEQ ID NO 1046
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1046
aaaggcugua gcgaugcucu u                                              21

<210> SEQ ID NO 1047
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1047
gcaaaggcug uagcgaugcu u                                              21

<210> SEQ ID NO 1048
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1048
ugcaaaggcu guagcgaugu u                                              21

<210> SEQ ID NO 1049
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1049
auugcaaagg cuguagcgau u                                              21

<210> SEQ ID NO 1050
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1050
```
agcauugcaa aggcuguagu u                                21

<210> SEQ ID NO 1051
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1051
agagcauugc aaaggcuguu u                                21

<210> SEQ ID NO 1052
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1052
ggaguuccug gaagccuucu u                                21

<210> SEQ ID NO 1053
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1053
uccaaaaacu uauccacuau u                                21

<210> SEQ ID NO 1054
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1054
aaggcuucug agugguacau u                                21

<210> SEQ ID NO 1055
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1055
gaaggcuucu gaguggurcu u                                21

<210> SEQ ID NO 1056
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1056
uucuuggccu cuucgguguu u                                21

<210> SEQ ID NO 1057
<211> LENGTH: 21
<212> TYPE: RNA

```
<213> ORGANISM: Artificial sequence
<220> FEATURE:
<223> OTHER INFORMATION: AAT RNAi agent antisense sequence

<400> SEQUENCE: 1057
guuucuuggc cucuucgguu u                                              21

<210> SEQ ID NO 1058
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1058
uugaucuguu ucuuggccuu u                                              21

<210> SEQ ID NO 1059
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1059
guugaucugu ucuuggccu u                                               21

<210> SEQ ID NO 1060
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1060
cguugaucug uuucuuggcu u                                              21

<210> SEQ ID NO 1061
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1061
cacaauuuuc ccuugaguau u                                              21

<210> SEQ ID NO 1062
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1062
uccacaauuu ucccuugagu u                                              21

<210> SEQ ID NO 1063
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1063
auccacaauu ucccuugau u                                               21
```

<210> SEQ ID NO 1064
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1064
ugucaagcuc cuugaccaau u              21

<210> SEQ ID NO 1065
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1065
gugucucugu caagcuccuu u              21

<210> SEQ ID NO 1066
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1066
acugugucuc ugucaagcuu u              21

<210> SEQ ID NO 1067
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1067
uguaauucac cagagcaaau u              21

<210> SEQ ID NO 1068
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1068
uuaaacaugc cuaaacgcuu u              21

<210> SEQ ID NO 1069
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1069
guuaaacaug ccuaaacgcu u              21

<210> SEQ ID NO 1070
<211> LENGTH: 21
<212> TYPE: RNA
<213> ORGANISM: Artificial sequence
<220> FEATURE:

<223> OTHER INFORMATION: AAT RNAi agent antisense sequence

<400> SEQUENCE: 1070
uguuaaacau gccuaaacgu u                                         21

<210> SEQ ID NO 1071
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1071
ggauguuaaa caugccuaau u                                         21

<210> SEQ ID NO 1072
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1072
auuucaucag cagcacccau u                                         21

<210> SEQ ID NO 1073
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1073
gaagaagaug gcgguggcau u                                         21

<210> SEQ ID NO 1074
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1074
ggugaguuca uuuuccaggu u                                         21

<210> SEQ ID NO 1075
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1075
gaacuuggug augauaucgu u                                         21

<210> SEQ ID NO 1076
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1076
cauuuuccag gaacuugguu u                                         21

```
<210> SEQ ID NO 1077
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1077
cauagguucc aguaauggau u                                                 21

<210> SEQ ID NO 1078
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1078
ucauagguuc caguaauggu u                                                 21

<210> SEQ ID NO 1079
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1079
ucagaucaua gguuccaguu u                                                 21

<210> SEQ ID NO 1080
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1080
ucuucagauc auagguuccu u                                                 21

<210> SEQ ID NO 1081
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1081
cucuucagau cauagguucu u                                                 21

<210> SEQ ID NO 1082
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1082
gaggucagcc ccauugcugu u                                                 21

<210> SEQ ID NO 1083
<211> LENGTH: 21
<212> TYPE: RNA
<213> ORGANISM: Artificial sequence
<220> FEATURE:
<223> OTHER INFORMATION: AAT RNAi agent antisense sequence
```

```
<400> SEQUENCE: 1083
gagaggucag ccccauugcu u                                              21

<210> SEQ ID NO 1084
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1084
cuucaggggu gccuccucuu u                                              21

<210> SEQ ID NO 1085
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1085
gagagcuuca ggggugccuu u                                              21

<210> SEQ ID NO 1086
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1086
uuaugcacgg ccuuggagau u                                              21

<210> SEQ ID NO 1087
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1087
ccuuaugcac ggccuuggau u                                              21

<210> SEQ ID NO 1088
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1088
gccuuaugca cggccuuggu u                                              21

<210> SEQ ID NO 1089
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1089
agccuuaugc acggccuugu u                                              21

<210> SEQ ID NO 1090
<211> LENGTH: 21
```

```
<212> TYPE: RNA
<213> ORGANISM: Artificial sequence
<220> FEATURE:
<223> OTHER INFORMATION: AAT RNAi agent antisense sequence

<400> SEQUENCE: 1090
cgauggucag cacagccuuu u                                              21

<210> SEQ ID NO 1091
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1091
gucgaugguc agcacagccu u                                              21

<210> SEQ ID NO 1092
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1092
aaaaacaugg ccccagcagu u                                              21

<210> SEQ ID NO 1093
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1093
cuaaaaacau ggccccagcu u                                              21

<210> SEQ ID NO 1094
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1094
ucuaaaaaca uggccccagu u                                              21

<210> SEQ ID NO 1095
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1095
ccucuaaaaa cauggccccu u                                              21

<210> SEQ ID NO 1096
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1096
```
gccucuaaaa acauggcccu u                                        21

<210> SEQ ID NO 1097
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1097
uagacauggg uauggccucu u                                        21

<210> SEQ ID NO 1098
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1098
gauagacaug gguauggccu u                                        21

<210> SEQ ID NO 1099
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1099
uguugaacuu gaccucgggu u                                        21

<210> SEQ ID NO 1100
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1100
gguuuguuga acuugaccuu u                                        21

<210> SEQ ID NO 1101
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1101
aaaggguuug uugaacuugu u                                        21

<210> SEQ ID NO 1102
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1102
acaaaggguu uguugaacuu u                                        21

<210> SEQ ID NO 1103
<211> LENGTH: 21
<212> TYPE: RNA
<213> ORGANISM: Artificial sequence

```
<220> FEATURE:
<223> OTHER INFORMATION: AAT RNAi agent antisense sequence

<400> SEQUENCE: 1103
gacaaagggu uguugaacu u                                          21

<210> SEQ ID NO 1104
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1104
aagacaaagg guuguugau u                                          21

<210> SEQ ID NO 1105
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1105
cauuaagaag acaaaggguu u                                         21

<210> SEQ ID NO 1106
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1106
aucauuaaga agacaaaggu u                                         21

<210> SEQ ID NO 1107
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1107
gaagagggga gacuuggau u                                          21

<210> SEQ ID NO 1108
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1108
ccaugaagag gggagacuuu u                                         21

<210> SEQ ID NO 1109
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1109
cccaugaaga ggggagacuu u                                         21
```

<210> SEQ ID NO 1110
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1110
uucccaugaa gagggagau u                                              21

<210> SEQ ID NO 1111
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1111
uuucccauga agagggagu u                                              21

<210> SEQ ID NO 1112
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1112
aacccuucuu uaaugucauu u                                             21

<210> SEQ ID NO 1113
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1113
uuguuggacu ggugugccau u                                             21

<210> SEQ ID NO 1114
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1114
uauauuggug cuguuggacu u                                             21

<210> SEQ ID NO 1115
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1115
uuagcgaugc ucacuggggu u                                             21

<210> SEQ ID NO 1116
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1116
ucaaaggcug uagcgaugcu u                                             21

<210> SEQ ID NO 1117
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1117
ugaguuccug gaagccuucu u                                             21

<210> SEQ ID NO 1118
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1118
uaaggcuucu gagugguacu u                                             21

<210> SEQ ID NO 1119
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1119
uuuucuuggc cucuucgguu u                                             21

<210> SEQ ID NO 1120
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1120
uuugaucugu uucuuggccu u                                             21

<210> SEQ ID NO 1121
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1121
uguugaucug uuucuuggcu u                                             21

<210> SEQ ID NO 1122
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1122
uacaauuuuc ccuugaguau u                                             21

<210> SEQ ID NO 1123

```
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1123
uugucucugu caagcuccuu u                                              21

<210> SEQ ID NO 1124
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1124
uuuaaacaug ccuaaacgcu u                                              21

<210> SEQ ID NO 1125
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1125
ugauguuaaa caugccuaau u                                              21

<210> SEQ ID NO 1126
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1126
uaagaagaug gcgguggcau u                                              21

<210> SEQ ID NO 1127
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1127
ugugaguuca uuuccaggu u                                               21

<210> SEQ ID NO 1128
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1128
uaacuuggug augauaucgu u                                              21

<210> SEQ ID NO 1129
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1129
```
uauuuuccag gaacuugguu u          21

<210> SEQ ID NO 1130
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1130
uauagguucc aguaauggau u          21

<210> SEQ ID NO 1131
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1131
uucuucagau cauagguucu u          21

<210> SEQ ID NO 1132
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1132
uaggucagcc ccauugcugu u          21

<210> SEQ ID NO 1133
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1133
uagaggucag ccccauugcu u          21

<210> SEQ ID NO 1134
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1134
uuucaggggu gccuccucuu u          21

<210> SEQ ID NO 1135
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1135
uagagcuuca ggggugccuu u          21

<210> SEQ ID NO 1136
<211> LENGTH: 21
<212> TYPE: RNA

```
<213> ORGANISM: Artificial sequence
<220> FEATURE:
<223> OTHER INFORMATION: AAT RNAi agent antisense sequence

<400> SEQUENCE: 1136
ucuuaugcac ggccuuggau u                                              21

<210> SEQ ID NO 1137
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1137
uccuuaugca cggccuuggu u                                              21

<210> SEQ ID NO 1138
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1138
ugauggucag cacagccuuu u                                              21

<210> SEQ ID NO 1139
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1139
uucgaugguc agcacagccu u                                              21

<210> SEQ ID NO 1140
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1140
uuaaaaacau ggccccagcu u                                              21

<210> SEQ ID NO 1141
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1141
ucucuaaaaa cauggccccu u                                              21

<210> SEQ ID NO 1142
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1142
uccucuaaaa acauggcccu u                                              21
```

<210> SEQ ID NO 1143
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1143
uauagacaug gguauggccu u                                          21

<210> SEQ ID NO 1144
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1144
uguuuguuga acuugaccuu u                                          21

<210> SEQ ID NO 1145
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1145
uacaaagggu uuguugaacu u                                          21

<210> SEQ ID NO 1146
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1146
uauuaagaag acaaagggua u                                          21

<210> SEQ ID NO 1147
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1147
uaagagggga gacuugguau u                                          21

<210> SEQ ID NO 1148
<211> LENGTH: 21
<212> TYPE: RNA
<213> ORGANISM: Artificial sequence
<220> FEATURE:
<223> OTHER INFORMATION: AAT RNAi agent antisense sequence

<400> SEQUENCE: 1148
ucaugaagag gggagacuuu u                                          21

<210> SEQ ID NO 1149
<211> LENGTH: 21
<212> TYPE: RNA
<213> ORGANISM: Artificial sequence
<220> FEATURE:

<223> OTHER INFORMATION: AAT RNAi agent antisense sequence

<400> SEQUENCE: 1149
uccaugaaga ggggagacuu u    21

<210> SEQ ID NO 1150
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1150
aacagcacca auaucuucuu u    21

<210> SEQ ID NO 1151
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1151
auaucaucac caaguuccuu u    21

<210> SEQ ID NO 1152
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1152
agaugcugcc cagaagacau u    21

<210> SEQ ID NO 1153
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1153
cuggcacacc aguccaacau u    21

<210> SEQ ID NO 1154
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1154
uggcacacca guccaacagu u    21

<210> SEQ ID NO 1155
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1155
gcacaccagu ccaacagcau u    21

<210> SEQ ID NO 1156
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1156
caguccaaca gcaccaauau u                                              21

<210> SEQ ID NO 1157
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1157
aguccaacag caccaauauu u                                              21

<210> SEQ ID NO 1158
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1158
guccaacagc accaauaucu u                                              21

<210> SEQ ID NO 1159
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1159
ccaacagcac caauaucuuu u                                              21

<210> SEQ ID NO 1160
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1160
ccccagugag caucgcuacu u                                              21

<210> SEQ ID NO 1161
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1161
gagcaucgcu acagccuuuu u                                              21

<210> SEQ ID NO 1162
<211> LENGTH: 21
<212> TYPE: RNA
<213> ORGANISM: Artificial sequence
<220> FEATURE:
<223> OTHER INFORMATION: AAT RNAi agent sense sequence

```
<400> SEQUENCE: 1162
gcaucgcuac agccuuugcu u                                              21

<210> SEQ ID NO 1163
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1163
caucgcuaca gccuuugcau u                                              21

<210> SEQ ID NO 1164
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1164
ucgcuacagc cuuugcaauu u                                              21

<210> SEQ ID NO 1165
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1165
cuacagccuu ugcaaugcuu u                                              21

<210> SEQ ID NO 1166
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1166
acagccuuug caaugcucuu u                                              21

<210> SEQ ID NO 1167
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1167
gaaggcuucc aggaacuccu u                                              21

<210> SEQ ID NO 1168
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1168
uaguggauaa guuuuuggau u                                              21

<210> SEQ ID NO 1169
<211> LENGTH: 21
```

```
<212> TYPE: RNA
<213> ORGANISM: Artificial sequence
<220> FEATURE:
<223> OTHER INFORMATION: AAT RNAi agent sense sequence

<400> SEQUENCE: 1169
uguaccacuc agaagccuuu u                                              21

<210> SEQ ID NO 1170
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1170
guaccacuca gaagccuucu u                                              21

<210> SEQ ID NO 1171
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1171
acaccgaaga ggccaagaau u                                              21

<210> SEQ ID NO 1172
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1172
accgaagagg ccaagaaacu u                                              21

<210> SEQ ID NO 1173
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1173
aggccaagaa acagaucaau u                                              21

<210> SEQ ID NO 1174
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1174
ggccaagaaa cagaucaacu u                                              21

<210> SEQ ID NO 1175
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1175
```
gccaagaaac agaucaacgu u                                              21

<210> SEQ ID NO 1176
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1176
uacucaaggg aaaauugugu u                                              21

<210> SEQ ID NO 1177
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1177
cucaagggaa aauguggau u                                               21

<210> SEQ ID NO 1178
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1178
ucaagggaaa auuguggauu u                                              21

<210> SEQ ID NO 1179
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1179
uuggucaagg agcuugacau u                                              21

<210> SEQ ID NO 1180
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1180
aggagcuuga cagagacacu u                                              21

<210> SEQ ID NO 1181
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1181
agcuugacag agacacaguu u                                              21

<210> SEQ ID NO 1182
<211> LENGTH: 21
<212> TYPE: RNA
<213> ORGANISM: Artificial sequence

```
<220> FEATURE:
<223> OTHER INFORMATION: AAT RNAi agent sense sequence

<400> SEQUENCE: 1182
uuugcucugg ugaauuacau u                                              21

<210> SEQ ID NO 1183
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1183
agcguuuagg cauguuuaau u                                              21

<210> SEQ ID NO 1184
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1184
gcguuuaggc auguuuaacu u                                              21

<210> SEQ ID NO 1185
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1185
cguuuaggca uguuuaacau u                                              21

<210> SEQ ID NO 1186
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1186
uuaggcaugu uuaacauccu u                                              21

<210> SEQ ID NO 1187
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1187
ugggugcugc ugaugaaauu u                                              21

<210> SEQ ID NO 1188
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1188
ugccaccgcc aucuucuucu u                                              21
```

```
<210> SEQ ID NO 1189
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1189
ccuggaaaau gaacucaccu u                                          21

<210> SEQ ID NO 1190
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1190
cgauaucauc accaaguucu u                                          21

<210> SEQ ID NO 1191
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1191
accaaguucc uggaaaaugu u                                          21

<210> SEQ ID NO 1192
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1192
uccauuacug gaaccuaugu u                                          21

<210> SEQ ID NO 1193
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1193
ccauuacugg aaccuaugau u                                          21

<210> SEQ ID NO 1194
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1194
acuggaaccu augaucugau u                                          21

<210> SEQ ID NO 1195
<211> LENGTH: 21
<212> TYPE: RNA
<213> ORGANISM: Artificial sequence
<220> FEATURE:
<223> OTHER INFORMATION: AAT RNAi agent sense sequence
```

```
<400> SEQUENCE: 1195
ggaaccuaug aucugaagau u                                              21

<210> SEQ ID NO 1196
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1196 gaaccauga ucugaagagu u                                               21

<210> SEQ ID NO 1197
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1197
cagcaauggg gcugaccucu u                                              21

<210> SEQ ID NO 1198
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1198 gcaaugggc ugaccucucu u                                               21

<210> SEQ ID NO 1199
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1199
agaggaggca ccccugaagu u                                              21

<210> SEQ ID NO 1200
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1200
aggcaccccu gaagcucucu u                                              21

<210> SEQ ID NO 1201
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1201
ucuccaaggc cgugcauaau u                                              21

<210> SEQ ID NO 1202
```

```
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1202
uccaaggccg ugcauaaggu u                                              21

<210> SEQ ID NO 1203
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1203
ccaaggccgu gcauaaggcu u                                              21

<210> SEQ ID NO 1204
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1204
caaggccgug cauaaggcuu u                                              21

<210> SEQ ID NO 1205
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1205
aaggcugugc ugaccaucgu u                                              21

<210> SEQ ID NO 1206
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1206
ggcugugcug accaucgacu u                                              21

<210> SEQ ID NO 1207
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1207
cugcuggggc cauguuuuuu u                                              21

<210> SEQ ID NO 1208
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1208
```

```
gcuggggcca uguuuuagu u                                                21
```

<210> SEQ ID NO 1209
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1209

```
cuggggccau guuuuagau u                                                21
```

<210> SEQ ID NO 1210
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1210

```
ggggccaugu uuuagaggu u                                                21
```

<210> SEQ ID NO 1211
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1211

```
gggccauguu uuagaggcu u                                                21
```

<210> SEQ ID NO 1212
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1212

```
gaggccauac ccaugucuau u                                               21
```

<210> SEQ ID NO 1213
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1213

```
ggccauaccc augcuaucu u                                                21
```

<210> SEQ ID NO 1214
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1214

```
cccgagguca aguucaacau u                                               21
```

<210> SEQ ID NO 1215
<211> LENGTH: 21
<212> TYPE: RNA

```
<213> ORGANISM: Artificial sequence
<220> FEATURE:
<223> OTHER INFORMATION: AAT RNAi agent sense sequence

<400> SEQUENCE: 1215
aggucaaguu caacaaaccu u                                              21

<210> SEQ ID NO 1216
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1216
caaguucaac aaacccuuuu u                                              21

<210> SEQ ID NO 1217
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1217
aguucaacaa acccuuuguu u                                              21

<210> SEQ ID NO 1218
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1218
guucaacaaa cccuuugucu u                                              21

<210> SEQ ID NO 1219
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1219
ucaacaaacc cuuugucuuu u                                              21

<210> SEQ ID NO 1220
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1220
acccuuuguc uucuuaaugu u                                              21

<210> SEQ ID NO 1221
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1221
ccuuugucuu cuuaaugauu u                                              21
```

<210> SEQ ID NO 1222
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1222
uaccaagucu ccccucuucu u                                              21

<210> SEQ ID NO 1223
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1223 aagucuccccc ucuucauggu u                                             21

<210> SEQ ID NO 1224
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1224
agucuccccu cuucaugggu u                                              21

<210> SEQ ID NO 1225
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1225
ucuccccucu caugggaau u                                               21

<210> SEQ ID NO 1226
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1226
cuccccucuu caugggaaau u                                              21

<210> SEQ ID NO 1227
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1227
augacauuaa agaaggguuu u                                              21

<210> SEQ ID NO 1228
<211> LENGTH: 21
<212> TYPE: RNA
<213> ORGANISM: Artificial sequence
<220> FEATURE:

-continued

<223> OTHER INFORMATION: AAT RNAi agent sense sequence

<400> SEQUENCE: 1228
uggcacacca guccaacaau u          21

<210> SEQ ID NO 1229
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1229
guccaacagc accaauauau u          21

<210> SEQ ID NO 1230
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1230
ccccagugag caucgcuaau u          21

<210> SEQ ID NO 1231
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1231
gcaucgcuac agccuuugau u          21

<210> SEQ ID NO 1232
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1232
gaaggcuucc aggaacucau u          21

<210> SEQ ID NO 1233
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1233
guaccacuca gaagccuuau u          21

<210> SEQ ID NO 1234
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1234
accgaagagg ccaagaaaau u          21

```
<210> SEQ ID NO 1235
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1235
ggccaagaaa cagaucaaau u                                              21

<210> SEQ ID NO 1236
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1236
gccaagaaac agaucaacau u                                              21

<210> SEQ ID NO 1237
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1237
uacucaaggg aaaauuguau u                                              21

<210> SEQ ID NO 1238
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1238
aggagcuuga cagagacaau u                                              21

<210> SEQ ID NO 1239
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1239
gcguuuaggc auguuuaaau u                                              21

<210> SEQ ID NO 1240
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1240
uuaggcaugu uuaacaucau u                                              21

<210> SEQ ID NO 1241
<211> LENGTH: 21
<212> TYPE: RNA
<213> ORGANISM: Artificial sequence
<220> FEATURE:
<223> OTHER INFORMATION: AAT RNAi agent sense sequence
```

```
<400> SEQUENCE: 1241
ugccaccgcc aucuucuuau u                                              21

<210> SEQ ID NO 1242
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1242
ccuggaaaau gaacucacau u                                              21

<210> SEQ ID NO 1243
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1243
cgauaucauc accaaguuau u                                              21

<210> SEQ ID NO 1244
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1244
accaaguucc uggaaaauau u                                              21

<210> SEQ ID NO 1245
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1245
uccauuacug gaaccuauau u                                              21

<210> SEQ ID NO 1246
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1246
gaaccuauga ucugaagaau u                                              21

<210> SEQ ID NO 1247
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1247
cagcaauggg gcugaccuau u                                              21

<210> SEQ ID NO 1248
<211> LENGTH: 21
```

-continued

```
<212> TYPE: RNA
<213> ORGANISM: Artificial sequence
<220> FEATURE:
<223> OTHER INFORMATION: AAT RNAi agent sense sequence

<400> SEQUENCE: 1248 gcaaugggc ugaccucuau u                                               21

<210> SEQ ID NO 1249
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1249
agaggaggca ccccugaaau u                                              21

<210> SEQ ID NO 1250
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1250 aggcacccu gaagcucuau u                                               21

<210> SEQ ID NO 1251
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1251
uccaaggccg ugcauaagau u                                              21

<210> SEQ ID NO 1252
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1252
ccaaggccgu gcauaaggau u                                              21

<210> SEQ ID NO 1253
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1253
aaggcugugc ugaccaucau u                                              21

<210> SEQ ID NO 1254
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1254
```

-continued ggcugugcug accaucgaau u                                              21

<210> SEQ ID NO 1255
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1255
gcuggggcca uguuuuuaau u                                              21

<210> SEQ ID NO 1256
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1256
ggggccaugu uuuagagau u                                               21

<210> SEQ ID NO 1257
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1257
gggccauguu uuagaggau u                                               21

<210> SEQ ID NO 1258
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1258
ggccauaccc augucuauau u                                              21

<210> SEQ ID NO 1259
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1259
aggucaaguu caacaaacau u                                              21

<210> SEQ ID NO 1260
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1260
guucaacaaa cccuuuguau u                                              21

<210> SEQ ID NO 1261
<211> LENGTH: 21
<212> TYPE: RNA
<213> ORGANISM: Artificial sequence

```
<220> FEATURE:
<223> OTHER INFORMATION: AAT RNAi agent sense sequence

<400> SEQUENCE: 1261
acccuuuguc uucuuaauau u                                                 21

<210> SEQ ID NO 1262
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1262
uaccaagucu ccccucuuau u                                                 21

<210> SEQ ID NO 1263
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1263
aagucccccu cuucaugau u                                                  21

<210> SEQ ID NO 1264
<211> LENGTH: 21
<212> TYPE: RNA
<213> ORGANISM: Artificial sequence
<220> FEATURE:
<223> OTHER INFORMATION: AAT RNAi agent sense sequence

<400> SEQUENCE: 1264 agucccccu cuucauggau u                                                  21

<210> SEQ ID NO 1265
<211> LENGTH: 19
<212> TYPE: RNA
<213> ORGANISM: Artificial sequence
<220> FEATURE:
<223> OTHER INFORMATION: AAT RNAi agent sense strand base sequence

<400> SEQUENCE: 1265
cguuuaggca uguuuaaca                                                    19

<210> SEQ ID NO 1266
<211> LENGTH: 19
<212> TYPE: RNA
<213> ORGANISM: Artificial sequence
<220> FEATURE:
<223> OTHER INFORMATION: AAT RNAi agent sense strand base sequence

<400> SEQUENCE: 1266
gcacaccagu ccaacagca                                                    19

<210> SEQ ID NO 1267
<211> LENGTH: 19
<212> TYPE: RNA
<213> ORGANISM: Artificial sequence
<220> FEATURE:
<223> OTHER INFORMATION: AAT RNAi agent sense strand base sequence

<400> SEQUENCE: 1267
guaccacuca gaagccuua                                                    19
```

```
<210> SEQ ID NO 1268
<211> LENGTH: 19
<212> TYPE: RNA
<213> ORGANISM: Artificial sequence
<220> FEATURE:
<223> OTHER INFORMATION: AAT RNAi agent sense strand base sequence

<400> SEQUENCE: 1268
guaccacuca gaagccuuc                                                   19

<210> SEQ ID NO 1269
<211> LENGTH: 19
<212> TYPE: RNA
<213> ORGANISM: Artificial sequence
<220> FEATURE:
<223> OTHER INFORMATION: AAT RNAi agent sense strand base sequence

<400> SEQUENCE: 1269
ucaacaaacc cuuugucuu                                                   19

<210> SEQ ID NO 1270
<211> LENGTH: 19
<212> TYPE: RNA
<213> ORGANISM: Artificial sequence
<220> FEATURE:
<223> OTHER INFORMATION: AAT RNAi agent sense strand base sequence

<400> SEQUENCE: 1270
gaggccauac ccaugucua                                                   19

<210> SEQ ID NO 1271
<211> LENGTH: 19
<212> TYPE: RNA
<213> ORGANISM: Artificial sequence
<220> FEATURE:
<223> OTHER INFORMATION: AAT RNAi agent sense strand base sequence

<400> SEQUENCE: 1271
ggccaagaaa cagaucaaa                                                   19

<210> SEQ ID NO 1272
<211> LENGTH: 19
<212> TYPE: RNA
<213> ORGANISM: Artificial sequence
<220> FEATURE:
<223> OTHER INFORMATION: AAT RNAi agent sense strand base sequence

<400> SEQUENCE: 1272
cuggcacacc aguccaaca                                                   19

<210> SEQ ID NO 1273
<211> LENGTH: 19
<212> TYPE: RNA
<213> ORGANISM: Artificial sequence
<220> FEATURE:
<223> OTHER INFORMATION: AAT RNAi agent sense strand base sequence

<400> SEQUENCE: 1273
caaguucaac aaacccuuu                                                   19

<210> SEQ ID NO 1274
<211> LENGTH: 19
<212> TYPE: RNA
<213> ORGANISM: Artificial sequence
<220> FEATURE:
<223> OTHER INFORMATION: AAT RNAi agent sense strand base sequence
```

```
<400> SEQUENCE: 1274
caguccaaca gcaccaaua                                              19

<210> SEQ ID NO 1275
<211> LENGTH: 19
<212> TYPE: RNA
<213> ORGANISM: Artificial sequence
<220> FEATURE:
<223> OTHER INFORMATION: AAT RNAi agent sense strand base sequence

<400> SEQUENCE: 1275
ggccauaccc augucuaua                                              19

<210> SEQ ID NO 1276
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1276
cguuuaggca uguuuaacau u                                           21

<210> SEQ ID NO 1277
<211> LENGTH: 22
<212> TYPE: RNA
<213> ORGANISM: Artificial sequence
<220> FEATURE:
<223> OTHER INFORMATION: AAT RNAi agent sense strand modified sequence

<400> SEQUENCE: 1277
gcguuuaggc auguuuaaca uu                                          22

<210> SEQ ID NO 1278
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1278
cgcguuuagg cauguuuaac a                                           21

<210> SEQ ID NO 1279
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 1279
agcguuuagg cauguuuaac a                                           21
```

ALPHA-1 ANTITRYPSIN (AAT) RNAI AGENTS, COMPOSITIONS INCLUDING AAT RNAI AGENTS, AND METHODS OF USE

CROSS REFERENCE TO RELATED APPLICATIONS

This application is a divisional of U.S. patent application Ser. No. 16/568,387, filed Sep. 12, 2019 which is a divisional of U.S. patent application Ser. No. 15/867,107, filed on Jan. 10, 2018, and claims priority to U.S. Provisional Patent Application Ser. No. 62/596,232, filed on Dec. 8, 2017, U.S. Provisional Patent Application Ser. No. 62/486,720, filed on Apr. 18, 2017, and U.S. Provisional Patent Application Ser. No. 62/444,452, filed on Jan. 10, 2017, the contents of each of which are incorporated herein by reference in their entirety.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Nov. 10, 2021, is named T083370014US05-SEQ-ZJG and is 348,582 bytes in size.

FIELD OF THE INVENTION

Disclosed herein are RNA interference (RNAi) agents for inhibition of alpha-1 antitrypsin gene expression, compositions that include alpha-1 antitrypsin RNAi agents, and methods of use thereof.

BACKGROUND

Alpha-1 antitrypsin (AAT, a1-antitrypsin, or A1AT) deficiency is an inherited, autosomal codominant genetic disorder that causes misfolding of the AAT protein and poor secretion of the misfolded protein leading to lung and liver diseases. AAT deficiency (AATD) occurs with a frequency of about 1 in every 1,500 to 3,500 individuals and most often affects persons with European ancestry.

Alpha-1 Antitrypsin is a protease inhibitor belonging to the serpin superfamily. Normal AAT protein is a circulating glycoprotein protease inhibitor primarily synthesized in the liver by hepatocytes and secreted into the blood. The known physiologic function of AAT is to inhibit neutrophil proteases, which serves to protect host tissues from non-specific injury during periods of inflammation.

The most clinically significant form of AATD, a genetic disorder associated with liver disease in children and adults, and pulmonary disease in adults, is caused by the Z mutation. The Z mutant allele (PiZ), through a single point mutation, renders the mutant Z form AAT protein (the "Z-AAT protein") prone to abnormal folding causing intracellular retention. The mutant Z-AAT protein monomers are able to form chains of polymers that amass into aggregates, which are sometimes referred to as "globules." The misfolded Z-AAT protein is ineffective in traversing the secretory pathway, and instead polymerizes and accumulates in the endoplasmic reticulum (ER) of hepatocytes. The polymeric globule masses stress the ER and trigger continuous hepatocyte injury, leading to fibrosis, cirrhosis, and increased risk of hepatocellular carcinoma. Further, the absence of circulating anti-protease activity leaves the lung vulnerable to injury by neutrophil elastase, resulting in the development of respiratory complications such as emphysema.

Individuals with the homozygous PiZZ genotype have severe deficiency of functional AAT, which leads to pulmonary disease. Weekly use of AAT augmentation therapy, using purified human AAT, results in near normal plasma levels of AAT in subjects with AATD, and helps prevent lung damage in affected individuals. However, while the administration of purified AAT can ameliorate or help prevent lung damage caused by the absence of endogenously secreted AAT, AATD patients remain vulnerable to endoplasmic reticulum liver storage disease caused by the deposition and accumulation of excessive abnormally folded AAT protein. Accumulated Z-AAT protein in the globule conformation in hepatocytes is a well-known characteristic of AATD liver disease and is believed to lead to proteotoxic effects that are responsible for inducing liver injury, including liver cell damage and death and chronic liver injury, in individuals with AATD. (see, e.g., D. Lindblad et al., Hepatology 2007, 46: 1228-1235). Patients with AATD often develop liver disease, which can be severe or fatal, even in infancy. Clinical presentations of injury in the liver include chronic hepatitis, cirrhosis, hepatocellular carcinoma, transaminitis, cholestasis, fibrosis, and even fulminant hepatic failure.

There is currently no clinically approved treatment to prevent the onset or slow the progression of liver disease due to AATD. Further, while U.S. Patent Application Publication No. 2015/0361427 discloses certain RNAi agents capable of inhibiting the expression of an AAT gene, there remains a need for novel and effective AAT RNAi agents having improved potency that can selectively, efficiently, and safely inhibit the expression of an AAT gene, thereby preventing and potentially reversing Z-AAT accumulation-related liver injury and fibrosis. Similarly, while U.S. Patent Application Publication No. 2015/0011607 to Brown et al. ("Brown '607") discloses various sequences for inhibiting expression of an AAT gene, Brown teaches the use of longer double-stranded constructs (referred to in Brown as DsiRNAs), which according to Brown have been found to give "unexpected effective results in terms of potency and duration of action" as compared to 19-23mer siRNA agents. (See, e.g., Brown '607 at paragraph [0376]). Moreover, many of the sequences disclosed in Brown '607 are designed to be used in DsiRNA constructs that are designed to target different locations of an AAT mRNA as compared to the sequences disclosed in the present invention. Such differences lead to different binding affinity to the AAT mRNA and produces a different cleavage site, which can impact the inhibitory effect of the compound, while also potentially leading to additional off-target issues (see, e.g., Piotr J. Kamola et al., PLoS Comput Biol, 2015, 11(12):e1004656 at FIG. 1 (illustrating the mechanism of siRNA-Mediated Gene Silencing)). For example, nothing in Brown '607 teaches or suggests the design of an RNAi agent (of any length) wherein the 5' terminal nucleobase or nucleotide of the antisense strand would be aligned with the position that is 19 nucleotides downstream (towards the 3' end) from position 1000 on an AAT gene (SEQ ID NO: 1). Put different, and again solely as an example involving one such potential AAT RNAi agent sequence, nothing in Brown '607 teaches or suggests the design of an RNAi agent wherein the 5' terminal nucleobase of the antisense strand of an RNAi agent corresponds to position 1018 on an AAT gene (SEQ ID NO: 1). Further, nothing in Brown '607 teaches or suggests the modified AAT RNAi agent constructs disclosed herein.

SUMMARY

There exists a need for novel AAT-specific RNA interference (RNAi) agents (also herein termed RNAi agent, RNAi trigger, or trigger) that are able to selectively and efficiently inhibit the expression of an AAT gene. Further, there exists a need for compositions of novel AAT-specific RNAi agents for the treatment of diseases associated with AAT deficiency.

Because liver damage resulting from AATD occurs through a gain-of-function mechanism, inhibition of AAT gene expression is useful in preventing accumulation of the Z-AAT protein in the liver. Further, the reduction or removal of the Z-AAT polymer aggregates reduces the ER stress in hepatocytes, and offers additional advantages in reducing the likelihood of occurrence of liver cell damage and assisting in the treatment of liver cell damage and chronic liver injury such as fibrosis, cirrhosis, hepatocellular carcinoma, and other conditions and diseases caused by AATD. Reduction of inflammatory Z-AAT protein, which has been clearly defined as the cause of progressive liver disease in AATD patients, is important as it can slow or halt the progression of liver disease and allow fibrotic tissue repair.

In general, the disclosure features novel AAT RNAi agents, compositions comprising the AAT RNAi agents, and methods for inhibiting the expression of an AAT gene in vivo and/or in vitro using AAT RNAi agents and compositions that include AAT RNAi agents. Further described herein are methods of treatment of AATD-related diseases using the AAT RNAi agents described herein and compositions that include AAT RNAi agents.

The AAT RNAi agents and methods disclosed herein can provide for the treatment of AATD, including the treatment of conditions and diseases caused by AATD, such as chronic hepatitis, cirrhosis, hepatocellular carcinoma, and fulminant hepatic failure. The AAT RNAi agents disclosed herein, when administered to a subject, can prevent and/or reverse Z-AAT accumulation-related liver injury and fibrosis. The AAT RNAi agents described herein may be administered to a subject, e.g., a human or animal subject, by any suitable methods known in the art, such as subcutaneous injection or intravenous administration.

In one aspect, the disclosure features RNAi agents for inhibiting the expression of an alpha-1 antitrypsin (AAT) gene, wherein the RNAi agent comprises a sense strand and an antisense strand. Also described herein are compositions comprising an RNAi agent capable of inhibiting the expression of an alpha-1 antitrypsin gene, wherein the RNAi agent comprises a sense strand and an antisense strand, and at least one pharmaceutically acceptable excipient.

Each AAT RNAi agent described herein includes a sense strand and an antisense strand. The sense strand and the antisense strand can be partially, substantially, or fully complementary to each other. The length of the RNAi agent sense and antisense strands described herein each can be 16 to 30 nucleotides in length. In some embodiments, the sense and antisense strands are independently 17 to 26 nucleotides in length. In some embodiments, the sense and antisense strands are independently 21 to 26 nucleotides in length. In some embodiments, the sense and antisense strands are independently 21 to 24 nucleotides in length. In some embodiments, the sense and/or antisense strands are independently 16, 17, 18, 19, 20, 21, 22, 23, 24, 25, 26, 27, 28, 29, or 30 nucleotides in length. The sense and antisense strands can be either the same length or different lengths.

The RNAi agents described herein, upon delivery to a cell expressing AAT, inhibit the expression of one or more AAT genes in vivo or in vitro.

An AAT RNAi agent includes a sense strand (also referred to as a passenger strand), and an antisense strand (also referred to as a guide strand). A sense strand of the AAT RNAi agents described herein includes a nucleotide sequence having at least 85% identity to a core stretch of at least 16 consecutive nucleotides to a sequence in an AAT mRNA. In some embodiments, the sense strand core stretch having at least 85% identity to a sequence in an AAT mRNA is 16, 17, 18, 19, 20, 21, 22, or 23 nucleotides in length. An antisense strand of an AAT RNAi agent includes a nucleotide sequence having at least 85% complementarity over a core stretch of at least 16 consecutive nucleotides to a sequence in an AAT mRNA and the corresponding sense strand. In some embodiments, the antisense strand core stretch having at least 85% complementarity to a sequence in an AAT mRNA or the corresponding sense strand is 16, 17, 18, 19, 20, 21, 22, or 23 nucleotides in length.

In some embodiments, the AAT RNAi agents disclosed herein target a portion of an AAT gene having the sequence of any of the sequences disclosed in Table 1.

Examples of AAT RNAi agent sense strands and antisense strands that can be used in AAT RNAi agents are provided in Tables 2, 3, 4 and 5. Examples of duplexes that include AAT RNAi agent are provided in Table 6. Examples of 19-nucleotide core stretch sequences that may consist of or may be included in the sense strands and antisense strands of certain AAT RNAi agents disclosed herein, are provided in Table 2.

In another aspect, the disclosure features methods for delivering AAT RNAi agents to liver cells in a subject, such as a mammal, in vivo. In some embodiments, one or more AAT RNAi agents are delivered to target cells or tissues using any oligonucleotide delivery technology known in the art. Nucleic acid delivery methods include, but are not limited to, encapsulation in liposomes, iontophoresis, or incorporation into other vehicles, such as hydrogels, cyclodextrins, biodegradable nanocapsules, and bioadhesive microspheres, proteinaceous vectors, or Dynamic Polyconjugates™ (DPCs) (see, for example WO 2000/053722, WO 2008/0022309, WO 2011/104169, and WO 2012/083185, each of which is incorporated herein by reference). In some embodiments, a delivery vehicle, such as a polymer, an amphipathic polymer, a membrane active polymer, a peptide, such as a melittin or melittin-like peptide, a reversibly modified polymer or peptide, or a lipid, can be used with the AAT RNAi agents disclosed herein.

In some embodiments, an AAT RNAi agent is delivered to target cells or tissues by covalently linking or conjugating the RNAi agent to a targeting group such as an asialoglycoprotein receptor ligand. In some embodiments, an asialoglycoprotein receptor ligand includes, consists of, or consists essentially of, a galactose or galactose-derivative cluster. In some embodiments, an AAT RNAi agent is linked to a targeting ligand comprising the galactose-derivative N-acetyl-galactosamine. In some embodiments, a galactose-derivative cluster includes an N-acetyl-galactosamine trimer or an N-acetyl-galactosamine tetramer. In some embodiments, a galactose derivative cluster is an N-acetyl-galactosamine trimer or an N-acetyl-galactosamine tetramer. Example targeting groups useful for delivering RNAi agents are disclosed, for example, in U.S. patent application Ser. No. 15/452,324 and WO 2017/156012, which are incorporated by reference herein in their entirety.

A targeting group can be linked to the 3' or 5' end of a sense strand or an antisense strand of an AAT RNAi agent. In some embodiments, a targeting group is linked to the 3' or 5' end of the sense strand. In some embodiments, a targeting group is linked to the 5' end of the sense strand. In some embodiments, a targeting group is linked internally to a nucleotide on the sense strand and/or the antisense strand of the RNAi agent. In some embodiments, a targeting group is linked to the RNAi agent via a linker.

A targeting group, with or without a linker, can be linked to the 5' or 3' end of any of the sense and/or antisense strands disclosed in Tables 2, 3, 4, and 5. A linker, with or without a targeting group, can be attached to the 5' or 3' end of any of the sense and/or antisense strands disclosed in Tables 2, 3, 4, and 5.

In another aspect, the disclosure features compositions that include one or more AAT RNAi agents that have the duplex structures disclosed in Table 6.

In some embodiments, described herein are compositions that include a combination or cocktail of at least two AAT RNAi agents having different nucleotide sequences. In some embodiments, the two or more different AAT RNAi agents are each separately and independently linked to targeting groups. In some embodiments, the two or more different AAT RNAi agents are each linked to targeting groups that include or consist of targeting ligands that include one or more moieties that target an asialoglycoprotein receptor. In some embodiments, the two or more different AAT RNAi agents are each linked to targeting groups that include or consist of targeting ligands that include one or more galactose-derivatives. In some embodiments, the two or more different AAT RNAi agents are each linked to targeting groups that include or consist of targeting ligands that include one or more N-acetyl-galactosomines. In some embodiments, when two or more RNAi agents are included in a composition, each RNAi agent is independently linked to the same targeting group. In some embodiments, when two or more RNAi agents are included in a composition, each RNAi agent is independently linked to a different targeting group, such as targeting groups having different chemical structures.

In some embodiments, targeting groups are linked to the AAT RNAi agents without the use of an additional linker. In some embodiments, the targeting group is designed having a linker readily present to facilitate the linkage to an AAT RNAi agent. In some embodiments, when two or more RNAi agents are included in a composition, the two or more RNAi agents may be linked to their respective targeting groups using the same linkers. In some embodiments, when two or more RNAi agents are included in a composition, the two or more RNAi agents are linked to their respective targeting groups using different linkers.

In another aspect, the disclosure features methods for inhibiting alpha-1 antitrypsin gene expression in a subject, the methods comprising administering to the subject an amount of an AAT RNAi agent capable of inhibiting the expression of an AAT gene, wherein the AAT RNAi agent comprises a sense strand and an antisense strand.

Also described herein are methods for the treatment of a condition or disease caused by AATD, comprising administering to a subject a therapeutically effective amount of an RNAi agent described herein. Further described are methods for inhibiting expression of an AAT gene, wherein the methods include administering to a cell an AAT RNAi agent described herein.

In some embodiments, disclosed herein are methods for the treatment of AATD (including the treatment of a condition or disease caused by AATD), the methods comprising administering to a subject a therapeutically effective amount of an RNAi agent having an antisense strand comprising the sequence of any of the sequences in Tables 2, 3, or 4.

In some embodiments, disclosed herein are methods for inhibiting expression of an AAT gene, the methods comprising administering to a cell an AAT RNAi agent that includes an antisense strand comprising the sequence of any of the sequences in Tables 2, 3, or 4.

In some embodiments, disclosed herein methods for the treatment of AATD (including the treatment of a condition or disease caused by AATD), the methods comprising administering to a subject a therapeutically effective amount of an RNAi agent that includes a sense strand comprising the sequence of any of the sequences in Tables 2, 3, or 5.

In some embodiments, disclosed herein are methods for inhibiting expression of an AAT gene, wherein the methods include administering to a cell an AAT RNAi agent that includes a sense strand comprising the sequence of any of the sequences in Tables 2, 3, or 5.

In some embodiments, disclosed herein are methods for the treatment of AATD (including the treatment of a condition or disease caused by AATD), wherein the methods include administering to a subject a therapeutically effective amount of an RNAi agent that includes a sense strand comprising the sequence of any of the sequences in Table 5, and an antisense strand comprising any of the sequences in Table 4.

In some embodiments, disclosed herein are methods for inhibiting expression of an AAT gene, wherein the methods include administering to a subject a therapeutically effective amount of an RNAi agent that includes a sense strand comprising the sequence of any of the sequences in Table 5, and an antisense strand comprising any of the sequences in Table 4.

In some embodiments, disclosed herein are methods of inhibiting expression of an AAT gene, wherein the methods include administering to a subject an AAT RNAi agent that includes a sense strand consisting of the nucleobase sequence of any of the sequences in Table 5, and the antisense strand consisting of the nucleobase sequence of any of the sequences in Table 4. In other embodiments, disclosed herein are methods of inhibiting expression of an AAT gene, wherein the methods include administering to a subject an AAT RNAi agent that includes a sense strand consisting of the modified sequence of any of the modified sequences in Table 5, and the antisense strand consisting of the modified sequence of any of the modified sequences in Table 4.

In some embodiments, disclosed herein are methods for inhibiting expression of an AAT gene in a cell, wherein the methods include administering one or more AAT RNAi agents having the duplex structure set forth in Table 6.

In some embodiments, the AAT RNAi agents disclosed herein have structures that include, consist of, or consist essentially of, the structure shown in any one of FIG. 1, FIG. 2, FIG. 3, FIG. 4, FIG. 5, FIG. 6, FIG. 7, or FIG. 8.

The AAT RNAi agents disclosed herein are designed to target specific positions on an AAT gene (SEQ ID NO:1). As defined herein, an antisense strand sequence is designed to target an AAT gene at a given position on the gene when the 5' terminal nucleobase of the antisense strand would be aligned with the position that is 19 nucleotides downstream (towards the 3' end) from the position on the gene when base pairing to the gene. For example, as illustrated in Tables 1, 2, and 3 herein, an antisense strand sequence designed to target an AAT gene at position 1000 requires that when base pairing to the gene, the 5' terminal nucleobase of the antisense strand is aligned with position 1018 of the AAT gene. As provided herein, an AAT RNAi agent does not require that the nucleobase at position 1 (5'→3') of the antisense strand be complementary to the gene, provided that there is at least 85% complementarity (e.g., at least 90, 91, 92, 93, 94, 95, 96, 97, 98, 99, or 100% complementarity) of the antisense strand and the gene across a core stretch sequence of at least 16 consecutive nucleotides. For example, for an AAT RNAi agent disclosed herein that is designed to target position 1000 of an AAT gene, the 5' terminal nucleobase of the antisense strand of the of the AAT RNAi agent must be aligned with position 1018 of the gene; however, the 5' terminal nucleobase of the antisense strand may be, but is not required to be, complementary to position 1018 of an AAT gene, provided that there is at least 85% complementarity (e.g., at least 90, 91, 92, 93, 94, 95, 96, 97, 98, 99, or 100% complementarity) of the antisense strand and the gene across a core stretch sequence of at least 16 consecutive nucleotides. As shown by, among other things, the various examples disclosed herein, the specific site of binding of the gene by the antisense strand of the AAT RNAi agent (e.g., whether the AAT RNAi agent is designed to target an AAT gene at position 1000, at position 1142, or at some other position) is highly important to the level of inhibition achieved by the AAT RNAi agent.

In some embodiments, the antisense strand sequence is designed to have a sequence target position 1000 of an AAT gene (SEQ ID NO: 1).

In some embodiments, the antisense strand of an AAT RNAi agent comprises or consists of the nucleobase sequence of UGUUAAACAUGCCUAAACGCU (SEQ ID NO: 801), wherein at least one or more nucleotides is a modified nucleotide. In some embodiments, the antisense strand of an AAT RNAi agent comprises or consists of the nucleobase sequence of UGUUAAACAUGCCUAAACGCU (SEQ ID NO: 801), wherein all or substantially all of the nucleotides are modified nucleotides.

In some embodiments, the antisense strand of an AAT RNAi agent comprises or consists of the nucleobase sequence of UGUUAAACAUGCCUAAACGUU (SEQ ID NO: 794), wherein at least one or more nucleotides is a modified nucleotide. In some embodiments, the antisense strand of an AAT RNAi agent comprises or consists of the nucleobase sequence of UGUUAAACAUGCCUAAACGUU (SEQ ID NO: 794), wherein all or substantially all of the nucleotides are modified nucleotides.

In some embodiments, the antisense strand of an AAT RNAi agent comprises or consists of the nucleobase sequence of UGUUAAACAUGCCUAAACGCUU (SEQ ID NO: 839), wherein at least one or more nucleotides is a modified nucleotide. In some embodiments, the antisense strand of an AAT RNAi agent comprises or consists of the nucleobase sequence of UGUUAAACAUGCCUAAACGCUU (SEQ ID NO: 839), wherein all or substantially all of the nucleotides are modified nucleotides.

In some embodiments, the antisense strand of an AAT RNAi agent comprises or consists of the nucleobase sequence of UGUUAAACAUGCCUAAACGCG (SEQ ID NO: 800), wherein at least one or more nucleotides is a modified nucleotide. In some embodiments, the antisense strand of an AAT RNAi agent comprises or consists of the nucleobase sequence of UGUUAAACAUGCCUAAACGCG (SEQ ID NO: 800), wherein all or substantially all of the nucleotides are modified nucleotides.

In some embodiments, the antisense strand of an AAT RNAi agent comprises or consists of the nucleobase sequence of UGUUAAACAUGCCUAAACG (SEQ ID NO: 80), wherein one or more nucleotides is a modified nucleotide. In some embodiments, the antisense strand of an AAT RNAi agent comprises or consists of the nucleobase sequence of UGUUAAACAUGCCUAAACG (SEQ ID NO: 80), wherein all or substantially all of the nucleotides are modified nucleotides.

In some embodiments, the antisense strand of an AAT RNAi agent comprises or consists of the nucleobase sequence of AGUUAAACAUGCCUAAACG (SEQ ID NO: 81), wherein one or more nucleotides is a modified nucleotide. In some embodiments, the antisense strand of an AAT RNAi agent comprises or consists of the nucleobase sequence of AGUUAAACAUGCCUAAACG (SEQ ID NO: 81), wherein all or substantially all of the nucleotides are modified nucleotides.

In some embodiments, the sense strand of an AAT RNAi agent comprises or consists of the nucleobase sequence of CGUUUAGGCAUGUUUAACA (SEQ ID NO: 429), wherein one or more nucleotides is a modified nucleotide. In some embodiments, the sense strand of an AAT RNAi agent comprises or consists of the nucleobase sequence of CGUUUAGGCAUGUUUAACA (SEQ ID NO: 429), wherein all or substantially all of the nucleotides are modified nucleotides.

In some embodiments, the sense strand of an AAT RNAi agent comprises or consists of the nucleobase sequence of CGUUUAGGCAUGUUUAACU (SEQ ID NO: 430), wherein one or more nucleotides is a modified nucleotide. In some embodiments, the sense strand of an AAT RNAi agent comprises or consists of the nucleobase sequence of CGUUUAGGCAUGUUUAACU (SEQ ID NO: 430), wherein all or substantially all of the nucleotides are modified nucleotides.

In some embodiments, the sense strand of an AAT RNAi agent comprises or consists of the nucleobase sequence of CGUUUAGGCAUGUUUAACA (SEQ ID NO: 429), wherein one or more nucleotides is a modified nucleotide, and the antisense strand of an AAT RNAi agent comprises or consists of the nucleobase sequence of UGUUAAACAUGCCUAAACG (SEQ ID NO: 80), wherein one or more nucleotides is a modified nucleotide.

In some embodiments, the sense strand of an AAT RNAi agent comprises or consists of the nucleobase sequence of CGUUUAGGCAUGUUUAACU (SEQ ID NO: 430), wherein one or more nucleotides is a modified nucleotide, and the antisense strand of an AAT RNAi agent comprises or consists of the nucleobase sequence of AGUUAAACAUGCCUAAACG (SEQ ID NO: 81), wherein one or more nucleotides is a modified nucleotide.

In some embodiments, the antisense strand of an AAT RNAi agent comprises or consists of the nucleobase sequence of UGUUAAACAUGCCUAAACGUU (SEQ ID NO: 794), wherein at least one or more nucleotides is a modified nucleotide, and the sense strand of an AAT RNAi agent comprises or consists of the nucleobase sequence of CGUUUAGGCAUGUUUAACAUU (SEQ ID NO: 857).

In some embodiments, the antisense strand of an AAT RNAi agent comprises or consists of the nucleobase sequence of UGUUAAACAUGCCUAAACGCUU (SEQ ID NO: 839), wherein at least one or more nucleotides is a modified nucleotide, and the sense strand of an AAT RNAi agent comprises or consists of the nucleobase sequence of GCGUUUAGGCAUGUUUAACAUU (SEQ ID NO: 885).

In some embodiments, the antisense strand of an AAT RNAi agent comprises or consists of the nucleobase sequence of UGUUAAACAUGCCUAAACGCG (SEQ ID NO: 800), wherein at least one or more nucleotides is a modified nucleotide, and the sense strand of an AAT RNAi agent comprises or consists of the nucleobase sequence of CGCGUUUAGGCAUGUUUAACA (SEQ ID NO: 864).

In some embodiments, the antisense strand of an AAT RNAi agent comprises or consists of the nucleobase sequence of UGUUAAACAUGCCUAAACGCU (SEQ ID NO: 801), wherein at least one or more nucleotides is a modified nucleotide, and the sense strand of an AAT RNAi agent comprises or consists of the nucleobase sequence of AGCGUUUAGGCAUGUUUAACA (SEQ ID NO: 866).

In some embodiments, the antisense strand of an AAT RNAi agent comprises or consists of the nucleobase sequence of UGUUAAACAUGCCUAAACGUU (SEQ ID NO: 794) differing by 0, 1, 2, or 3 nucleotides, wherein at least one or more nucleotides is a modified nucleotide, and the sense strand of an AAT RNAi agent comprises or consists of the nucleobase sequence of CGUUUAGGCAUGUUUAACAUU (SEQ ID NO: 857) differing by 0, 1, 2, or 3 nucleotides.

In some embodiments, the antisense strand of an AAT RNAi agent comprises or consists of the nucleobase sequence of UGUUAAACAUGCCUAAACGCUU (SEQ ID NO: 839) differing by 0, 1, 2, or 3 nucleotides, wherein at least one or more nucleotides is a modified nucleotide, and the sense strand of an AAT RNAi agent comprises or consists of the nucleobase sequence of GCGUUUAGGCAUGUUUAACAUU (SEQ ID NO: 885) differing by 0, 1, 2, or 3 nucleotides.

In some embodiments, the antisense strand of an AAT RNAi agent comprises or consists of the nucleobase sequence of UGUUAAACAUGCCUAAACGCG (SEQ ID NO: 800) differing by 0, 1, 2, or 3 nucleotides, wherein at least one or more nucleotides is a modified nucleotide, and the sense strand of an AAT RNAi agent comprises or consists of the nucleobase sequence of CGCGUUUAGGCAUGUUUAACA (SEQ ID NO: 864) differing by 0, 1, 2, or 3 nucleotides.

In some embodiments, the antisense strand of an AAT RNAi agent comprises or consists of the nucleobase sequence of UGUUAAACAUGCCUAAACGCU (SEQ ID NO: 801) differing by 0, 1, 2, or 3 nucleotides, wherein at least one or more nucleotides is a modified nucleotide, and the sense strand of an AAT RNAi agent comprises or consists of the nucleobase sequence of AGCGUUUAGGCAUGUUUAACA (SEQ ID NO: 866) differing by 0, 1, 2, or 3 nucleotides.

In some embodiments, the AAT RNAi agent comprises, consists of, or consists essentially of the duplex structure of AD04824.

In some embodiments, the AAT RNAi agent comprises, consists of, or consists essentially of the duplex structure of AD04825.

In some embodiments, the AAT RNAi agent comprises, consists of, or consists essentially of the duplex structure of AD04826.

In some embodiments, the AAT RNAi agent comprises, consists of, or consists essentially of the duplex structure of AD04827.

In some embodiments, the AAT RNAi agent comprises, consists of, or consists essentially of the duplex structure of AD04828.

In some embodiments, the AAT RNAi agent comprises, consists of, or consists essentially of the duplex structure of AD04829.

In some embodiments, the AAT RNAi agent comprises, consists of, or consists essentially of the duplex structure of AD04830.

In some embodiments, the AAT RNAi agent comprises, consists of, or consists essentially of the duplex structure of AD04831.

In some embodiments, the AAT RNAi agent comprises, consists of, or consists essentially of the duplex AD04832.

In some embodiments, the AAT RNAi agent comprises, consists of, or consists essentially of the duplex structure of AD04833.

In some embodiments, the AAT RNAi agent comprises, consists of, or consists essentially of the duplex structure of AD04834.

In some embodiments, the AAT RNAi agent comprises, consists of, or consists essentially of the duplex structure of AD04835.

In some embodiments, the AAT RNAi agent comprises, consists of, or consists essentially of the duplex structure of AD04836.

In some embodiments, the AAT RNAi agent comprises, consists of, or consists essentially of the duplex structure of AD04837.

In some embodiments, the antisense strand of an AAT RNAi agent comprises or consists of the nucleobase sequence of UGUUAAACAUGCCUAAACG (SEQ ID NO: 80), wherein one or more nucleotides is a modified nucleotide, and wherein SEQ ID NO: 80 is located at positions 1 to 19 (5'→3') of the antisense strand. In some embodiments, the antisense strand of an AAT RNAi agent comprises or consists of the nucleobase sequence of UGUUAAACAUGCCUAAACG (SEQ ID NO: 80), wherein all or substantially all of the nucleotides are modified nucleotides, and wherein SEQ ID NO: 80 is located at positions 1 to 19 (5'→3') of the antisense strand.

In some embodiments, the antisense strand of an AAT RNAi agent comprises or consists of the nucleobase sequence of AGUUAAACAUGCCUAAACG (SEQ ID NO: 81), wherein one or more nucleotides is a modified nucleotide, and wherein SEQ ID NO: 81 is located at positions 1 to 19 (5'→3') of the antisense strand. In some embodiments, the antisense strand of an AAT RNAi agent comprises or consists of the nucleobase sequence of AGUUAAACAUGCCUAAACG (SEQ ID NO: 81), wherein all or substantially all of the nucleotides are modified nucleotides, and wherein SEQ ID NO: 81 is located at positions 1 to 19 (5'→3') of the antisense strand.

In some embodiments, the sense strand of an AAT RNAi agent comprises the nucleobase sequence of CGUUUAGGCAUGUUUAACA (SEQ ID NO: 429), wherein one or more nucleotides is a modified nucleotide, and wherein position 19 of SEQ ID NO: 429 forms a base pair with the nucleotide located at the 5' terminal end of the antisense strand. In some embodiments, the sense strand of an AAT RNAi agent comprises or consists of the nucleobase sequence of CGUUUAGGCAUGUUUAACA (SEQ ID NO: 429), wherein all or substantially all of the nucleotides are modified nucleotides, and wherein position 19 of SEQ ID NO: 429 forms a base pair with the nucleotide located at the 5' terminal end of the antisense strand.

In some embodiments, the sense strand of an AAT RNAi agent comprises the nucleobase sequence of CGUUUAGGCAUGUUUAACU (SEQ ID NO: 430), wherein one or more nucleotides is a modified nucleotide, and wherein position 19 of SEQ ID NO: 430 forms a base pair with the nucleotide located at the 5' terminal end of the antisense strand. In some embodiments, the sense strand of AN AAT RNAi agent comprises the nucleobase sequence of CGUUUAGGCAUGUUUAACU (SEQ ID NO: 430), wherein all or substantially all of the nucleotides are modified nucleotides, and wherein position 19 of SEQ ID NO: 430 forms a base pair with the nucleotide located at the 5' terminal end of the antisense strand.

In some embodiments, the antisense strand of an AAT RNAi agent comprises or consists of the nucleobase sequence of UGUUAAACAUGCCUAAACGUU (SEQ ID NO: 794), wherein at least one or more nucleotides is a modified nucleotide, and wherein SEQ ID NO: 794 is located at positions 1 to 21 (5'→3') of the antisense strand. In some embodiments, the antisense strand of an AAT RNAi agent comprises or consists of the nucleobase sequence of UGUUAAACAUGCCUAAACGUU (SEQ ID NO: 794), wherein all or substantially all of the nucleotides are modified nucleotides, and wherein SEQ ID NO: 794 is located at positions 1 to 21 (5'→3') of the antisense strand.

In some embodiments, the antisense strand of an AAT RNAi agent comprises or consists of the nucleobase sequence of UGUUAAACAUGCCUAAACGCUU (SEQ ID NO: 839), wherein at least one or more nucleotides is a modified nucleotide, and wherein SEQ ID NO: 839 is located at positions 1 to 22 (5'→3') of the antisense strand. In some embodiments, the antisense strand of an AAT RNAi agent comprises or consists of the nucleobase sequence of UGUUAAACAUGCCUAAACGCUU (SEQ ID NO: 839), wherein all or substantially all of the nucleotides are modified nucleotides, and wherein SEQ ID NO: 839 is located at positions 1 to 22 (5'→3') of the antisense strand.

In some embodiments, the antisense strand of an AAT RNAi agent comprises or consists of the nucleobase sequence of UGUUAAACAUGCCUAAACGCG (SEQ ID NO: 800), wherein at least one or more nucleotides is a modified nucleotide, and wherein SEQ ID NO: 800 is located at positions 1 to 21 (5'→3') of the antisense strand. In some embodiments, the antisense strand of an AAT RNAi agent comprises or consists of the nucleobase sequence of UGUUAAACAUGCCUAAACGCG (SEQ ID NO: 800), wherein all or substantially all of the nucleotides are modified nucleotides, and wherein SEQ ID NO: 800 is located at positions 1 to 21 (5'→3') of the antisense strand.

In some embodiments, the antisense strand of an AAT RNAi agent comprises or consists of the nucleobase sequence of UGUUAAACAUGCCUAAACGCU (SEQ ID NO: 801), wherein at least one or more nucleotides is a modified nucleotide, and wherein SEQ ID NO: 801 is located at positions 1 to 21 (5'→3') of the antisense strand. In some embodiments, the antisense strand of an AAT RNAi agent comprises or consists of the nucleobase sequence of UGUUAAACAUGCCUAAACGCU (SEQ ID NO: 801), wherein all or substantially all of the nucleotides are modified nucleotides, and wherein SEQ ID NO: 801 is located at positions 1 to 21 (5'→3') of the antisense strand.

In some embodiments, the antisense strand of an AAT RNAi agent comprises or consists of the nucleobase sequence of UGUUAAACAUGCCUAAACGUU (SEQ ID NO: 794), wherein at least one or more nucleotides is a modified nucleotide, and wherein SEQ ID NO: 794 is located at the 5' the terminal end of the antisense strand, and wherein sense strand of an AAT RNAi agent comprises or consists of the nucleobase sequence of CGUUUAGGCAUGUUUAACAUU (SEQ ID NO: 857).

In some embodiments, the antisense strand of an AAT RNAi agent comprises or consists of the nucleobase sequence of UGUUAAACAUGCCUAAACGCUU (SEQ ID NO: 839), wherein at least one or more nucleotides is a modified nucleotide, and wherein SEQ ID NO: 839 is located at the 5' the terminal end of the antisense strand, and the sense strand of an AAT RNAi agent comprises or consists of the nucleobase sequence of GCGUUUAGGCAUGUUUAACAUU (SEQ ID NO: 885).

In some embodiments, the antisense strand of an AAT RNAi agent comprises or consists of the nucleobase sequence of UGUUAAACAUGCCUAAACGCG (SEQ ID NO: 800), wherein at least one or more nucleotides is a modified nucleotide, and wherein SEQ ID NO: 800 is located at the 5' the terminal end of the antisense strand, and the sense strand of an AAT RNAi agent comprises or consists of the nucleobase sequence of CGCGUUUAGGCAUGUUUAACA (SEQ ID NO: 864).

In some embodiments, the antisense strand of an AAT RNAi agent comprises or consists of the nucleobase sequence of UGUUAAACAUGCCUAAACGCU (SEQ ID NO: 801), wherein at least one or more nucleotides is a modified nucleotide, and wherein SEQ ID NO: 801 is located at the 5' the terminal end of the antisense strand, and the sense strand of an AAT RNAi agent comprises or consists of the nucleobase sequence of AGCGUUUAGGCAUGUUUAACA (SEQ ID NO: 866).

In some embodiments, the antisense strand of an AAT RNAi agent comprises or consists of the nucleobase sequence of UGUUAAACAUGCCUAAACGUU (SEQ ID NO: 794) differing by 0, 1, 2, or 3 nucleotides, wherein at least one or more nucleotides is a modified nucleotide, and wherein SEQ ID NO: 794 is located at the 5' the terminal end of the antisense strand, and the sense strand of an AAT RNAi agent comprises or consists of the nucleobase sequence of CGUUUAGGCAUGUUUAACAUU (SEQ ID NO: 857) differing by 0, 1, 2, or 3 nucleotides.

In some embodiments, the antisense strand of an AAT RNAi agent comprises or consists of the nucleobase sequence of UGUUAAACAUGCCUAAACGCUU (SEQ ID NO: 839) differing by 0, 1, 2, or 3 nucleotides, wherein at least one or more nucleotides is a modified nucleotide, and wherein SEQ ID NO: 839 is located at the 5' the terminal end of the antisense strand, and the sense strand of an AAT RNAi agent comprises or consists of the nucleobase sequence of GCGUUUAGGCAUGUUUAACAUU (SEQ ID NO: 885) differing by 0, 1, 2, or 3 nucleotides.

In some embodiments, the antisense strand of an AAT RNAi agent comprises or consists of the nucleobase sequence of UGUUAAACAUGCCUAAACGCG (SEQ ID NO: 800) differing by 0, 1, 2, or 3 nucleotides, wherein at least one or more nucleotides is a modified nucleotide, and wherein SEQ ID NO: 800 is located at the 5' the terminal end of the antisense strand, and the sense strand of an AAT RNAi agent comprises or consists of the nucleobase sequence of CGCGUUUAGGCAUGUUUAACA (SEQ ID NO: 864) differing by 0, 1, 2, or 3 nucleotides.

In some embodiments, the antisense strand of an AAT RNAi agent comprises or consists of the nucleobase sequence of UGUUAAACAUGCCUAAACGCU (SEQ ID NO: 801) differing by 0, 1, 2, or 3 nucleotides, wherein at least one or more nucleotides is a modified nucleotide, and wherein SEQ ID NO: 801 is located at the 5' the terminal end of the antisense strand, and the sense strand of an AAT RNAi agent comprises or consists of the nucleobase sequence of AGCGUUUAGGCAUGUUUAACA (SEQ ID NO: 866) differing by 0, 1, 2, or 3 nucleotides.

The AAT RNAi agents described herein can include one or more modified nucleotides. The AAT RNAi agents described herein can also include one or more phosphorothioate internucleoside linkages.

The AAT RNAi agents described herein can also include one or more targeting groups or linking groups. In some embodiments, the AAT RNAi agents disclosed herein include one or more targeting groups. In some embodiments, the targeting groups are comprised of an asialoglycoprotein receptor ligand. In some embodiments, the asialoglycoprotein receptor ligand comprises a galactose or galactose-derivative cluster. In some embodiments, the galactose-derivative cluster comprises N-acetyl-galactosamine. In some embodiments, the targeting ligand comprises an N-acetyl-galactosamine trimer. In some embodiments, a targeting group is conjugated to the sense strand of the AAT RNAi agents disclosed herein.

In some embodiments, the antisense strand of an AAT RNAi agent comprises or consists of the sequence (5'→3') usGfsusUfaAfaCfaUfgCfcUfaAfaCfgusu (SEQ ID NO: 913), wherein a, c, g, and u are 2'-O-methyl adenosine, cytidine, guanosine, or uridine, respectively; Af, Cf, Gf, and Uf are 2'-fluoro adenosine, cytidine, guanosine, or uridine, respectively; and s is a phosphorothioate linkage, and the sense strand is at least substantially complementary to the antisense strand.

In some embodiments, the antisense strand of an AAT RNAi agent comprises or consists of the sequence (5'→3') usGfsusUfaAfaCfaUfgCfcUfaAfaCfgcusu (SEQ ID NO: 958), wherein a, c, g, and u are 2'-O-methyl adenosine, cytidine, guanosine, or uridine, respectively; Af, Cf, Gf, and Uf are 2'-fluoro adenosine, cytidine, guanosine, or uridine, respectively; and s is a phosphorothioate linkage, and the sense strand is at least substantially complementary to the antisense strand.

In some embodiments, the antisense strand of an AAT RNAi agent comprises or consists of the sequence (5'→3') usGfsuUfaAfaCfaUfgCfcUfaAfaCfgsCfsg (SEQ ID NO: 959), wherein a, c, g, and u are 2'-O-methyl adenosine, cytidine, guanosine, or uridine, respectively; Af, Cf, Gf, and Uf are 2'-fluoro adenosine, cytidine, guanosine, or uridine, respectively; and s is a phosphorothioate linkage, and the sense strand is at least substantially complementary to the antisense strand.

In some embodiments, the antisense strand of an AAT RNAi agent comprises or consists of the sequence (5'→3') usGfsuUfaAfacaugCfcUfaAfaCfgCfsu (SEQ ID NO: 960), wherein a, c, g, and u are 2'-O-methyl adenosine, cytidine, guanosine, or uridine, respectively; Af, Cf, Gf, and Uf are 2'-fluoro adenosine, cytidine, guanosine, or uridine, respectively; and s is a phosphorothioate linkage, and the sense strand is at least substantially complementary to the antisense strand.

In some embodiments, the antisense strand of an AAT RNAi agent comprises or consists of the sequence (5'→3') usGfsusUfaAfaCfaUfgCfcUfaAfaCfgusu (SEQ ID NO: 913) and the sense strand of an AAT RNAi agent comprises or consists of the sequence (5'→3') cgcguuuaGfGfCfauguuuaacausu (SEQ ID NO: 1276), wherein a, c, g, and u are 2'-O-methyl adenosine, cytidine, guanosine, or uridine, respectively; Af, Cf, Gf, and Uf are 2'-fluoro adenosine, cytidine, guanosine, or uridine, respectively; s is a phosphorothioate linkage; wherein optionally present on the sense strand is one, two, or more inverted abasic deoxyribose (invAb); and wherein optionally linked to the 5' terminal end of the sense strand is a targeting ligand that includes N-acetyl-galactosamine.

In some embodiments, the antisense strand of an AAT RNAi agent comprises or consists of the sequence (5'→3') usGfsusUfaAfaCfaUfgCfcUfaAfaCfgcusu (SEQ ID NO: 958) and the sense strand of an AAT RNAi agent comprises or consists of the sequence (5'→3') gcguuuaGfGfCfauguuuaacausu (SEQ ID NO: 1277), wherein a, c, g, and u are 2'-O-methyl adenosine, cytidine, guanosine, or uridine, respectively; Af, Cf, Gf, and Uf are 2'-fluoro adenosine, cytidine, guanosine, or uridine, respectively; s is a phosphorothioate linkage; wherein optionally present on the sense strand is one, two, or more inverted abasic deoxyribose (invAb); and wherein optionally linked to the 5' terminal end of the sense strand is a targeting ligand that includes N-acetyl-galactosamine.

In some embodiments, the antisense strand of an AAT RNAi agent comprises or consists of the sequence (5'→3') usGfsuUfaAfaCfaUfgCfcUfaAfaCfgsCfsg (SEQ ID NO: 959) and the sense strand of an AAT RNAi agent comprises or consists of the sequence (5'→3') cgcguuuaGfGfCfauguuuaaca (SEQ ID NO: 1278), wherein a, c, g, and u are 2'-O-methyl adenosine, cytidine, guanosine, or uridine, respectively; Af, Cf, Gf, and Uf are 2'-fluoro adenosine, cytidine, guanosine, or uridine, respectively; s is a phosphorothioate linkage; wherein optionally present on the sense strand is one, two, or more inverted abasic deoxyribose (invAb); and wherein optionally linked to the 5' terminal end of the sense strand is a targeting ligand that includes N-acetyl-galactosamine.

In some embodiments, the antisense strand of an AAT RNAi agent comprises or consists of the sequence (5'→3') usGfsuUfaAfacaugCfcUfaAfaCfgCfsu (SEQ ID NO: 960) and the sense strand of an AAT RNAi agent comprises or consists of the sequence (5'→3') agcguuuaGfGfCfauguuuaaca (SEQ ID NO: 1279), wherein a, c, g, and u are 2'-O-methyl adenosine, cytidine, guanosine, or uridine, respectively; Af, Cf, Gf, and Uf are 2'-fluoro adenosine, cytidine, guanosine, or uridine, respectively; s is a phosphorothioate linkage; wherein optionally present on the sense strand is one, two, or more inverted abasic deoxyribose (invAb); and wherein optionally linked to the 5' terminal end of the sense strand is a targeting ligand that includes N-acetyl-galactosamine.

In some embodiments, the antisense strand of an AAT RNAi agent comprises or consists of the sequence (5'→3') usGfsusUfaAfaCfaUfgCfcUfaAfaCfgusu (SEQ ID NO: 913) and the sense strand of an AAT RNAi agent comprises or consists of (5'→3') (NAG37)s(invAb)scguuuaGfGfCfauguuaacausu(invAb) (SEQ ID NO: 1028), wherein a, c, g, and u are 2'-O-methyl adenosine, cytidine, guanosine, or uridine, respectively; Af, Cf, Gf, and Uf are 2'-fluoro adenosine, cytidine, guanosine, or uridine, respectively; s is a phosphorothioate linkage; (invAb) is inverted abasic deoxyribose (invAb); and (NAG37) is the targeting ligand that includes N-acetyl-galactosamine having the structure shown in Table 7 herein.

In some embodiments, the antisense strand of an AAT RNAi agent comprises or consists of the sequence (5'→3') usGfsusUfaAfaCfaUfgCfcUfaAfaCfgcusu (SEQ ID NO: 958) and the sense strand of an AAT RNAi agent comprises or consists of the sequence (5'→3') (NAG37)s(invAb)sgcguuuaGfGfCfauguuuaacausu(invAb) (SEQ ID NO: 1030), wherein a, c, g, and u are 2'-O-methyl adenosine, cytidine, guanosine, or uridine, respectively; Af, Cf, Gf, and Uf are 2'-fluoro adenosine, cytidine, guanosine, or uridine, respectively; s is a phosphorothioate linkage; (invAb) is inverted abasic deoxyribose (invAb); and (NAG37) is the targeting ligand that includes N-acetyl-galactosamine having the structure shown in Table 7 herein.

In some embodiments, the antisense strand of an AAT RNAi agent comprises or consists of the sequence (5'→3') usGfsuUfaAfaCfaUfgCfcUfaAfaCfgsCfsg (SEQ ID NO:

959) and the sense strand of an AAT RNAi agent comprises or consists of the sequence (5'→3') (NAG37)s(invAb)scgcguuuaGfGfCfauguuuaacas(invAb) (SEQ ID NO: 1024), wherein a, c, g, and u are 2'-O-methyl adenosine, cytidine, guanosine, or uridine, respectively; Af, Cf, Gf, and Uf are 2'-fluoro adenosine, cytidine, guanosine, or uridine, respectively; s is a phosphorothioate linkage; (invAb) is inverted abasic deoxyribose (invAb); and (NAG37) is the targeting ligand that includes N-acetyl-galactosamine having the structure shown in Table 7 herein.

In some embodiments, the antisense strand of an AAT RNAi agent comprises or consists of the sequence (5'→3') usGfsuUfaAfacaugCfcUfaAfaCfgCfsu (SEQ ID NO: 960) and the sense strand of an AAT RNAi agent comprises or consists of the sequence (5'→3') (NAG37)s(invAb)sagcguuuaGfGfCfauguuuaacas(invAb) (SEQ ID NO: 1033), wherein a, c, g, and u are 2'-O-methyl adenosine, cytidine, guanosine, or uridine, respectively; Af, Cf, Gf, and Uf are 2'-fluoro adenosine, cytidine, guanosine, or uridine, respectively; s is a phosphorothioate linkage; (invAb) is inverted abasic deoxyribose (invAb); and (NAG37) is the targeting ligand that includes N-acetyl-galactosamine having the structure shown in Table 7 herein.

In some embodiments, the AAT RNAi agents described herein can include one or more targeting groups having the structure of (PAZ), (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s, as defined herein in Table 7.

In some embodiments, the AAT RNAi agents described herein include one targeting group at the 5' end of the sense strand having the structure of (PAZ), (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s, as defined herein in Table 7.

The AAT RNAi agents disclosed herein can be incorporated into a composition comprising one or more disclosed AAT RNAi agent and at least one pharmaceutically acceptable excipient. In some embodiments, the compositions disclosed herein comprising one or more of the disclosed AAT RNAi agents and at least one pharmaceutically acceptable excipient is a pharmaceutical composition.

The pharmaceutical compositions comprising one or more AAT RNAi agents can be administered in a number of ways depending upon whether local or systemic treatment is desired. Administration can be, but is not limited to, intravenous, intraarterial, subcutaneous, intraperitoneal, subdermal (e.g., via an implanted device), and intraparenchymal administration. In some embodiments, the pharmaceutical compositions described herein are administered by subcutaneous injection.

In some embodiments, the compositions comprising one or more disclosed AAT RNAi agents and at least one pharmaceutically acceptable excipient can further comprise one or more additional therapeutics or treatments.

In some embodiments, the compositions described herein comprising one or more AAT RNAi agents are packaged in a kit, container, pack, dispenser, pre-filled syringes, or vials. In some embodiments, the compositions described herein are administered parenterally.

The AAT RNAi agents and compositions comprising same that are disclosed herein can be administered to a subject to inhibit the expression of the alpha-1 antitrypsin gene in the subject. In some embodiments, the subject is a human. In some embodiments, the subject is a human that has been diagnosed with having AATD.

In some embodiments, disclosed herein are methods for inhibiting expression of an AAT gene in a cell, the methods comprising administering an AAT RNAi agent that has an antisense strand that is at least partially complementary to the portion of an AAT mRNA having any one of the sequences listed in Table 1.

The AAT RNAi agents and compositions comprising same disclosed herein may be administered to a subject for the treatment of AATD (including a condition or disease caused by alpha-1 antitrypsin deficiency). The condition or disease that may be treated, prevented, and/or managed by administration of the AAT RNAi agents and compositions comprising same disclosed herein include chronic hepatitis, cirrhosis, hepatocellular carcinoma, transaminitis, cholestasis, fibrosis, or fulminant hepatic failure.

As used herein, the terms "oligonucleotide" and "polynucleotide" mean a polymer of linked nucleosides each of which can be independently modified or unmodified.

As used herein, an "RNAi agent" or "RNAi trigger" means a composition that contains an RNA or RNA-like (e.g., chemically modified RNA) oligonucleotide molecule that is capable of degrading or inhibiting translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short interfering RNAs (siRNAs), double-strand RNAs (dsRNA), micro RNAs (miRNAs), short hairpin RNAs (shRNA), and dicer substrates. The antisense strand of the RNAi agents described herein is at least partially complementary to the mRNA being targeted (e.g. AAT mRNA). RNAi agents can include one or more modified nucleotides and/or one or more non-phosphodiester linkages.

As used herein, the terms "silence," "reduce," "inhibit," "down-regulate," or "knockdown" when referring to expression of a given gene, mean that the expression of the gene, as measured by the level of RNA transcribed from the gene or the level of polypeptide, protein or protein subunit translated from the mRNA in a cell, group of cells, tissue, organ, or subject in which the gene is transcribed, is reduced when the cell, group of cells, tissue, organ, or subject is treated with the RNAi agents described herein as compared to a second cell, group of cells, tissue, organ, or subject that has not or have not been so treated.

As used herein, the terms "sequence" and "nucleotide sequence" mean a succession or order of nucleobases or nucleotides, described with a succession of letters using standard nomenclature.

As used herein, a "base", "nucleotide base," or "nucleobase," is a heterocyclic pyrimidine or purine compound, which is a standard constituent of all nucleic acids, and includes the bases that form the nucleotides adenine (A), guanine (G), cytosine (C), thymine (T), and uracil (U). A nucleobase may further be modified to include, without limitation, universal bases, hydrophobic bases, promiscuous bases, size-expanded bases, and fluorinated bases. As used herein, the term "nucleotide" can include a modified nucleotide (such as, for example, a nucleotide mimic, abasic residue (Ab), or a surrogate replacement moiety).

As used herein, and unless otherwise indicated, the term "complementary," when used to describe a first nucleobase or nucleotide sequence (e.g., RNAi agent sense strand or targeted mRNA) in relation to a second nucleobase or nucleotide sequence (e.g., RNAi agent antisense strand or a single-stranded antisense oligonucleotide), means the ability of an oligonucleotide or polynucleotide including the first nucleotide sequence to hybridize (form base pair hydrogen bonds under mammalian physiological conditions (or similar conditions in vitro)) and form a duplex or double helical structure under certain standard conditions with an oligonucleotide or polynucleotide including the second nucleotide sequence. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification. For example, a and Af, as defined herein, are complementary to U (or T) and identical to A for the purposes of determining identity or complementarity.

As used herein, "perfectly complementary" or "fully complementary" means that all (100%) of the nucleobases or nucleotides in a contiguous sequence of a first polynucleotide will hybridize with the same number of nucleobases or nucleotides in a contiguous sequence of a second polynucleotide. The contiguous sequence may comprise all or a part of a first or second nucleotide sequence.

As used herein, "partially complementary" means that in a hybridized pair of nucleobase sequences, at least 70%, but not all, of the bases in a contiguous sequence of a first polynucleotide will hybridize with the same number of bases in a contiguous sequence of a second polynucleotide.

As used herein, "substantially complementary" means that in a hybridized pair of nucleobase sequences, at least 85%, but not all, of the bases in a contiguous sequence of a first polynucleotide will hybridize with the same number of bases in a contiguous sequence of a second polynucleotide. The terms "complementary," "fully complementary," "partially complementary," and "substantially complementary" herein are used with respect to the nucleobase or nucleotide matching between the sense strand and the antisense strand of an RNAi agent, or between the antisense strand of an RNAi agent and a sequence of an AAT mRNA.

As used herein, the term "substantially identical" or "substantially identity" as applied to nucleic acid sequence means that a nucleic acid sequence comprises a sequence that has at least about 85% sequence identity or more, e.g., at least 90%, at least 95%, or at least 99% identity, compared to a reference sequence. Percentage of sequence identity is determined by comparing two optimally aligned sequences over a comparison window. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity. The inventions disclosed herein encompass nucleotide sequences substantially identical to those disclosed herein.

As used herein, the terms "treat," "treatment," and the like, mean the methods or steps taken to provide relief from or alleviation of the number, severity, and/or frequency of one or more symptoms of a disease in a subject. As used herein, "treat" and treatment" may include the prevention, management, prophylactic treatment, and/or inhibition of the number, severity, and/or frequency of one or more symptoms of a disease in a subject.

As used herein, the phrase "introducing into a cell," when referring to an RNAi agent, means functionally delivering the RNAi agent into a cell. The phrase "functional delivery," means that delivering the RNAi agent to the cell in a manner that enables the RNAi agent to have the expected biological activity, e.g., sequence-specific inhibition of gene expression.

Unless stated otherwise, use of the symbol as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the environment (such as pH), as would be readily understood by the person of ordinary skill in the art.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

In addition, the materials, methods, and examples are illustrative only and not intended to be limiting.

Other objects, features, aspects, and advantages of the invention will be apparent from the following detailed description, accompanying figures, and from the claims.

DETAILED DESCRIPTION

RNAi Agents

Figure 1A:
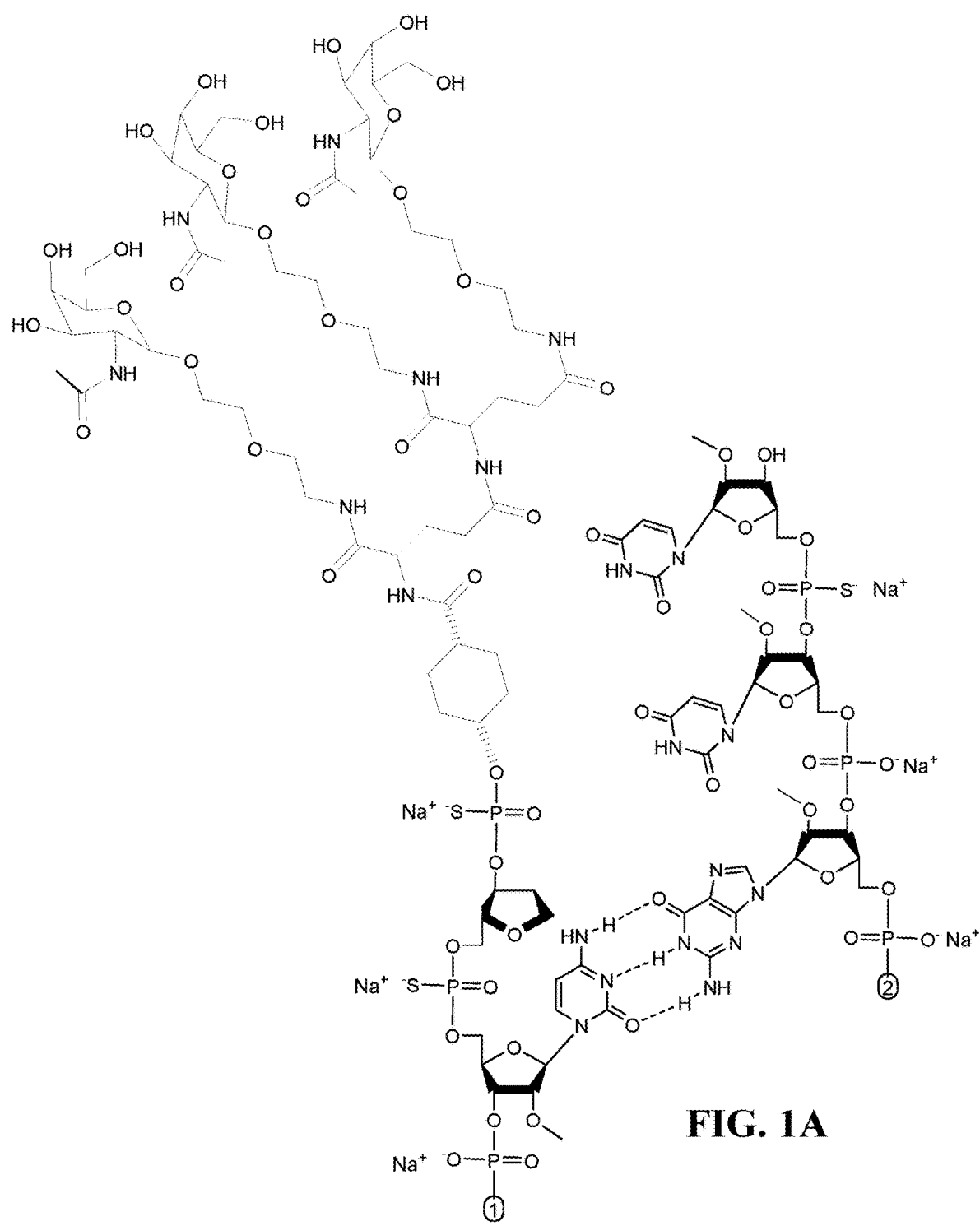
FIGS. 1A to 1E represent the chemical duplex structure of AD04828 shown as a sodium salt.
Figure 1B:
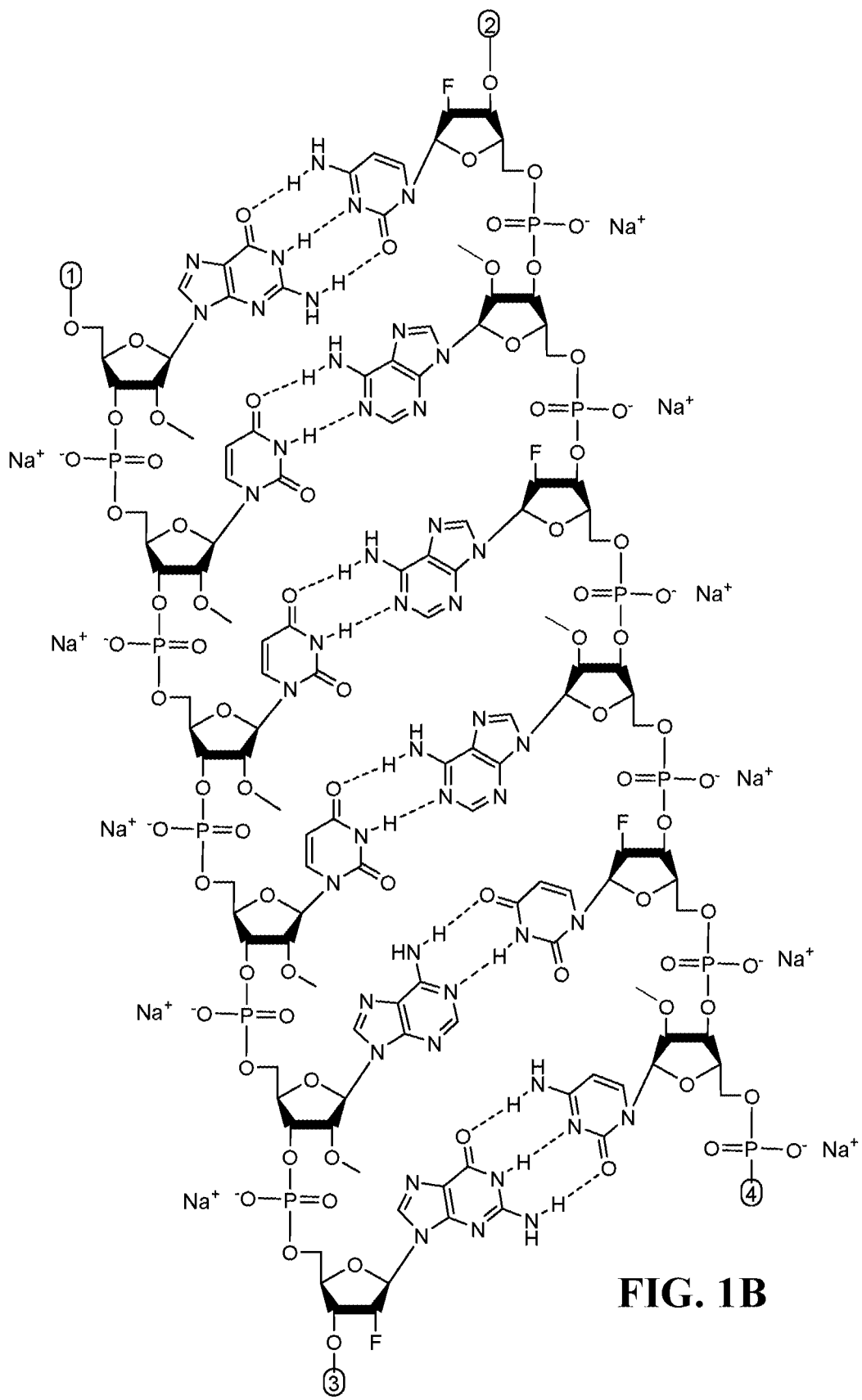
Figure 1C:
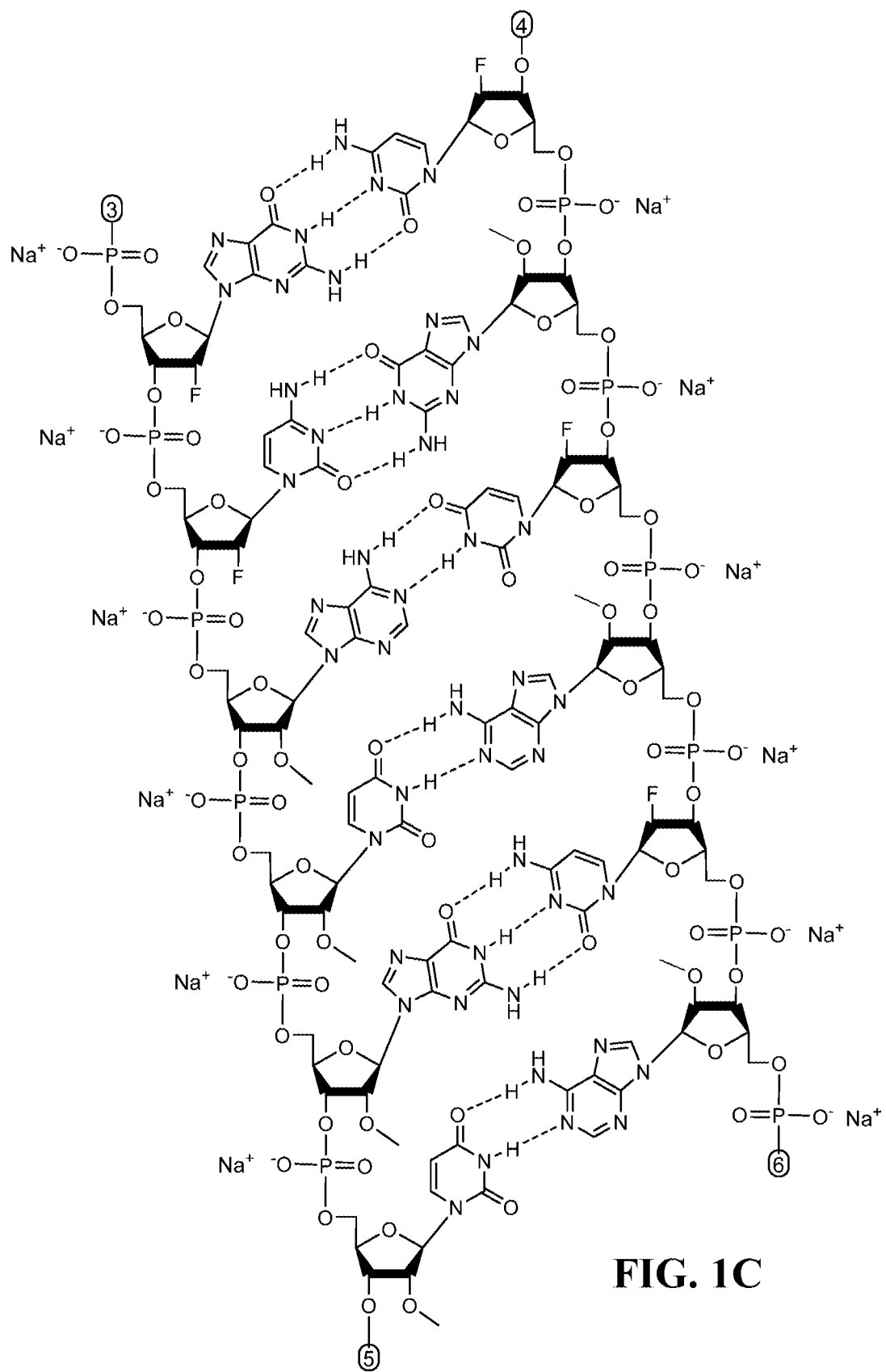
Figure 1D:
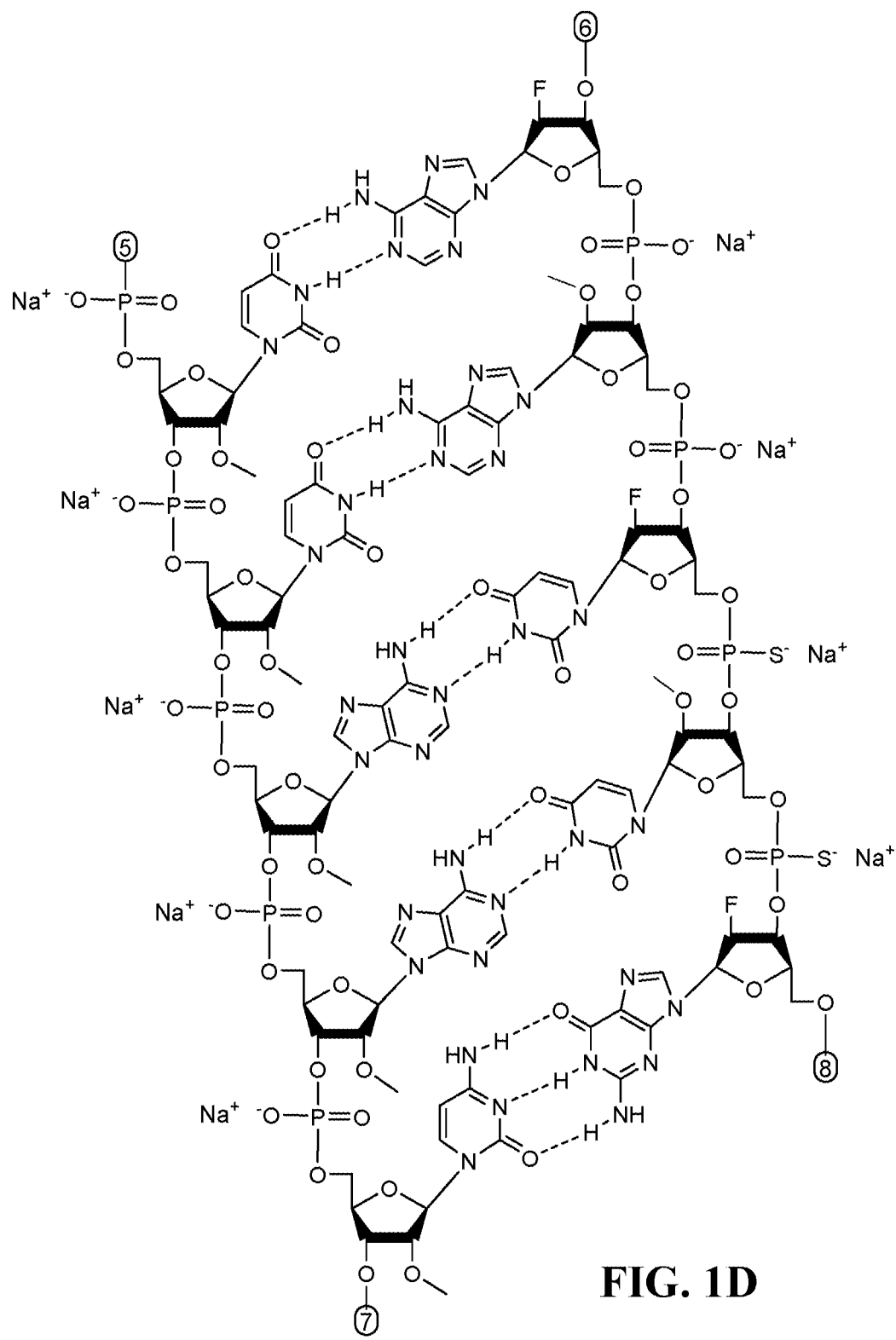
Figure 1E:
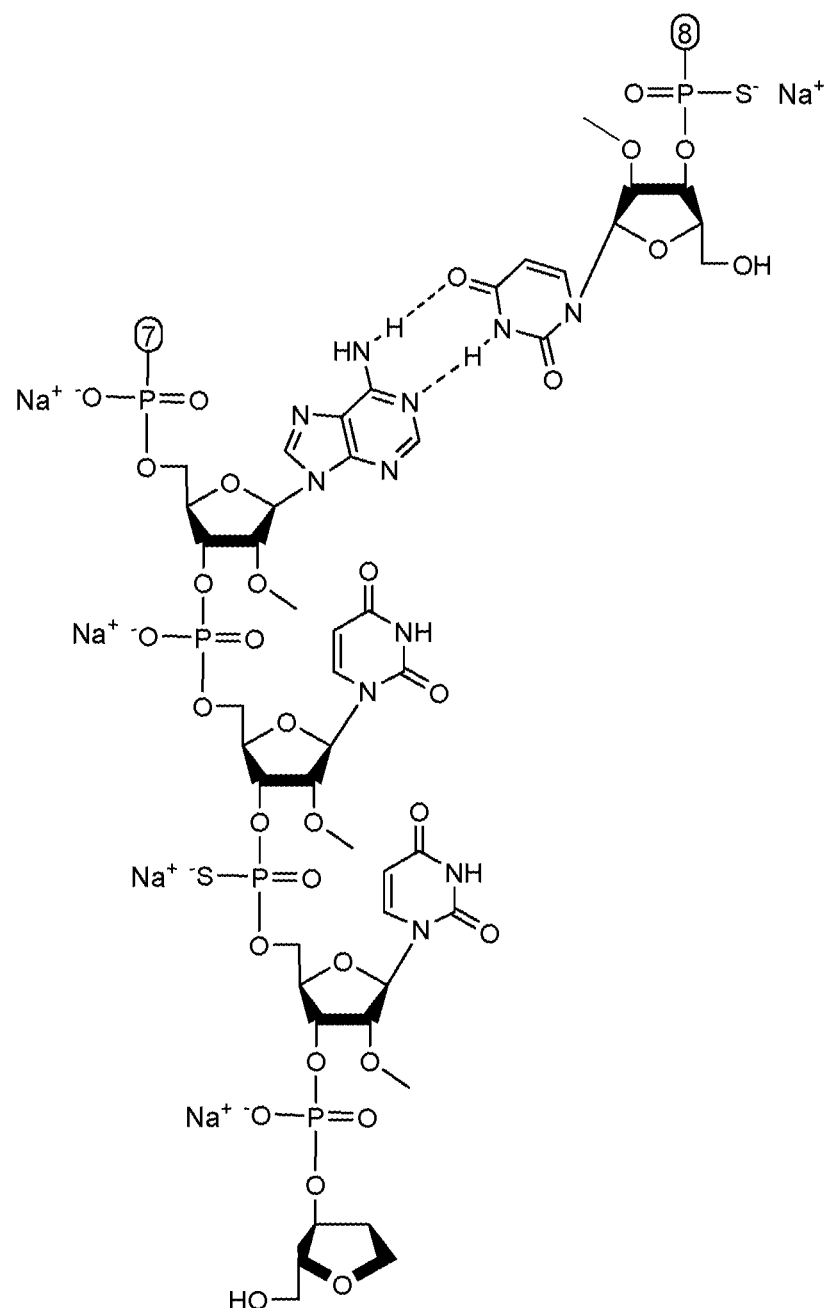
Figure 2A:
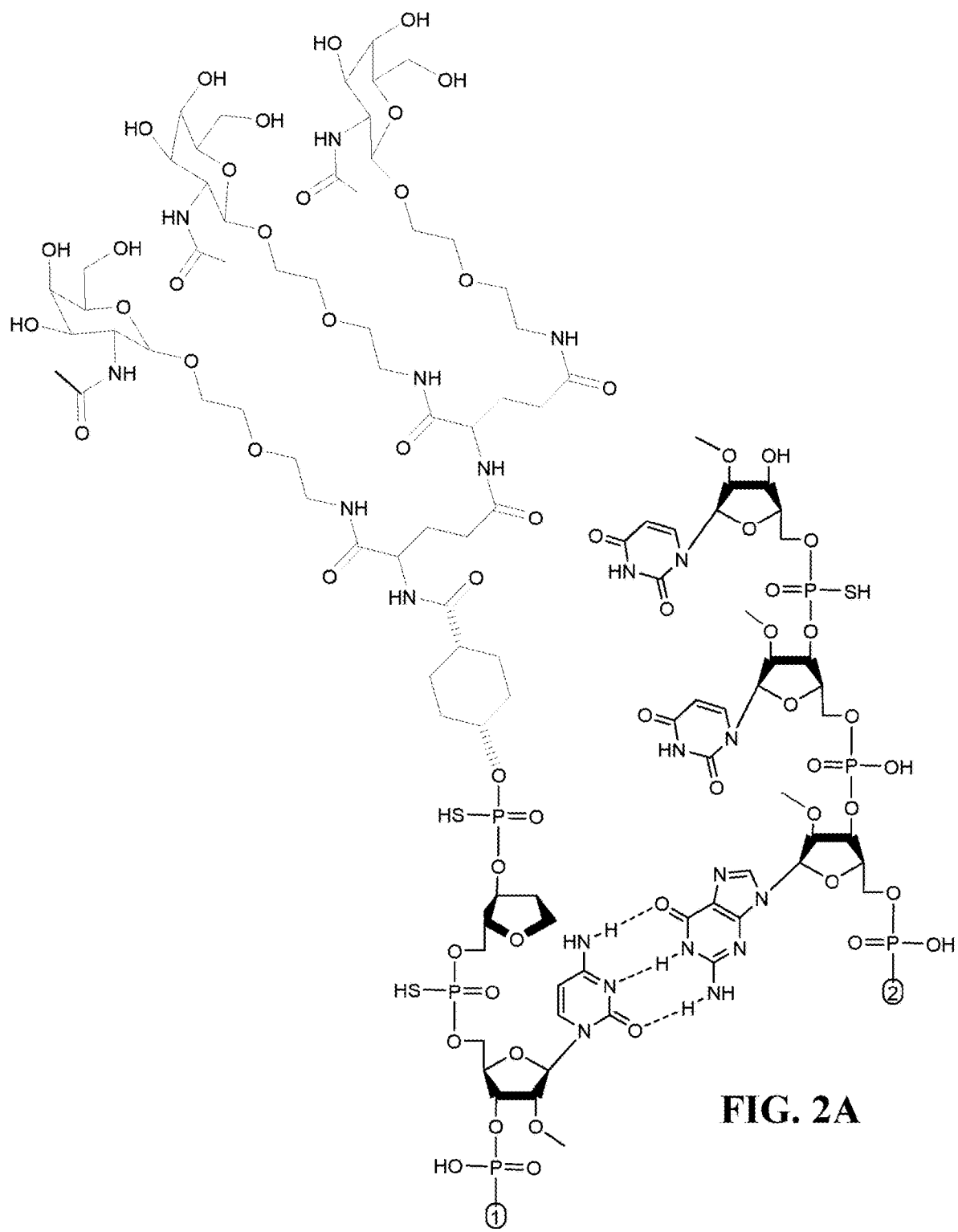
FIGS. 2A to 2E represent the chemical duplex structure of AD04828 shown as a free acid.
Figure 2B:
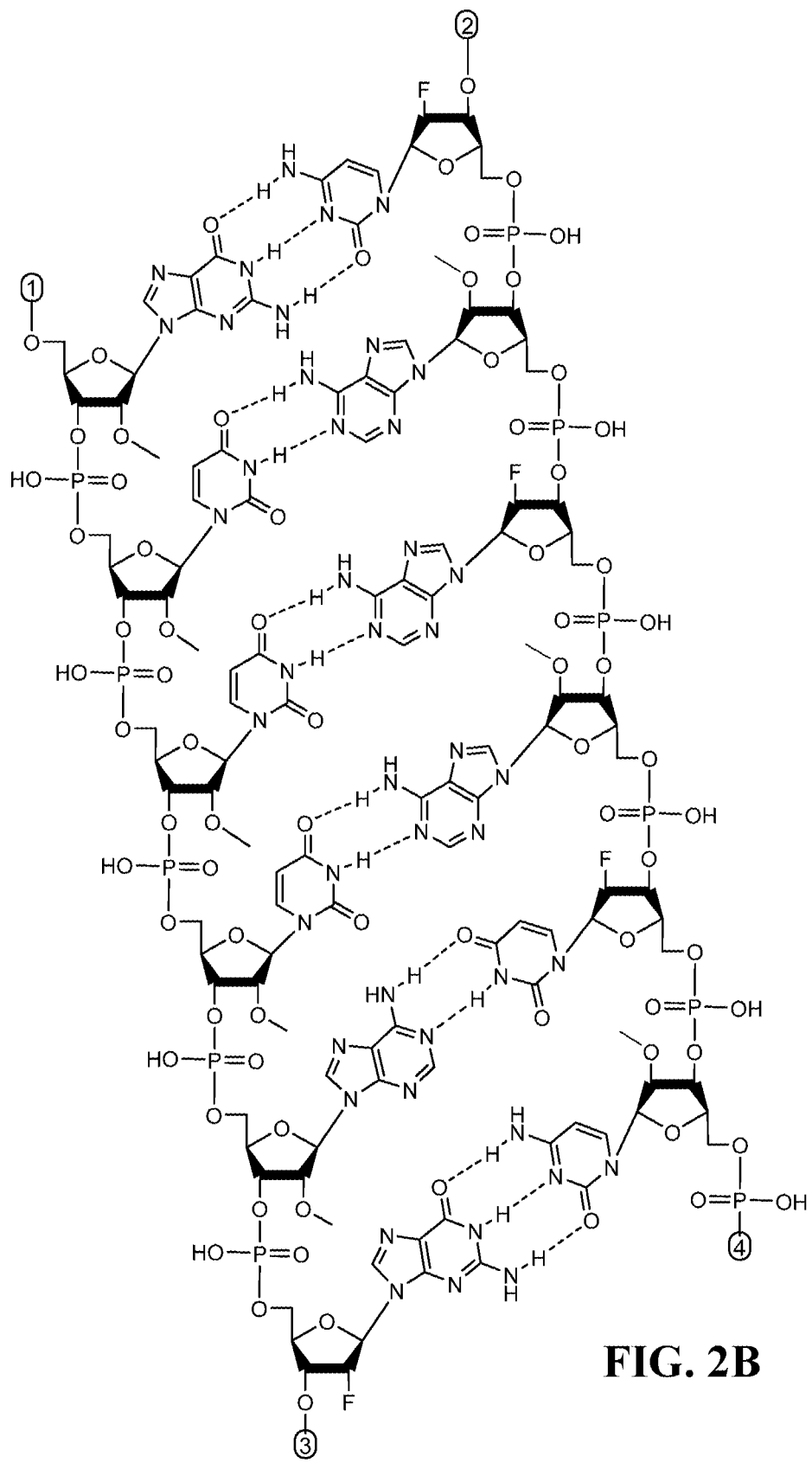
Figure 2C:
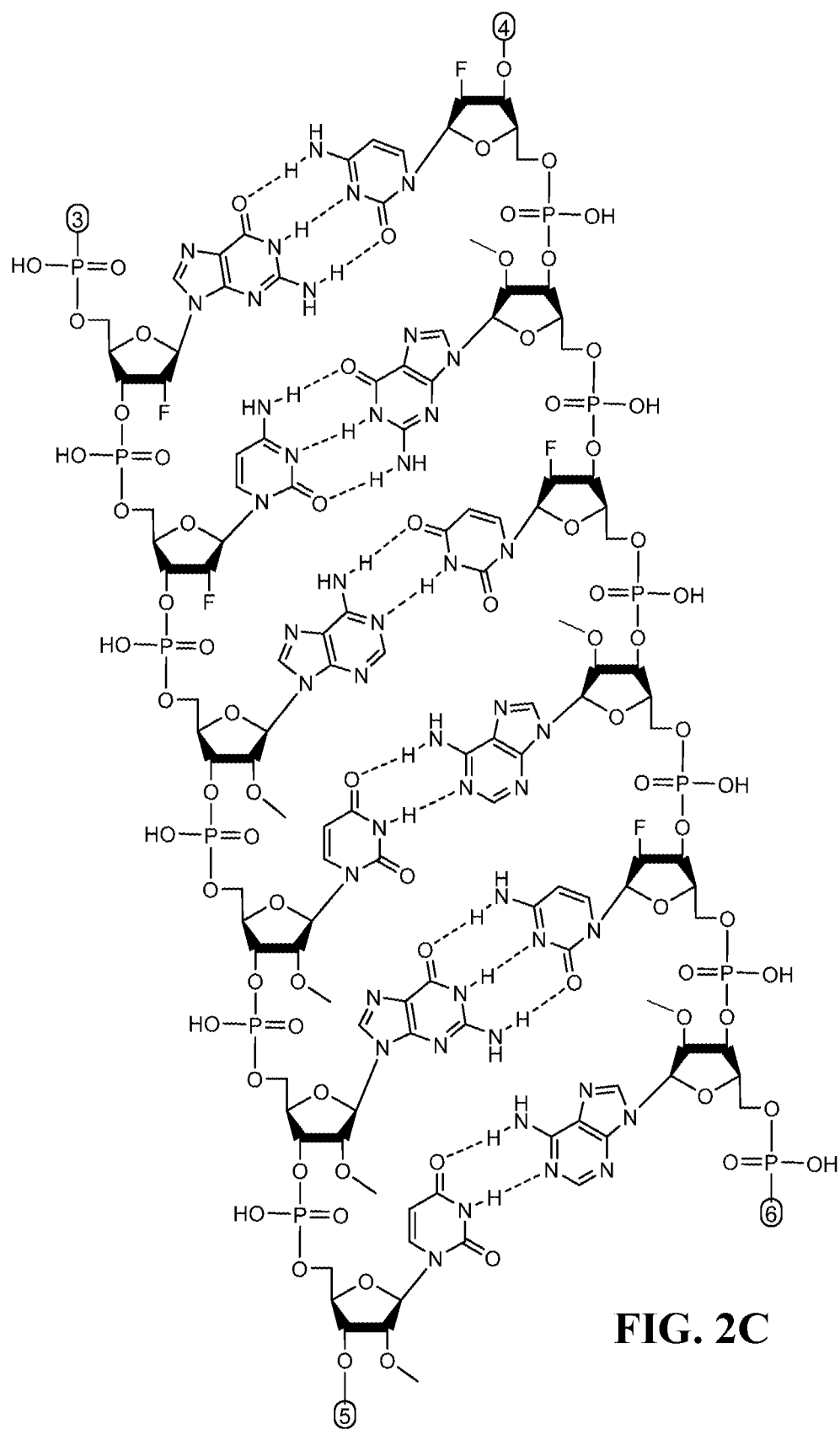
Figure 2D:
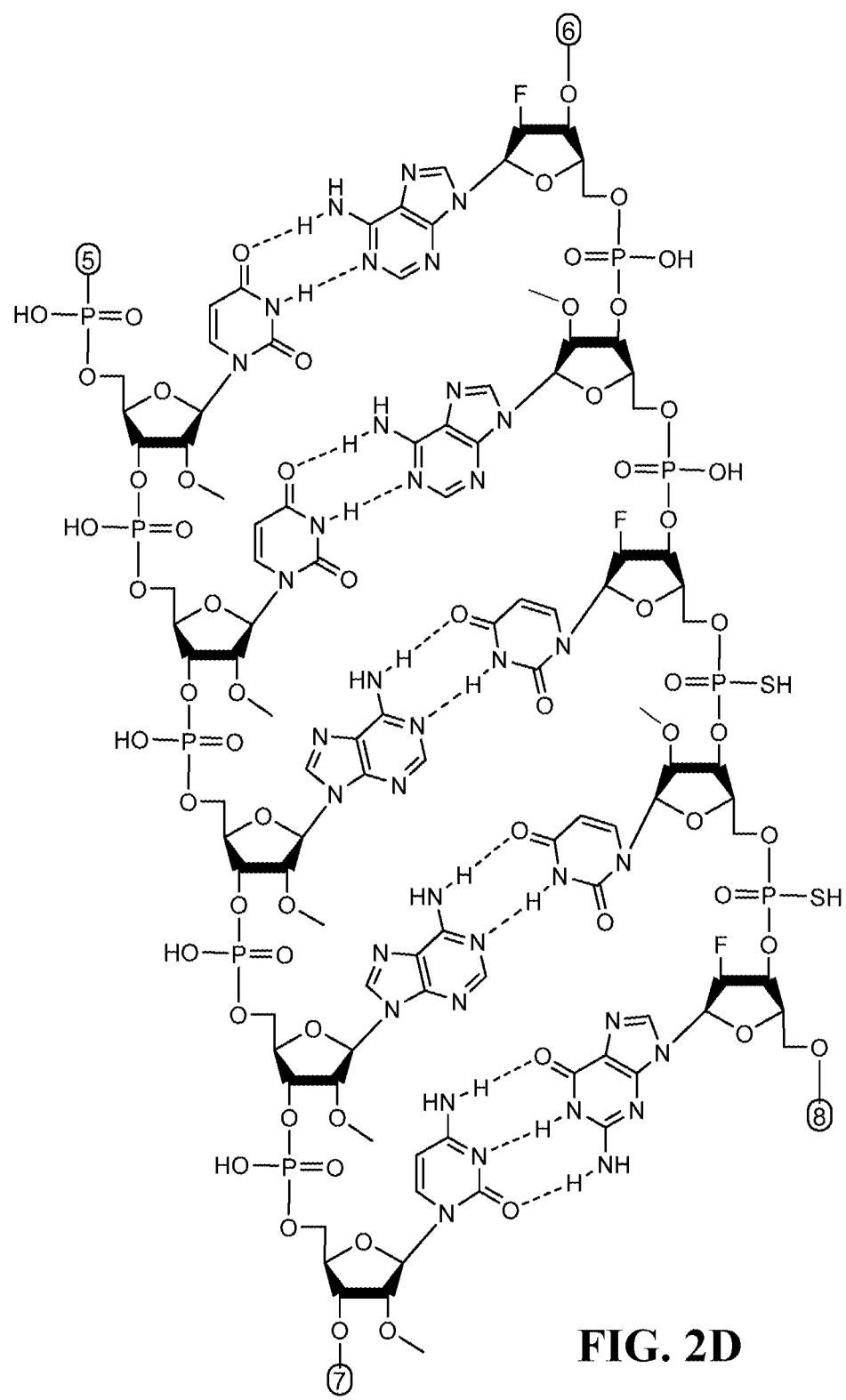
Figure 2E:
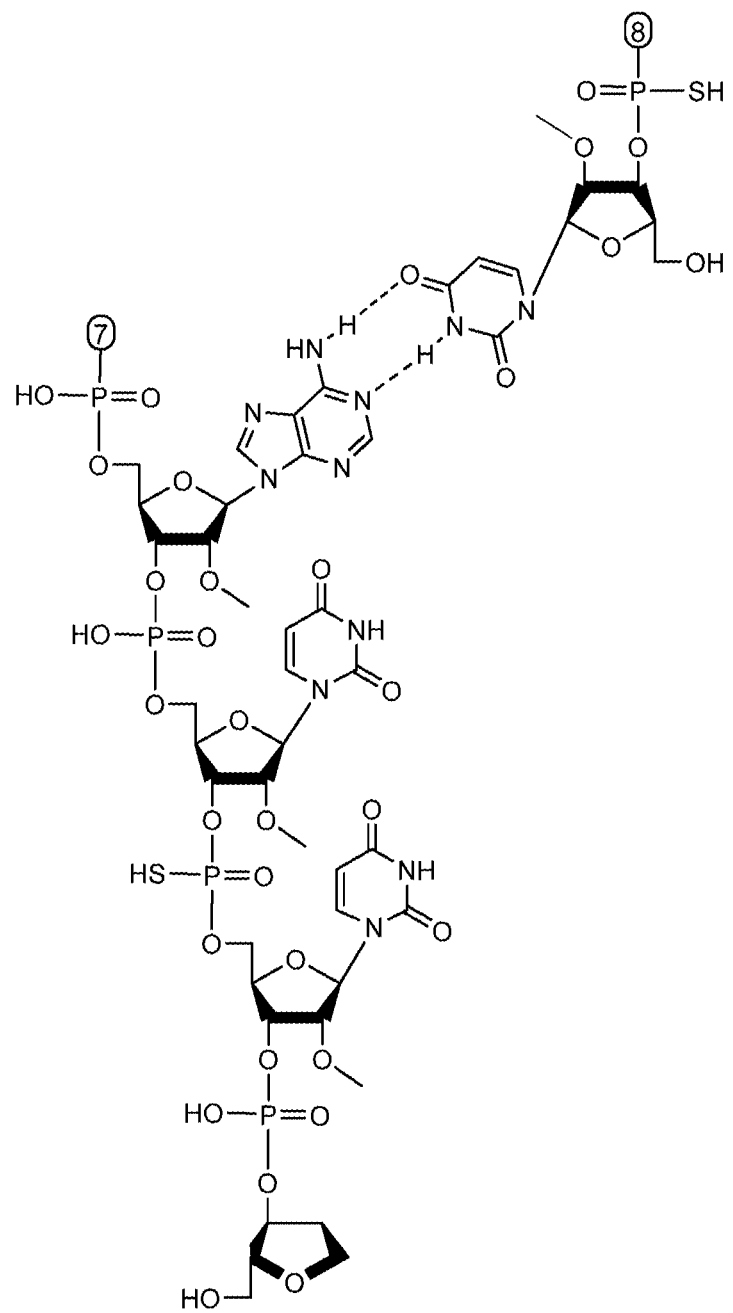
Figure 3A:
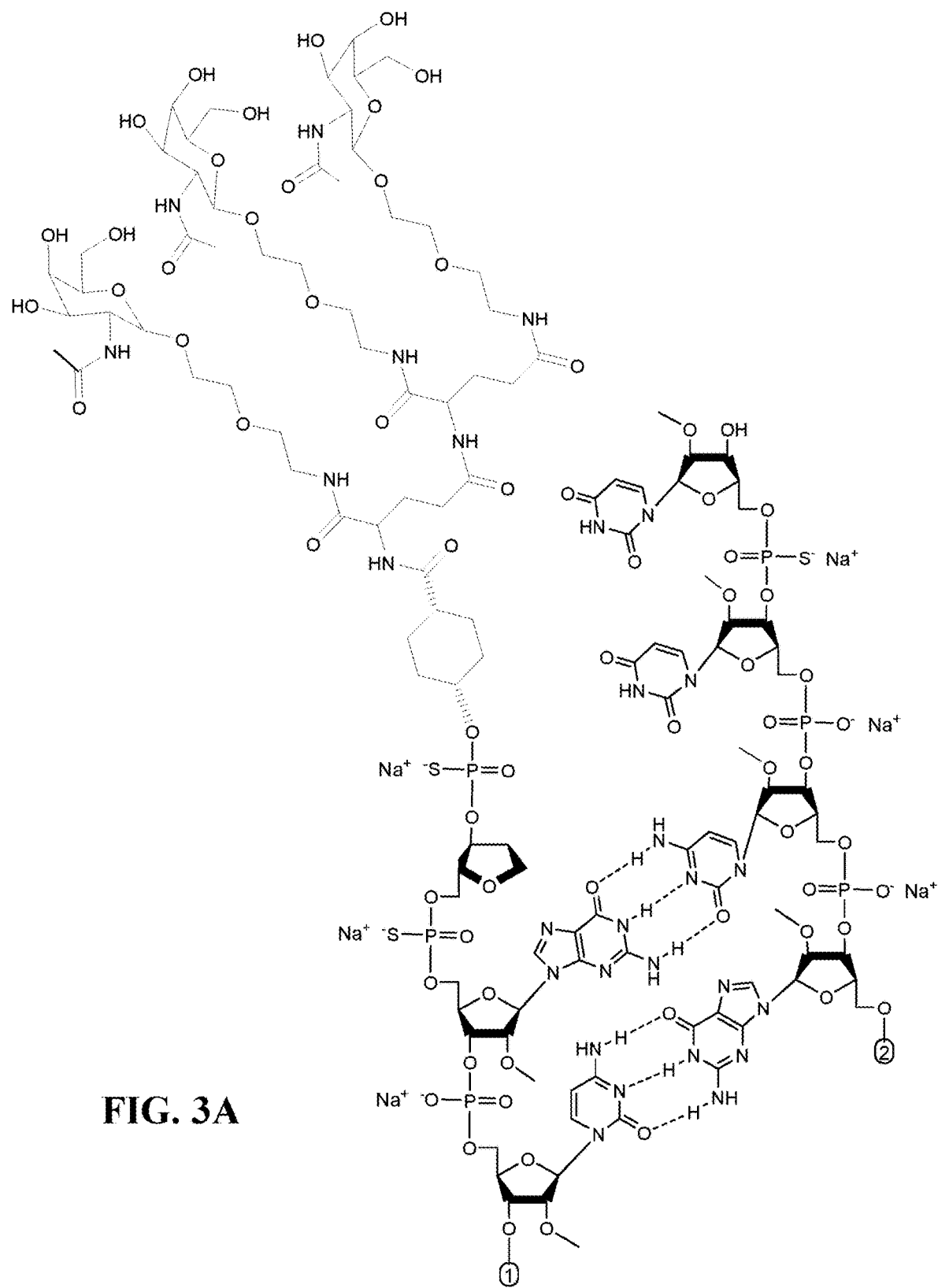
FIGS. 3A to 3E represent the chemical duplex structure of AD04831 shown as a sodium salt.
Figure 3B:
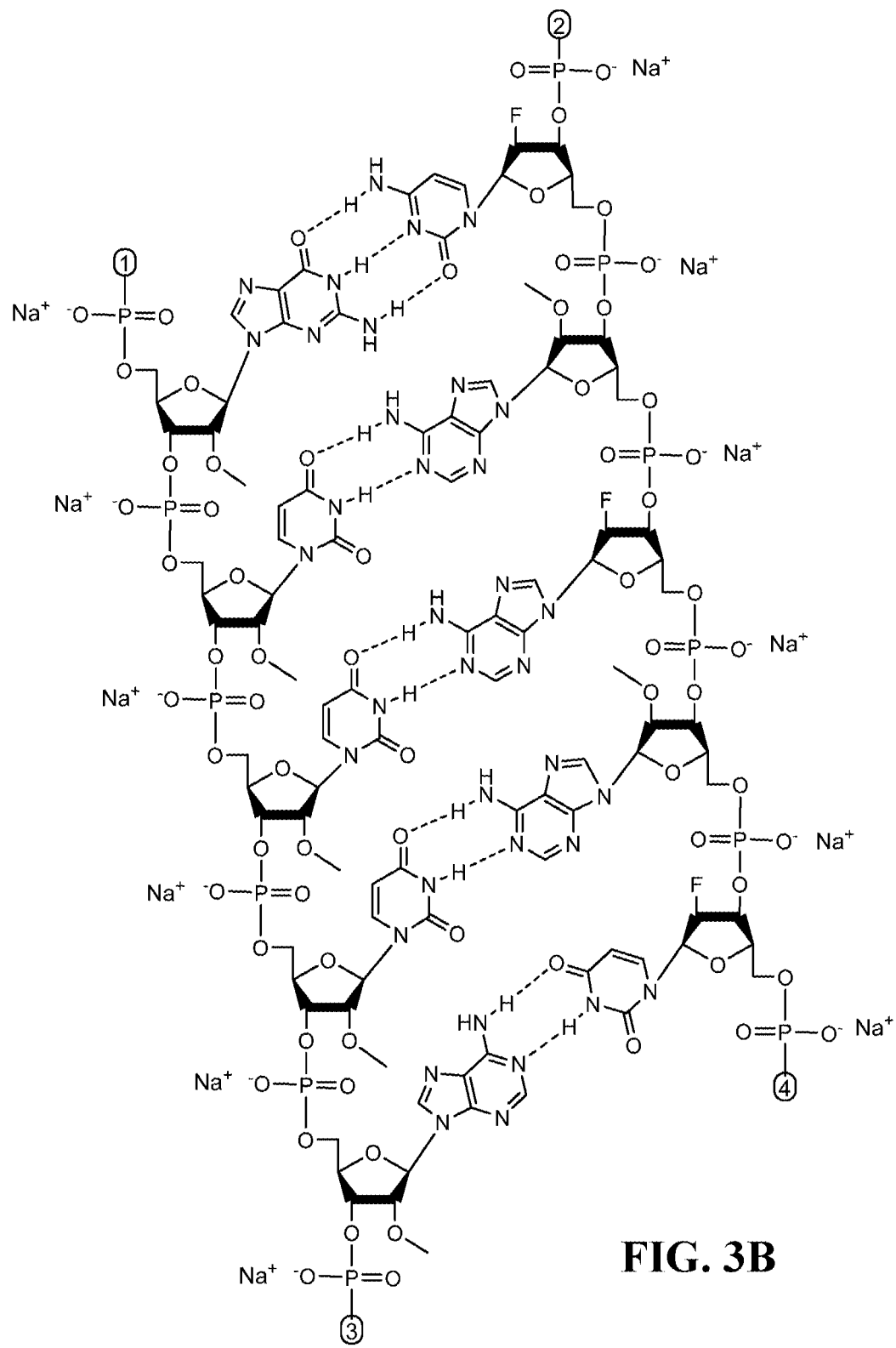
Figure 3C:
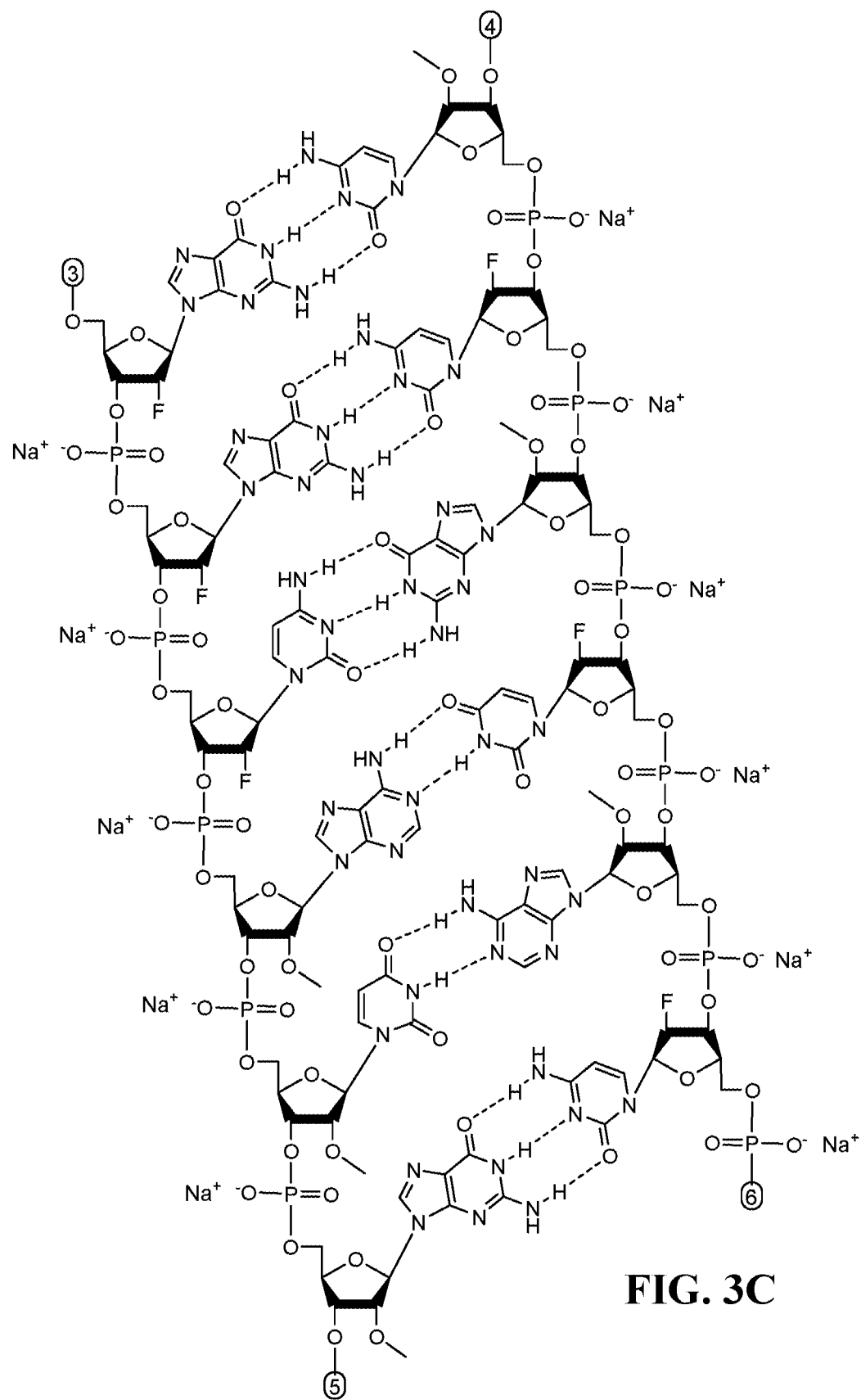
Figure 3D:
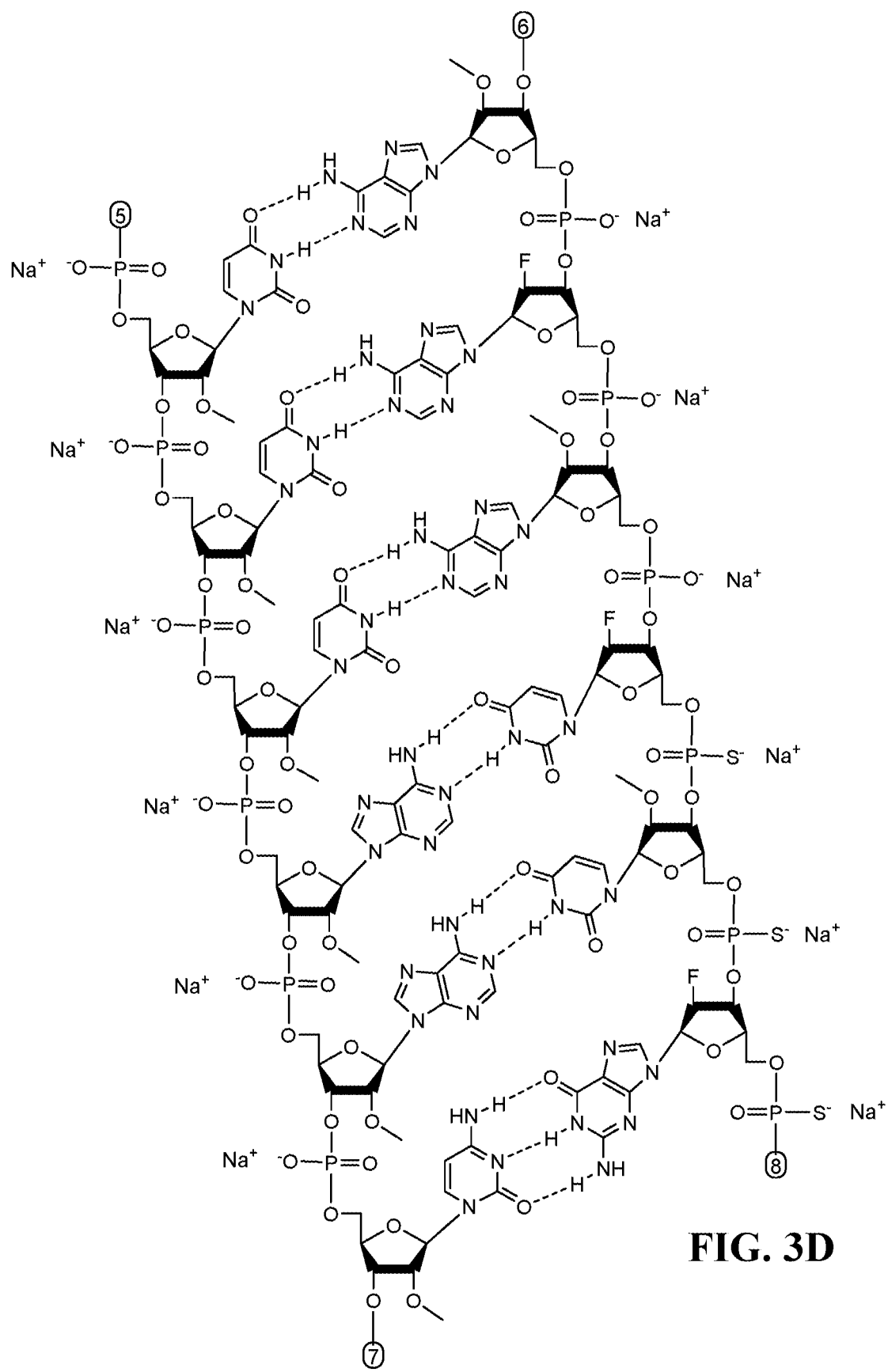
Figure 3E:
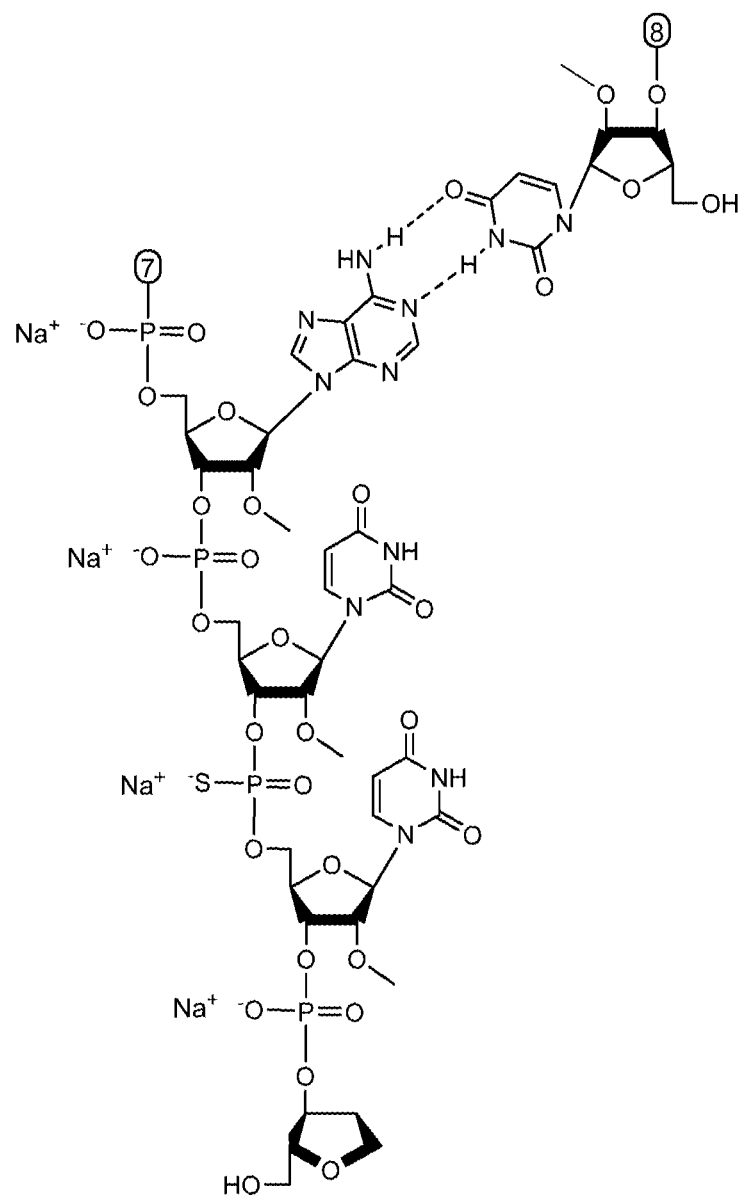
Figure 4A:
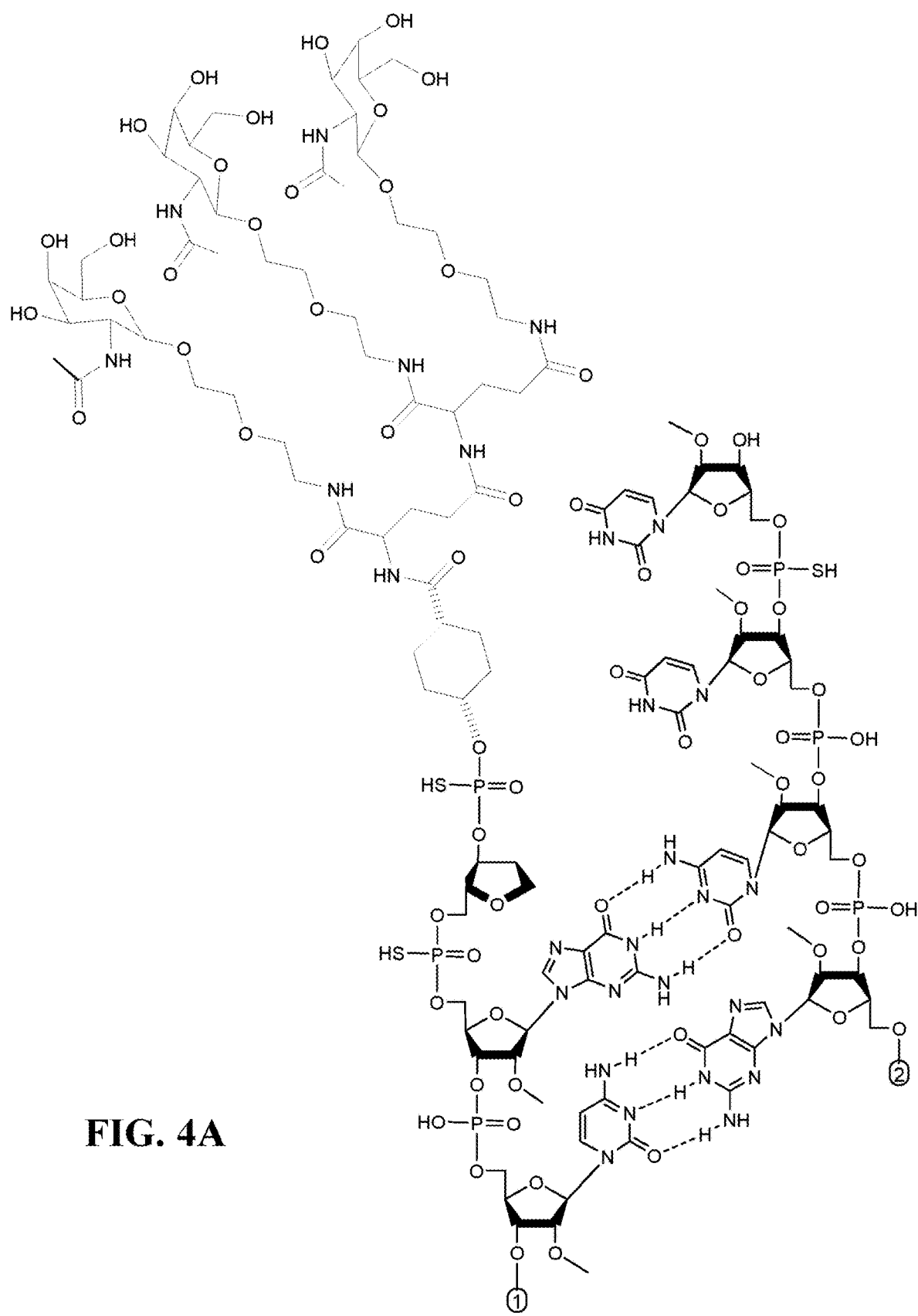
FIG. 4A to 4E represent the chemical duplex structure of AD04831 shown as a free acid.
Figure 4B:
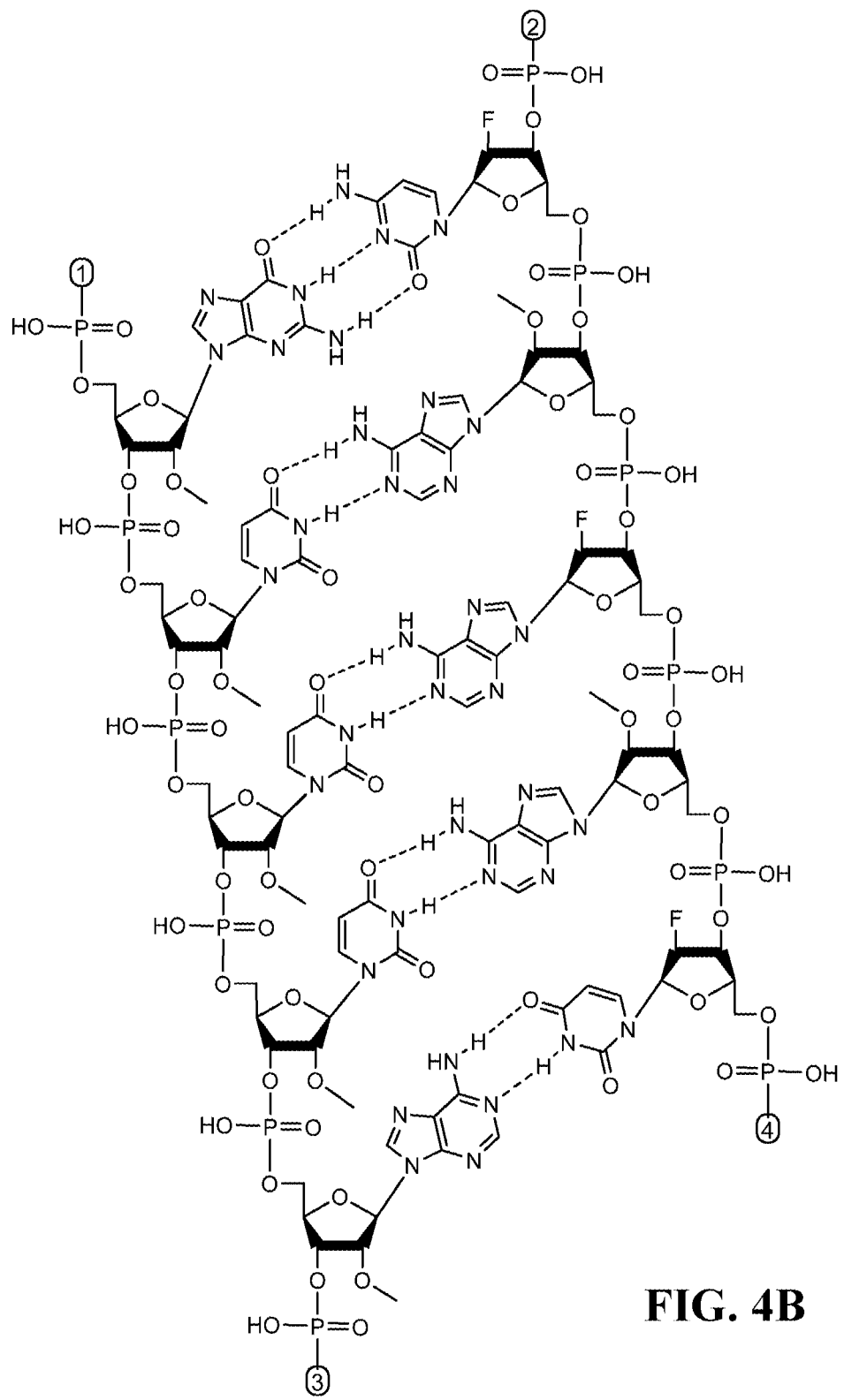
Figure 4C:
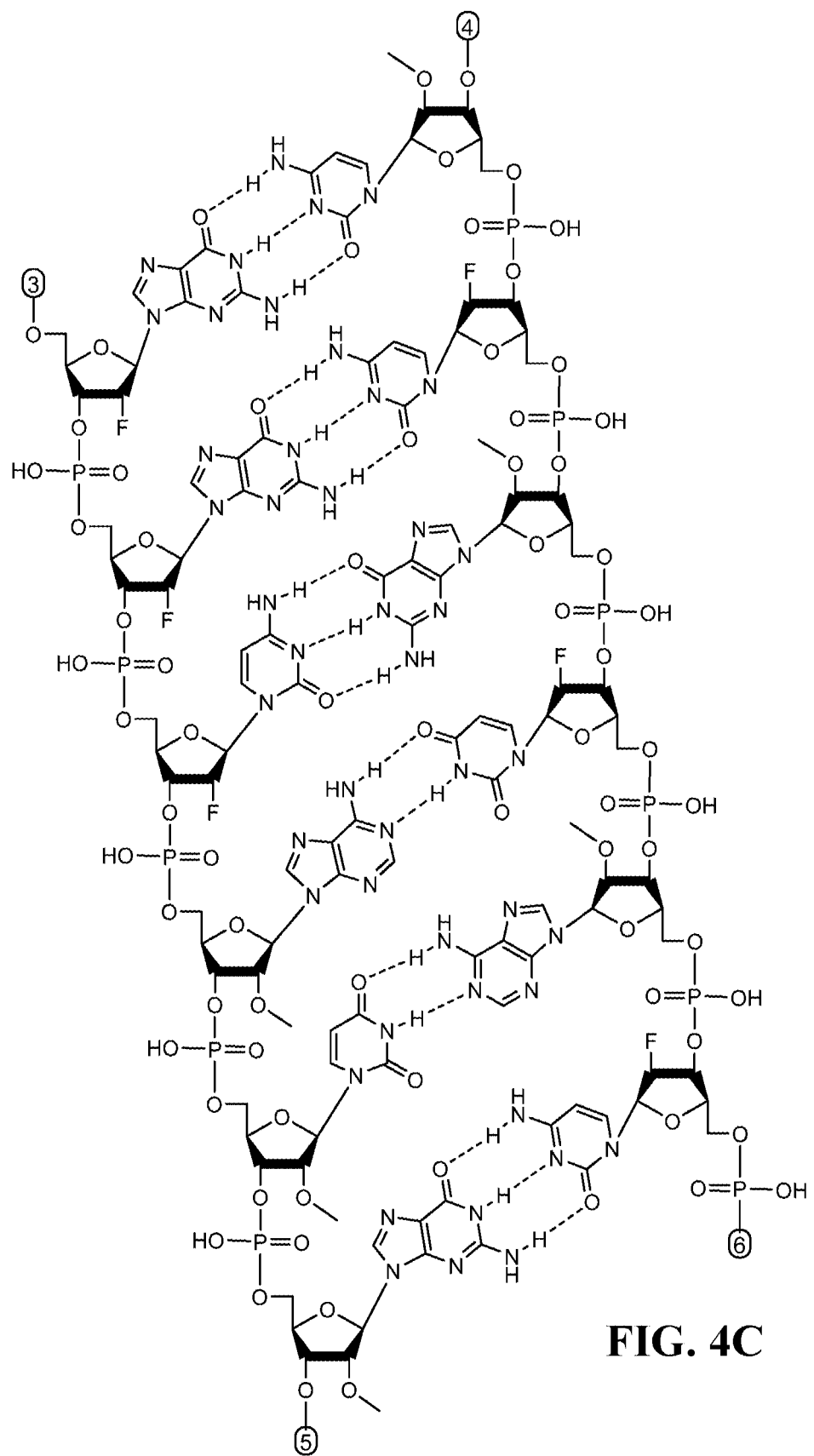
Figure 4D:
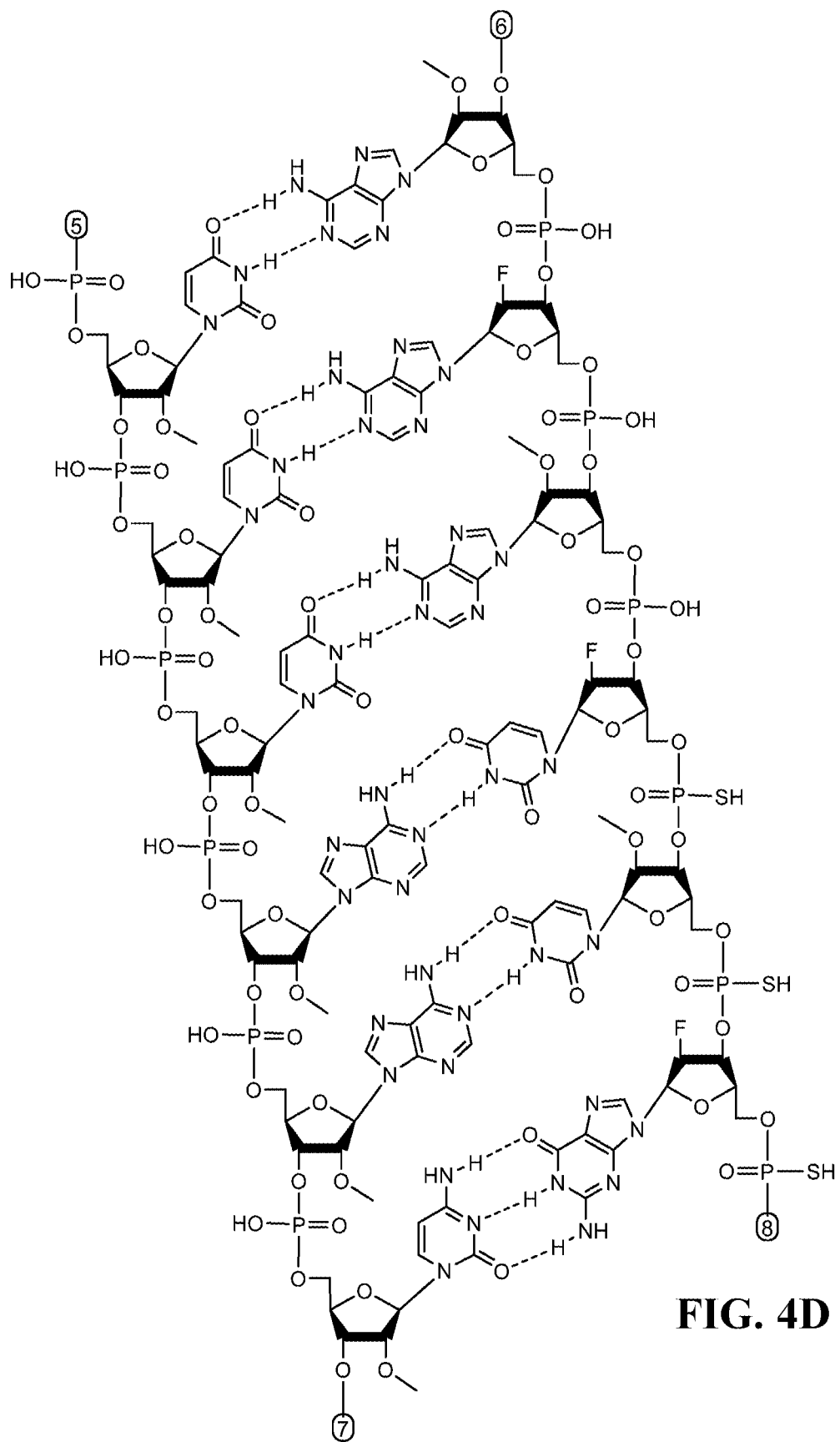
Figure 4E:
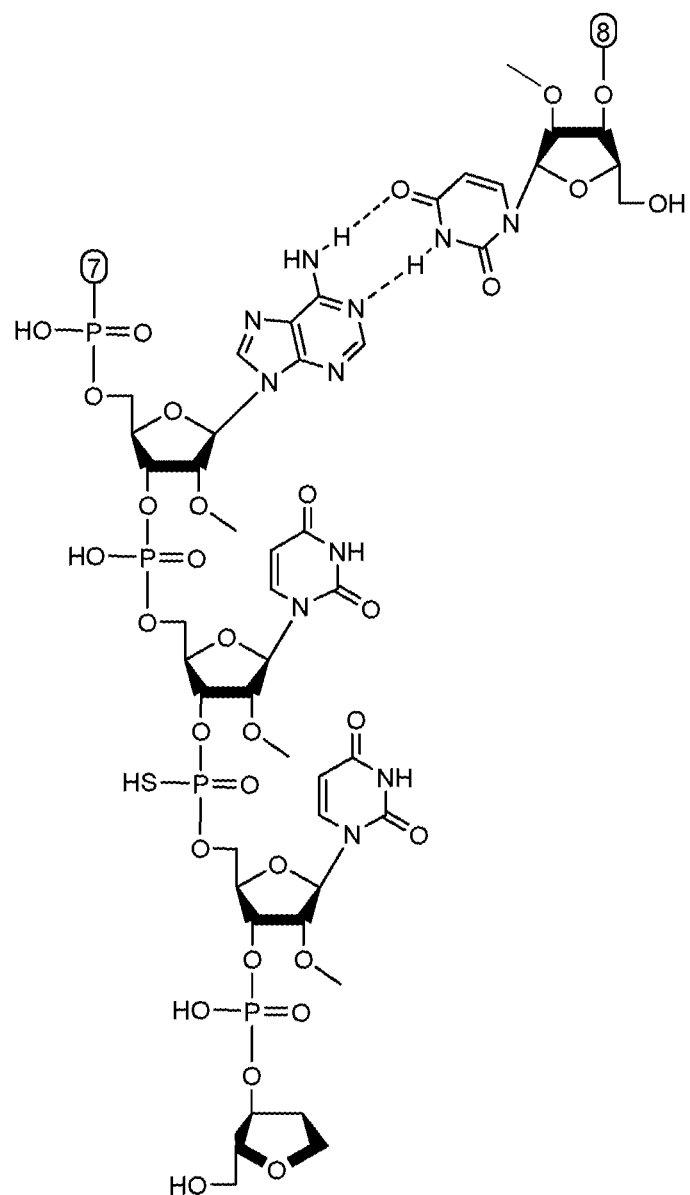
Figure 5A:
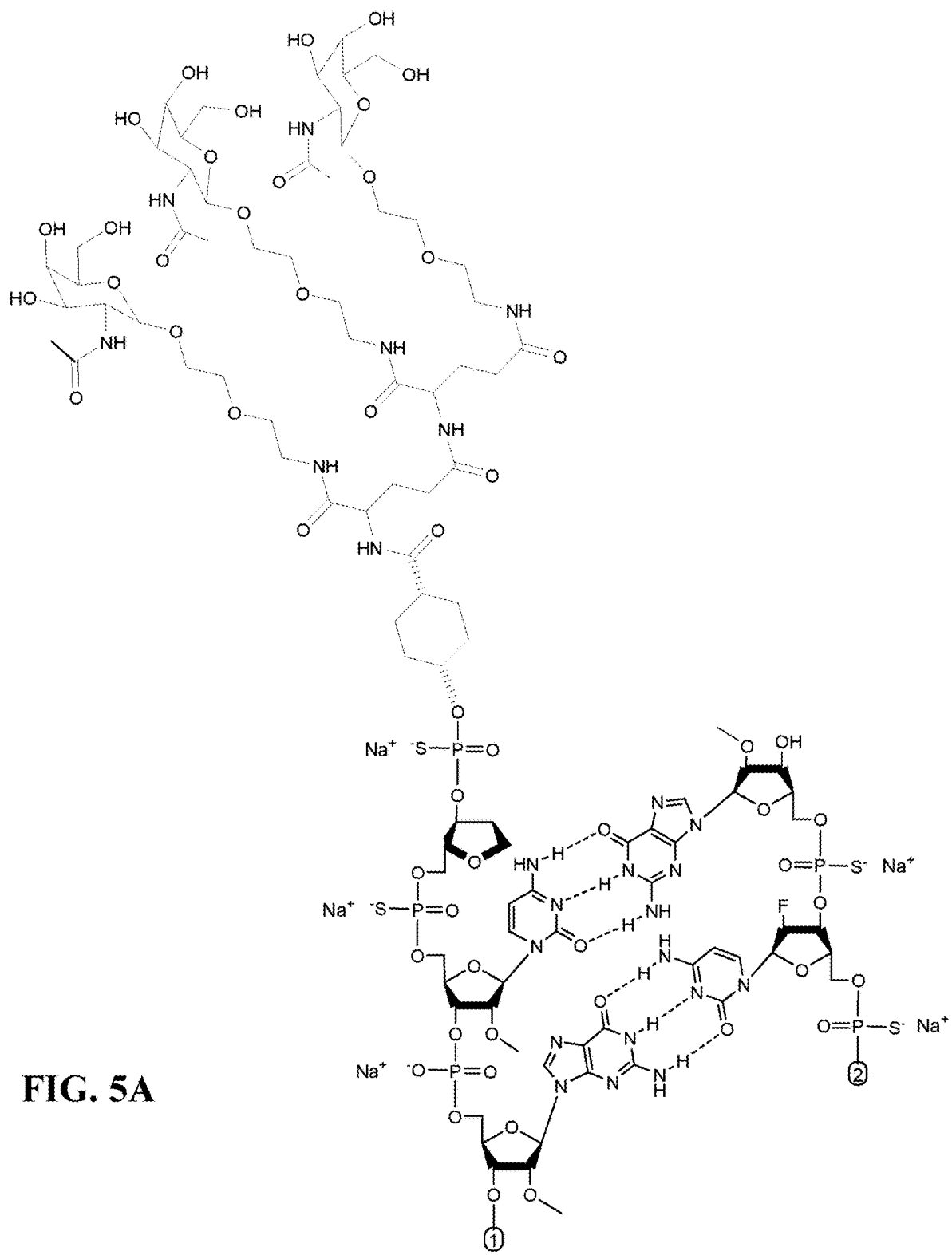
FIG. 5A to 5E represent the chemical duplex structure of AD04836 shown as a sodium salt.
Figure 5B:
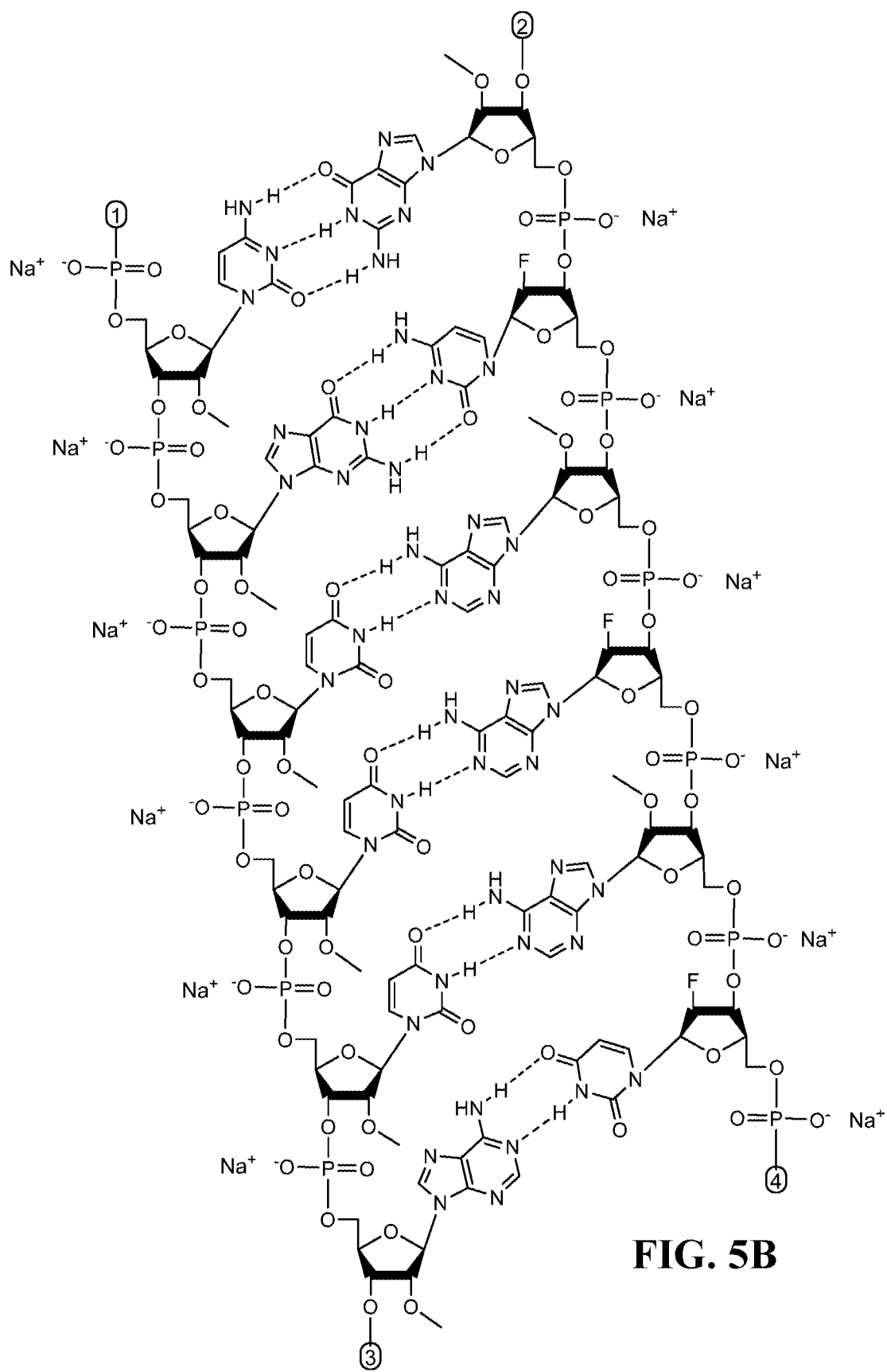
Figure 5C:
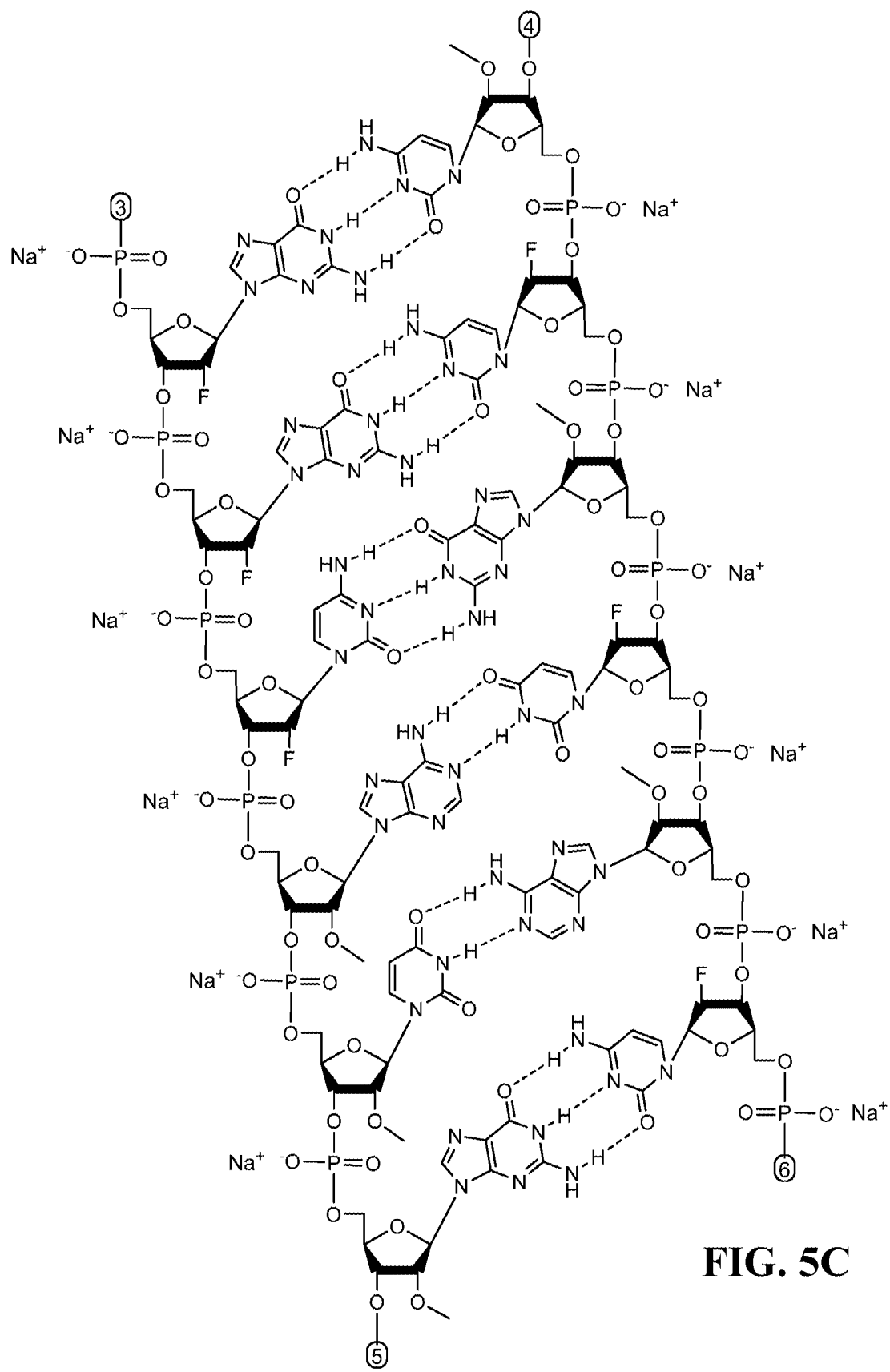
Figure 5D:
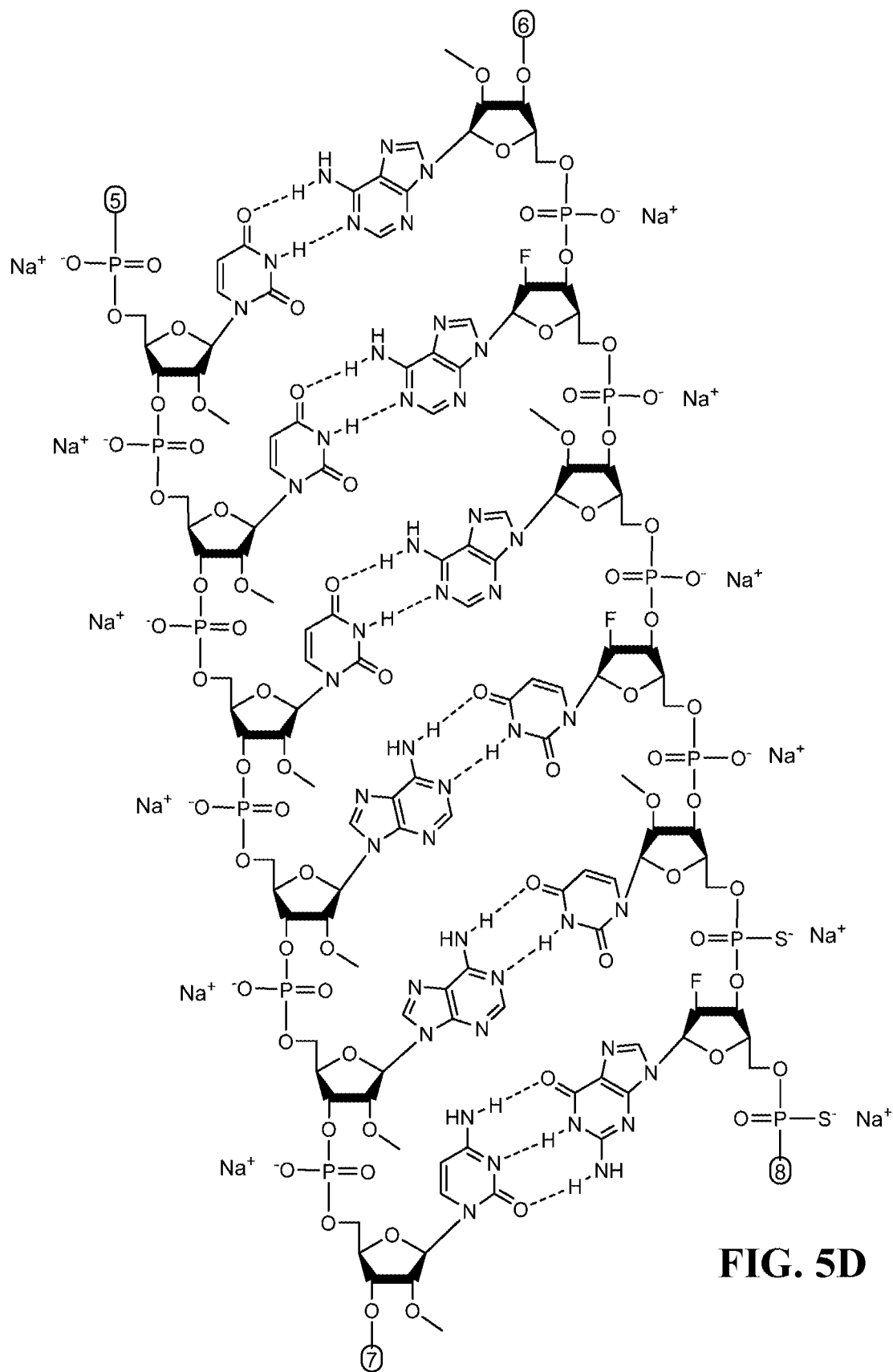
Figure 5E:
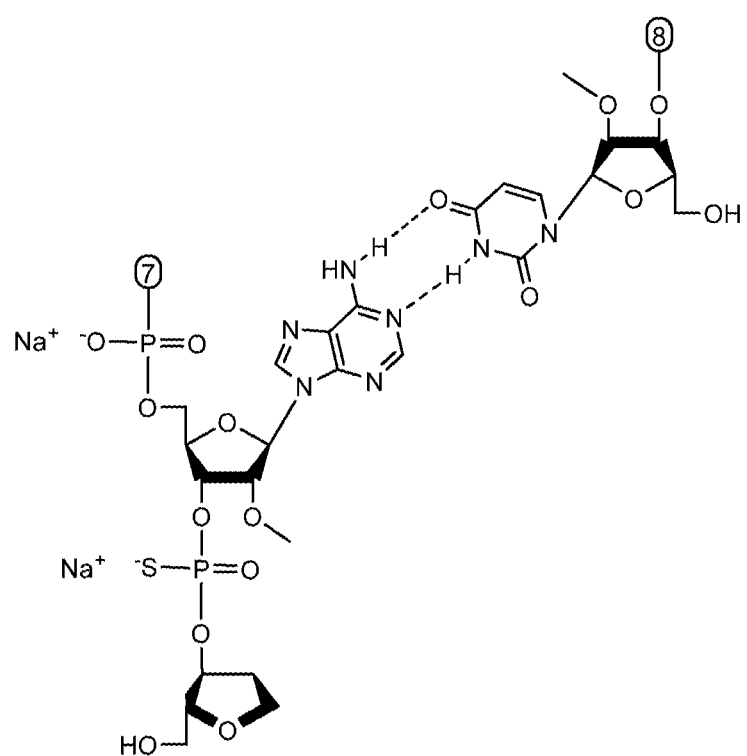
Figure 6A:
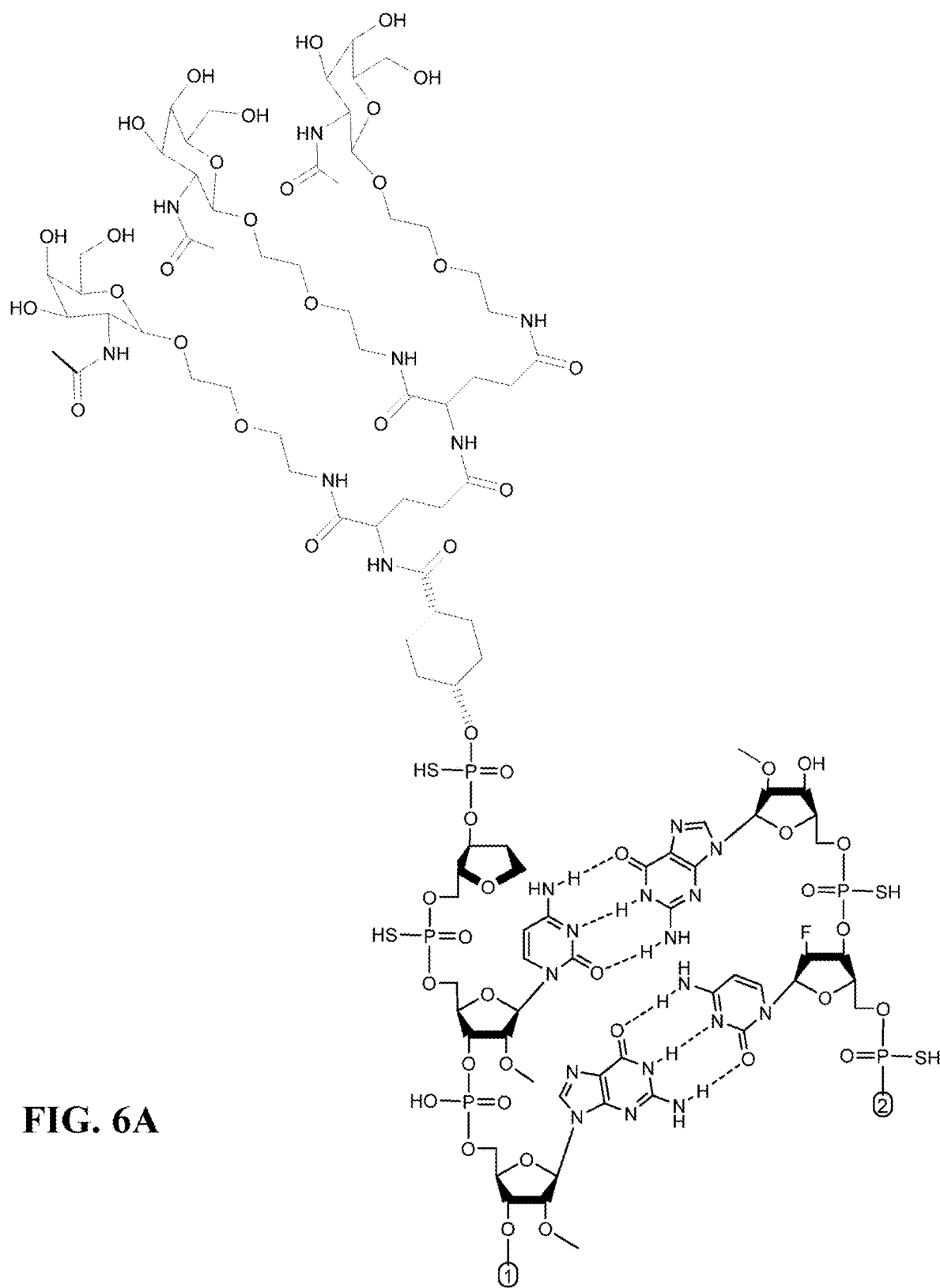
FIG. 6A to 6E represent the chemical duplex structure of AD04836 shown as a free acid.
Figure 6B:
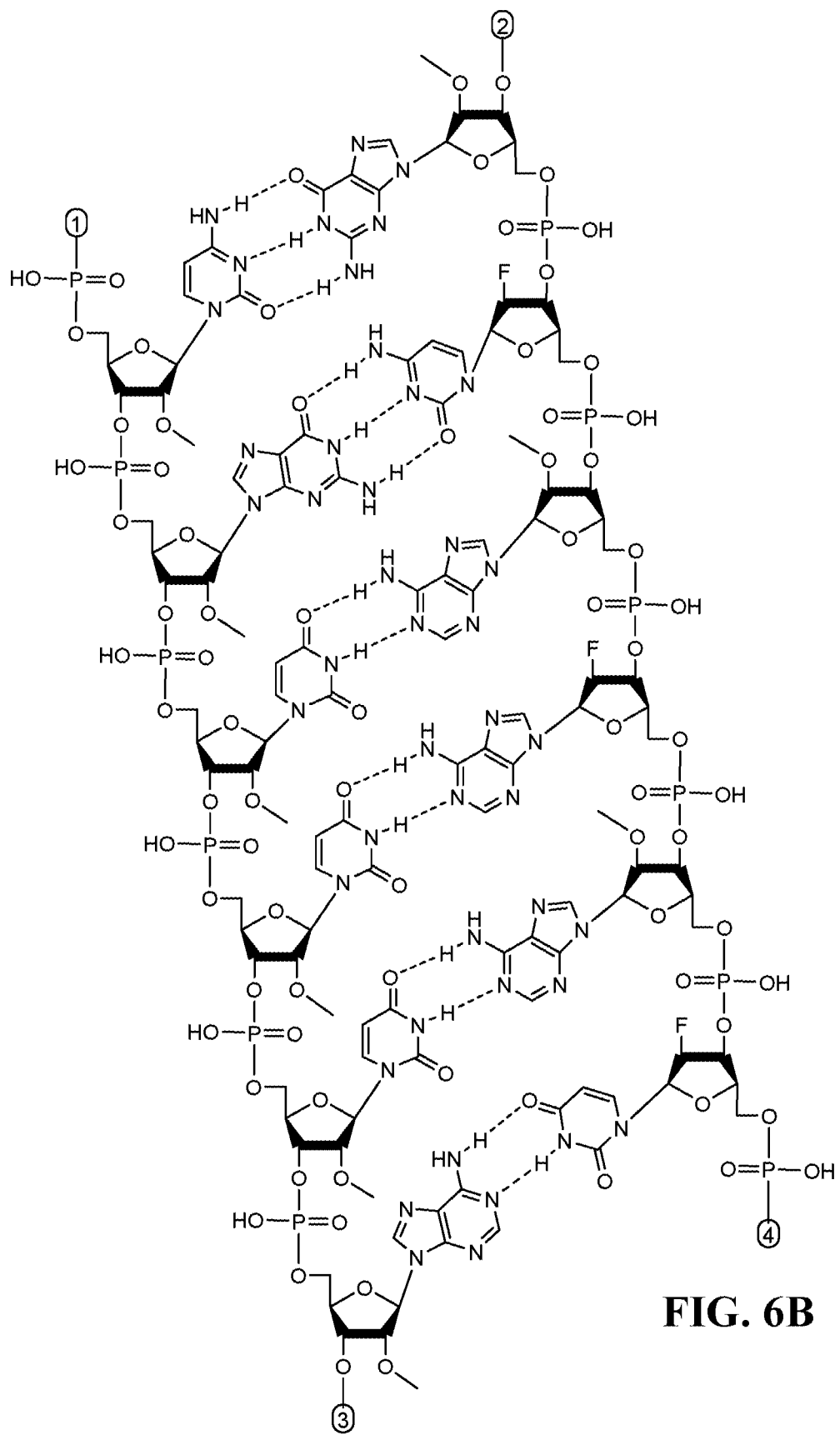
Figure 6C:
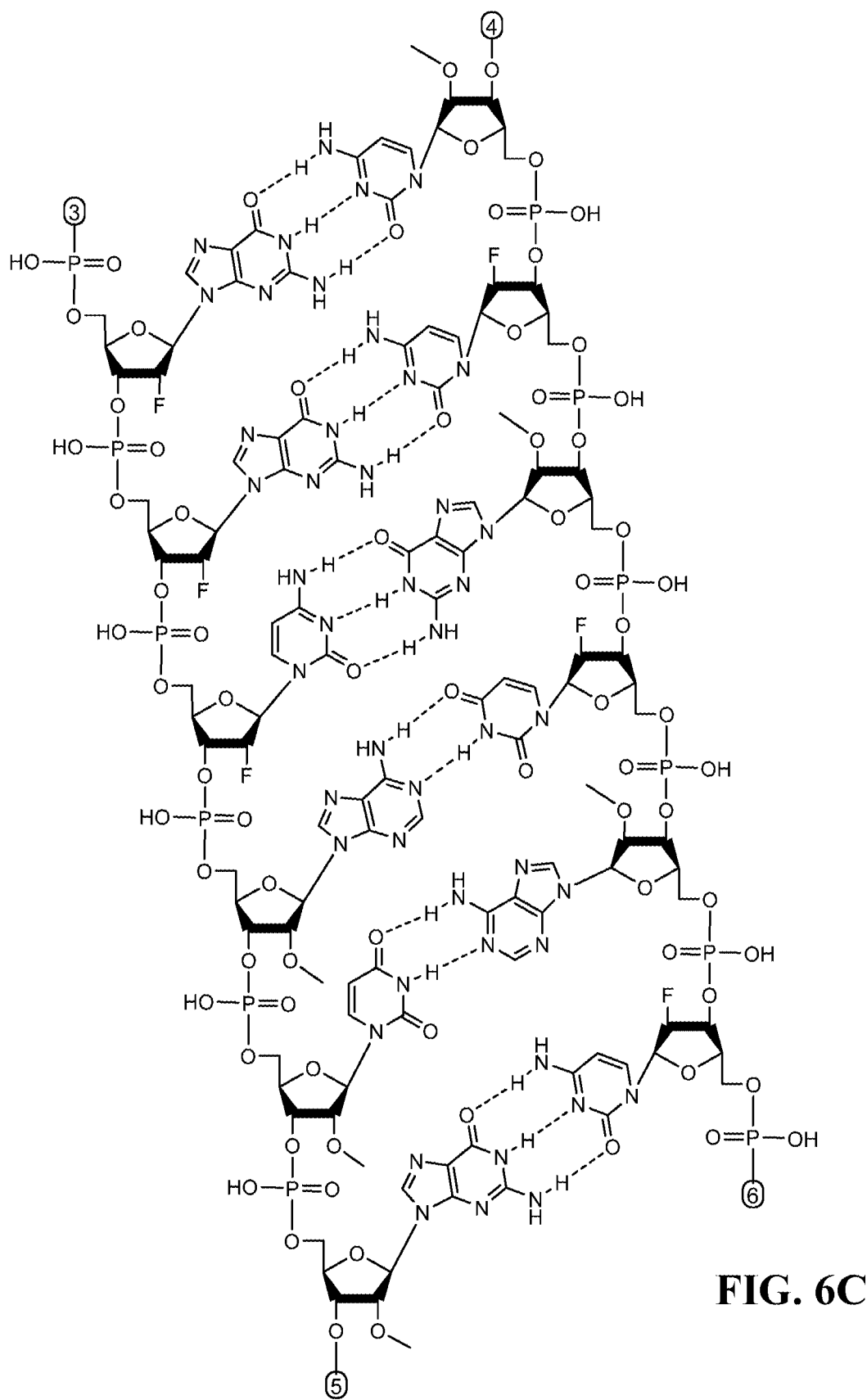
Figure 6D:
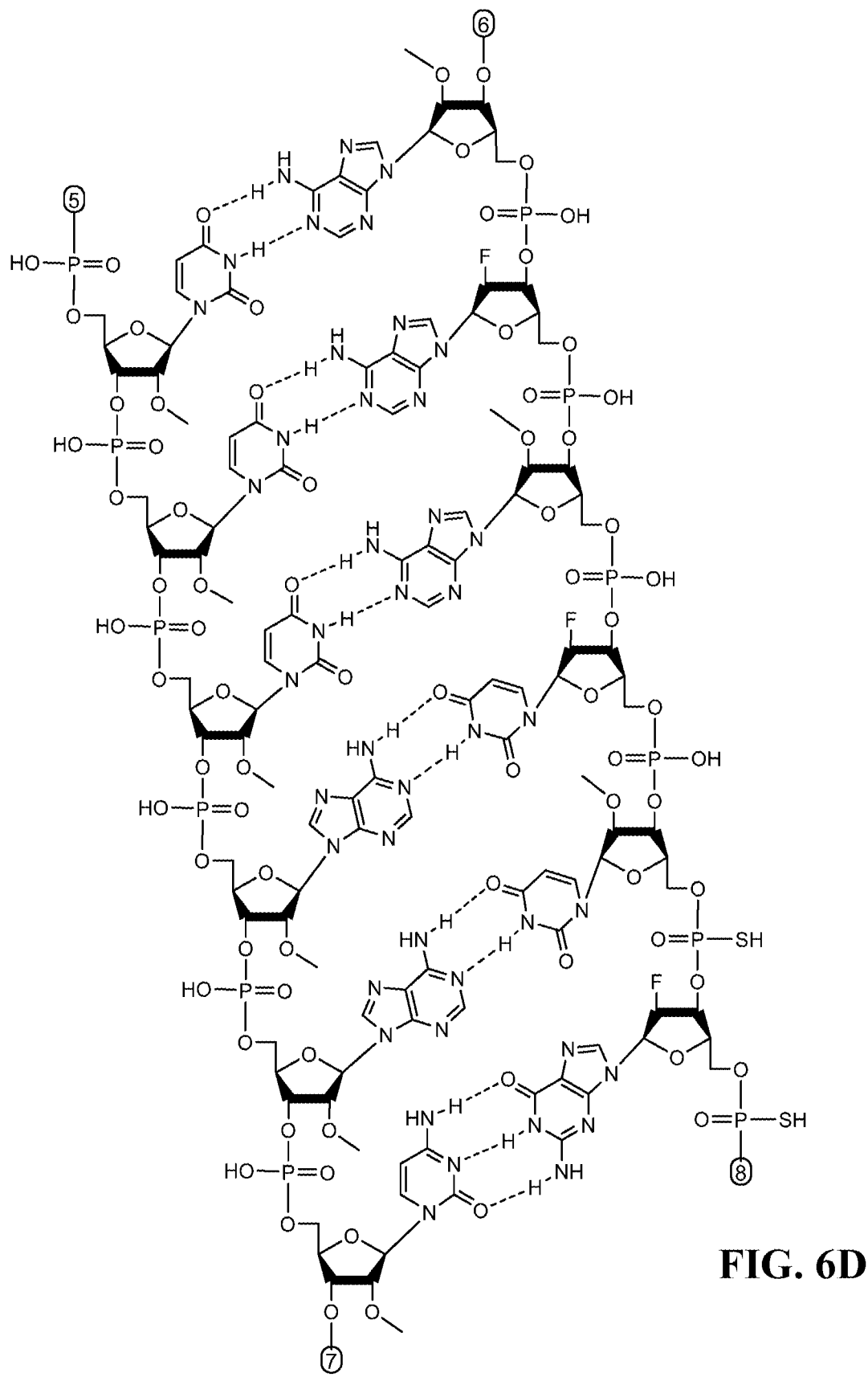
Figure 6E:
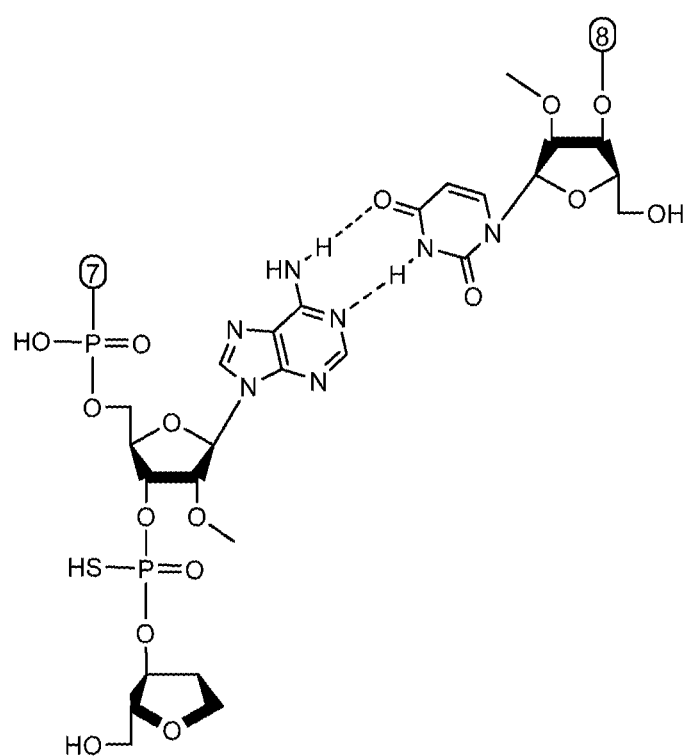
Figure 7A:
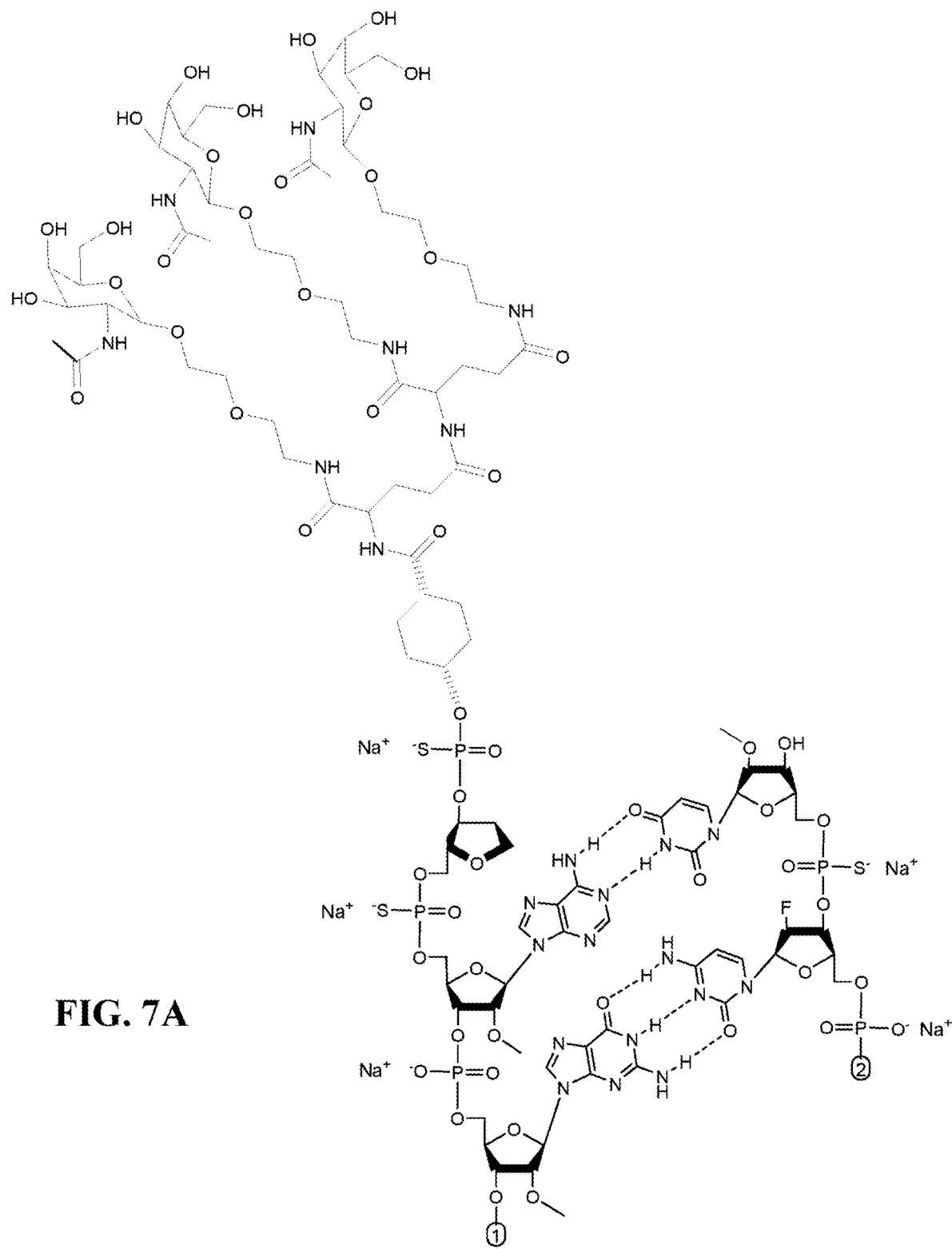
FIG. 7A to 7E represent the chemical duplex structure of AD04837 shown as a sodium salt.
Figure 7B:
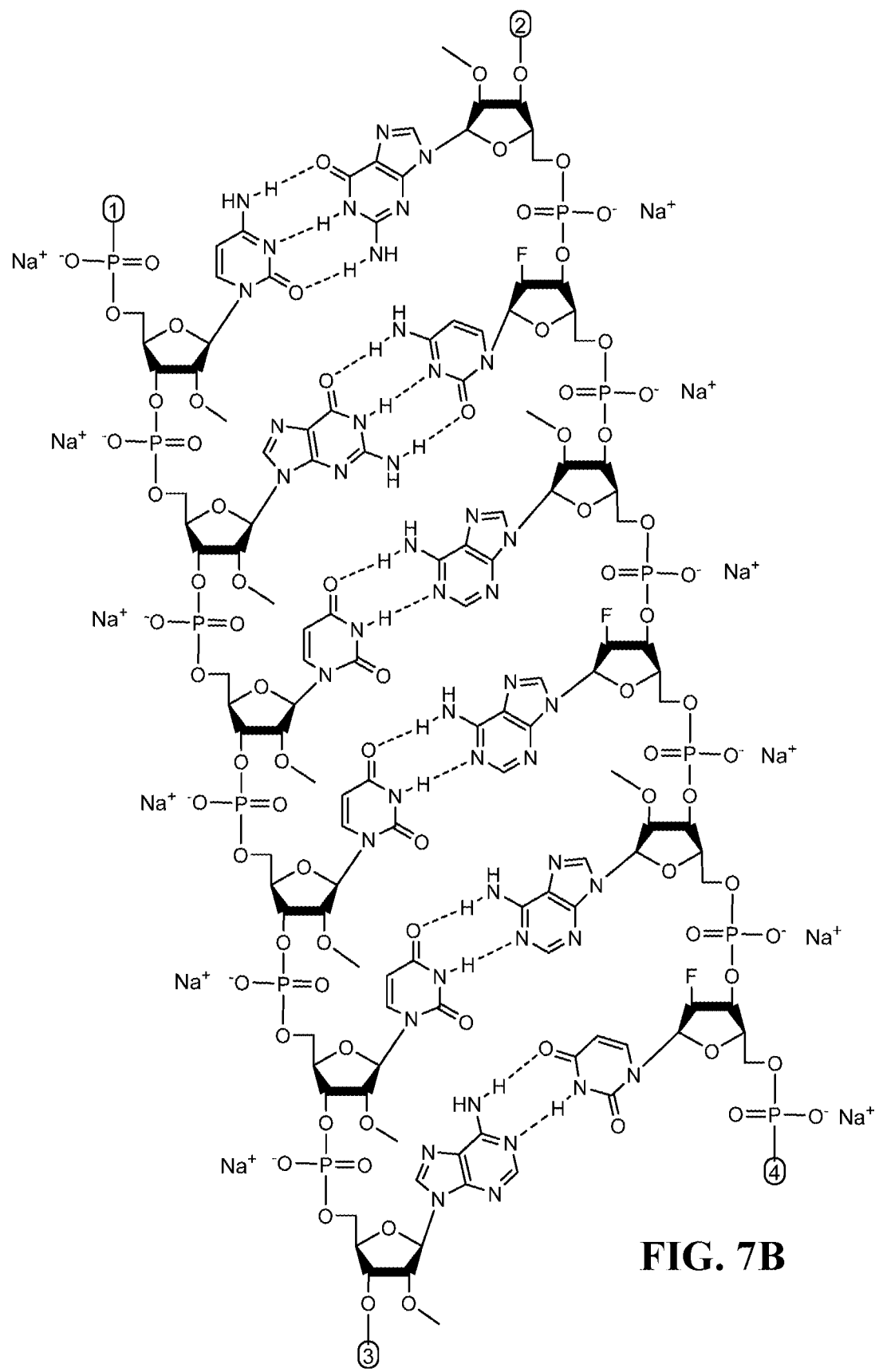
Figure 7C:
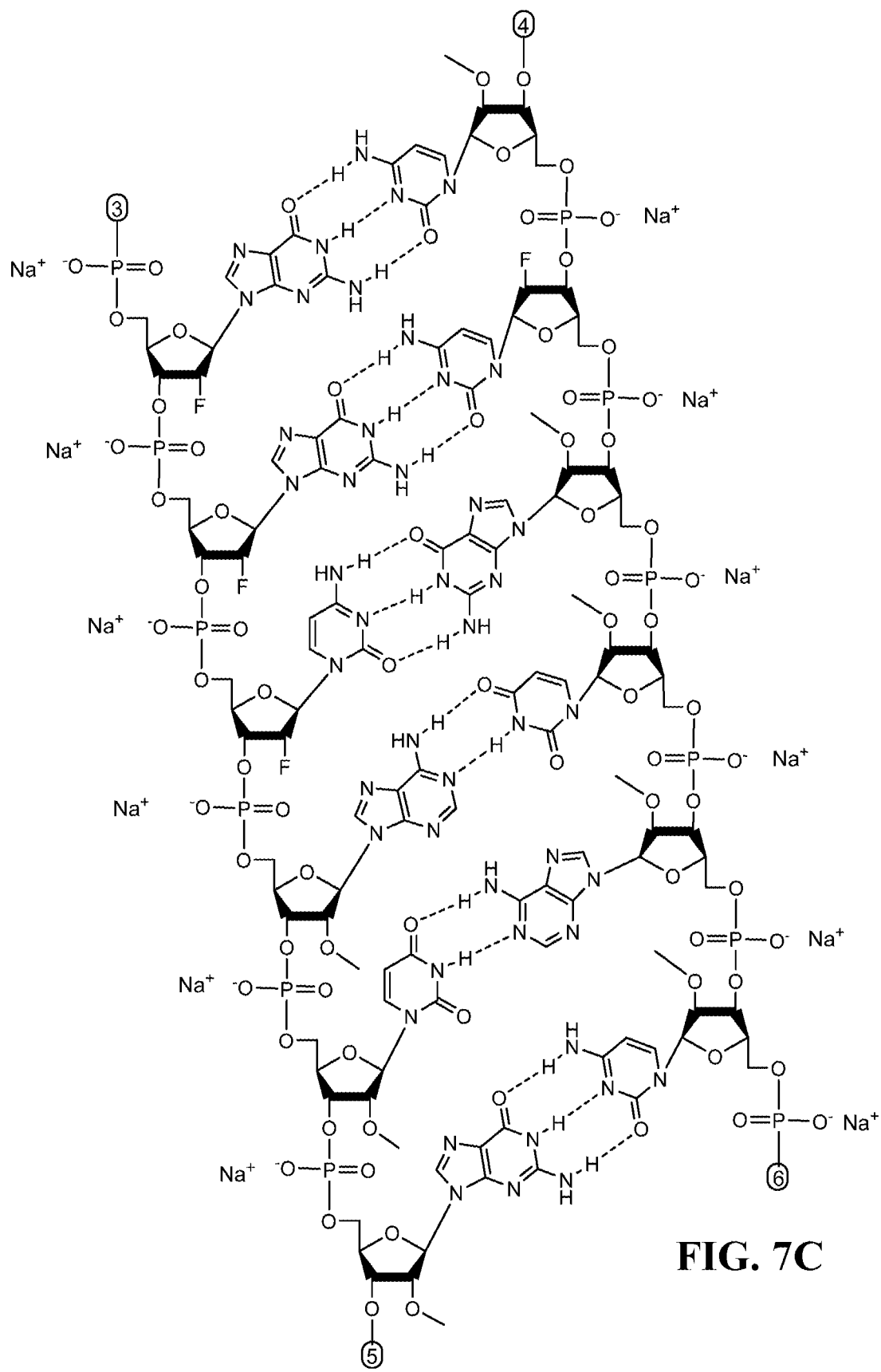
Figure 7D:
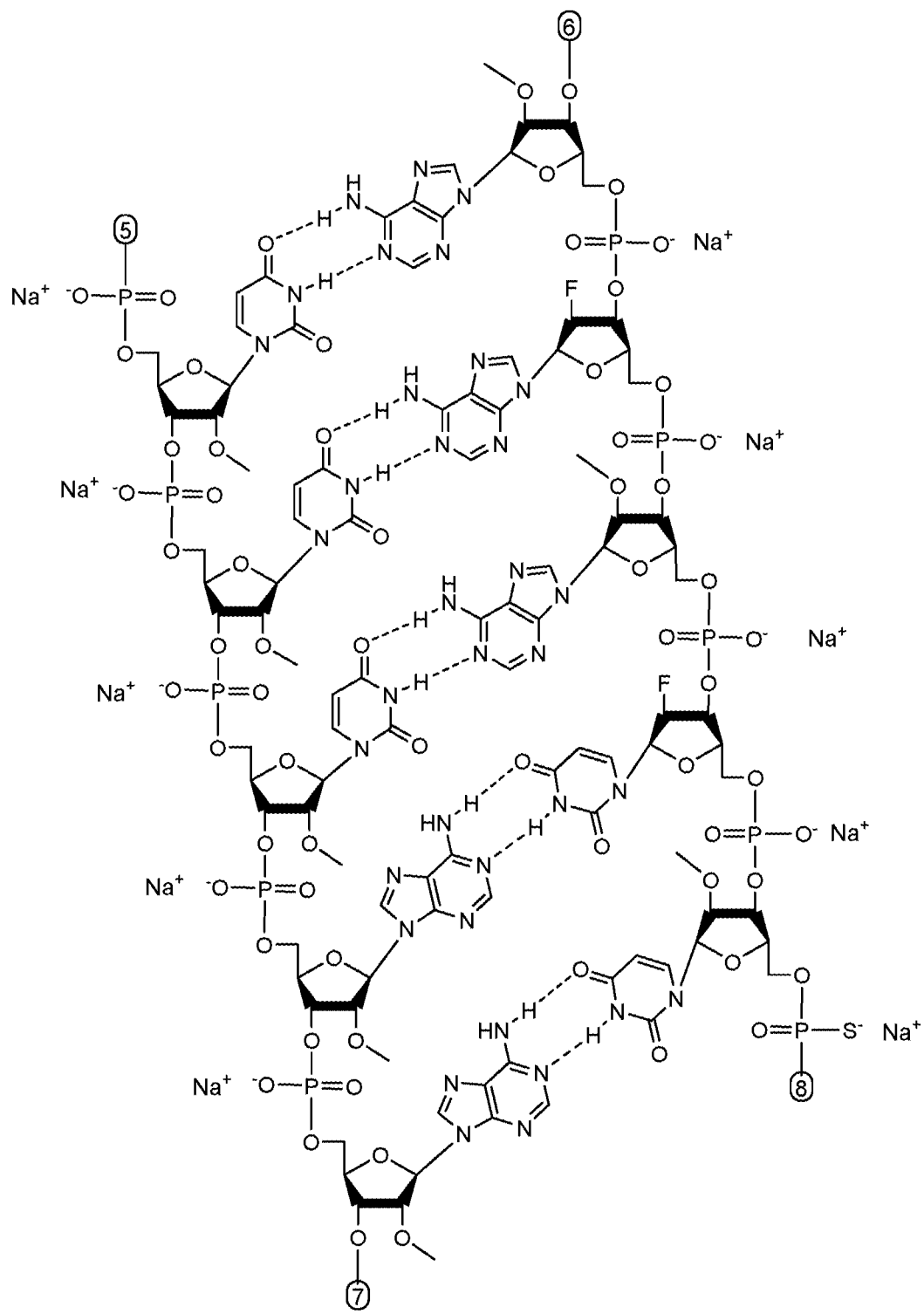
Figure 7E:
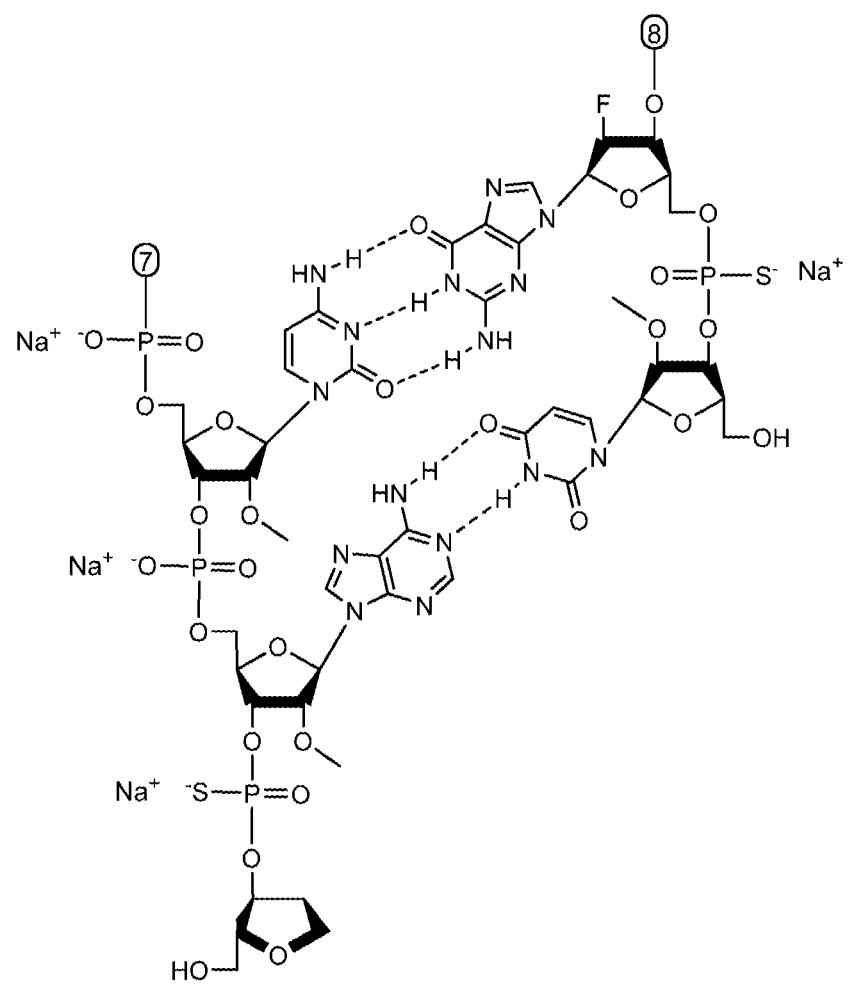
Figure 8A:
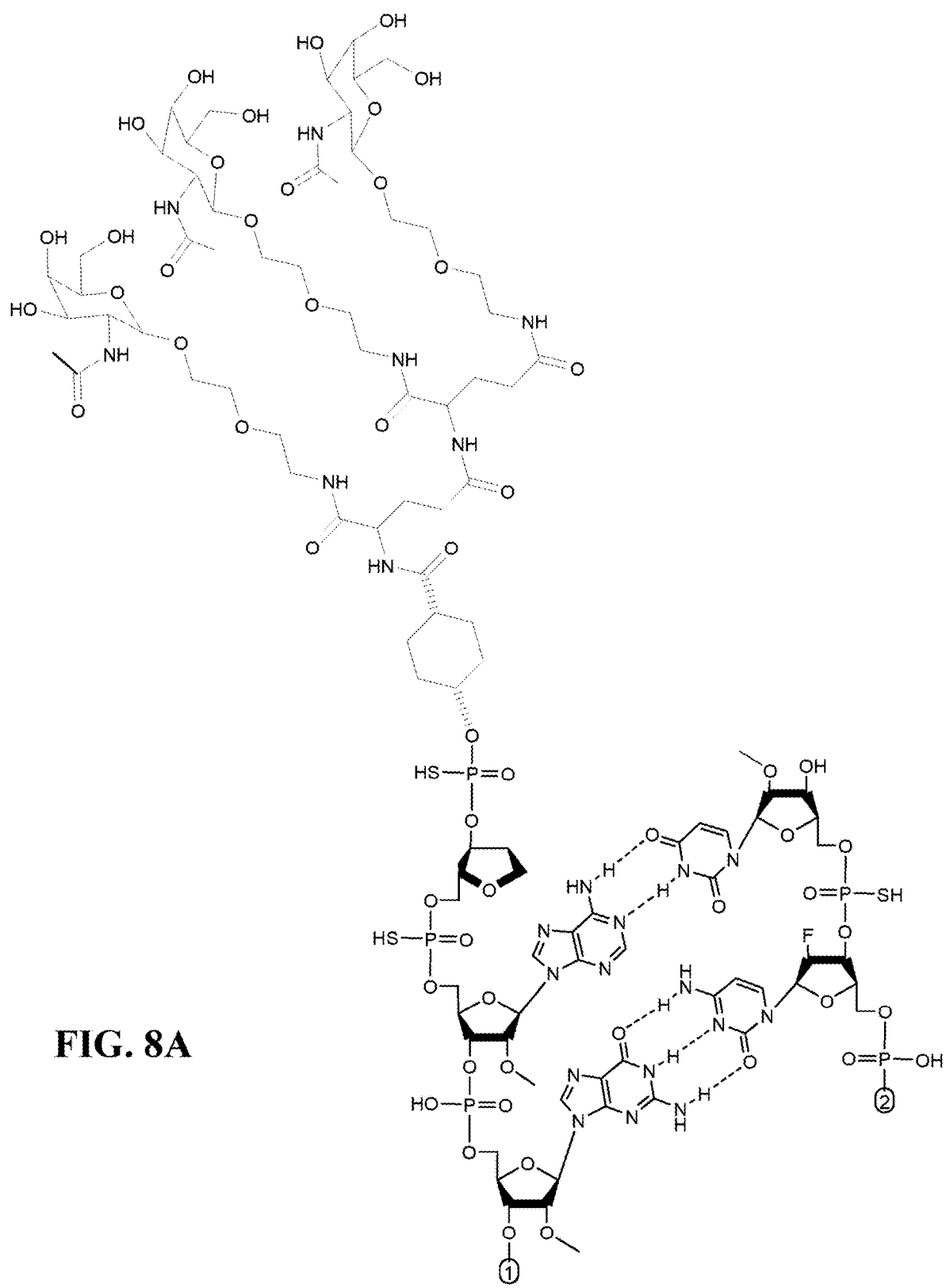
FIG. 8A to 8E represent the chemical duplex structure of AD04837 shown as a free acid.
Figure 8B:
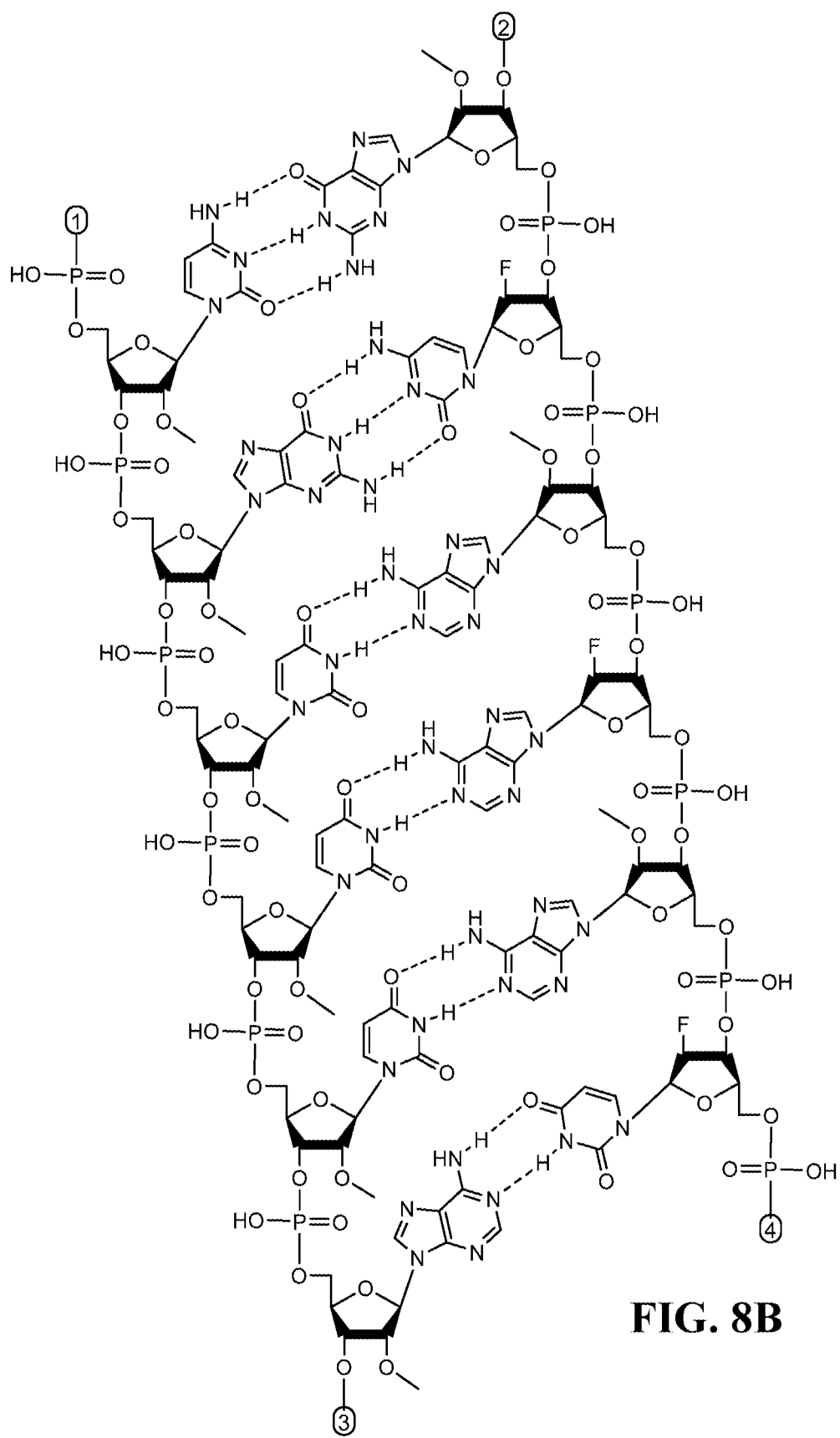
Figure 8C:
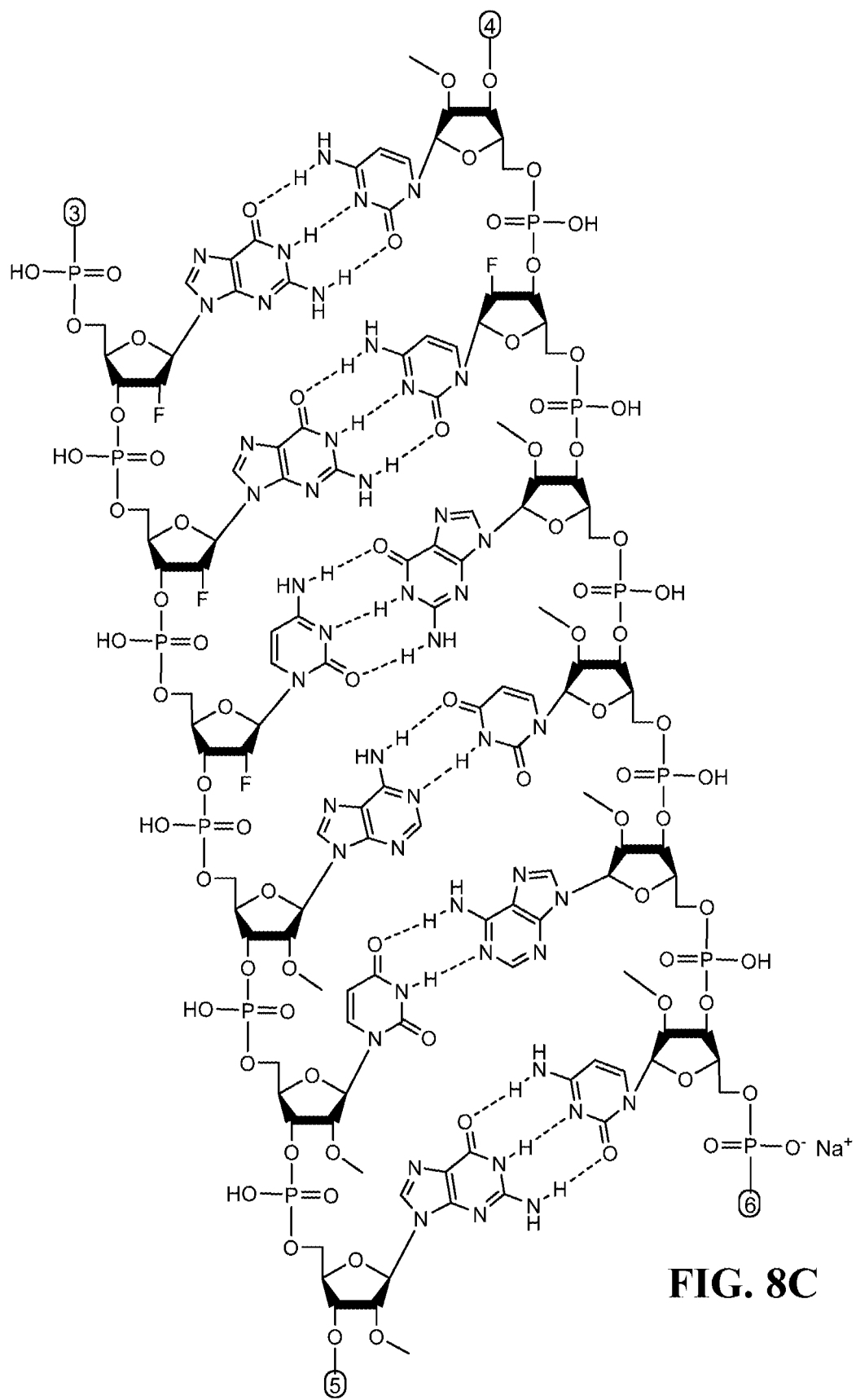
Figure 8D:
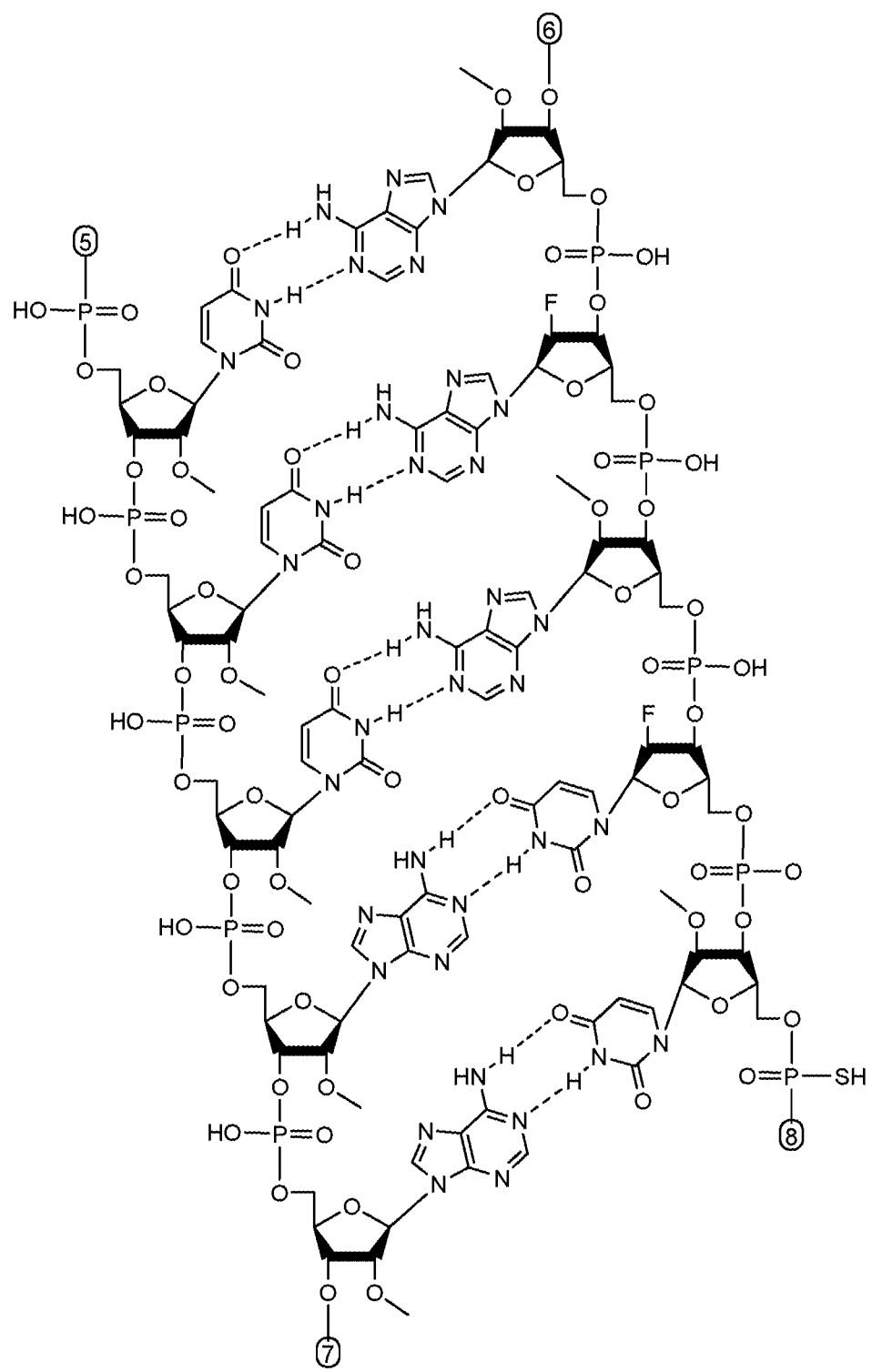
Figure 8E:
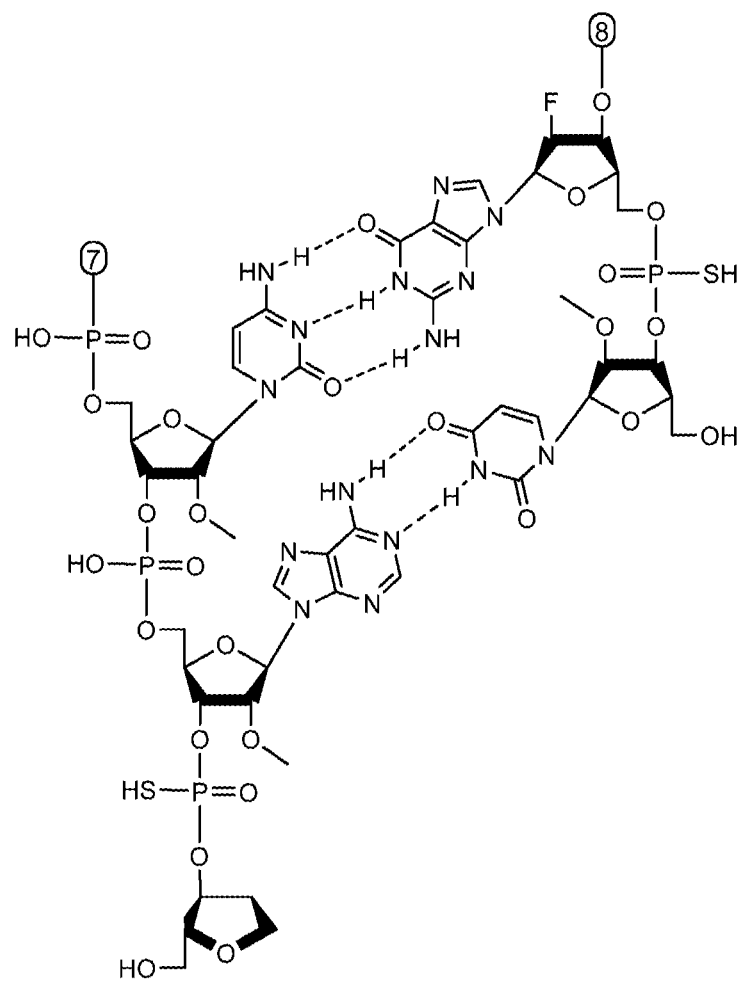

Described herein are RNAi agents for inhibiting expression of an AAT gene (referred to herein as AAT RNAi agents or AAT RNAi triggers). Each AAT RNAi agent comprises a sense strand and an antisense strand. The sense strand and the antisense strand each can be 16 to 30 nucleotides in length. In some embodiments, the sense and antisense strands each can be 17 to 26 nucleotides in length. The sense and antisense strands can be either the same length or they can be different lengths. In some embodiments, the sense and antisense strands are each independently 17-21 nucleotides in length. In some embodiments, the sense and antisense strands are each 21-26 nucleotides in length. In some embodiments, the sense and antisense strands are each 21-24 nucleotides in length. In some embodiments, the sense strand is about 19 nucleotides in length while the antisense strand is about 21 nucleotides in length. In some embodiments, the sense strand is about 21 nucleotides in length while the antisense strand is about 23 nucleotides in length. In some embodiments, a sense strand is 23 nucleotides in length and an antisense strand is 21 nucleotides in length. In some embodiments, both the sense and antisense strands are each 21 nucleotides in length. In some embodiments, a sense strand is 22 nucleotides in length and an antisense strand is 21 nucleotides in length. In some embodiments, a sense strand is 19 nucleotides in length and an antisense strand is 21 nucleotides in length. In some embodiments, the RNAi agent sense and antisense strands are each independently 17, 18, 19, 20, 21, 22, 23, 24, 25, or 26 nucleotides in length. In some embodiments, a double-stranded RNAi agent has a duplex length of about 16, 17, 18, 19, 20, 21, 22, 23 or 24 nucleotides.

In some embodiments, the region of perfect or substantial complementarity between the sense strand and the antisense strand is 16-26 (e.g., 16, 17, 18, 19, 20, 21, 22, 23, 24, 25, or 26) nucleotides in length and occurs at or near the 5' end of the antisense strand (e.g., this region may be separated from the 5' end of the antisense strand by 0, 1, 2, 3, or 4 nucleotides that are not perfectly or substantially complementary).

The sense strand and antisense strand each contain a core stretch sequence that is 16 to 23 nucleobases in length. An antisense strand core stretch sequence is 100% (perfectly) complementary or at least about 85% (substantially) complementary to a nucleotide sequence (sometimes referred to, e.g., as a target sequence) present in the AAT mRNA target. A sense strand core stretch sequence is 100% (perfectly) complementary or at least about 85% (substantially) complementary to a core stretch sequence in the antisense strand, and thus the sense strand core stretch sequence is perfectly identical or at least about 85% identical to a nucleotide sequence (target sequence) present in the AAT mRNA target. A sense strand core stretch sequence can be the same length as a corresponding antisense core sequence or it can be a different length. In some embodiments, the antisense strand core stretch sequence is 16, 17, 18, 19, 20, 21, 22, or 23 nucleotides in length. In some embodiments, the sense strand core stretch sequence is 16, 17, 18, 19, 20, 21, 22, or 23 nucleotides in length.

Examples of nucleotide sequences used in forming AAT RNAi agents are provided in Tables 2, 3, 4 and 5. Examples of AAT RNAi agent duplexes, that include the sense strand and antisense strand sequences in Tables 2, 3, 4, and 5, are shown in Table 6.

The AAT RNAi agent sense and antisense strands anneal to form a duplex. A sense strand and an antisense strand of an AAT RNAi agent may be partially, substantially, or fully complementary to each other. Within the complementary duplex region, the sense strand core stretch sequence is at least 85% complementary or 100% complementary to the antisense core stretch sequence. In some embodiments, the sense strand core stretch sequence contains a sequence of at least 16, at least 17, at least 18, at least 19, at least 20, at least 21, at least 22, or at least 23 nucleotides that is at least 85% or 100% complementary to a corresponding 16, 17, 18, 19, 20, 21, 22, or 23 nucleotide sequence of the antisense strand core stretch sequence (i.e., the sense and antisense core stretch sequences of an AAT RNAi agent have a region of at least 16, at least 17, at least 18, at least 19, at least 20, at least 21, at least 22, or at least 23 nucleotides that is at least 85% base paired or 100% base paired.)

In some embodiments, the antisense strand of an AAT RNAi agent disclosed herein differs by 0, 1, 2, or 3 nucleotides from any of the antisense strand sequences in Table 2, Table 3, or Table 4. In some embodiments, the sense strand of an AAT RNAi agent disclosed herein differs by 0, 1, 2, or 3 nucleotides from any of the sense strand sequences in Table 2, Table 3, or Table 5.

The sense strand and/or the antisense strand may optionally and independently contain an additional 1, 2, 3, 4, 5, or 6 nucleotides (extension) at the 3' end, the 5' end, or both the 3' and 5' ends of the core stretch sequences. The antisense strand additional nucleotides, if present, may or may not be complementary to the corresponding sequence in an AAT mRNA. The sense strand additional nucleotides, if present, may or may not be identical to the corresponding sequence in an AAT mRNA. The antisense strand additional nucleotides, if present, may or may not be complementary to the corresponding sense strand's additional nucleotides, if present.

As used herein, an extension comprises 1, 2, 3, 4, 5, or 6 nucleotides at the 5' and/or 3' end of the sense strand core stretch sequence and/or antisense strand core stretch sequence. The extension nucleotides on a sense strand may or may not be complementary to nucleotides, either core stretch sequence nucleotides or extension nucleotides, in the corresponding antisense strand. Conversely, the extension nucleotides on an antisense strand may or may not be complementary to nucleotides, either core stretch nucleotides or extension nucleotides, in the corresponding sense strand. In some embodiments, both the sense strand and the antisense strand of an RNAi agent contain 3' and 5' extensions. In some embodiments, one or more of the 3' extension nucleotides of one strand base pairs with one or more 5' extension nucleotides of the other strand. In other embodiments, one or more of 3' extension nucleotides of one strand do not base pair with one or more 5' extension nucleotides of the other strand. In some embodiments, an AAT RNAi agent has an antisense strand having a 3' extension and a sense strand having a 5' extension.

In some embodiments, an AAT RNAi agent comprises an antisense strand having a 3' extension of 1, 2, 3, 4, 5, or 6 nucleotides in length. In other embodiments, an AAT RNAi agent comprises an antisense strand having a 3' extension of 1, 2, or 3 nucleotides in length. In some embodiments, one or more of the antisense strand extension nucleotides comprise uracil or thymidine nucleotides or nucleotides that are complementary to the corresponding AAT mRNA sequence. In some embodiments, a 3' antisense strand extension includes or consists of one of the following sequences, but is not limited to: AUA, UGCUU, CUG, UG, UGCC, CUGCC, CGU, CUU, UGCCUA, CUGCCU, UGCCU, UGAUU, GCCUAU, T, TT, U, UU (each listed 5'→3').

In some embodiments, the 3' end of the antisense strand can include additional abasic residues (Ab). An "abasic residue" or "abasic site" is a nucleotide or nucleoside that lacks a nucleobase at the 1' position of the sugar. In some embodiments, Ab or AbAb can be added to the 3' end of the antisense strand. In some embodiments, the abasic residue(s) can be added as inverted abasic residues (invAb) (see Table 7). (See, e.g., F. Czauderna, Nucleic Acids Res., 2003, 31(11), 2705-16).

In some embodiments, an AAT RNAi agent comprises a sense strand having a 3' extension of 1, 2, 3, 4, or 5 nucleotides in length. In some embodiments, one or more of the sense strand extension nucleotides comprises adenosine, uracil, or thymidine nucleotides, AT dinucleotide, or nucleotides that correspond to nucleotides in the AAT mRNA sequence. In some embodiments, the 3' sense strand extension includes or consists of one of the following sequences, but is not limited to: T, UT, TT, UU, UUT, TTT, or TTTT (each listed 5' to 3').

In some embodiments, the 3' end of the sense strand may include additional abasic residues. In some embodiments, UUAb, UAb, or Ab are added to the 3' end of the sense strand. In some embodiments, the one or more abasic residues added to the 3' end of the sense strand are inverted (invAb). In some embodiments, one or more inverted abasic residues or abasic sites may be inserted between the targeting ligand and the nucleobase sequence of the sense strand of the RNAi agent. In some embodiments, the inclusion of one or more inverted abasic residues or abasic sites at or near the terminal end or terminal ends of the sense strand of an RNAi agent allows for enhanced activity or other desired properties of an RNAi agent.

In some embodiments, an AAT RNAi agent comprises a sense strand having a 5' extension of 1, 2, 3, 4, 5, or 6 nucleotides in length. In some embodiments, one or more of the sense strand extension nucleotides comprise uracil or adenosine nucleotides or nucleotides that correspond to nucleotides in the AAT mRNA sequence. In some embodiments, the sense strand 5' extension is one of the following sequences, but is not limited to: CA, AUAGGC, AUAGG, AUAG, AUA, A, AA, AC, GCA, GGCA, GGC, UAUCA, UAUC, UCA, UAU, U, UU (each listed 5' to 3'). A sense strand can have a 3' extension and/or a 5' extension.

In some embodiments, the 5' end of the sense strand can include one or more additional abasic residues (e.g., (Ab) or (AbAb)). In some embodiments, the one or more abasic residues added to the 5' end of the sense strand can be inverted (e.g., invAb). In some embodiments, one or more inverted abasic residues can be inserted between the targeting ligand and the nucleobase sequence of the sense strand of the RNAi agent. In some embodiments, the inclusion of one or more inverted abasic residues at or near the terminal end or terminal ends of the sense strand of an RNAi agent may allow for enhanced activity or other desired properties of an RNAi agent. In some embodiments, an abasic (deoxyribose) residue can be replaced with a ribitol (abasic ribose) residue.

In some embodiments, the 3' end of the antisense strand core stretch sequence, or the 3' end of the antisense strand sequence, may include an inverted abasic residue (invAb (see Table 7)).

Examples of sequences used in forming AAT RNAi agents are provided in Tables 2, 3, 4, and 5. In some embodiments, an AAT RNAi agent antisense strand includes a sequence of any of the sequences in Tables 2, 3, or 4. In some embodiments, an AAT RNAi agent antisense strand includes the sequence of nucleotides (from 5' end→3' end) 1-17, 2-15, 2-17, 1-18, 2-18, 1-19, 2-19, 1-20, 2-20, 1-21, 2-21, 1-22, 2-22, 1-23, 2-23, 1-24, or 2-24, of any of the sequences in Table 2, Table 3, or Table 4. In certain embodiments, an AAT RNAi agent antisense strand comprises or consists of a modified sequence of any one of the modified sequences in Table 4. In some embodiments, an AAT RNAi agent sense strand includes the sequence of any of the sequences in Tables 2, 3, or 5. In some embodiments, an AAT RNAi agent sense strand includes the sequence of nucleotides (from 5' end→3' end) 1-18, 1-19, 1-20, 1-21, 1-22, 1-23, 1-24, 2-19, 2-20, 2-21, 2-22, 2-23, 2-24, 3-20, 3-21, 3-22, 3-23, 3-24, 4-21, 4-22, 4-23, 4-24, 5-22, 5-23, 5-24, 6-23, 6-24, 7-24, of any of the sequences in Tables 2, 3, or 5. In certain embodiments, an AAT RNAi agent sense strand comprises or consists of a modified sequence of any one of the modified sequences in Table 5.

In some embodiments, the sense and antisense strands of the RNAi agents described herein contain the same number of nucleotides. In some embodiments, the sense and antisense strands of the RNAi agents described herein contain different numbers of nucleotides. In some embodiments, the sense strand 5' end and the antisense strand 3' end of an RNAi agent form a blunt end. In some embodiments, the sense strand 3' end and the antisense strand 5' end of an RNAi agent form a blunt end. In some embodiments, both ends of an RNAi agent form blunt ends. In some embodiments, neither end of an RNAi agent is blunt-ended. As used herein a blunt end refers to an end of a double stranded RNAi agent in which the terminal nucleotides of the two annealed strands are complementary (form a complementary base-pair).

In some embodiments, the sense strand 5' end and the antisense strand 3' end of an RNAi agent form a frayed end. In some embodiments, the sense strand 3' end and the antisense strand 5' end of an RNAi agent form a frayed end. In some embodiments, both ends of an RNAi agent form a frayed end. In some embodiments, neither end of an RNAi agent is a frayed end. As used herein a frayed end refers to an end of a double stranded RNAi agent in which the terminal nucleotides of the two annealed strands from a pair (i.e., do not form an overhang) but are not complementary (i.e. form a non-complementary pair). As used herein, an overhang is a stretch of one or more unpaired nucleotides at the end of one strand of a double stranded RNAi agent. The unpaired nucleotides may be on the sense strand or the antisense strand, creating either 3' or 5' overhangs. In some embodiments, the RNAi agent contains: a blunt end and a frayed end, a blunt end and 5' overhang end, a blunt end and a 3' overhang end, a frayed end and a 5' overhang end, a frayed end and a 3' overhang end, two 5' overhang ends, two 3' overhang ends, a 5' overhang end and a 3' overhang end, two frayed ends, or two blunt ends.

Modified nucleotides, when used in various polynucleotide or oligonucleotide constructs, can preserve activity of the compound in cells while at the same time increasing the serum stability of these compounds, and can also minimize the possibility of activating interferon activity in humans upon administering of the polynucleotide or oligonucleotide construct.

In some embodiments, an AAT RNAi agent is prepared or provided as a salt, mixed salt, or a free-acid. In some embodiments, an AAT RNAi agent is prepared as a sodium salt. Such forms are within the scope of the inventions disclosed herein.

Modified Nucleotides

In some embodiments, an AAT RNAi agent contains one or more modified nucleotides. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides include, but are not limited to, deoxyribonucleotides, nucleotide mimics, abasic nucleotides (represented herein as Ab), 2'-modified nucleotides, 3' to 3' linkages (inverted) nucleotides (represented herein as invdN, invN, invn), modified nucleobase-comprising nucleotides, bridged nucleotides, peptide nucleic acids (PNAs), 2',3'-seco nucleotide mimics (unlocked nucleobase analogues, represented herein as $N_{UNA}$ or NUNA), locked nucleotides (represented herein as $N_{LNA}$ or NLNA), 3'-O-methoxy (2' internucleoside linked) nucleotides (represented herein as 3'-OMen), 2'-F-Arabino nucleotides (represented herein as NfANA or $Nf_{ANA}$), 5'-Me, 2'-fluoro nucleotide (represented herein as 5Me-Nf), morpholino nucleotides, vinyl phosphonate deoxyribonucleotides (represented herein as vpdN), vinyl phosphonate containing nucleotides, and cyclopropyl phosphonate containing nucleotides (cPrpN). 2'-modified nucleotides (i.e. a nucleotide with a group other than a hydroxyl group at the 2' position of the five-membered sugar ring) include, but are not limited to, 2'-O-methyl nucleotides (represented herein as a lower case letter 'n' in a nucleotide sequence), 2'-deoxy-2'-fluoro nucleotides (represented herein as Nf, also represented herein as 2'-fluoro nucleotide), 2'-deoxy nucleotides (represented herein as dN), 2'-methoxyethyl (2'-O-2-methoxylethyl) nucleotides (represented herein as NM or 2'-MOE), 2'-amino nucleotides, and 2'-alkyl nucleotides. It is not necessary for all positions in a given compound to be uniformly modified. Conversely, more than one modification can be incorporated in a single AAT RNAi agent or even in a single nucleotide thereof. The AAT RNAi agent sense strands and antisense strands can be synthesized and/or modified by methods known in the art. Modification at one nucleotide is independent of modification at another nucleotide.

Modified nucleobases include synthetic and natural nucleobases, such as 5-substituted pyrimidines, 6-azapyrimidines and N-2, N-6 and 0-6 substituted purines, (e.g., 2-aminopropyladenine, 5-propynyluracil, or 5-propynylcytosine), 5-methylcytosine (5-me-C), 5-hydroxymethyl cytosine, inosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, all or substantially all of the nucleotides of an RNAi agent are modified nucleotides. As used herein, an RNAi agent wherein substantially all of the nucleotides present are modified nucleotides is an RNAi agent having four or fewer (i.e., 0, 1, 2, 3, or 4) nucleotides in both the sense strand and the antisense strand being ribonucleotides (i.e., unmodified). As used herein, a sense strand wherein substantially all of the nucleotides present are modified nucleotides is a sense strand having two or fewer (i.e., 0, 1, or 2) nucleotides in the sense strand being ribonucleotides. As used herein, an antisense sense strand wherein substantially all of the nucleotides present are modified nucleotides is an antisense strand having two or fewer (i.e., 0, 1, or 2) nucleotides in the sense strand being ribonucleotides. In some embodiments, one or more nucleotides of an RNAi agent is a ribonucleotide.

Modified Internucleoside Linkages

In some embodiments, one or more nucleotides of an AAT RNAi agent are linked by non-standard linkages or backbones (i.e., modified internucleoside linkages or modified backbones). Modified internucleoside linkages or backbones include, but are not limited to, 5'-phosphorothioate groups (represented herein as a lower case "s"), chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, a sense strand of an AAT RNAi agent can contain 1, 2, 3, 4, 5, or 6 phosphorothioate linkages, an antisense strand of an AAT RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some embodiments, a sense strand of an AAT RNAi agent can contain 1, 2, 3, or 4 phosphorothioate linkages, an antisense strand of an AAT RNAi agent can contain 1, 2, 3, or 4 phosphorothioate linkages, or both the sense strand and the antisense strand independently can contain 1, 2, 3, or 4 phosphorothioate linkages.

In some embodiments, an AAT RNAi agent sense strand contains at least two phosphorothioate internucleoside linkages. In some embodiments, the at least two phosphorothioate internucleoside linkages are between the nucleotides at positions 1-3 from the 3' end of the sense strand. In some embodiments, the at least two phosphorothioate internucleoside linkages are between the nucleotides at positions 1-3, 2-4, 3-5, 4-6, 4-5, or 6-8 from the 5' end of the sense strand. In some embodiments, an AAT RNAi agent antisense strand contains four phosphorothioate internucleoside linkages. In some embodiments, the four phosphorothioate internucleoside linkages are between the nucleotides at positions 1-3 from the 5' end of the antisense strand and between the nucleotides at positions 19-21, 20-22, 21-23, 22-24, 23-25, or 24-26 from the 5' end. In some embodiments, an AAT RNAi agent contains at least two phosphorothioate internucleoside linkages in the sense strand and three or four phosphorothioate internucleoside linkages in the antisense strand.

In some embodiments, an AAT RNAi agent contains one or more modified nucleotides and one or more modified internucleoside linkages. In some embodiments, a 2'-modified nucleoside is combined with modified internucleoside linkage.

AAT RNAi Agents

In some embodiments, the AAT RNAi agents disclosed herein target an AAT gene at or near the positions of the AAT gene shown in Table 1. In some embodiments, the antisense strand of an AAT RNAi agent disclosed herein includes a core stretch sequence that is fully, substantially, or at least partially complementary to a target AAT 19-mer sequence disclosed in Table 1.

TABLE 1

AAT 19-mer mRNA Target Sequences
(taken from human AAT cDNA, GenBank
NM_000295.4 (SEQ ID NO: 1))

| SEQ ID NO: | AAT 19-mer Target Sequences (5' → 3') | Corresponding Gene Position (taken from SEQ ID NO: 1) |
|---|---|---|
| 2 | CGUUUAGGCAUGUUUAACA | 1000-1018 |
| 3 | AACAGCACCAAUAUCUUCU | 469-487 |
| 4 | AUAUCAUCACCAAGUUCCU | 1142-1160 |
| 5 | AGAUGCUGCCCAGAAGACA | 348-366 |
| 6 | CUGGCACACCAGUCCAACA | 454-472 |
| 7 | UGGCACACCAGUCCAACAG | 455-473 |
| 8 | GCACACCAGUCCAACAGCA | 457-475 |
| 9 | CAGUCCAACAGCACCAAUA | 463-481 |
| 10 | AGUCCAACAGCACCAAUAU | 464-482 |
| 11 | GUCCAACAGCACCAAUAUC | 465-483 |
| 12 | CCAACAGCACCAAUAUCUU | 467-485 |
| 13 | CCCCAGUGAGCAUCGCUAC | 491-509 |
| 14 | GAGCAUCGCUACAGCCUUU | 498-516 |
| 15 | GCAUCGCUACAGCCUUUGC | 500-518 |
| 16 | CAUCGCUACAGCCUUUGCA | 501-519 |
| 17 | UCGCUACAGCCUUUGCAAU | 503-521 |
| 18 | CUACAGCCUUUGCAAUGCU | 506-524 |
| 19 | ACAGCCUUUGCAAUGCUCU | 508-526 |
| 20 | GAAGGCUUCCAGGAACUCC | 613-631 |
| 21 | UAGUGGAUAAGUUUUUGGA | 710-728 |
| 22 | UGUACCACUCAGAAGCCUU | 743-761 |
| 23 | GUACCACUCAGAAGCCUUC | 744-762 |
| 24 | ACACCGAAGAGGCCAAGAA | 779-797 |
| 25 | ACCGAAGAGGCCAAGAAAC | 781-799 |
| 26 | AGGCCAAGAAACAGAUCAA | 788-806 |
| 27 | GGCCAAGAAACAGAUCAAC | 789-807 |
| 28 | GCCAAGAAACAGAUCAACG | 790-808 |
| 29 | UACUCAAGGGAAAAUUGUG | 825-843 |
| 30 | CUCAAGGGAAAAUUGUGGA | 827-845 |
| 31 | UCAAGGGAAAAUUGUGGAU | 828-846 |

TABLE 1-continued

AAT 19-mer mRNA Target Sequences
(taken from human AAT cDNA, GenBank
NM_000295.4 (SEQ ID NO: 1))

| SEQ ID NO: | AAT 19-mer Target Sequences (5' → 3') | Corresponding Gene Position (taken from SEQ ID NO: 1) |
|---|---|---|
| 32 | UUGGUCAAGGAGCUUGACA | 847-865 |
| 33 | AGGAGCUUGACAGAGACAC | 854-872 |
| 34 | AGCUUGACAGAGACACAGU | 857-875 |
| 35 | UUUGCUCUGGUGAAUUACA | 877-895 |
| 36 | AGCGUUUAGGCAUGUUUAA | 998-1016 |
| 37 | GCGUUUAGGCAUGUUUAAC | 999-1017 |
| 38 | UUAGGCAUGUUUAACAUCC | 1003-1021 |
| 39 | UGGGUGCUGCUGAUGAAAU | 1045-1063 |
| 40 | UGCCACCGCCAUCUUCUUC | 1074-1092 |
| 41 | CCUGGAAAAUGAACUCACC | 1119-1137 |
| 42 | CGAUAUCAUCACCAAGUUC | 1140-1158 |
| 43 | ACCAAGUUCCUGGAAAAUG | 1150-1168 |
| 44 | UCCAUUACUGGAACCUAUG | 1207-1225 |
| 45 | CCAUUACUGGAACCUAUGA | 1208-1226 |
| 46 | ACUGGAACCUAUGAUCUGA | 1213-1231 |
| 47 | GGAACCUAUGAUCUGAAGA | 1216-1234 |
| 48 | GAACCUAUGAUCUGAAGAG | 1217-1235 |
| 49 | CAGCAAUGGGGCUGACCUC | 1269-1287 |
| 50 | GCAAUGGGGCUGACCUCUC | 1271-1289 |
| 51 | AGAGGAGGCACCCCUGAAG | 1299-1317 |
| 52 | AGGCACCCCUGAAGCUCUC | 1304-1322 |
| 53 | UCUCCAAGGCCGUGCAUAA | 1319-1337 |
| 54 | UCCAAGGCCGUGCAUAAGG | 1321-1339 |
| 55 | CCAAGGCCGUGCAUAAGGC | 1322-1340 |
| 56 | CAAGGCCGUGCAUAAGGCU | 1323-1341 |
| 57 | AAGGCUGUGCUGACCAUCG | 1336-1354 |
| 58 | GGCUGUGCUGACCAUCGAC | 1338-1356 |
| 59 | CUGCUGGGGCCAUGUUUUU | 1373-1391 |
| 60 | GCUGGGGCCAUGUUUUUAG | 1375-1393 |
| 61 | CUGGGGCCAUGUUUUUAGA | 1376-1394 |
| 62 | GGGGCCAUGUUUUUAGAGG | 1378-1396 |
| 63 | GGGCCAUGUUUUUAGAGGC | 1379-1397 |
| 64 | GAGGCCAUACCCAUGUCUA | 1393-1411 |
| 65 | GGCCAUACCCAUGUCUAUC | 1395-1413 |
| 66 | CCCGAGGUCAAGUUCAACA | 1417-1435 |
| 67 | AGGUCAAGUUCAACAAACC | 1421-1439 |
| 68 | CAAGUUCAACAAACCCUUU | 1425-1443 |
| 69 | AGUUCAACAAACCCUUUGU | 1427-1445 |
| 70 | GUUCAACAAACCCUUUGUC | 1428-1446 |
| 71 | UCAACAAACCCUUUGUCUU | 1430-1448 |
| 72 | ACCCUUUGUCUUCUUAAUG | 1437-1455 |
| 73 | CCUUUGUCUUCUUAAUGAU | 1439-1457 |
| 74 | UACCAAGUCUCCCCUCUUC | 1467-1485 |
| 75 | AAGUCUCCCCUCUUCAUGG | 1471-1489 |
| 76 | AGUCUCCCCUCUUCAUGGG | 1472-1490 |
| 77 | UCUCCCCUCUUCAUGGGAA | 1474-1492 |
| 78 | CUCCCCUCUUCAUGGGAAA | 1475-1493 |
| 79 | AUGACAUUAAAGAAGGGUU | 1569-1587 |

In some embodiments, an AAT RNAi agent includes an antisense strand wherein position 19 of the antisense strand (5'→3') is capable of forming a base pair with position 1 of a 19-mer target sequence disclosed in Table 1. In some embodiments, an AAT RNAi agent includes an antisense strand wherein position 1 of the antisense strand (5'→3') is capable of forming a base pair with position 19 of the 19-mer target sequence disclosed in Table 1.

In some embodiments, an AAT RNAi agent includes an antisense strand wherein position 2 of the antisense strand (5'→3') is capable of forming a base pair with position 18 of the 19-mer target sequence disclosed in Table 1. In some embodiments, an AAT RNAi agent includes an antisense strand wherein positions 2 through 18 of the antisense strand (5→3') are capable of forming base pairs with each of the respective complementary bases located at positions 18 through 2 of the 19-mer target sequence disclosed in Table 1.

For the RNAi agents disclosed herein, the nucleotide at position 1 of the antisense strand (from 5' end→3' end) can be perfectly complementary to the AAT gene, or can be non-complementary to the AAT gene. In some embodiments, the nucleotide at position 1 of the antisense strand (from 5' end→3' end) is a U, A, or dT. In some embodiments, the nucleotide at position 1 of the antisense strand (from 5' end→3' end) forms an A:U or U:A base pair with the sense strand.

In some embodiments, an AAT RNAi agent antisense strand comprises the sequence of nucleotides (from 5' end→3' end) 2-18 or 2-19 of any of the antisense strand sequences in Table 2, Table 3, or Table 4. In some embodiments, an AAT RNAi sense strand comprises the sequence of nucleotides (from 5' end→3' end) 1-17, 1-18, or 2-18 of any of the sense strand sequences in Table 2, Table 3, or Table 5.

In some embodiments, an AAT RNAi agent is comprised of (i) an antisense strand comprising the sequence of nucleotides (from 5' end→3' end) 2-18 or 2-19 of any of the antisense strand sequences in Table 2, Table 3, or Table 4, and (ii) a sense strand comprising the sequence of nucleotides (from 5' end→3' end) 1-17 or 1-18 of any of the sense strand sequences in Table 2, Table 3, or Table 5.

In some embodiments, the AAT RNAi agents include core 19-mer nucleotide sequences shown in the following Table 2.

TABLE 2

Example AAT RNAi Agent Antisense Strand and Sense Strand Core Stretch Base Sequences
(N = any nucleobase)

| SEQ ID NO: | Antisense Base Sequence (5' → 3') (19-mers) | SEQ ID NO: | Sense Base Sequence (5' → 3') (19-mers) | Gene Position of SEQ ID NO: 1 |
|---|---|---|---|---|
| 80 | UGUUAAACAUGCCUAAACG | 429 | CGUUUAGGCAUGUUUAACA | 1000-1018 |
| 81 | AGUUAAACAUGCCUAAACG | 430 | CGUUUAGGCAUGUUUAACU | 1000-1018 |
| 82 | NGUUAAACAUGCCUAAACG | 431 | CGUUUAGGCAUGUUUAACN | 1000-1018 |
| 83 | NGUUAAACAUGCCUAAACN | 432 | NGUUUAGGCAUGUUUAACN | 1000-1018 |
| 84 | AGAAGAUAUUGGUGCUGUU | 433 | AACAGCACCAAUAUCUUCU | 469-487 |
| 85 | UGAAGAUAUUGGUGCUGUU | 434 | AACAGCACCAAUAUCUUCA | 469-487 |
| 86 | NGAAGAUAUUGGUGCUGUU | 435 | AACAGCACCAAUAUCUUCN | 469-487 |
| 87 | NGAAGAUAUUGGUGCUGUN | 436 | NACAGCACCAAUAUCUUCN | 469-487 |
| 88 | AGGAACUUGGUGAUGAUAU | 437 | AUAUCAUCACCAAGUUCCU | 1142-1160 |
| 89 | UGGAACUUGGUGAUGAUAU | 438 | AUAUCAUCACCAAGUUCCA | 1142-1160 |
| 90 | NGGAACUUGGUGAUGAUAU | 439 | AUAUCAUCACCAAGUUCCN | 1142-1160 |
| 91 | NGGAACUUGGUGAUGAUAN | 440 | NUAUCAUCACCAAGUUCCN | 1142-1160 |
| 92 | UGUCUUCUGGGCAGCAUCU | 441 | AGAUGCUGCCCAGAAGACA | 348-366 |
| 93 | AGUCUUCUGGGCAGCAUCU | 442 | AGAUGCUGCCCAGAAGACU | 348-366 |
| 94 | NGUCUUCUGGGCAGCAUCU | 443 | AGAUGCUGCCCAGAAGACN | 348-366 |
| 95 | NGUCUUCUGGGCAGCAUCN | 444 | NGAUGCUGCCCAGAAGACN | 348-366 |
| 96 | UGUUGGACUGGUGUGCCAG | 445 | CUGGCACACCAGUCCAACA | 454-472 |
| 97 | AGUUGGACUGGUGUGCCAG | 446 | CUGGCACACCAGUCCAACU | 454-472 |
| 98 | NGUUGGACUGGUGUGCCAG | 447 | CUGGCACACCAGUCCAACN | 454-472 |
| 99 | NGUUGGACUGGUGUGCCAN | 448 | NUGGCACACCAGUCCAACN | 454-472 |
| 100 | CUGUUGGACUGGUGUGCCA | 449 | UGGCACACCAGUCCAACAG | 455-473 |
| 101 | UUGUUGGACUGGUGUGCCA | 450 | UGGCACACCAGUCCAACAA | 455-473 |
| 102 | AUGUUGGACUGGUGUGCCA | 451 | UGGCACACCAGUCCAACAU | 455-473 |
| 103 | NUGUUGGACUGGUGUGCCA | 452 | UGGCACACCAGUCCAACAN | 455-473 |
| 104 | NUGUUGGACUGGUGUGCCN | 453 | NGGCACACCAGUCCAACAN | 455-473 |
| 105 | UGCUGUUGGACUGGUGUGC | 454 | GCACACCAGUCCAACAGCA | 457-475 |
| 106 | AGCUGUUGGACUGGUGUGC | 455 | GCACACCAGUCCAACAGCU | 457-475 |
| 107 | NGCUGUUGGACUGGUGUGC | 456 | GCACACCAGUCCAACAGCN | 457-475 |
| 108 | NGCUGUUGGACUGGUGUGN | 457 | NCACACCAGUCCAACAGCN | 457-475 |
| 109 | UAUUGGUGCUGUUGGACUG | 458 | CAGUCCAACAGCACCAAUA | 463-481 |
| 110 | AAUUGGUGCUGUUGGACUG | 459 | CAGUCCAACAGCACCAAUU | 463-481 |
| 111 | NAUUGGUGCUGUUGGACUG | 460 | CAGUCCAACAGCACCAAUN | 463-481 |

TABLE 2-continued

Example AAT RNAi Agent Antisense Strand and
Sense Strand Core Stretch Base Sequences
(N = any nucleobase)

| SEQ ID NO: | Antisense Base Sequence (5' → 3') (19-mers) | SEQ ID NO: | Sense Base Sequence (5' → 3') (19-mers) | Gene Position of SEQ ID NO: 1 |
|---|---|---|---|---|
| 112 | NAUUGGUGCUGUUGGACUN | 461 | NAGUCCAACAGCACCAAUN | 463-481 |
| 113 | AUAUUGGUGCUGUUGGACU | 462 | AGUCCAACAGCACCAAUAU | 464-482 |
| 114 | UUAUUGGUGCUGUUGGACU | 463 | AGUCCAACAGCACCAAUAA | 464-482 |
| 115 | NUAUUGGUGCUGUUGGACU | 464 | AGUCCAACAGCACCAAUAN | 464-482 |
| 116 | NUAUUGGUGCUGUUGGACN | 465 | NGUCCAACAGCACCAAUAN | 464-482 |
| 117 | GAUAUUGGUGCUGUUGGAC | 466 | GUCCAACAGCACCAAUAUC | 465-483 |
| 118 | UAUAUUGGUGCUGUUGGAC | 467 | GUCCAACAGCACCAAUAUA | 465-483 |
| 119 | AAUAUUGGUGCUGUUGGAC | 468 | GUCCAACAGCACCAAUAUU | 465-483 |
| 120 | NAUAUUGGUGCUGUUGGAC | 469 | GUCCAACAGCACCAAUAUN | 465-483 |
| 121 | NAUAUUGGUGCUGUUGGAN | 470 | NUCCAACAGCACCAAUAUN | 465-483 |
| 122 | AAGAUAUUGGUGCUGUUGG | 471 | CCAACAGCACCAAUAUCUU | 467-485 |
| 123 | UAGAUAUUGGUGCUGUUGG | 472 | CCAACAGCACCAAUAUCUA | 467-485 |
| 124 | NAGAUAUUGGUGCUGUUGG | 473 | CCAACAGCACCAAUAUCUN | 467-485 |
| 125 | NAGAUAUUGGUGCUGUUGN | 474 | NCAACAGCACCAAUAUCUN | 467-485 |
| 126 | GUAGCGAUGCUCACUGGGG | 475 | CCCCAGUGAGCAUCGCUAC | 491-509 |
| 127 | UUAGCGAUGCUCACUGGGG | 476 | CCCCAGUGAGCAUCGCUAA | 491-509 |
| 128 | AUAGCGAUGCUCACUGGGG | 477 | CCCCAGUGAGCAUCGCUAU | 491-509 |
| 129 | NUAGCGAUGCUCACUGGGG | 478 | CCCCAGUGAGCAUCGCUAN | 491-509 |
| 130 | NUAGCGAUGCUCACUGGGN | 479 | NCCCAGUGAGCAUCGCUAN | 491-509 |
| 131 | AAAGGCUGUAGCGAUGCUC | 480 | GAGCAUCGCUACAGCCUUU | 498-516 |
| 132 | UAAGGCUGUAGCGAUGCUC | 481 | GAGCAUCGCUACAGCCUUA | 498-516 |
| 133 | NAAGGCUGUAGCGAUGCUC | 482 | GAGCAUCGCUACAGCCUUN | 498-516 |
| 134 | NAAGGCUGUAGCGAUGCUN | 483 | NAGCAUCGCUACAGCCUUN | 498-516 |
| 135 | GCAAAGGCUGUAGCGAUGC | 484 | GCAUCGCUACAGCCUUUGC | 500-518 |
| 136 | UCAAAGGCUGUAGCGAUGC | 485 | GCAUCGCUACAGCCUUUGA | 500-518 |
| 137 | ACAAAGGCUGUAGCGAUGC | 486 | GCAUCGCUACAGCCUUUGU | 500-518 |
| 138 | NCAAAGGCUGUAGCGAUGC | 487 | GCAUCGCUACAGCCUUUGN | 500-518 |
| 139 | NCAAAGGCUGUAGCGAUGN | 488 | NCAUCGCUACAGCCUUUGN | 500-518 |
| 140 | UGCAAAGGCUGUAGCGAUG | 489 | CAUCGCUACAGCCUUUGCA | 501-519 |
| 141 | AGCAAAGGCUGUAGCGAUG | 490 | CAUCGCUACAGCCUUUGCU | 501-519 |
| 142 | NGCAAAGGCUGUAGCGAUG | 491 | NAUCGCUACAGCCUUUGCN | 501-519 |
| 143 | NGCAAAGGCUGUAGCGAUN | 492 | NAUCGCUACAGCCUUUGCN | 501-519 |
| 144 | AUUGCAAAGGCUGUAGCGA | 493 | UCGCUACAGCCUUUGCAAU | 503-521 |
| 145 | UUUGCAAAGGCUGUAGCGA | 494 | UCGCUACAGCCUUUGCAAA | 503-521 |
| 146 | NUUGCAAAGGCUGUAGCGA | 495 | UCGCUACAGCCUUUGCAAN | 503-521 |
| 147 | NUUGCAAAGGCUGUAGCGN | 496 | NCGCUACAGCCUUUGCAAN | 503-521 |

TABLE 2-continued

Example AAT RNAi Agent Antisense Strand and
Sense Strand Core Stretch Base Sequences
(N = any nucleobase)

| SEQ ID NO: | Antisense Base Sequence (5' → 3') (19-mers) | SEQ ID NO: | Sense Base Sequence (5' → 3') (19-mers) | Gene Position of SEQ ID NO: 1 |
|---|---|---|---|---|
| 148 | AGCAUUGCAAAGGCUGUAG | 497 | CUACAGCCUUUGCAAUGCU | 506-524 |
| 149 | UGCAUUGCAAAGGCUGUAG | 498 | CUACAGCCUUUGCAAUGCA | 506-524 |
| 150 | NGCAUUGCAAAGGCUGUAG | 499 | CUACAGCCUUUGCAAUGCN | 506-524 |
| 151 | NGCAUUGCAAAGGCUGUAN | 500 | NUACAGCCUUUGCAAUGCN | 506-524 |
| 152 | AGAGCAUUGCAAAGGCUGU | 501 | ACAGCCUUUGCAAUGCUCU | 508-526 |
| 153 | UGAGCAUUGCAAAGGCUGU | 502 | ACAGCCUUUGCAAUGCUCA | 508-526 |
| 154 | NGAGCAUUGCAAAGGCUGU | 503 | ACAGCCUUUGCAAUGCUCN | 508-526 |
| 155 | NGAGCAUUGCAAAGGCUGU | 504 | NCAGCCUUUGCAAUGCUCN | 508-526 |
| 156 | GGAGUUCCUGGAAGCCUUC | 505 | GAAGGCUUCCAGGAACUCC | 613-631 |
| 157 | UGAGUUCCUGGAAGCCUUC | 506 | GAAGGCUUCCAGGAACUCA | 613-631 |
| 158 | AGAGUUCCUGGAAGCCUUC | 507 | GAAGGCUUCCAGGAACUCU | 613-631 |
| 159 | NGAGUUCCUGGAAGCCUUC | 508 | GAAGGCUUCCAGGAACUCN | 613-631 |
| 160 | NGAGUUCCUGGAAGCCUUN | 509 | NAAGGCUUCCAGGAACUCN | 613-631 |
| 161 | UCCAAAAACUUAUCCACUA | 510 | UAGUGGAUAAGUUUUUGGA | 710-728 |
| 162 | ACCAAAAACUUAUCCACUA | 511 | UAGUGGAUAAGUUUUUGGU | 710-728 |
| 163 | NCCAAAAACUUAUCCACUA | 512 | UAGUGGAUAAGUUUUUGGN | 710-728 |
| 164 | NCCAAAAACUUAUCCACUN | 513 | NAGUGGAUAAGUUUUUGGN | 710-728 |
| 165 | AAGGCUUCUGAGUGGUACA | 514 | UGUACCACUCAGAAGCCUU | 743-761 |
| 166 | UAGGCUUCUGAGUGGUACA | 515 | UGUACCACUCAGAAGCCUA | 743-761 |
| 167 | NAGGCUUCUGAGUGGUACA | 516 | UGUACCACUCAGAAGCCUN | 743-761 |
| 168 | NAGGCUUCUGAGUGGUACN | 517 | NGUACCACUCAGAAGCCUN | 743-761 |
| 169 | GAAGGCUUCUGAGUGGUAC | 518 | GUACCACUCAGAAGCCUUC | 744-762 |
| 170 | UAAGGCUUCUGAGUGGUAC | 519 | GUACCACUCAGAAGCCUUA | 744-762 |
| 171 | AAAGGCUUCUGAGUGGUAC | 520 | GUACCACUCAGAAGCCUUU | 744-762 |
| 172 | NAAGGCUUCUGAGUGGUAC | 521 | GUACCACUCAGAAGCCUUN | 744-762 |
| 173 | NAAGGCUUCUGAGUGGUAN | 522 | NUACCACUCAGAAGCCUUN | 744-762 |
| 174 | UUCUUGGCCUCUUCGGUGU | 523 | ACACCGAAGAGGCCAAGAA | 779-797 |
| 175 | AUCUUGGCCUCUUCGGUGU | 524 | ACACCGAAGAGGCCAAGAU | 779-797 |
| 176 | NUCUUGGCCUCUUCGGUGU | 525 | ACACCGAAGAGGCCAAGAN | 779-797 |
| 177 | NUCUUGGCCUCUUCGGUGN | 526 | NCACCGAAGAGGCCAAGAN | 779-797 |
| 178 | GUUUCUUGGCCUCUUCGGU | 527 | ACCGAAGAGGCCAAGAAAC | 781-799 |
| 179 | UUUUCUUGGCCUCUUCGGU | 528 | ACCGAAGAGGCCAAGAAAA | 781-799 |
| 180 | AUUUCUUGGCCUCUUCGGU | 529 | ACCGAAGAGGCCAAGAAAU | 781-799 |
| 181 | NUUUCUUGGCCUCUUCGGU | 530 | ACCGAAGAGGCCAAGAAAN | 781-799 |
| 182 | NUUUCUUGGCCUCUUCGGN | 531 | NCCGAAGAGGCCAAGAAAN | 781-799 |

TABLE 2-continued

Example AAT RNAi Agent Antisense Strand and
Sense Strand Core Stretch Base Sequences
(N = any nucleobase)

| SEQ ID NO: | Antisense Base Sequence (5' → 3') (19-mers) | SEQ ID NO: | Sense Base Sequence (5' → 3') (19-mers) | Gene Position of SEQ ID NO: 1 |
|---|---|---|---|---|
| 183 | UUGAUCUGUUUCUUGGCCU | 532 | AGGCCAAGAAACAGAUCAA | 788-806 |
| 184 | AUGAUCUGUUUCUUGGCCU | 533 | AGGCCAAGAAACAGAUCAU | 788-806 |
| 185 | NUGAUCUGUUUCUUGGCCU | 534 | AGGCCAAGAAACAGAUCAN | 788-806 |
| 186 | NUGAUCUGUUUCUUGGCCN | 535 | NGGCCAAGAAACAGAUCAN | 788-806 |
| 187 | GUUGAUCUGUUUCUUGGCC | 536 | GGCCAAGAAACAGAUCAAC | 789-807 |
| 188 | UUUGAUCUGUUUCUUGGCC | 537 | GGCCAAGAAACAGAUCAAA | 789-807 |
| 189 | AUUGAUCUGUUUCUUGGCC | 538 | GGCCAAGAAACAGAUCAAU | 789-807 |
| 190 | NUUGAUCUGUUUCUUGGCC | 539 | GGCCAAGAAACAGAUCAAN | 789-807 |
| 191 | NUUGAUCUGUUUCUUGGCN | 540 | NGCCAAGAAACAGAUCAAN | 789-807 |
| 192 | CGUUGAUCUGUUUCUUGGC | 541 | GCCAAGAAACAGAUCAACG | 790-808 |
| 193 | UGUUGAUCUGUUUCUUGGC | 542 | GCCAAGAAACAGAUCAACA | 790-808 |
| 194 | AGUUGAUCUGUUUCUUGGC | 543 | GCCAAGAAACAGAUCAACU | 790-808 |
| 195 | NGUUGAUCUGUUUCUUGGC | 544 | GCCAAGAAACAGAUCAACN | 790-808 |
| 196 | NGUUGAUCUGUUUCUUGGN | 545 | NCCAAGAAACAGAUCAACN | 790-808 |
| 197 | CACAAUUUUCCCUUGAGUA | 546 | UACUCAAGGGAAAAUUGUG | 825-843 |
| 198 | UACAAUUUUCCCUUGAGUA | 547 | UACUCAAGGGAAAAUUGUA | 825-843 |
| 199 | AACAAUUUUCCCUUGAGUA | 548 | UACUCAAGGGAAAAUUGUU | 825-843 |
| 200 | NACAAUUUUCCCUUGAGUA | 549 | UACUCAAGGGAAAAUUGUN | 825-843 |
| 201 | NACAAUUUUCCCUUGAGUN | 550 | NACUCAAGGGAAAAUUGUN | 825-843 |
| 202 | UCCACAAUUUUCCCUUGAG | 551 | CUCAAGGGAAAAUUGUGGA | 827-845 |
| 203 | ACCACAAUUUUCCCUUGAG | 552 | CUCAAGGGAAAAUUGUGGU | 827-845 |
| 204 | NCCACAAUUUUCCCUUGAG | 553 | CUCAAGGGAAAAUUGUGGN | 827-845 |
| 205 | NCCACAAUUUUCCCUUGAN | 554 | NUCAAGGGAAAAUUGUGGN | 827-845 |
| 206 | AUCCACAAUUUUCCCUUGA | 555 | UCAAGGGAAAAUUGUGGAU | 828-846 |
| 207 | UUCCACAAUUUUCCCUUGA | 556 | UCAAGGGAAAAUUGUGGAA | 828-846 |
| 208 | NUCCACAAUUUUCCCUUGA | 557 | UCAAGGGAAAAUUGUGGAN | 828-846 |
| 209 | NUCCACAAUUUUCCCUUGN | 558 | NCAAGGGAAAAUUGUGGAN | 828-846 |
| 210 | UGUCAAGCUCCUUGACCAA | 559 | UUGGUCAAGGAGCUUGACA | 847-865 |
| 211 | AGUCAAGCUCCUUGACCAA | 560 | UUGGUCAAGGAGCUUGACU | 847-865 |
| 212 | NGUCAAGCUCCUUGACCAA | 561 | NUGGUCAAGGAGCUUGACA | 847-865 |
| 213 | NGUCAAGCUCCUUGACCAN | 562 | NUGGUCAAGGAGCUUGACN | 847-865 |
| 214 | GUGUCUCUGUCAAGCUCCU | 563 | AGGAGCUUGACAGAGACAC | 854-872 |
| 215 | UUGUCUCUGUCAAGCUCCU | 564 | AGGAGCUUGACAGAGACAA | 854-872 |
| 216 | AUGUCUCUGUCAAGCUCCU | 565 | AGGAGCUUGACAGAGACAU | 854-872 |
| 217 | NUGUCUCUGUCAAGCUCCU | 566 | AGGAGCUUGACAGAGACAN | 854-872 |
| 218 | NUGUCUCUGUCAAGCUCCN | 567 | NGGAGCUUGACAGAGACAN | 854-872 |

TABLE 2-continued

Example AAT RNAi Agent Antisense Strand and
Sense Strand Core Stretch Base Sequences
(N = any nucleobase)

| SEQ ID NO: | Antisense Base Sequence (5' → 3') (19-mers) | SEQ ID NO: | Sense Base Sequence (5' → 3') (19-mers) | Gene Position of SEQ ID NO: 1 |
|---|---|---|---|---|
| 219 | ACUGUGUCUCUGUCAAGCU | 568 | AGCUUGACAGAGACACAGU | 857-875 |
| 220 | UCUGUGUCUCUGUCAAGCU | 569 | AGCUUGACAGAGACACAGA | 857-875 |
| 221 | NCUGUGUCUCUGUCAAGCU | 570 | AGCUUGACAGAGACACAGN | 857-875 |
| 222 | NCUGUGUCUCUGUCAAGCN | 571 | NGCUUGACAGAGACACAGN | 857-875 |
| 223 | UGUAAUUCACCAGAGCAAA | 572 | UUUGCUCUGGUGAAUUACA | 877-895 |
| 224 | AGUAAUUCACCAGAGCAAA | 573 | UUUGCUCUGGUGAAUUACU | 877-895 |
| 225 | NGUAAUUCACCAGAGCAAA | 574 | UUUGCUCUGGUGAAUUACN | 877-895 |
| 226 | NGUAAUUCACCAGAGCAAN | 575 | NUUGCUCUGGUGAAUUACN | 877-895 |
| 227 | UUAAACAUGCCUAAACGCU | 576 | AGCGUUUAGGCAUGUUUAA | 998-1016 |
| 228 | AUAAACAUGCCUAAACGCU | 577 | AGCGUUUAGGCAUGUUUAU | 998-1016 |
| 229 | NUAAACAUGCCUAAACGCU | 578 | AGCGUUUAGGCAUGUUUAN | 998-1016 |
| 230 | NUAAACAUGCCUAAACGCN | 579 | NGCGUUUAGGCAUGUUUAN | 998-1016 |
| 231 | GUUAAACAUGCCUAAACGC | 580 | GCGUUUAGGCAUGUUUAAC | 999-1017 |
| 232 | UUUAAACAUGCCUAAACGC | 581 | GCGUUUAGGCAUGUUUAAA | 999-1017 |
| 233 | AUUAAACAUGCCUAAACGC | 582 | GCGUUUAGGCAUGUUUAAU | 999-1017 |
| 234 | NUUAAACAUGCCUAAACGC | 583 | GCGUUUAGGCAUGUUUAAN | 999-1017 |
| 235 | NUUAAACAUGCCUAAACGN | 584 | NCGUUUAGGCAUGUUUAAN | 999-1017 |
| 236 | GGAUGUUAAACAUGCCUAA | 585 | UUAGGCAUGUUUAACAUCC | 1003-1021 |
| 237 | UGAUGUUAAACAUGCCUAA | 586 | UUAGGCAUGUUUAACAUCA | 1003-1021 |
| 238 | AGAUGUUAAACAUGCCUAA | 587 | UUAGGCAUGUUUAACAUCU | 1003-1021 |
| 239 | NGAUGUUAAACAUGCCUAA | 588 | UUAGGCAUGUUUAACAUCN | 1003-1021 |
| 240 | NGAUGUUAAACAUGCCUAN | 589 | NUAGGCAUGUUUAACAUCN | 1003-1021 |
| 241 | AUUUCAUCAGCAGCACCCA | 590 | UGGGUGCUGCUGAUGAAAU | 1045-1063 |
| 242 | UUUUCAUCAGCAGCACCCA | 591 | UGGGUGCUGCUGAUGAAAA | 1045-1063 |
| 243 | NUUUCAUCAGCAGCACCCA | 592 | UGGGUGCUGCUGAUGAAAN | 1045-1063 |
| 244 | NUUUCAUCAGCAGCACCCN | 593 | NGGGUGCUGCUGAUGAAAN | 1045-1063 |
| 245 | GAAGAAGAUGGCGGUGGCA | 594 | UGCCACCGCCAUCUUCUUC | 1074-1092 |
| 246 | UAAGAAGAUGGCGGUGGCA | 595 | UGCCACCGCCAUCUUCUUA | 1074-1092 |
| 247 | AAAGAAGAUGGCGGUGGCA | 596 | UGCCACCGCCAUCUUCUUU | 1074-1092 |
| 248 | NAAGAAGAUGGCGGUGGCA | 597 | UGCCACCGCCAUCUUCUUN | 1074-1092 |
| 249 | NAAGAAGAUGGCGGUGGCN | 598 | NGCCACCGCCAUCUUCUUN | 1074-1092 |
| 250 | GGUGAGUUCAUUUUCCAGG | 599 | CCUGGAAAAUGAACUCACC | 1119-1137 |
| 251 | UGUGAGUUCAUUUUCCAGG | 600 | CCUGGAAAAUGAACUCACA | 1119-1137 |
| 252 | AGUGAGUUCAUUUUCCAGG | 601 | CCUGGAAAAUGAACUCACU | 1119-1137 |
| 253 | NGUGAGUUCAUUUUCCAGG | 602 | CCUGGAAAAUGAACUCACN | 1119-1137 |

TABLE 2-continued

Example AAT RNAi Agent Antisense Strand and
Sense Strand Core Stretch Base Sequences
(N = any nucleobase)

| SEQ ID NO: | Antisense Base Sequence (5' → 3') (19-mers) | SEQ ID NO: | Sense Base Sequence (5' → 3') (19-mers) | Gene Position of SEQ ID NO: 1 |
|---|---|---|---|---|
| 254 | NGUGAGUUCAUUUUCCAGN | 603 | NCUGGAAAAUGAACUCACN | 1119-1137 |
| 255 | GAACUUGGUGAUGAUAUCG | 604 | CGAUAUCAUCACCAAGUUC | 1140-1158 |
| 256 | UAACUUGGUGAUGAUAUCG | 605 | CGAUAUCAUCACCAAGUUA | 1140-1158 |
| 257 | AAACUUGGUGAUGAUAUCG | 606 | CGAUAUCAUCACCAAGUUU | 1140-1158 |
| 258 | NAACUUGGUGAUGAUAUCG | 607 | CGAUAUCAUCACCAAGUUN | 1140-1158 |
| 259 | NAACUUGGUGAUGAUAUCN | 608 | NGAUAUCAUCACCAAGUUN | 1140-1158 |
| 260 | CAUUUUCCAGGAACUUGGU | 609 | ACCAAGUUCCUGGAAAAUG | 1150-1168 |
| 261 | UAUUUUCCAGGAACUUGGU | 610 | ACCAAGUUCCUGGAAAAUA | 1150-1168 |
| 262 | AAUUUUCCAGGAACUUGGU | 611 | ACCAAGUUCCUGGAAAAUU | 1150-1168 |
| 263 | NAUUUUCCAGGAACUUGGU | 612 | ACCAAGUUCCUGGAAAAUN | 1150-1168 |
| 264 | NAUUUUCCAGGAACUUGGN | 613 | NCCAAGUUCCUGGAAAAUN | 1150-1168 |
| 265 | CAUAGGUUCCAGUAAUGGA | 614 | UCCAUUACUGGAACCUAUG | 1207-1225 |
| 266 | UAUAGGUUCCAGUAAUGGA | 615 | UCCAUUACUGGAACCUAUA | 1207-1225 |
| 267 | AAUAGGUUCCAGUAAUGGA | 616 | UCCAUUACUGGAACCUAUU | 1207-1225 |
| 268 | NAUAGGUUCCAGUAAUGGA | 617 | UCCAUUACUGGAACCUAUN | 1207-1225 |
| 269 | NAUAGGUUCCAGUAAUGGN | 618 | NCCAUUACUGGAACCUAUN | 1207-1225 |
| 270 | UCAUAGGUUCCAGUAAUGG | 619 | CCAUUACUGGAACCUAUGA | 1208-1226 |
| 271 | ACAUAGGUUCCAGUAAUGG | 620 | CCAUUACUGGAACCUAUGU | 1208-1226 |
| 272 | NCAUAGGUUCCAGUAAUGG | 621 | CCAUUACUGGAACCUAUGN | 1208-1226 |
| 273 | NCAUAGGUUCCAGUAAUGN | 622 | NCAUUACUGGAACCUAUGN | 1208-1226 |
| 274 | UCAGAUCAUAGGUUCCAGU | 623 | ACUGGAACCUAUGAUCUGA | 1213-1231 |
| 275 | ACAGAUCAUAGGUUCCAGU | 624 | ACUGGAACCUAUGAUCUGU | 1213-1231 |
| 276 | NCAGAUCAUAGGUUCCAGU | 625 | ACUGGAACCUAUGAUCUGN | 1213-1231 |
| 277 | NCAGAUCAUAGGUUCCAGN | 626 | NCUGGAACCUAUGAUCUGN | 1213-1231 |
| 278 | UCUUCAGAUCAUAGGUUCC | 627 | GGAACCUAUGAUCUGAAGA | 1216-1234 |
| 279 | ACUUCAGAUCAUAGGUUCC | 628 | GGAACCUAUGAUCUGAAGU | 1216-1234 |
| 280 | NCUUCAGAUCAUAGGUUCC | 629 | GGAACCUAUGAUCUGAAGN | 1216-1234 |
| 281 | NCUUCAGAUCAUAGGUUCN | 630 | NGAACCUAUGAUCUGAAGN | 1216-1234 |
| 282 | CUCUUCAGAUCAUAGGUUC | 631 | GAACCUAUGAUCUGAAGAG | 1217-1235 |
| 283 | UUCUUCAGAUCAUAGGUUC | 632 | GAACCUAUGAUCUGAAGAA | 1217-1235 |
| 284 | AUCUUCAGAUCAUAGGUUC | 633 | GAACCUAUGAUCUGAAGAU | 1217-1235 |
| 285 | NUCUUCAGAUCAUAGGUUC | 634 | GAACCUAUGAUCUGAAGAG | 1217-1235 |
| 286 | NUCUUCAGAUCAUAGGUUN | 635 | NAACCUAUGAUCUGAAGAN | 1217-1235 |
| 287 | GAGGUCAGCCCCAUUGCUG | 636 | CAGCAAUGGGGCUGACCUC | 1269-1287 |
| 288 | UAGGUCAGCCCCAUUGCUG | 637 | CAGCAAUGGGGCUGACCUA | 1269-1287 |
| 289 | AAGGUCAGCCCCAUUGCUG | 638 | CAGCAAUGGGGCUGACCUU | 1269-1287 |

TABLE 2-continued

Example AAT RNAi Agent Antisense Strand and
Sense Strand Core Stretch Base Sequences
(N = any nucleobase)

| SEQ ID NO: | Antisense Base Sequence (5' → 3') (19-mers) | SEQ ID NO: | Sense Base Sequence (5' → 3') (19-mers) | Gene Position of SEQ ID NO: 1 |
|---|---|---|---|---|
| 290 | NAGGUCAGCCCCAUUGCUG | 639 | CAGCAAUGGGGCUGACCUN | 1269-1287 |
| 291 | NAGGUCAGCCCCAUUGCUN | 640 | NAGCAAUGGGGCUGACCUN | 1269-1287 |
| 292 | GAGAGGUCAGCCCCAUUGC | 641 | GCAAUGGGGCUGACCUCUC | 1271-1289 |
| 293 | UAGAGGUCAGCCCCAUUGC | 642 | GCAAUGGGGCUGACCUCUA | 1271-1289 |
| 294 | AAGAGGUCAGCCCCAUUGC | 643 | GCAAUGGGGCUGACCUCUU | 1271-1289 |
| 295 | NAGAGGUCAGCCCCAUUGC | 644 | GCAAUGGGGCUGACCUCUN | 1271-1289 |
| 296 | NAGAGGUCAGCCCCAUUGN | 645 | NCAAUGGGGCUGACCUCUN | 1271-1289 |
| 297 | CUUCAGGGGUGCCUCCUCU | 646 | AGAGGAGGCACCCCUGAAG | 1299-1317 |
| 298 | UUUCAGGGGUGCCUCCUCU | 647 | AGAGGAGGCACCCCUGAAA | 1299-1317 |
| 299 | AUUCAGGGGUGCCUCCUCU | 648 | AGAGGAGGCACCCCUGAAU | 1299-1317 |
| 300 | NUUCAGGGGUGCCUCCUCU | 649 | AGAGGAGGCACCCCUGAAN | 1299-1317 |
| 301 | NUUCAGGGGUGCCUCCUCN | 650 | NGAGGAGGCACCCCUGAAN | 1299-1317 |
| 302 | GAGAGCUUCAGGGGUGCCU | 651 | AGGCACCCCUGAAGCUCUC | 1304-1322 |
| 303 | UAGAGCUUCAGGGGUGCCU | 652 | AGGCACCCCUGAAGCUCUA | 1304-1322 |
| 304 | AAGAGCUUCAGGGGUGCCU | 653 | AGGCACCCCUGAAGCUCUU | 1304-1322 |
| 305 | NAGAGCUUCAGGGGUGCCU | 654 | AGGCACCCCUGAAGCUCUN | 1304-1322 |
| 306 | NAGAGCUUCAGGGGUGCCN | 655 | NGGCACCCCUGAAGCUCUN | 1304-1322 |
| 307 | UUAUGCACGGCCUUGGAGA | 656 | UCUCCAAGGCCGUGCAUAA | 1319-1337 |
| 308 | AUAUGCACGGCCUUGGAGA | 657 | UCUCCAAGGCCGUGCAUAU | 1319-1337 |
| 309 | NUAUGCACGGCCUUGGAGA | 658 | UCUCCAAGGCCGUGCAUAN | 1319-1337 |
| 310 | NUAUGCACGGCCUUGGAGN | 659 | NCUCCAAGGCCGUGCAUAN | 1319-1337 |
| 311 | CCUUAUGCACGGCCUUGGA | 660 | UCCAAGGCCGUGCAUAAGG | 1321-1339 |
| 312 | UCUUAUGCACGGCCUUGGA | 661 | UCCAAGGCCGUGCAUAAGA | 1321-1339 |
| 313 | ACUUAUGCACGGCCUUGGA | 662 | UCCAAGGCCGUGCAUAAGU | 1321-1339 |
| 314 | NCUUAUGCACGGCCUUGGA | 663 | UCCAAGGCCGUGCAUAAGN | 1321-1339 |
| 315 | NCUUAUGCACGGCCUUGGN | 664 | NCCAAGGCCGUGCAUAAGN | 1321-1339 |
| 316 | GCCUUAUGCACGGCCUUGG | 665 | CCAAGGCCGUGCAUAAGGC | 1322-1340 |
| 317 | UCCUUAUGCACGGCCUUGG | 666 | CCAAGGCCGUGCAUAAGGA | 1322-1340 |
| 318 | ACCUUAUGCACGGCCUUGG | 667 | CCAAGGCCGUGCAUAAGGU | 1322-1340 |
| 319 | NCCUUAUGCACGGCCUUGG | 668 | CCAAGGCCGUGCAUAAGGN | 1322-1340 |
| 320 | NCCUUAUGCACGGCCUUGN | 669 | NCAAGGCCGUGCAUAAGGN | 1322-1340 |
| 321 | AGCCUUAUGCACGGCCUUG | 670 | CAAGGCCGUGCAUAAGGCU | 1323-1341 |
| 322 | UGCCUUAUGCACGGCCUUG | 671 | CAAGGCCGUGCAUAAGGCA | 1323-1341 |
| 323 | NGCCUUAUGCACGGCCUUG | 672 | CAAGGCCGUGCAUAAGGCN | 1323-1341 |
| 324 | NGCCUUAUGCACGGCCUUN | 673 | NAAGGCCGUGCAUAAGGCN | 1323-1341 |

TABLE 2-continued

Example AAT RNAi Agent Antisense Strand and
Sense Strand Core Stretch Base Sequences
(N = any nucleobase)

| SEQ ID NO: | Antisense Base Sequence (5' → 3') (19-mers) | SEQ ID NO: | Sense Base Sequence (5' → 3') (19-mers) | Gene Position of SEQ ID NO: 1 |
|---|---|---|---|---|
| 325 | CGAUGGUCAGCACAGCCUU | 674 | AAGGCUGUGCUGACCAUCG | 1336-1354 |
| 326 | UGAUGGUCAGCACAGCCUU | 675 | AAGGCUGUGCUGACCAUCA | 1336-1354 |
| 327 | AGAUGGUCAGCACAGCCUU | 676 | AAGGCUGUGCUGACCAUCU | 1336-1354 |
| 328 | NGAUGGUCAGCACAGCCUU | 677 | AAGGCUGUGCUGACCAUCN | 1336-1354 |
| 329 | NGAUGGUCAGCACAGCCUN | 678 | NAGGCUGUGCUGACCAUCN | 1336-1354 |
| 330 | GUCGAUGGUCAGCACAGCC | 679 | GGCUGUGCUGACCAUCGAC | 1338-1356 |
| 331 | UUCGAUGGUCAGCACAGCC | 680 | GGCUGUGCUGACCAUCGAA | 1338-1356 |
| 332 | AUCGAUGGUCAGCACAGCC | 681 | GGCUGUGCUGACCAUCGAU | 1338-1356 |
| 333 | NUCGAUGGUCAGCACAGCC | 682 | GGCUGUGCUGACCAUCGAN | 1338-1356 |
| 334 | NUCGAUGGUCAGCACAGCN | 683 | NGCUGUGCUGACCAUCGAN | 1338-1356 |
| 335 | AAAAACAUGGCCCCAGCAG | 684 | CUGCUGGGGCCAUGUUUUU | 1373-1391 |
| 336 | UAAAACAUGGCCCCAGCAG | 685 | CUGCUGGGGCCAUGUUUUA | 1373-1391 |
| 337 | NAAAACAUGGCCCCAGCAG | 686 | CUGCUGGGGCCAUGUUUUN | 1373-1391 |
| 338 | NAAAACAUGGCCCCAGCAN | 687 | NUGCUGGGGCCAUGUUUUN | 1373-1391 |
| 339 | CUAAAAACAUGGCCCCAGC | 688 | GCUGGGGCCAUGUUUUUAG | 1375-1393 |
| 340 | UUAAAAACAUGGCCCCAGC | 689 | GCUGGGGCCAUGUUUUUAA | 1375-1393 |
| 341 | AUAAAAACAUGGCCCCAGC | 690 | GCUGGGGCCAUGUUUUUAU | 1375-1393 |
| 342 | NUAAAAACAUGGCCCCAGC | 691 | GCUGGGGCCAUGUUUUUAN | 1375-1393 |
| 343 | NUAAAAACAUGGCCCCAGN | 692 | NCUGGGGCCAUGUUUUUAN | 1375-1393 |
| 344 | UCUAAAAACAUGGCCCCAG | 693 | CUGGGGCCAUGUUUUUAGA | 1376-1394 |
| 345 | ACUAAAAACAUGGCCCCAG | 694 | CUGGGGCCAUGUUUUUAGU | 1376-1394 |
| 346 | NCUAAAAACAUGGCCCCAG | 695 | CUGGGGCCAUGUUUUUAGN | 1376-1394 |
| 347 | NCUAAAAACAUGGCCCCAN | 696 | NUGGGGCCAUGUUUUUAGN | 1376-1394 |
| 348 | CCUCUAAAAACAUGGCCCC | 697 | GGGGCCAUGUUUUUAGAGG | 1378-1396 |
| 349 | UCUCUAAAAACAUGGCCCC | 698 | GGGGCCAUGUUUUUAGAGA | 1378-1396 |
| 350 | ACUCUAAAAACAUGGCCCC | 699 | GGGGCCAUGUUUUUAGAGU | 1378-1396 |
| 351 | NCUCUAAAAACAUGGCCCC | 700 | GGGGCCAUGUUUUUAGAGN | 1378-1396 |
| 352 | NCUCUAAAAACAUGGCCCN | 701 | NGGGCCAUGUUUUUAGAGN | 1378-1396 |
| 353 | GCCUCUAAAAACAUGGCCC | 702 | GGGCCAUGUUUUUAGAGGC | 1379-1397 |
| 354 | UCCUCUAAAAACAUGGCCC | 703 | GGGCCAUGUUUUUAGAGGA | 1379-1397 |
| 355 | ACCUCUAAAAACAUGGCCC | 704 | GGGCCAUGUUUUUAGAGGU | 1379-1397 |
| 356 | NCCUCUAAAAACAUGGCCC | 705 | GGGCCAUGUUUUUAGAGGN | 1379-1397 |
| 357 | NCCUCUAAAAACAUGGCCN | 706 | NGGCCAUGUUUUUAGAGGN | 1379-1397 |
| 358 | UAGACAUGGGUAUGGCCUC | 707 | GAGGCCAUACCCAUGUCUA | 1393-1411 |
| 359 | AAGACAUGGGUAUGGCCUC | 708 | GAGGCCAUACCCAUGUCUU | 1393-1411 |
| 360 | NAGACAUGGGUAUGGCCUC | 709 | GAGGCCAUACCCAUGUCUN | 1393-1411 |

TABLE 2-continued

Example AAT RNAi Agent Antisense Strand and
Sense Strand Core Stretch Base Sequences
(N = any nucleobase)

| SEQ ID NO: | Antisense Base Sequence (5' → 3') (19-mers) | SEQ ID NO: | Sense Base Sequence (5' → 3') (19-mers) | Gene Position of SEQ ID NO: 1 |
|---|---|---|---|---|
| 361 | NAGACAUGGGUAUGGCCUN | 710 | NAGGCCAUACCCAUGUCUN | 1393-1411 |
| 362 | GAUAGACAUGGGUAUGGCC | 711 | GGCCAUACCCAUGUCUAUC | 1395-1413 |
| 363 | UAUAGACAUGGGUAUGGCC | 712 | GGCCAUACCCAUGUCUAUA | 1395-1413 |
| 364 | AAUAGACAUGGGUAUGGCC | 713 | GGCCAUACCCAUGUCUAUU | 1395-1413 |
| 365 | NAUAGACAUGGGUAUGGCC | 714 | GGCCAUACCCAUGUCUAUN | 1395-1413 |
| 366 | NAUAGACAUGGGUAUGGCN | 715 | NGCCAUACCCAUGUCUAUN | 1395-1413 |
| 367 | UGUUGAACUUGACCUCGGG | 716 | CCCGAGGUCAAGUUCAACA | 1417-1435 |
| 368 | AGUUGAACUUGACCUCGGG | 717 | CCCGAGGUCAAGUUCAACU | 1417-1435 |
| 369 | NGUUGAACUUGACCUCGGG | 718 | CCCGAGGUCAAGUUCAACN | 1417-1435 |
| 370 | NGUUGAACUUGACCUCGGN | 719 | NCCGAGGUCAAGUUCAACN | 1417-1435 |
| 371 | GGUUUGUUGAACUUGACCU | 720 | AGGUCAAGUUCAACAAACC | 1421-1439 |
| 372 | UGUUUGUUGAACUUGACCU | 721 | AGGUCAAGUUCAACAAACA | 1421-1439 |
| 373 | AGUUUGUUGAACUUGACCU | 722 | AGGUCAAGUUCAACAAACU | 1421-1439 |
| 374 | NGUUUGUUGAACUUGACCU | 723 | AGGUCAAGUUCAACAAACN | 1421-1439 |
| 375 | NGUUUGUUGAACUUGACCN | 724 | NGGUCAAGUUCAACAAACN | 1421-1439 |
| 376 | AAAGGGUUUGUUGAACUUG | 725 | CAAGUUCAACAAACCCUUU | 1425-1443 |
| 377 | UAAGGGUUUGUUGAACUUG | 726 | CAAGUUCAACAAACCCUUA | 1425-1443 |
| 378 | NAAGGGUUUGUUGAACUUG | 727 | CAAGUUCAACAAACCCUUN | 1425-1443 |
| 379 | NAAGGGUUUGUUGAACUUN | 728 | NAAGUUCAACAAACCCUUN | 1425-1443 |
| 380 | ACAAAGGGUUUGUUGAACU | 729 | AGUUCAACAAACCCUUUGU | 1427-1445 |
| 381 | UCAAAGGGUUUGUUGAACU | 730 | AGUUCAACAAACCCUUUGA | 1427-1445 |
| 382 | NCAAAGGGUUUGUUGAACU | 731 | AGUUCAACAAACCCUUUGN | 1427-1445 |
| 383 | NCAAAGGGUUUGUUGAACN | 732 | NGUUCAACAAACCCUUUGN | 1427-1445 |
| 384 | GACAAAGGGUUUGUUGAAC | 733 | GUUCAACAAACCCUUUGUC | 1428-1446 |
| 385 | UACAAAGGGUUUGUUGAAC | 734 | GUUCAACAAACCCUUUGUA | 1428-1446 |
| 386 | AACAAAGGGUUUGUUGAAC | 735 | GUUCAACAAACCCUUUGUU | 1428-1446 |
| 387 | NACAAAGGGUUUGUUGAAC | 736 | GUUCAACAAACCCUUUGUN | 1428-1446 |
| 388 | NACAAAGGGUUUGUUGAAN | 737 | NUUCAACAAACCCUUUGUN | 1428-1446 |
| 389 | AAGACAAAGGGUUUGUUGA | 738 | UCAACAAACCCUUUGUCUU | 1430-1448 |
| 390 | UAGACAAAGGGUUUGUUGA | 739 | UCAACAAACCCUUUGUCUA | 1430-1448 |
| 391 | NAGACAAAGGGUUUGUUGA | 740 | UCAACAAACCCUUUGUCUN | 1430-1448 |
| 392 | NAGACAAAGGGUUUGUUGN | 741 | NCAACAAACCCUUUGUCUN | 1430-1448 |
| 393 | CAUUAAGAAGACAAAGGGU | 742 | ACCCUUUGUCUUCUUAAUG | 1437-1455 |
| 394 | UAUUAAGAAGACAAAGGGU | 743 | ACCCUUUGUCUUCUUAAUA | 1437-1455 |
| 395 | AAUUAAGAAGACAAAGGGU | 744 | ACCCUUUGUCUUCUUAAUU | 1437-1455 |

TABLE 2-continued

Example AAT RNAi Agent Antisense Strand and
Sense Strand Core Stretch Base Sequences
(N = any nucleobase)

| SEQ ID NO: | Antisense Base Sequence (5' → 3') (19-mers) | SEQ ID NO: | Sense Base Sequence (5' → 3') (19-mers) | Gene Position of SEQ ID NO: 1 |
|---|---|---|---|---|
| 396 | NAUUAAGAAGACAAAGGGU | 745 | ACCCUUUGUCUUCUUAAUN | 1437-1455 |
| 397 | NAUUAAGAAGACAAAGGGN | 746 | NCCCUUUGUCUUCUUAAUN | 1437-1455 |
| 398 | AUCAUUAAGAAGACAAAGG | 747 | CCUUUGUCUUCUUAAUGAU | 1439-1457 |
| 399 | UUCAUUAAGAAGACAAAGG | 748 | CCUUUGUCUUCUUAAUGAA | 1439-1457 |
| 400 | NUCAUUAAGAAGACAAAGG | 749 | CCUUUGUCUUCUUAAUGAN | 1439-1457 |
| 401 | NUCAUUAAGAAGACAAAGN | 750 | NCUUUGUCUUCUUAAUGAN | 1439-1457 |
| 402 | GAAGAGGGGAGACUUGGUA | 751 | UACCAAGUCUCCCCUCUUC | 1467-1485 |
| 403 | UAAGAGGGGAGACUUGGUA | 752 | UACCAAGUCUCCCCUCUUA | 1467-1485 |
| 404 | AAAGAGGGGAGACUUGGUA | 753 | UACCAAGUCUCCCCUCUUU | 1467-1485 |
| 405 | NAAGAGGGGAGACUUGGUA | 754 | UACCAAGUCUCCCCUCUUN | 1467-1485 |
| 406 | NAAGAGGGGAGACUUGGUN | 755 | NACCAAGUCUCCCCUCUUN | 1467-1485 |
| 407 | CCAUGAAGAGGGGAGACUU | 756 | AAGUCUCCCCUCUUCAUGG | 1471-1489 |
| 408 | UCAUGAAGAGGGGAGACUU | 757 | AAGUCUCCCCUCUUCAUGA | 1471-1489 |
| 409 | ACAUGAAGAGGGGAGACUU | 758 | AAGUCUCCCCUCUUCAUGU | 1471-1489 |
| 410 | NCAUGAAGAGGGGAGACUU | 759 | AAGUCUCCCCUCUUCAUGN | 1471-1489 |
| 411 | NCAUGAAGAGGGGAGACUN | 760 | NAGUCUCCCCUCUUCAUGN | 1471-1489 |
| 412 | CCCAUGAAGAGGGGAGACU | 761 | AGUCUCCCCUCUUCAUGGG | 1472-1490 |
| 413 | UCCAUGAAGAGGGGAGACU | 762 | AGUCUCCCCUCUUCAUGGA | 1472-1490 |
| 414 | ACCAUGAAGAGGGGAGACU | 763 | AGUCUCCCCUCUUCAUGGU | 1472-1490 |
| 415 | NCCAUGAAGAGGGGAGACU | 764 | AGUCUCCCCUCUUCAUGGN | 1472-1490 |
| 416 | NCCAUGAAGAGGGGAGACN | 765 | NGUCUCCCCUCUUCAUGGN | 1472-1490 |
| 417 | UUCCCAUGAAGAGGGGAGA | 766 | UCUCCCCUCUUCAUGGGAA | 1474-1492 |
| 418 | AUCCCAUGAAGAGGGGAGA | 767 | UCUCCCCUCUUCAUGGGAU | 1474-1492 |
| 419 | NUCCCAUGAAGAGGGGAGA | 768 | UCUCCCCUCUUCAUGGGAN | 1474-1492 |
| 420 | NUCCCAUGAAGAGGGGAGN | 769 | NCUCCCCUCUUCAUGGGAN | 1474-1492 |
| 421 | UUUCCCAUGAAGAGGGGAG | 770 | CUCCCCUCUUCAUGGGAAA | 1475-1493 |
| 422 | AUUCCCAUGAAGAGGGGAG | 771 | CUCCCCUCUUCAUGGGAAU | 1475-1493 |
| 423 | NUUCCCAUGAAGAGGGGAG | 772 | CUCCCCUCUUCAUGGGAAN | 1475-1493 |
| 424 | NUUCCCAUGAAGAGGGGAN | 773 | NUCCCCUCUUCAUGGGAAN | 1475-1493 |
| 425 | AACCCUUCUUUAAUGUCAU | 774 | AUGACAUUAAAGAAGGGUU | 1569-1587 |
| 426 | UACCCUUCUUUAAUGUCAU | 775 | AUGACAUUAAAGAAGGGUA | 1569-1587 |
| 427 | NACCCUUCUUUAAUGUCAU | 776 | AUGACAUUAAAGAAGGGUN | 1569-1587 |
| 428 | NACCCUUCUUUAAUGUCAN | 777 | NUGACAUUAAAGAAGGGUN | 1569-1587 |

TABLE 3

Example AAT RNAi Agent Antisense Strand and Sense Strand Base Sequences

| SEQ ID NO: | Antisense Base Sequence (5' → 3') | SEQ ID NO: | Sense Base Sequence (5' → 3') |
|---|---|---|---|
| 778 | GGAACUUGGUGAUGAUAU | 840 | AUAUCAUCACCAAGUUCC |
| 779 | GAUCAUAGGUUCCAGUAA | 841 | UUACUGGAACCUAUGAUC |
| 780 | ACAGCCUUAUGCACGGCC | 842 | GGCCGUGCAUAAGGCUGU |
| 781 | UCGAUGGUCAGCACAGCC | 843 | GGCUGUGCUGACCAUCGA |
| 782 | CAAAGGGUUUGUUGAACU | 844 | AGUUCAACAAACCCUUUG |
| 783 | TGGAACUUGGUGAUGAUAUTT | 845 | UAUAUAUCAUCACCAAGUUCCAT |
| 783 | TGGAACUUGGUGAUGAUAUTT | 846 | AUAUCAUCACCAAGUUCCAT |
| 784 | TGGAACUUGGUGAUGAUAUCGUG | 847 | CGAUAUCAUCACCAAGUUCCA |
| 785 | ACUUGGUGAUGAUAUTT | 848 | UAUCAUCACCAAGUUCCAT |
| 786 | TGGAACTTGGTGATGATATTT | 849 | TATATATCATCACCAAGTTCCAT |
| 787 | UUUAAACAUGCCUAAACGCUU | 850 | GCGUUUAGGCAUGUUUAAAUU |
| 788 | UGCAUUGCCCAGGUAUUUCUU | 851 | GAAAUACCUGGGCAAUGCAUU |
| 789 | UGGAACUUGGUGAUGAUAUUU | 852 | AUAUCAUCACCAAGUUCCAUU |
| 790 | UGAUCAUAGGUUCCAGUAAUU | 853 | UUACUGGAACCUAUGAUCAUU |
| 791 | UACAGCCUUAUGCACGGCCUU | 854 | GGCCGUGCAUAAGGCUGUAUU |
| 792 | UUCGAUGGUCAGCACAGCCUU | 855 | GGCUGUGCUGACCAUCGAAUU |
| 793 | UCAAAGGGUUUGUUGAACUUU | 856 | AGUUCAACAAACCCUUUGAUU |
| 794 | UGUUAAACAUGCCUAAACGUU | 857 | CGUUUAGGCAUGUUUAACAUU |
| 795 | UUUAAACGUGCCUAAACGCUG | 858 | CAGCGUUUAGGCAUGUUUAAA |
| 796 | UGCAUUGCCCAGGUAUUUCAG | 859 | CUGAAAUACCUGGGCAAUGCA |
| 797 | UGGAACUUGGUGAUGAUAUCG | 847 | CGAUAUCAUCACCAAGUUCCA |
| 798 | UGAUCAUAGGUUCCAGUAAUG | 860 | CAUUACUGGAACCUAUGAUCA |
| 791 | UACAGCCUUAUGCACGGCCUU | 861 | AAGGCCGUGCAUAAGGCUGUA |
| 792 | UUCGAUGGUCAGCACAGCCUU | 862 | AAGGCUGUGCUGACCAUCGAA |
| 799 | UCAAAGGGUUUGUUGAACUUG | 863 | CAAGUUCAACAAACCCUUUGA |
| 800 | UGUUAAACAUGCCUAAACGCG | 864 | CGCGUUUAGGCAUGUUUAACA |
| 801 | UGUUAAACAUGCCUAAACGCU | 857 | CGUUUAGGCAUGUUUAACAUU |
| 794 | UGUUAAACAUGCCUAAACGUU | 1265 | CGUUUAGGCAUGUUUAACA |
| 801 | UGUUAAACAUGCCUAAACGCU | 1265 | CGUUUAGGCAUGUUUAACA |
| 794 | UGUUAAACAUGCCUAAACGUU | 865 | AACGUUUAGGCAUGUUUAACA |
| 801 | UGUUAAACAUGCCUAAACGCU | 866 | AGCGUUUAGGCAUGUUUAACA |
| 802 | UGUUAAACAUGCCUAAACGCUUC | 866 | AGCGUUUAGGCAUGUUUAACA |
| 803 | UGCUGUUGGACUGGUGUGCUU | 1266 | GCACACCAGUCCAACAGCA |
| 804 | UGCUGUUGGACUGGUGUGCCA | 1266 | GCACACCAGUCCAACAGCA |
| 804 | UGCUGUUGGACUGGUGUGCCA | 867 | UGGCACACCAGUCCAACAGCA |
| 803 | UGCUGUUGGACUGGUGUGCUU | 868 | AAGCACACCAGUCCAACAGCA |
| 805 | UGCUGUUGGACUGGUGUGCCAUU | 867 | UGGCACACCAGUCCAACAGCA |

TABLE 3-continued

Example AAT RNAi Agent Antisense Strand and
Sense Strand Base Sequences

| SEQ ID NO: | Antisense Base Sequence (5' → 3') | SEQ ID NO: | Sense Base Sequence (5' → 3') |
|---|---|---|---|
| 806 | UGCUGUUGGACUGGUGUGCCAGC | 867 | UGGCACACCAGUCCAACAGCA |
| 807 | UAAGGCUUCUGAGUGGUACUU | 1267 | GUACCACUCAGAAGCCUUA |
| 808 | UAAGGCUUCUGAGUGGUACAA | 1267 | GUACCACUCAGAAGCCUUA |
| 808 | UAAGGCUUCUGAGUGGUACAA | 869 | UUGUACCACUCAGAAGCCUUA |
| 809 | UAAGGCUUCUGAGUGGUACAACU | 869 | UUGUACCACUCAGAAGCCUUA |
| 810 | GAAGGCUUCUGAGUGGUACUU | 1268 | GUACCACUCAGAAGCCUUC |
| 811 | AAGACAAAGGGUUUGUUGAUU | 1269 | UCAACAAACCCUUUGUCUU |
| 812 | AAGACAAAGGGUUUGUUGAAC | 1269 | UCAACAAACCCUUUGUCUU |
| 812 | AAGACAAAGGGUUUGUUGAAC | 870 | GUUCAACAAACCCUUUGUCUU |
| 813 | UAGACAAAGGGUUUGUUGAAC | 871 | GUUCAACAAACCCUUUGUCUA |
| 814 | AAGACAAAGGGUUUGUUGAACUU | 870 | GUUCAACAAACCCUUUGUCUU |
| 815 | UAGACAUGGGUAUGGCCUCUU | 1270 | GAGGCCAUACCCAUGUCUA |
| 816 | UAGACAUGGGUAUGGCCUCUA | 1270 | GAGGCCAUACCCAUGUCUA |
| 816 | UAGACAUGGGUAUGGCCUCUA | 872 | UAGAGGCCAUACCCAUGUCUA |
| 817 | UAGACAUGGGUAUGGCCUCUAAA | 872 | UAGAGGCCAUACCCAUGUCUA |
| 818 | UAGACAUGGGUAUGGCCUCUAUU | 872 | UAGAGGCCAUACCCAUGUCUA |
| 819 | UUUGAUCUGUUUCUUGGCCUU | 1271 | GGCCAAGAAACAGAUCAAA |
| 820 | UUUGAUCUGUUUCUUGGCCUC | 1271 | GGCCAAGAAACAGAUCAAA |
| 820 | UUUGAUCUGUUUCUUGGCCUC | 873 | GAGGCCAAGAAACAGAUCAAA |
| 821 | UUUGAUCUGUUUCUUGGCCUCUU | 873 | GAGGCCAAGAAACAGAUCAAA |
| 822 | UGUUGGACUGGUGUGCCAGUU | 1272 | CUGGCACACCAGUCCAACA |
| 823 | UGUUGGACUGGUGUGCCAGCU | 874 | AGCUGGCACACCAGUCCAACA |
| 824 | UGUUGGACUGGUGUGCCAGCUGG | 874 | AGCUGGCACACCAGUCCAACA |
| 825 | UGUUGGACUGGUGUGCCAGCUG | 875 | GCUGGCACACCAGUCCAACA |
| 826 | AAAGGGUUUGUUGAACUUGUU | 1273 | CAAGUUCAACAAACCCUUU |
| 827 | AAAGGGUUUGUUGAACUUGAC | 876 | GUCAAGUUCAACAAACCCUUU |
| 828 | UAAGGGUUUGUUGAACUUGACCU | 877 | GUCAAGUUCAACAAACCCUUA |
| 829 | UAAGGGUUUGUUGAACUUGAC | 877 | GUCAAGUUCAACAAACCCUUA |
| 830 | UAUUGGUGCUGUUGGACUGUU | 1274 | CAGUCCAACAGCACCAAUA |
| 831 | UAUUGGUGCUGUUGGACUGGU | 878 | ACCAGUCCAACAGCACCAAUA |
| 832 | UAUUGGUGCUGUUGGACUGGUU | 879 | CCAGUCCAACAGCACCAAUA |
| 833 | UUGUUGGACUGGUGUGCCAG | 880 | CUGGCACACCAGUCCAACAA |
| 834 | UUGUUGGACUGGUGUGCCAGCU | 880 | CUGGCACACCAGUCCAACAA |
| 835 | UAUAGACAUGGGUAUGGCCUC | 1275 | GGCCAUACCCAUGUCUAUA |
| 835 | UAUAGACAUGGGUAUGGCCUC | 881 | GAGGCCAUACCCAUGUCUAUA |
| 836 | UCAAGGGUUUGUUGAACUUGAC | 882 | GUCAAGUUCAACAAACCCUUUGA |
| 836 | UCAAGGGUUUGUUGAACUUGAC | 863 | CAAGUUCAACAAACCCUUUGA |

TABLE 3-continued

Example AAT RNAi Agent Antisense Strand and Sense Strand Base Sequences

| SEQ ID NO: | Antisense Base Sequence (5' → 3') | SEQ ID NO: | Sense Base Sequence (5' → 3') |
|---|---|---|---|
| 837 | UUAUUGGUGCUGUUGGACUGG | 883 | CCAGUCCAACAGCACCAAUAA |
| 838 | UGUUAAACAUGCCUAAACGC | 884 | GCGUUUAGGCAUGUUUAACA |
| 839 | UGUUAAACAUGCCUAAACGCUU | 884 | GCGUUUAGGCAUGUUUAACA |
| 839 | UGUUAAACAUGCCUAAACGCUU | 885 | GCGUUUAGGCAUGUUUAACAUU |
| 800 | UGUUAAACAUGCCUAAACGCG | 886 | CGCGUUUAGGCAUGUUUAACAUU |
| 801 | UGUUAAACAUGCCUAAACGCU | 887 | AGCGUUUAGGCAUGUUUAACAUU |
| 838 | UGUUAAACAUGCCUAAACGC | 885 | GCGUUUAGGCAUGUUUAACAUU |

The AAT RNAi agent sense strands and antisense strands that comprise or consist of the nucleotide sequences in Table 2 or Table 3 can be modified nucleotides or unmodified nucleotides. In some embodiments, the AAT RNAi agents having the sense and antisense strand sequences that comprise or consist of any of the nucleotide sequences in Table 2 or Table 3 are all or substantially all modified nucleotides.

In some embodiments, the antisense strand of an AAT RNAi agent disclosed herein differs by 0, 1, 2, or 3 nucleotides from any of the antisense strand sequences in Table 2 or Table 3. In some embodiments, the sense strand of an AAT RNAi agent disclosed herein differs by 0, 1, 2, or 3 nucleotides from any of the sense strand sequences in Table 2 or Table 3.

As used herein, each N listed in a sequence disclosed in Table 2 may be independently selected. In some embodiments, an N nucleotide listed in a sequence disclosed in Table 2 has a nucleobase that is complementary to the N nucleotide at the corresponding position on the other strand. In some embodiments, an N nucleotide listed in a sequence disclosed in Table 2 has a nucleobase that is not complementary to the N nucleotide at the corresponding position on the other strand. In some embodiments, an N nucleotide listed in a sequence disclosed in Table 2 has a nucleobase that is the same as the N nucleotide at the corresponding position on the other strand. In some embodiments, an N nucleotide listed in a sequence disclosed in Table 2 has a nucleobase that is different from the N nucleotide at the corresponding position on the other strand.

Certain modified AAT RNAi agent sense and antisense strands are provided in Table 4 and Table 5. Modified AAT RNAi agent antisense strands, as well as their underlying unmodified nucleobase sequences, are provided in Table 4. Modified AAT RNAi agent sense strands, as well as their underlying unmodified sequences, are provided in Table 5. In forming AAT RNAi agents, each of the nucleotides in each of the unmodified sequences listed in Tables 4 and 5, as well as in Table 2 and Table 3, above, can be a modified nucleotide.

The AAT RNAi agents described herein are formed by annealing an antisense strand with a sense strand. A sense strand containing a sequence listed in Table 2, Table 3, or Table 5, can be hybridized to any antisense strand containing a sequence listed in Table 2, Table 3, or Table 4, provided the two sequences have a region of at least 85% complementarity over a contiguous 16, 17, 18, 19, 20, or 21 nucleotide sequence.

In some embodiments, an AAT RNAi agent antisense strand comprises a nucleotide sequence of any of the sequences in Table 2, Table 3, or Table 4.

In some embodiments, an AAT RNAi agent comprises or consists of a duplex having the nucleobase sequences of the sense strand and the antisense strand of any of the sequences in Table 2 or Table 3.

Examples of antisense strands containing modified nucleotides are provided in Table 4. Examples of sense strands containing modified nucleotides are provided in Table 5.

As used in Tables 4 and 5, the following notations are used to indicate modified nucleotides, targeting groups, and linking groups. As the person of ordinary skill in the art would readily understand, unless otherwise indicated by the sequence, that when present in an oligonucleotide, the monomers are mutually linked by 5'-3'-phosphodiester bonds:

A=adenosine-3'-phosphate;
C=cytidine-3'-phosphate;
G=guanosine-3'-phosphate;
U=uridine-3'-phosphate
n=any 2'-OMe modified nucleotide
a=2'-O-methyladenosine-3'-phosphate
as=2'-O-methyladenosine-3'-phosphorothioate
c=2'-O-methylcytidine-3'-phosphate
cs=2'-O-methylcytidine-3'-phosphorothioate
g=2'-O-methylguanosine-3'-phosphate
gs=2'-O-methylguanosine-3'-phosphorothioate
t=2'-O-methyl-5-methyluridine-3'-phosphate
ts=2'-O-methyl-5-methyluridine-3'-phosphorothioate
u=2'-O-methyluridine-3'-phosphate
us=2'-O-methyluridine-3'-phosphorothioate
Nf=any 2'-fluoro modified nucleotide
Af=2'-fluoroadenosine-3'-phosphate
Afs=2'-fluoroadenosine-3'-phosorothioate
Cf=2'-fluorocytidine-3'-phosphate
Cfs=2'-fluorocytidine-3'-phosphorothioate
Gf=2'-fluoroguanosine-3'-phosphate
Gfs=2'-fluoroguanosine-3'-phosphorothioate
Tf=2'-fluoro-5'-methyluridine-3'-phosphate
Tfs=2'-fluoro-5'-methyluridine-3'-phosphorothioate
Uf=2'-fluorouridine-3'-phosphate
Ufs=2'-fluorouridine-3'-phosphorothioate
dN=any 2'-deoxyribonucleotide
dT=2'-deoxythymidine-3'-phosphate N$_{UNA}$=2',3'-seco nucleotide mimics (unlocked nucleobase analogs)-3'-Phosphate
N$_{UNAS}$=2',3'-seco nucleotide mimics (unlocked nucleobase analogs)-3'-phosphorothioate
U$_{UNA}$=2',3'-seco-uridine-3'-phosphate
U$_{UNAS}$=2',3'-seco-uridine-3'-phosphorothioate
a_2N=see Table 7
a_2Ns=see Table 7
pu_2N=see Table 7
pu_2Ns=see Table 7
Npu=see Table 7
Nus=see Table 7
N$_{LNA}$=locked nucleotide
Nf$_{ANA}$=2'-F-Arabino nucleotide
NM=2'-methoxyethyl nucleotide
AM=2'-methoxyethyladenosine-3'-phosphate
AMs=2'-methoxyethyladenosine-3'-phosphorothioate
TM=2'-methoxyethylthymidine-3'-phosphate
TMs=2'-methoxyethylthymidine-3'-phosphorothioate
R=ribitol
(invdN)=any inverted deoxyribonucleotide (3'-3' linked nucleotide)
(invAb)=inverted (3'-3' linked) abasic deoxyribonucleotide, see Table 7
(invAb)s=inverted (3'-3' linked) abasic deoxyribonucleotide-5'-phosphorothioate, see Table 7
(invn)=any inverted 2'-OMe nucleotide (3'-3' linked nucleotide)
s=phosphorothioate linkage
vpdN=vinyl phosphonate deoxyribonucleotide
(5Me-Nf)=5'-Me, 2'-fluoro nucleotide
cPrp=cyclopropyl phosphonate, see Table 7
epTcPr=see Table 7
epTM=see Table 7
(Chol-TEG)=see Table 7
(TEG-Biotin)=see Table 7
(PEG-C3-SS)=see Table 7
(Alk-SS-C6)=see Table 7
(C6-SS-Alk)=see Table 7
(C6-SS-Alk-Me)=see Table 7

The person or ordinary skill in the art would readily understand that the terminal nucleotide at the 3" end of a given oligonucleotide sequence would typically have a hydroxyl (—OH) group at the respective 3° position of the given monomer instead of a phosphate moiety ex vivo. Unless expressly indicated otherwise herein, such understandings of the person of ordinary skill in the art are used when describing the AAT RNAi agents and compositions of AAT RNAi agents disclosed herein.

Targeting groups and linking groups include the following, for which their chemical structures are provided below in Table 7: (PAZ), (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s. Each sense strand and/or antisense strand can have any targeting groups or linking groups listed above, as well as other targeting or linking groups, conjugated to the 5' and/or 3' end of the sequence.

TABLE 4

AAT RNAi Agent Antisense Strand Sequences

| Antisense Strand ID: | SEQ ID NO. | Antisense Sequence (Modified) (5' → 3') | SEQ ID NO. | Underlying Base Sequence (5' → 3') |
|---|---|---|---|---|
| AM00516-AS | 888 | dTGfgAfaCfUuNAUfgGfuGfaUfgAfuAfudTsdT | 783 | TGGAACUUGGUGAUGAUAUTT |
| AM02129-AS | 889 | dTsGfsgAfaCfUuNAUfgGfuGfaUfgAfuAfudTsdT | 783 | TGGAACUUGGUGAUGAUAUTT |
| AM02130-AS | 890 | dTsGfsgAfaCfUuNAUfgGfuGfaUfgAfuAfuCfgsusg | 784 | TGGAACUUGGUGAUGAUAUCGUG |
| AM04786-AS | 891 | aCfUuNAUfgGfuGfaUfgAfuAfudTsdT | 785 | ACUUGGUGAUGAUAUTT |
| AM05303-AS | 892 | dTdGdGdAdAdCdTdTdGdGdTdGdAdTdGdAdTdAdTdTsdT | 786 | TGGAACTTGGTGATGATATTT |
| AM05643-AS | 893 | usUfsusAfaAfcAfUfGfcCfuAfaAfcGfcusu | 787 | UUUAAACAUGCCUAAACGCUU |
| AM05645-AS | 894 | usGfscsAfuUfgCfCfCfaGfgUfaUfuUfcusu | 788 | UGCAUUGCCCAGGUAUUUCUU |
| AM05647-AS | 895 | usGfsgsAfaCfuUfGfGfuGfaUfgAfuAfuusu | 789 | UGGAACUUGGUGAUGAUAUUU |
| AM05649-AS | 896 | usGfsasUfcAftiAfGfGfuucCfaGfuAfausu | 790 | UGAUCAUAGGUUCCAGUAAUU |
| AM05651-AS | 897 | usAfscsAfgCfCfUfUfAfuGfcAfcGfgCfcusu | 791 | UACAGCCUUAUGCACGGCCUU |
| AM05653-AS | 898 | usUfscsGfaUfgGfUfCfaGfcAfcAfgCfcusu | 792 | UUCGAUGGUCAGCACAGCCUU |
| AM05655-AS | 899 | usCfsasAfaGfgGfUfUfuGfuUfgAfaCfuusu | 793 | UCAAAGGGUUUGUUGAACUUU |
| AM05657-AS | 900 | usGfsusUfaAfaCfAfUfgCfcUfaAfaCfgusu | 794 | UGUUAAACAUGCCUAAACGUU |
| AM05659-AS | 901 | usUfuAfaAfcgugcCfuAfaAfcGfcsUfsg | 795 | UUUAAACGUGCCUAAACGCUG |
| AM05661-AS | 902 | usGfscAfuUfgcccaGfgUfaUfuUfcsAfsg | 796 | UGCAUUGCCCAGGUAUUUCAG |
| AM05663-AS | 903 | usGfsgAfaCfuuugguGfaUfgAfuAfusCfsg | 797 | UGGAACUUGGUGAUGAUAUCG |

TABLE 4-continued

AAT RNAi Agent Antisense Strand Sequences

| Antisense Strand ID: | SEQ ID NO. | Antisense Sequence (Modified) (5' → 3') | SEQ ID NO. | Underlying Base Sequence (5' → 3') |
|---|---|---|---|---|
| AM05665-AS | 904 | usGfsaUfcAfuagguUfcCfaGfuAfasUfsg | 798 | UGAUCAUAGGUUCCAGUAAUG |
| AM05667-AS | 905 | usAfscAfgCfcuuauGfcAfcGfgCfcsUfsu | 791 | UACAGCCUUAUGCACGGCCUU |
| AM05669-AS | 906 | usUfscGfaUfggucaGfcAfcAfgCfcsUfsu | 792 | UUCGAUGGUCAGCACAGCCUU |
| AM05671-AS | 907 | usCfsaAfaGfgguuuGfuUfgAfaCfusUfsg | 799 | UCAAAGGGUUUGUUGAACUUG |
| AM05673-AS | 908 | usGfsuUfaAfacaugCfcUfaAfaCfgsCfsg | 800 | UGUUAAACAUGCCUAAACGCG |
| AM05677-AS | 909 | usUfsuAfaAfcgugcCfuAfaAfcGfcsUfsg | 795 | UUUAAACGUGCCUAAACGCUG |
| AM05884-AS | 910 | vpusGfsusUfaAfaCfAfUfgCfcUfaAfaCfgusu | 794 | UGUUAAACAUGCCUAAACGUU |
| AM05885-AS | 911 | cPrpusGfsusUfaAfaCfAfUfgCfcUfaAfaCfgusu | 794 | UGUUAAACAUGCCUAAACGUU |
| AM05886-AS | 912 | usGfsusUfaAfaCfAfUfgCfcUfaAfaCfgcsu | 801 | UGUUAAACAUGCCUAAACGCU |
| AM05887-AS | 913 | usGfsusUfaAfaCfaUfgCfcUfaAfaCfgusu | 794 | UGUUAAACAUGCCUAAACGUU |
| AM05888-AS | 914 | usGfsusUfaAfaCfaUfgCfcUfaAfaCfgcsu | 801 | UGUUAAACAUGCCUAAACGCU |
| AM05889-AS | 915 | usGfsusUfaAfaCfAfUfgCfcUfaAfaCfgCfsu | 801 | UGUUAAACAUGCCUAAACGCU |
| AM05890-AS | 916 | usGfsusUfaAfaCfAfUfgCfcUfaAfaCfgCfuusc | 802 | UGUUAAACAUGCCUAAACGCUUC |
| AM05891-AS | 917 | usGfsusUfaAfaCfaUfgCfcUfaAfaCfgCfsu | 801 | UGUUAAACAUGCCUAAACGCU |
| AM05892-AS | 918 | usGfsusUfaAfaCfaUfgCfcUfaAfaCfgCfuusc | 802 | UGUUAAACAUGCCUAAACGCUUC |
| AM05900-AS | 919 | cPrpusGfsuUfaAfacaugCfcUfaAfaCfgsCfsg | 800 | UGUUAAACAUGCCUAAACGCG |
| AM05901-AS | 920 | usGfsgsAfaCfUuNAUfGfGfuGfaUfgAfuAfuusu | 789 | UGGAACUUGGUGAUGAUAUUU |
| AM05954-AS | 921 | usGfscsUfgUfuggacUfgGfuGfuGfcusu | 803 | UGCUGUUGGACUGGUGUGCUU |
| AM05955-AS | 922 | usGfscsUfgUfuggacUfgGfuGfuGfccsa | 804 | UGCUGUUGGACUGGUGUGCCA |
| AM05956-AS | 923 | usGfscsUfgUfuggacUfgGfuGfuGfccausu | 805 | UGCUGUUGGACUGGUGUGCCAUU |
| AM05957-AS | 924 | usGfscsUfgUfuggacUfgGfuGfuGfccagsc | 806 | UGCUGUUGGACUGGUGUGCCAGC |
| AM05961-AS | 925 | usAfsasGfgCfuUfcUfgAfgUfgGfuAfcusu | 807 | UAAGGCUUCUGAGUGGUACUU |
| AM05962-AS | 926 | usAfsasGfgCfuUfcUfgAfgUfgGfuAfcasa | 808 | UAAGGCUUCUGAGUGGUACAA |
| AM05963-AS | 927 | usAfsasGfgCfuUfcUfgAfgUfgGfuAfcaacsu | 809 | UAAGGCUUCUGAGUGGUACAACU |
| AM05964-AS | 928 | gsAfsasGfgCfuUfcUfgAfgUfgGfuAfcusu | 810 | GAAGGCUUCUGAGUGGUACUU |
| AM05969-AS | 929 | asAfsgsAfcAfaAfgGfgUfuUfgUfuGfausu | 811 | AAGACAAAGGGUUUGUUGAUU |
| AM05970-AS | 930 | asAfsgsAfcAfaAfgGfgUfuUfgUfuGfaasc | 812 | AAGACAAAGGGUUUGUUGAAC |
| AM05973-AS | 931 | usAfsgsAfcAfaAfgGfgUfuUfgUfuGfaasc | 813 | UAGACAAAGGGUUUGUUGAAC |
| AM05974-AS | 932 | asAfsgsAfcAfaAfgGfgUfuUfgUfuGfaacusu | 814 | AAGACAAAGGGUUUGUUGAACUU |
| AM05976-AS | 933 | usAfsgsAfcAfuGfgGfuAfuGfgCfcUfcusu | 815 | UAGACAUGGGUAUGGCCUCUU |
| AM05977-AS | 934 | usAfsgsAfcAfuGfgGfuAfuGfgCfcUfcusa | 816 | UAGACAUGGGUAUGGCCUCUA |
| AM05979-AS | 935 | usAfsgsAfcAfuGfgGfuAfuGfgCfcticuaasa | 817 | UAGACAUGGGUAUGGCCUCUAAA |
| AM05980-AS | 936 | usAfsgsAfcAfuGfgGfuAfuGfgCfcUfcuausu | 818 | UAGACAUGGGUAUGGCCUCUAUU |
| AM05982-AS | 937 | usUfsusGfaUfcUfgUfuUfcUfuGfgCfcusu | 819 | UUUGAUCUGUUUCUUGGCCUU |
| AM05983-AS | 938 | usUfsusGfaUfcUfgUfuUfcUfuGfgCfcusc | 820 | UUUGAUCUGUUUCUUGGCCUC |
| AM05985-AS | 939 | usUfsusGfaUfcUfgUfuUfcUfuGfgCfcucusu | 821 | UUUGAUCUGUUUCUUGGCCUCUU |
| AM05987-AS | 940 | usGfsusUfgGfacuggUfgUfgCfcAfgusu | 822 | UGUUGGACUGGUGUGCCAGUU |

TABLE 4-continued

AAT RNAi Agent Antisense Strand Sequences

| Antisense Strand ID: | SEQ ID NO. | Antisense Sequence (Modified) (5' → 3') | SEQ ID NO. | Underlying Base Sequence (5' → 3') |
|---|---|---|---|---|
| AM05989-AS | 941 | usGfsusUfgGfacuggUfgUfgCfcAfgcsu | 823 | UGUUGGACUGGUGUGCCAGCU |
| AM05990-AS | 942 | usGfsusUfgGfacuggUfgUfgCfcAfgcugsg | 824 | UGUUGGACUGGUGUGCCAGCUGG |
| AM05992-AS | 943 | usGfsusUfgGfacuggUfgUfgCfcAfgcusg | 825 | UGUUGGACUGGUGUGCCAGCUG |
| AM05994-AS | 944 | asAfsasGfgGfuUfuGfuUfgAfaCfuUfgusu | 826 | AAAGGGUUUGUUGAACUUGUU |
| AM05996-AS | 945 | asAfsasGfgGfuUfuGfuUfgAfaCfuUfgasc | 827 | AAAGGGUUUGUUGAACUUGAC |
| AM05998-AS | 946 | usAfsasGfgGfuUfuGfuUfgAfaCfuUfgaccsu | 828 | UAAGGGUUUGUUGAACUUGACCU |
| AM05999-AS | 947 | usAfsasGfgGfuUfuGfuUfgAfaCfuUfgasc | 829 | UAAGGGUUUGUUGAACUUGAC |
| AM06124-AS | 948 | usAfsusUfgGfuGfcUfgUfuGfgAfcUfgusu | 830 | UAUUGGUGCUGUUGGACUGUU |
| AM06125-AS | 949 | usAfsusUfgGfuGfcUfgUfuGfgAfcUfggsu | 831 | UAUUGGUGCUGUUGGACUGGU |
| AM06126-AS | 950 | usAfsusUfgGfuGfcUfgUfuGfgAfcUfggusu | 832 | UAUUGGUGCUGUUGGACUGGUU |
| AM06130-AS | 951 | usUfsgsUfuGfgacugGfuGfuGfcCfasg | 833 | UUGUUGGACUGGUGUGCCAG |
| AM06131-AS | 952 | usUfsgsUfuGfgacugGfuGfuGfcCfagcsu | 834 | UUGUUGGACUGGUGUGCCAGCU |
| AM06133-AS | 953 | usAfsusAfgAfcAfuGfgGfuAfuGfgCfcusc | 835 | UAUAGACAUGGGUAUGGCCUC |
| AM06134-AS | 954 | usAfsusAfgAfcauggGfuAfuGfgCfcusc | 835 | UAUAGACAUGGGUAUGGCCUC |
| AM06137-AS | 955 | usCfsasAfaGfgGfuUfuGfuUfgAfaCfuugasc | 836 | UCAAAGGGUUUGUUGAACUUGAC |
| AM06140-AS | 956 | usUfsasUfuGfgugcuGfuUfgGfaCfugsg | 837 | UUAUUGGUGCUGUUGGACUGG |
| AM06227-AS | 957 | usGfsusUfaAfaCfaUfgCfcUfaAfaCfgsc | 838 | UGUUAAACAUGCCUAAACGC |
| AM06228-AS | 958 | usGfsusUfaAfaCfaUfgCfcUfaAfaCfgcusu | 839 | UGUUAAACAUGCCUAAACGCUU |
| AM06234-AS | 959 | usGfsuUfaAfaCfaUfgCfcUfaAfaCfgsCfsg | 800 | UGUUAAACAUGCCUAAACGCG |
| AM06235-AS | 960 | usGfsuUfaAfacaugCfcUfaAfaCfgCfsu | 801 | UGUUAAACAUGCCUAAACGCU |
| AM06237-AS | 961 | usGfsuUfaAfaCfAfUfgCfcUfaAfaCfgsCfsg | 800 | UGUUAAACAUGCCUAAACGCG |
| AM06238-AS | 962 | NpusGfsusUfaAfaCfaUfgCfcUfaAfaCfgusu | 794 | UGUUAAACAUGCCUAAACGUU |
| AM06261-AS | 963 | NusGfsusUfaAfaCfaUfgCfcUfaAfaCfgusu | 794 | UGUUAAACAUGCCUAAACGUU |

TABLE 5

AAT RNAi Agent Sense Strand Sequences

| Sense Strand ID: | SEQ ID NO. | Sense Sequence (Modified) (5' → 3') | SEQ ID NO. | Underlying Base Sequence (5' → 3') |
|---|---|---|---|---|
| AM01887-SS | 964 | (Chol-TEG)uAuAfuAfuCfaUfcAfcCfaAfgUfuCfcAf(invdT)(TEG-Biotin) | 845 | UAUAUAUCAUCACCAAGUUCCAT |
| AM01888-SS | 965 | (Chol-TEG)uAuAfuAfuCfaUfcAfcCfaAfgUthCfcAf(invdT)(PEG-C3-SS) | 845 | UAUAUAUCAUCACCAAGUUCCAT |
| AM01855-SS | 966 | (Alk-SS-C6)AfuAfuCfaUfcAfcCfaAfgUfuCfcAf(invdT) | 846 | AUAUCAUCACCAAGUUCCAT |
| AM02132-SS | 967 | CfsgsAfuAfuCfaUfcAfcCfaAfgUfuCfcAf(C6-SS-Alk) | 847 | CGAUAUCAUCACCAAGUUCCA |
| AM02390-SS | 968 | CfsgsAfuAfuCfaUfcAfcCfaAfgUfuCfcAf(C6-SS-Alk-Me) | 847 | CGAUAUCAUCACCAAGUUCCA |
| AM04785-SS | 969 | uAfuCfaUfcAfcCfaAfgUfuCfcAf(invdT) | 848 | UAUCAUCACCAAGUUCCAT |
| AM05304-SS | 970 | (Chol-TEG)dTdAdTdAdTdAdTdCdAdTdCdAdCdCdAdAdGdTdTdCdCsdA(invdT)(TEG-Biotin) | 849 | TATATATCATCACCAAGTTCCAT |

TABLE 5-continued

AAT RNAi Agent Sense Strand Sequences

| Sense Strand ID: | SEQ ID NO. | Sense Sequence (Modified) (5' → 3') | SEQ ID NO. | Underlying Base Sequence (5' → 3') |
|---|---|---|---|---|
| AM05599-SS | 971 | (Chol-TEG)dTdAdTdAdTdAdTdCdAdTdCdAdCdCdAdAdGdTdTdCdCsdA(invdT) | 849 | TATATATCATCACCAAGTTCCAT |
| AM05642-SS | 972 | (NAG25)(invAb)GfcGfuUfuAfGfGfcAfuGfuUfuAfaausu(invAb) | 850 | GCGUUUAGGCAUGUUUAAAUU |
| AM05644-SS | 973 | (NAG25)(invAb)GfaAfaUfaCfCfUfgGfgCfaAfuGfcausu(invAb) | 851 | GAAAUACCUGGGCAAUGCAUU |
| AM05646-SS | 974 | (NAG25)(invAb)AfuAfuCfaUfCfAfcCfaAfgUfuCfcausu(invAb) | 852 | AUAUCAUCACCAAGUUCCAUU |
| AM05648-SS | 975 | (NAG25)(invAb)UfuAfcUfgGfAfAfcCfuAfuGfaUfcausu(invAb) | 853 | UUACUGGAACCUAUGAUCAUU |
| AM05650-SS | 976 | (NAG25)(invAb)GfgCfcGfuGfCfAfuAfaGfgCfuGfuausu(invAb) | 854 | GGCCGUGCAUAAGGCUGUAUU |
| AM05652-SS | 977 | (NAG25)(invAb)GfgCfuGfuGfCfUfgAfcCfaUfcGfaausu(invAb) | 855 | GGCUGUGCUGACCAUCGAAUU |
| AM05654-SS | 978 | (NAG25)(invAb)AfgUfuCfaAfCfAfaAfcCfcUfuUfgausu(invAb) | 856 | AGUUCAACAAACCCUUUGAUU |
| AM05656-SS | 979 | (NAG25)(invAb)CfgUfuUfaGfGfCfaUfgUfuUfaAfcausu(invAb) | 857 | CGUUUAGGCAUGUUUAACAUU |
| AM05658-SS | 980 | (NAG25)scsagcguuuAfGfGfcauguuuaasa(invAb) | 858 | CAGCGUUUAGGCAUGUUUAAA |
| AM05660-SS | 981 | (NAG25)scsugaaauaCfCfUfgggcaaugcsa(invAb) | 859 | CUGAAAUACCUGGGCAAUGCA |
| AM05662-SS | 982 | (NAG25)scsgauaucaUfCfAfccaaguuccsa(invAb) | 847 | CGAUAUCAUCACCAAGUUCCA |
| AM05664-SS | 983 | (NAG25)scsauuacugGfAfAfccuaugaucsa(invAb) | 860 | CAUUACUGGAACCUAUGAUCA |
| AM05666-SS | 984 | (NAG25)sasaggccguGfCfAfuaaggcugsa(invAb) | 861 | AAGGCCGUGCAUAAGGCUGUA |
| AM05668-SS | 985 | (NAG25)sasaggcuguGfCfUfgaccaucgasa(invAb) | 862 | AAGGCUGUGCUGACCAUCGAA |
| AM05670-SS | 986 | (NAG25)scsaaguucaAfCfAfaacccuuugsa(invAb) | 863 | CAAGUUCAACAAACCCUUUGA |
| AM05672-SS | 987 | (NAG25)scsgcguuuaGfGfCfauguuuaacsa(invAb) | 864 | CGCGUUUAGGCAUGUUUAACA |
| AM05658-SS | 988 | (NAG25)scsagcguuuAfGfGfcauguuuaasa(invAb) | 858 | CAGCGUUUAGGCAUGUUUAAA |
| AM05893-SS | 989 | (NAG25)s(invAb)scguuuaGfGfCfauguuuaacausu(invAb) | 857 | CGUUUAGGCAUGUUUAACAUU |
| AM05894-SS | 990 | (NAG25)s(invAb)sCfgUfuUfaGfGfCfaUfgUfuUfaAfcas(invAb) | 429 | CGUUUAGGCAUGUUUAACA |
| AM05895-SS | 991 | (NAG25)s(invAb)scguuuaGfGfCfauguuuaacas(invAb) | 429 | CGUUUAGGCAUGUUUAACA |
| AM05896-SS | 992 | (NAG25)s(invAb)saaCfgUfuUfaGfGfCfaUfgUfuUfaAfcas(invAb) | 865 | AACGUUUAGGCAUGUUUAACA |
| AM05897-SS | 993 | (NAG25)s(invAb)sagCfgUfuUfaGfGfCfaUfgUfuUfaAfcas(invAb) | 866 | AGCGUUUAGGCAUGUUUAACA |
| AM05898-SS | 994 | (NAG25)s(invAb)saacguuuaGfGfCfauguuuaacas(invAb) | 865 | AACGUUUAGGCAUGUUUAACA |
| AM05899-SS | 995 | (NAG25)s(invAb)sagcguuuaGfGfCfauguuuaacas(invAb) | 866 | AGCGUUUAGGCAUGUUUAACA |
| AM05958-SS | 996 | (NAG37)s(invAb)sgcacacCfAfGfuccaacagcas(invAb) | 454 | GCACACCAGUCCAACAGCA |
| AM05959-SS | 997 | (NAG37)s(invAb)suggcacacCfAfGfuccaacagcas(invAb) | 867 | UGGCACACCAGUCCAACAGCA |
| AM05960-SS | 998 | (NAG37)s(invAb)saagcacacCfAfGfuccaacagcas(invAb) | 868 | AAGCACACCAGUCCAACAGCA |
| AM05965-SS | 999 | (NAG37)s(invAb)sguaccaCfUfCfagaagccuuas(invAb) | 519 | GUACCACUCAGAAGCCUUA |
| AM05966-SS | 1000 | (NAG37)s(invAb)suuguaccaCfUfCfagaagccuuas(invAb) | 869 | UUGUACCACUCAGAAGCCUUA |
| AM05967-SS | 1001 | (NAG37)s(invAb)sguaccaCfUfCfagaagccuucs(invAb) | 518 | GUACCACUCAGAAGCCUUC |
| AM05968-SS | 1002 | (NAG37)s(invAb)sucaacaAfAfCfccuuugucuus(invAb) | 738 | UCAACAAACCCUUUGUCUU |
| AM05971-SS | 1003 | (NAG37)s(invAb)sguucaacaAfAfCfccuuugucuus(invAb) | 870 | GUUCAACAAACCCUUUGUCUU |
| AM05972-SS | 1004 | (NAG37)s(invAb)sguucaacaAfAfCfccuuugucuas(invAb) | 871 | GUUCAACAAACCCUUUGUCUA |
| AM05975-SS | 1005 | (NAG37)s(invAb)sgaggccAfUfAfcccaugucuas(invAb) | 707 | GAGGCCAUACCCAUGUCUA |
| AM05978-SS | 1006 | (NAG37)s(invAb)suagaggccAfUfAfcccaugucuas(invAb) | 872 | UAGAGGCCAUACCCAUGUCUA |
| AM05981-SS | 1007 | (NAG37)s(invAb)sggccaaGfAfAfacagaucaaas(invAb) | 537 | GGCCAAGAAACAGAUCAAA |

TABLE 5-continued

AAT RNAi Agent Sense Strand Sequences

| Sense Strand ID: | SEQ ID NO. | Sense Sequence (Modified) (5' → 3') | SEQ ID NO. | Underlying Base Sequence (5' → 3') |
|---|---|---|---|---|
| AM05984-SS | 1008 | (NAG37)s(invAb)sgaggccaaGfAfAfacagaucalas(invAb) | 873 | GAGGCCAAGAAACAGAUCAAA |
| AM05986-SS | 1009 | (NAG37)s(invAb)scuggcaCfAfCfcaguccaacas(invAb) | 445 | CUGGCACACCAGUCCAACA |
| AM05988-SS | 1010 | (NAG37)s(invAb)sagcuggcaCfAfCfcaguccaacas(invAb) | 874 | AGCUGGCACACCAGUCCAACA |
| AM05991-SS | 1011 | (NAG37)s(invAb)sgcuggcaCfAfCfcaguccaacas(invAb) | 875 | GCUGGCACACCAGUCCAACA |
| AM05993-SS | 1012 | (NAG37)s(invAb)scaaguuCfAfAfcaaacccuuus(invAb) | 725 | CAAGUUCAACAAACCCUUU |
| AM05995-SS | 1013 | (NAG37)s(invAb)sgucaaguuCfAfAfcaaacccuuus(invAb) | 876 | GUCAAGUUCAACAAACCCUUU |
| AM05997-SS | 1014 | (NAG37)s(invAb)sgucaaguuCfAfAfcaaacccuuas(invAb) | 877 | GUCAAGUUCAACAAACCCUUA |
| AM06127-SS | 1015 | (NAG37)s(invAb)scaguccAfAfCfagcaccaauas(invAb) | 458 | CAGUCCAACAGCACCAAUA |
| AM06128-SS | 1016 | (NAG37)s(invAb)saccaguccAfAfCfagcaccaauas(invAb) | 878 | ACCAGUCCAACAGCACCAAUA |
| AM06129-SS | 1017 | (NAG37)s(invAb)sccaguccAfAfCfagcaccaauas(invAb) | 879 | CCAGUCCAACAGCACCAAUA |
| AM06132-SS | 1018 | (NAG37)s(invAb)scuggcacAfCfCfaguccaacaas(invAb) | 880 | CUGGCACACCAGUCCAACAA |
| AM06135-SS | 1019 | (NAG37)s(invAb)sggccauAfCfCfcaugucuauas(invAb) | 712 | GGCCAUACCCAUGUCUAUA |
| AM06136-SS | 1020 | (NAG37)s(invAb)sgaggccauAfCfCfcaugucuauas(invAb) | 881 | GAGGCCAUACCCAUGUCUAUA |
| AM06138-SS | 1021 | (NAG37)s(invAb)sgucaaguucaAfCfAfaacccuuugas(invAb) | 882 | GUCAAGUUCAACAAACCCUUUGA |
| AM06139-SS | 1022 | (NAG37)s(invAb)scaaguucaAfCfAfaacccuuugas(invAb) | 863 | CAAGUUCAACAAACCCUUUGA |
| AM06141-SS | 1023 | (NAG37)s(invAb)sccaguccaAfCfAfgcaccaauaas(invAb) | 883 | CCAGUCCAACAGCACCAAUAA |
| AM06195-SS | 1024 | (NAG37)s(invAb)scgcguuuaGfGfCfauguuuaacas(invAb) | 864 | CGCGUUUAGGCAUGUUUAACA |
| AM06223-SS | 1025 | (NAG37)s(invAb)scguuuaGfGfCfauguuuaacas(invAb) | 429 | CGUUUAGGCAUGUUUAACA |
| AM06224-SS | 1026 | (NAG37)s(invAb)scsgcguuuaGfGfCfauguuuaacsa(invAb) | 864 | CGCGUUUAGGCAUGUUUAACA |
| AM06225-SS | 1027 | (NAG37)s(invAb)sagCfgUfuUfaGfGfCfaUfgUfuUfaAfcas(invAb) | 866 | AGCGUUUAGGCAUGUUUAACA |
| AM06226-SS | 1028 | (NAG37)s(invAb)scguuuaGfGfCfauguuuaacausu(invAb) | 857 | CGUUUAGGCAUGUUUAACAUU |
| AM06229-SS | 1029 | (NAG37)s(invAb)sgcguuuaGfGfCfauguuuaacas(invAb) | 884 | GCGUUUAGGCAUGUUUAACA |
| AM06230-SS | 1030 | (NAG37)s(invAb)sgcguuuaGfGfCfauguuuaacausu(invAb) | 885 | GCGUUUAGGCAUGUUUAACAUU |
| AM06231-SS | 1031 | (NAG37)s(invAb)scgcguuuaGfGfCfauguuuaacsausu(invAb) | 886 | CGCGUUUAGGCAUGUUUAACAUU |
| AM06232-SS | 1032 | (NAG37)s(invAb)sagCfgUfuUfaGfGfCfaUfgUfuUfaAfcausu(invAb) | 887 | AGCGUUUAGGCAUGUUUAACAUU |
| AM06236-SS | 1033 | (NAG37)s(invAb)sagcguuuaGfGfCfauguuuaacas(invAb) | 866 | AGCGUUUAGGCAUGUUUAACA |
| AM06239-SS | 1034 | (NAG37)s(invAb)scgcguuuaGfGfCfauguuuaacsas(invAb) | 864 | CGCGUUUAGGCAUGUUUAACA |

The AAT RNAi agents described herein are formed by annealing an antisense strand with a sense strand. A sense strand containing a sequence listed in Table 2, Table 3, or Table 5 can be hybridized to any antisense strand containing a sequence listed in Table 2, Table 3, or Table 4, provided the two sequences have a region of at least 85% complementarity over a contiguous 16, 17, 18, 19, 20, or 21 nucleotide sequence.

In some embodiments, the antisense strand of an AAT RNAi agent disclosed herein differs by 0, 1, 2, or 3 nucleotides from any of the antisense strand sequences in Table 4. In some embodiments, the sense strand of an AAT RNAi agent disclosed herein differs by 0, 1, 2, or 3 nucleotides from any of the sense strand sequences in Table 5.

In some embodiments, an AAT RNAi agent antisense strand comprises a nucleotide sequence of any of the sequences in Table 2, Table 3, or Table 4. In some embodiments, an AAT RNAi agent antisense strand comprises the sequence of nucleotides (from 5' end→3' end) 1-17, 2-17, 1-18, 2-18, 1-19, 2-19, 1-20, 2-20, 1-21, 2-21, 1-22, 2-22, 1-23, 2-23, 1-24, or 2-24, of any of the sequences in Table 2, Table 3, or Table 4. In certain embodiments, an AAT RNAi agent antisense strand comprises or consists of a modified sequence of any one of the modified sequences in Table 4.

In some embodiments, an AAT RNAi agent sense strand comprises the nucleotide sequence of any of the sequences in Table 2, Table 3, or Table 5. In some embodiments, an AAT RNAi agent sense strand comprises the sequence of nucleotides (from 5' end→3' end) 1-17, 2-17, 3-17, 4-17, 1-18, 2-18, 3-18, 4-18, 1-19, 2-19, 3-19, 4-19, 1-20, 2-20, 3-20, 4-20, 1-21, 2-21, 3-21, 4-21, 1-22, 2-22, 3-22, 4-22, 1-23, 2-23, 3-23, 4-23, 1-24, 2-24, 3-24, or 4-24 of any of the sequences in Table 2, Table 3, or Table 5. In certain embodiments, an AAT RNAi agent sense strand comprises or consists of a modified sequence of any one of the modified sequences in Table 5.

For the AAT RNAi agents disclosed herein, the nucleotide at position 1 of the antisense strand (from 5' end→3' end) can be perfectly complementary to an AAT gene, or can be non-complementary to an AAT gene. In some embodiments, the nucleotide at position 1 of the antisense strand (from 5' end→3' end) is a U, A, or dT (or a modified version of U, A or dT). In some embodiments, the nucleotide at position 1 of the antisense strand (from 5' end→3' end) forms an A:U or U:A base pair with the sense strand.

In some embodiments, an AAT RNAi agent antisense strand comprises the sequence of nucleotides (from 5' end→3' end) 2-18 or 2-19 of any of the antisense strand sequences in Table 2, Table 3, or Table 4. In some embodiments, an AAT RNAi sense strand comprises the sequence of nucleotides (from 5' end→3' end) 1-17 or 1-18 of any of the sense strand sequences in Table 2, Table 3, or Table 5.

In some embodiments, an AAT RNAi agent includes (i) an antisense strand comprising the sequence of nucleotides (from 5' end→3' end) 2-18 or 2-19 of any of the antisense strand sequences in Table 2, Table 3, or Table 4, and (ii) a sense strand comprising the sequence of nucleotides (from 5' end→3' end) 1-17 or 1-18 of any of the sense strand sequences in Table 2, Table 3, or Table 5.

A sense strand containing a sequence listed in Table 2, Table 3, or Table 5 can be hybridized to any antisense strand containing a sequence listed in Table 2, Table 3, or Table 5, provided the two sequences have a region of at least 85% complementarity over a contiguous 16, 17, 18, 19, 20, or 21 nucleotide sequence. In some embodiments, the AAT RNAi agent has a sense strand consisting of the modified sequence of any of the modified sequences in Table 5, and an antisense strand consisting of the modified sequence of any of the modified sequences in Table 4. Representative sequence pairings are exemplified by the Duplex ID Nos. shown in Table 6.

In some embodiments, an AAT RNAi agent comprises any of the duplexes represented by any of the Duplex ID Nos. presented herein. In some embodiments, an AAT RNAi agent consists of any of the duplexes represented by any of the Duplex ID Nos. presented herein. In some embodiments, an AAT RNAi agent comprises the sense strand and antisense strand nucleotide sequences of any of the duplexes represented by any of the Duplex ID Nos. presented herein. In some embodiments, an AAT RNAi agent includes the sense strand and antisense strand nucleotide sequences of any of the duplexes represented by any of the Duplex ID Nos. presented herein and a targeting group and/or linking group, wherein the targeting group and/or linking group is covalently linked (i.e., conjugated) to the sense strand or the antisense strand. In some embodiments, an AAT RNAi agent includes the sense strand and antisense strand modified nucleotide sequences of any of the duplexes represented by any of the Duplex ID Nos. presented herein. In some embodiments, an AAT RNAi agent comprises the sense strand and antisense strand modified nucleotide sequences of any of the duplexes represented by any of the Duplex ID Nos. presented herein and a targeting group and/or linking group, wherein the targeting group and/or linking group is covalently linked to the sense strand or the antisense strand.

In some embodiments, an AAT RNAi agent comprises an antisense strand and a sense strand having the nucleotide sequences of any of the antisense strand/sense strand duplexes of Table 2, Table 3, or Table 6, and comprises an asialoglycoprotein receptor ligand targeting group.

In some embodiments, an AAT RNAi agent comprises an antisense strand and a sense strand having the nucleotide sequences of any of the antisense strand/sense strand duplexes of Table 2 or Table 5, and further comprises a targeting group selected from the group consisting of (PAZ), (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s. In some embodiments, the targeting group is (NAG25) or (NAG25)s as defined in Table 7. In other embodiments, the targeting group is (NAG37) or (NAG37)s as defined in Table 7.

In some embodiments, an AAT RNAi agent comprises an antisense strand and a sense strand having the modified nucleotide sequence of any of the antisense strand and/or sense strand nucleotide sequences of any of the duplexes of Table 6.

In some embodiments, an AAT RNAi agent comprises an antisense strand and a sense strand having a modified nucleotide sequence of any of the antisense strand and/or sense strand nucleotide sequences of any of the duplexes of Table 6, and comprises an asialoglycoprotein receptor ligand targeting group.

In some embodiments, an AAT RNAi agent comprises the duplex structure of any of the duplexes in Table 6.

In some embodiments, an AAT RNAi agent consists of the duplex structure of any of the duplexes in Table 6.

TABLE 6

AAT RNAi Agents Identified by Duplex ID No. with Corresponding Sense and Antisense Strands

| Duplex ID | Antisense Strand ID | Sense Strand ID |
| --- | --- | --- |
| AD01131 | AM00516-AS | AM01887-SS |
| AD01132 | AM00516-AS | AM01888-SS |
| AD01174 | AM00516-AS | AM01855-SS |
| AD01286 | AM02129-AS | AM01855-SS |
| AD01287 | AM02130-AS | AM02132-SS |
| AD01442 | AM02130-AS | AM02390-SS |
| AD03752 | AM04786-AS | AM04785-SS |
| AD04156 | AM05303-AS | AM05304-SS |
| AD04406 | AM05303-AS | AM05599-SS |
| AD04444 | AM05643-AS | AM05642-SS |
| AD04445 | AM05645-AS | AM05644-SS |
| AD04446 | AM05647-AS | AM05646-SS |
| AD04447 | AM05649-AS | AM05648-SS |
| AD04448 | AM05651-AS | AM05650-SS |
| AD04449 | AM05653-AS | AM05652-SS |
| AD04450 | AM05655-AS | AM05654-SS |
| AD04451 | AM05657-AS | AM05656-SS |
| AD04452 | AM05659-AS | AM05658-SS |
| AD04453 | AM05661-AS | AM05660-SS |
| AD04454 | AM05663-AS | AM05662-SS |
| AD04455 | AM05665-AS | AM05664-SS |
| AD04456 | AM05667-AS | AM05666-SS |
| AD04457 | AM05669-AS | AM05668-SS |
| AD04458 | AM05671-AS | AM05670-SS |
| AD04459 | AM05673-AS | AM05672-SS |

TABLE 6-continued

AAT RNAi Agents Identified by Duplex ID No. with Corresponding Sense and Antisense Strands

| Duplex ID | Antisense Strand ID | Sense Strand ID |
|---|---|---|
| AD04464 | AM05677-AS | AM05658-SS |
| AD04601 | AM05884-AS | AM05656-SS |
| AD04602 | AM05885-AS | AM05656-SS |
| AD04603 | AM05886-AS | AM05656-SS |
| AD04604 | AM05887-AS | AM05893-SS |
| AD04605 | AM05888-AS | AM05893-SS |
| AD04606 | AM05657-AS | AM05894-SS |
| AD04607 | AM05886-AS | AM05894-SS |
| AD04608 | AM05887-AS | AM05895-SS |
| AD04609 | AM05888-AS | AM05895-SS |
| AD04610 | AM05657-AS | AM05896-SS |
| AD04611 | AM05889-AS | AM05897-SS |
| AD04612 | AM05890-AS | AM05897-SS |
| AD04613 | AM05887-AS | AM05898-SS |
| AD04614 | AM05891-AS | AM05899-SS |
| AD04615 | AM05892-AS | AM05899-SS |
| AD04616 | AM05900-AS | AM05672-SS |
| AD04617 | AM05901-AS | AM05646-SS |
| AD04652 | AM05954-AS | AM05958-SS |
| AD04653 | AM05955-AS | AM05958-SS |
| AD04654 | AM05955-AS | AM05959-SS |
| AD04655 | AM05954-AS | AM05960-SS |
| AD04656 | AM05956-AS | AM05959-SS |
| AD04657 | AM05957-AS | AM05959-SS |
| AD04658 | AM05961-AS | AM05965-SS |
| AD04659 | AM05962-AS | AM05965-SS |
| AD04660 | AM05962-AS | AM05966-SS |
| AD04661 | AM05963-AS | AM05966-SS |
| AD04662 | AM05964-AS | AM05967-SS |
| AD04663 | AM05969-AS | AM05968-SS |
| AD04664 | AM05970-AS | AM05968-SS |
| AD04665 | AM05970-AS | AM05971-SS |
| AD04666 | AM05973-AS | AM05972-SS |
| AD04667 | AM05974-AS | AM05971-SS |
| AD04668 | AM05976-AS | AM05975-SS |
| AD04669 | AM05977-AS | AM05975-SS |
| AD04670 | AM05977-AS | AM05978-SS |
| AD04671 | AM05979-AS | AM05978-SS |
| AD04672 | AM05980-AS | AM05978-SS |
| AD04673 | AM05982-AS | AM05981-SS |
| AD04674 | AM05983-AS | AM05981-SS |
| AD04675 | AM05983-AS | AM05984-SS |
| AD04676 | AM05985-AS | AM05984-SS |
| AD04677 | AM05987-AS | AM05986-SS |
| AD04678 | AM05989-AS | AM05988-SS |
| AD04679 | AM05990-AS | AM05988-SS |
| AD04680 | AM05992-AS | AM05991-SS |
| AD04681 | AM05994-AS | AM05993-SS |
| AD04682 | AM05996-AS | AM05995-SS |
| AD04683 | AM05998-AS | AM05997-SS |
| AD04684 | AM05999-AS | AM05997-SS |
| AD04761 | AM06124-AS | AM06127-SS |
| AD04762 | AM06125-AS | AM06128-SS |
| AD04763 | AM06126-AS | AM06129-SS |
| AD04764 | AM06130-AS | AM06132-SS |
| AD04765 | AM06131-AS | AM06132-SS |
| AD04766 | AM06133-AS | AM06135-SS |
| AD04767 | AM06134-AS | AM06136-SS |
| AD04768 | AM06137-AS | AM06138-SS |
| AD04769 | AM06137-AS | AM06139-SS |
| AD04770 | AM06140-AS | AM06141-SS |
| AD04805 | AM05673-AS | AM06195-SS |
| AD04824 | AM05887-AS | AM06223-SS |
| AD04825 | AM05900-AS | AM06224-SS |
| AD04826 | AM05889-AS | AM06225-SS |
| AD04827 | AM05888-AS | AM06223-SS |
| AD04828 | AM05887-AS | AM06226-SS |
| AD04829 | AM06227-AS | AM06229-SS |
| AD04830 | AM06228-AS | AM06229-SS |
| AD04831 | AM06228-AS | AM06230-SS |
| AD04832 | AM05673-AS | AM06231-SS |
| AD04833 | AM05889-AS | AM06232-SS |
| AD04834 | AM06227-AS | AM06230-SS |
| AD04836 | AM06234-AS | AM06195-SS |
| AD04837 | AM06235-AS | AM06236-SS |
| AD04838 | AM06237-AS | AM06239-SS |
| AD04839 | AM05673-AS | AM06239-SS |
| AD04840 | AM06238-AS | AM06223-SS |
| AD04857 | AM06261-AS | AM06223-SS |

In some embodiments, an AAT RNAi agent is prepared or provided as a salt, mixed salt, or a free-acid. The RNAi agents described herein, upon delivery to a cell expressing an AAT gene, inhibit or knockdown expression of one or more AAT genes in vivo.

Targeting Groups, Linking Groups, and Delivery Vehicles

In some embodiments, an AAT RNAi agent is conjugated to one or more non-nucleotide groups including, but not limited to, a targeting group, linking group, delivery polymer, or a delivery vehicle. The non-nucleotide group can enhance targeting, delivery or attachment of the RNAi agent. Examples of targeting groups and linking groups are provided in Table 7. The non-nucleotide group can be covalently linked to the 3' and/or 5' end of either the sense strand and/or the antisense strand. In some embodiments, an AAT RNAi agent contains a non-nucleotide group linked to the 3' and/or 5' end of the sense strand. In some embodiments, a non-nucleotide group is linked to the 5' end of an AAT RNAi agent sense strand. A non-nucleotide group can be linked directly or indirectly to the RNAi agent via a linker/linking group. In some embodiments, a non-nucleotide group is linked to the RNAi agent via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the RNAi agent or conjugate. In some embodiments, a non-nucleotide group enhances endocytosis of the RNAi agent.

Targeting groups or targeting moieties can enhance the pharmacokinetic or biodistribution properties of a conjugate or RNAi agent to which they are attached to improve cell-specific distribution and cell-specific uptake of the conjugate or RNAi agent. A targeting group can be monovalent, divalent, trivalent, tetravalent, or have higher valency for the target to which it is directed. Representative targeting groups include, without limitation, compounds with affinity to cell surface molecules, cell receptor ligands, haptens, antibodies, monoclonal antibodies, antibody fragments, and antibody mimics with affinity to cell surface molecules. In some embodiments, a targeting group is linked to an RNAi agent using a linker, such as a PEG linker or one, two, or three abasic and/or ribitol (abasic ribose) residues, which in some instances can serve as linkers. In some embodiments, a targeting group comprises a galactose derivative cluster.

The AAT RNAi agents described herein can be synthesized having a reactive group, such as an amine group, at the 5'-terminus. The reactive group can be used to subsequently attach a targeting group using methods typical in the art.

In some embodiments, a targeting group comprises an asialoglycoprotein receptor ligand. In some embodiments, an asialoglycoprotein receptor ligand includes or consists of one or more galactose derivatives. As used herein, the term galactose derivative includes both galactose and derivatives of galactose having affinity for the asialoglycoprotein receptor that is equal to or greater than that of galactose. Galactose derivatives include, but are not limited to: galactose, galactosamine, N-formylgalactosamine, N-acetyl-galactosamine, N-propionyl-galactosamine, N-n-butanoyl-galactosamine, and N-iso-butanoylgalactos-amine (see for example: S. T. Iobst and K. Drickamer, J. B. C., 1996, 271, 6686). Galactose derivatives, and clusters of galactose derivatives, that are useful for in vivo targeting of oligonucleotides and other molecules to the liver are known in the art (see, for example, Baenziger and Fiete, 1980, Cell, 22, 611-620; Connolly et al., 1982, J. Biol. Chem., 257, 939-945).

Galactose derivatives have been used to target molecules to hepatocytes in vivo through their binding to the asialoglycoprotein receptor expressed on the surface of hepatocytes. Binding of asialoglycoprotein receptor ligands to the asialoglycoprotein receptor(s) facilitates cell-specific targeting to hepatocytes and endocytosis of the molecule into hepatocytes. Asialoglycoprotein receptor ligands can be monomeric (e.g., having a single galactose derivative) or multimeric (e.g., having multiple galactose derivatives). The galactose derivative or galactose derivative cluster can be attached to the 3' or 5' end of the sense or antisense strand of the RNAi agent using methods known in the art. The preparation of targeting groups, such as galactose derivative clusters, is described in, for example, U.S. patent application Ser. No. 15/452,324 and U.S. Patent Publication No. US 2017/0253875, the contents of both of which are incorporated by reference herein in their entirety.

As used herein, a galactose derivative cluster comprises a molecule having two to four terminal galactose derivatives. A terminal galactose derivative is attached to a molecule through its C-1 carbon. In some embodiments, the galactose derivative cluster is a galactose derivative trimer (also referred to as tri-antennary galactose derivative or tri-valent galactose derivative). In some embodiments, the galactose derivative cluster comprises N-acetyl-galactosomines. In some embodiments, the galactose derivative cluster comprises three N-acetyl-galactosomines. In some embodiments, the galactose derivative cluster is a galactose derivative tetramer (also referred to as tetra-antennary galactose derivative or tetra-valent galactose derivative). In some embodiments, the galactose derivative cluster comprises four N-acetyl-galactosamines.

As used herein, a galactose derivative trimer contains three galactose derivatives, each linked to a central branch point. As used herein, a galactose derivative tetramer contains four galactose derivatives, each linked to a central branch point. The galactose derivatives can be attached to the central branch point through the C-1 carbons of the saccharides. In some embodiments, the galactose derivatives are linked to the branch point via linkers or spacers. In some embodiments, the linker or spacer is a flexible hydrophilic spacer, such as a PEG group (see, for example, U.S. Pat. No. 5,885,968; Biessen et al. J. Med. Chem. 1995 Vol. 39 p. 1538-1546). In some embodiments, the PEG spacer is a PEGS spacer. The branch point can be any small molecule which permits attachment of three galactose derivatives and further permits attachment of the branch point to the RNAi agent. An example of branch point group is a di-lysine or di-glutamate. Attachment of the branch point to the RNAi agent can occur through a linker or spacer. In some embodiments, the linker or spacer comprises a flexible hydrophilic spacer, such as, but not limited to, a PEG spacer. In some embodiments, the linker comprises a rigid linker, such as a cyclic group. In some embodiments, a galactose derivative comprises or consists of N-acetyl-galactosamine. In some embodiments, the galactose derivative cluster is comprised of a galactose derivative tetramer, which can be, for example, an N-acetyl-galactosamine tetramer.

Embodiments of the present disclosure include pharmaceutical compositions for delivering an AAT RNAi agent to a liver cell in vivo. Such pharmaceutical compositions can include, for example, an AAT RNAi agent conjugated to a galactose derivative cluster. In some embodiments, the galactose derivative cluster is comprised of a galactose derivative trimer, which can be, for example, an N-acetyl-galactosamine trimer, or galactose derivative tetramer, which can be, for example, an N-acetyl-galactosamine tetramer.

Targeting groups include, but are not limited to, (PAZ), (NAG13), (NAG13)s, (NAG18), (NAG18)s, (NAG24), (NAG24)s, (NAG25), (NAG25)s, (NAG26), (NAG26)s, (NAG27) (NAG27)s, (NAG28) (NAG28)s, (NAG29) (NAG29)s, (NAG30) (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), and (NAG39)s as defined in Table 7. Other targeting groups, including galactose cluster targeting ligands, are known in the art.

In some embodiments, a linking group is conjugated to the RNAi agent. The linking group facilitates covalent linkage of the agent to a targeting group or delivery polymer or delivery vehicle. The linking group can be linked to the 3' or the 5' end of the RNAi agent sense strand or antisense strand. In some embodiments, the linking group is linked to the RNAi agent sense strand. In some embodiments, the linking group is conjugated to the 5' or 3' end of an RNAi agent sense strand. In some embodiments, a linking group is conjugated to the 5' end of an RNAi agent sense strand. Examples of linking groups, can include, but are not limited to: reactive groups such a primary amines and alkynes, alkyl groups, abasic nucleotides, ribitol (abasic ribose), and/or PEG groups.

A linker or linking group is a connection between two atoms that links one chemical group (such as an RNAi agent) or segment of interest to another chemical group (such as a targeting group or delivery polymer) or segment of interest via one or more covalent bonds. A labile linkage contains a labile bond. A linkage may optionally include a spacer that increases the distance between the two joined atoms. A spacer can further add flexibility and/or length to the linkage. Spacers can include, but are not be limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description.

Any of the AAT RNAi agent nucleotide sequences listed in Tables 2, 3, 4, or 5, whether modified or unmodified, may contain 3' or 5' targeting groups or linking groups. Any of the AAT RNAi agent sequences listed in Tables 4 or 5 which contain a 3' or 5' targeting group or linking group, may alternatively contain no 3' or 5' targeting group or linking group, or may contain a different 3' or 5' targeting group or linking group including, but not limited to, those depicted in Table 7. Any of the AAT RNAi agent duplexes listed in Table 2, Table 3, or Table 6, whether modified or unmodified, may further comprise a targeting group or linking group, including, but not limited to, those depicted in Table 7, and the targeting group or linking group may be attached to the 3' or 5' terminus of either the sense strand or the antisense strand of the AAT RNAi agent duplex.

Examples of targeting groups and linking groups are provided in Table 7. Table 5 provides several embodiments of AAT RNAi agent sense strands having a targeting group or linking group linked to the 5' or 3' end.
TABLE 7
Structures Representing Various Modified Nucleotides, Targeting Groups, and Linking Groups
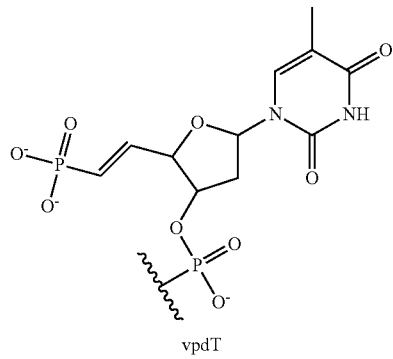 [SMILES: *P(=O)([O-])OC1CC(n2cc(C)c(=O)[nH]c2=O)OC1/C=C/P(=O)([O-])[O-]]
vpdT
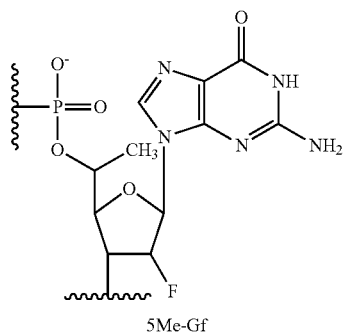 [SMILES: *C1C(F)C(n2cnc3c(=O)[nH]c(N)nc32)OC1C(C)OP(*)(=O)[O-]]
5Me-Gf
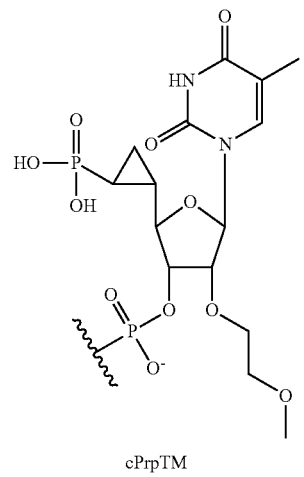 [SMILES: *P(=O)([O-])OC1C(C2CC2P(=O)(O)O)OC(n2cc(C)c(=O)[nH]c2=O)C1OCCOC]
cPrpTM TABLE 7-continued
Structures Representing Various Modified Nucleotides, Targeting Groups, and Linking Groups
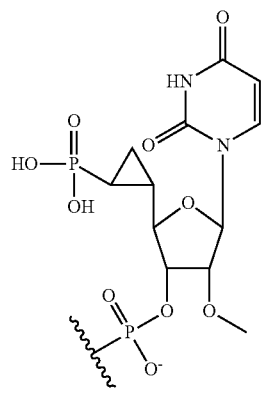
(cPrp)u
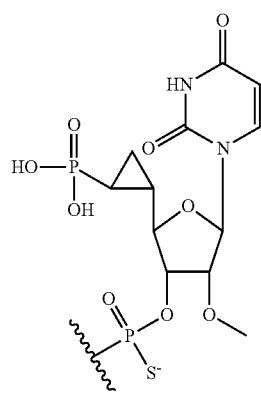
cPrpus
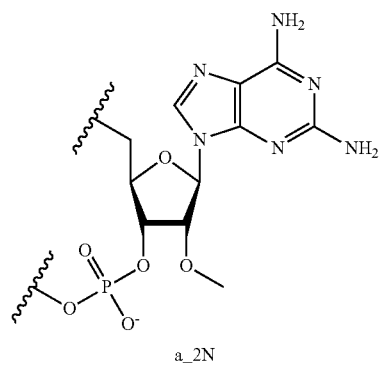
a_2N
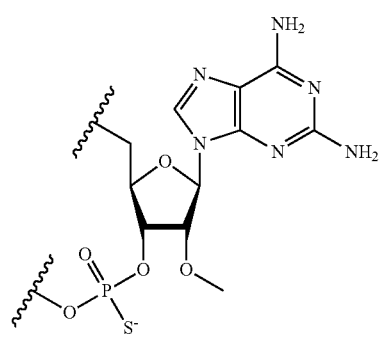
a_2Ns TABLE 7-continued
Structures Representing Various Modified Nucleotides, Targeting Groups, and Linking Groups
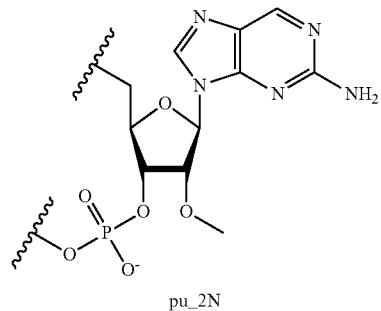
pu_2N
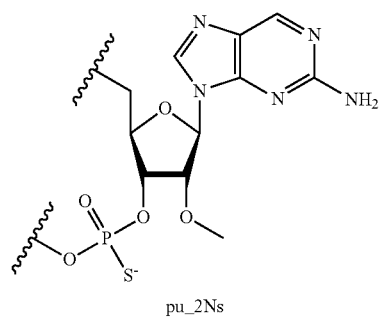
pu_2Ns
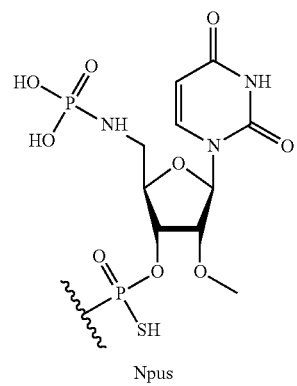
Npus
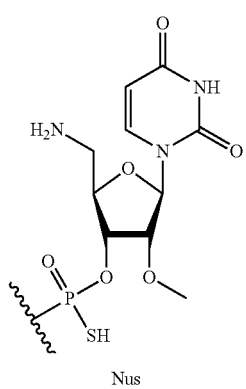
Nus TABLE 7-continued
Structures Representing Various Modified Nucleotides, Targeting Groups, and Linking Groups
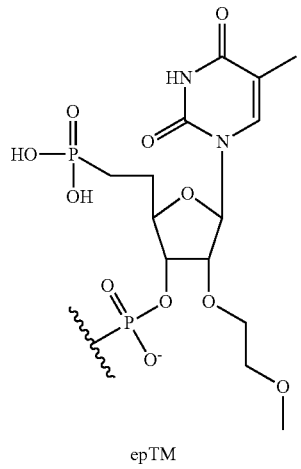 [SMILES: *P(=O)([O-])OC1C(CCP(=O)(O)O)OC(n2cc(C)c(=O)[nH]c2=O)C1OCCOC]
epTM
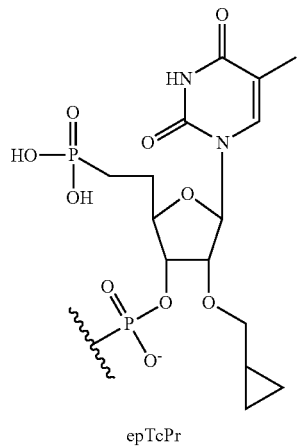 [SMILES: *P(=O)([O-])OC1C(CCP(=O)(O)O)OC(n2cc(C)c(=O)[nH]c2=O)C1OCC1CC1]
epTcPr
When positioned internally on oligonucleotide:
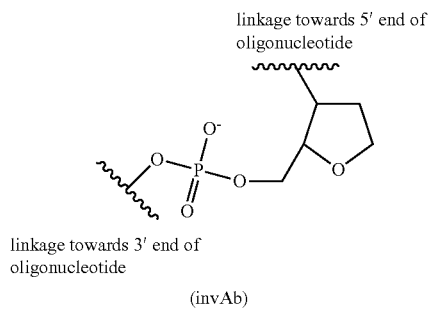 [SMILES: *OP(=O)([O-])OCC1OCCC1*]
(invAb)

TABLE 7-continued
Structures Representing Various Modified Nucleotides, Targeting Groups, and Linking Groups
When positioned internally on oligonucleotide:
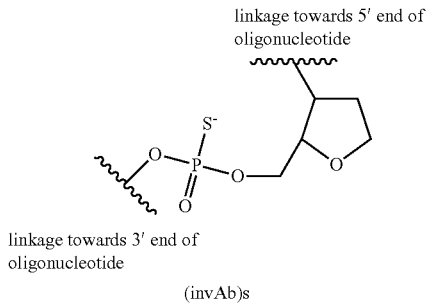 [SMILES: *OP(=O)([S-])OCC1OCCC1*]
(invAb)s
When positioned at the 3' terminal end of oligonucleotide:
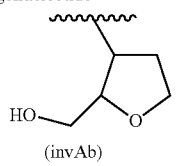
(invAb)
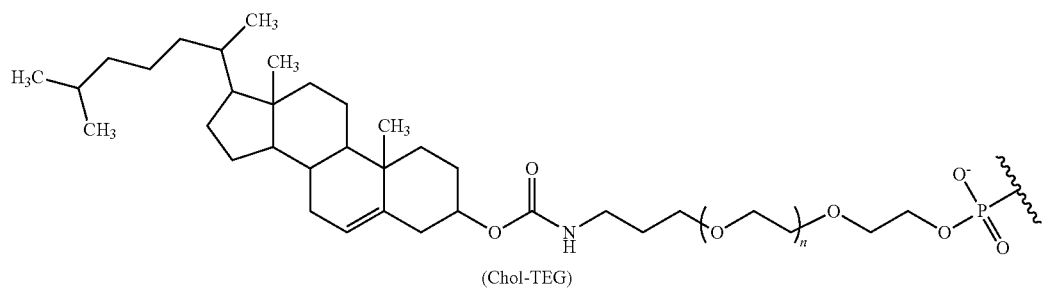
(Chol-TEG)
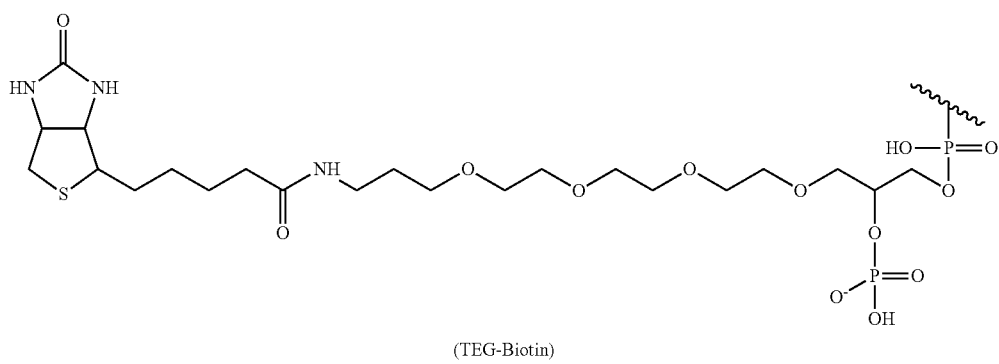 [SMILES: *P(=O)(O)OCC(COCCOCCOCCOCCCNC(=O)CCCCC1SCC2NC(=O)NC21)OP(=O)([O-])O]
(TEG-Biotin)
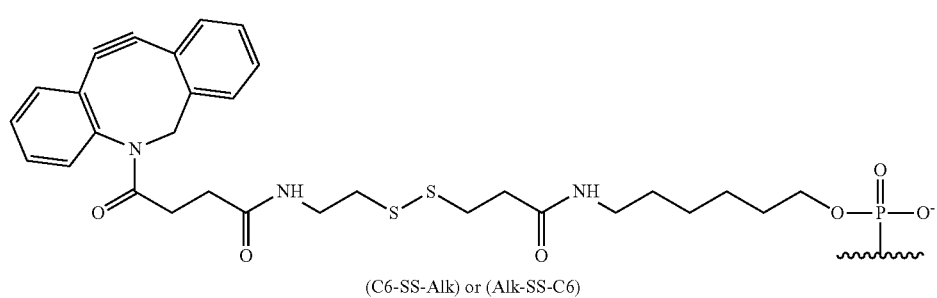 [SMILES: *P(=O)([O-])OCCCCCCNC(=O)CCSSCCNC(=O)CCC(=O)N1Cc2ccccc2C#Cc2ccccc21]
(C6-SS-Alk) or (Alk-SS-C6)

TABLE 7-continued
Structures Representing Various Modified Nucleotides, Targeting Groups, and Linking Groups
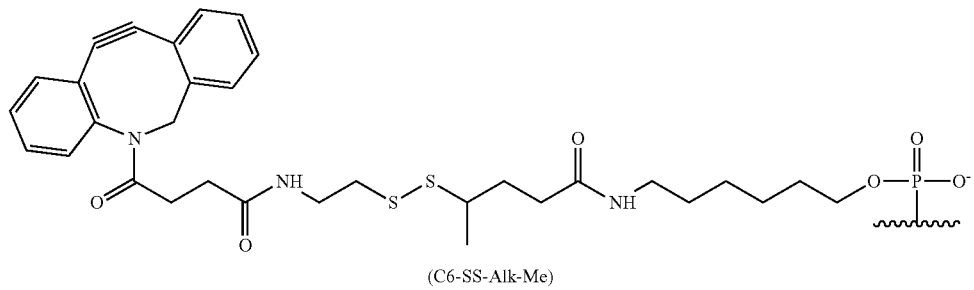 [SMILES: *P(=O)([O-])OCCCCCCNC(=O)CCC(C)SSCCNC(=O)CCC(=O)N1Cc2ccccc2C#Cc2ccccc21]
(C6-SS-Alk-Me)
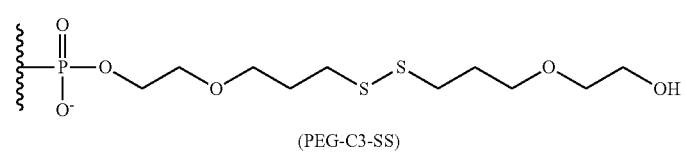 [SMILES: *P(=O)([O-])OCCOCCCSSCCCOCCO]
(PEG-C3-SS)
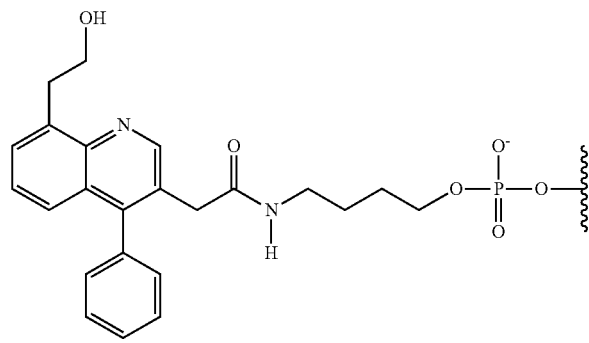
(PAZ)
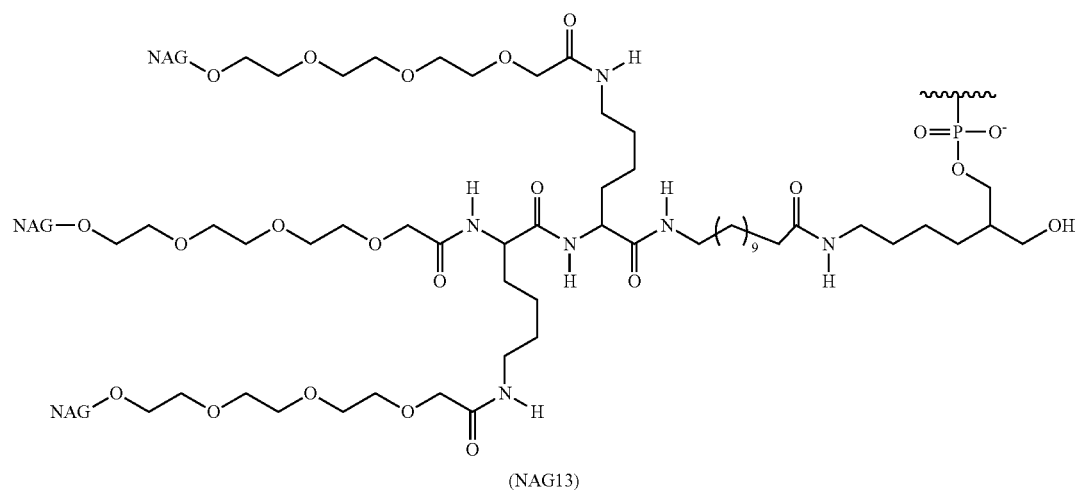
(NAG13)

TABLE 7-continued
Structures Representing Various Modified Nucleotides, Targeting Groups, and Linking Groups
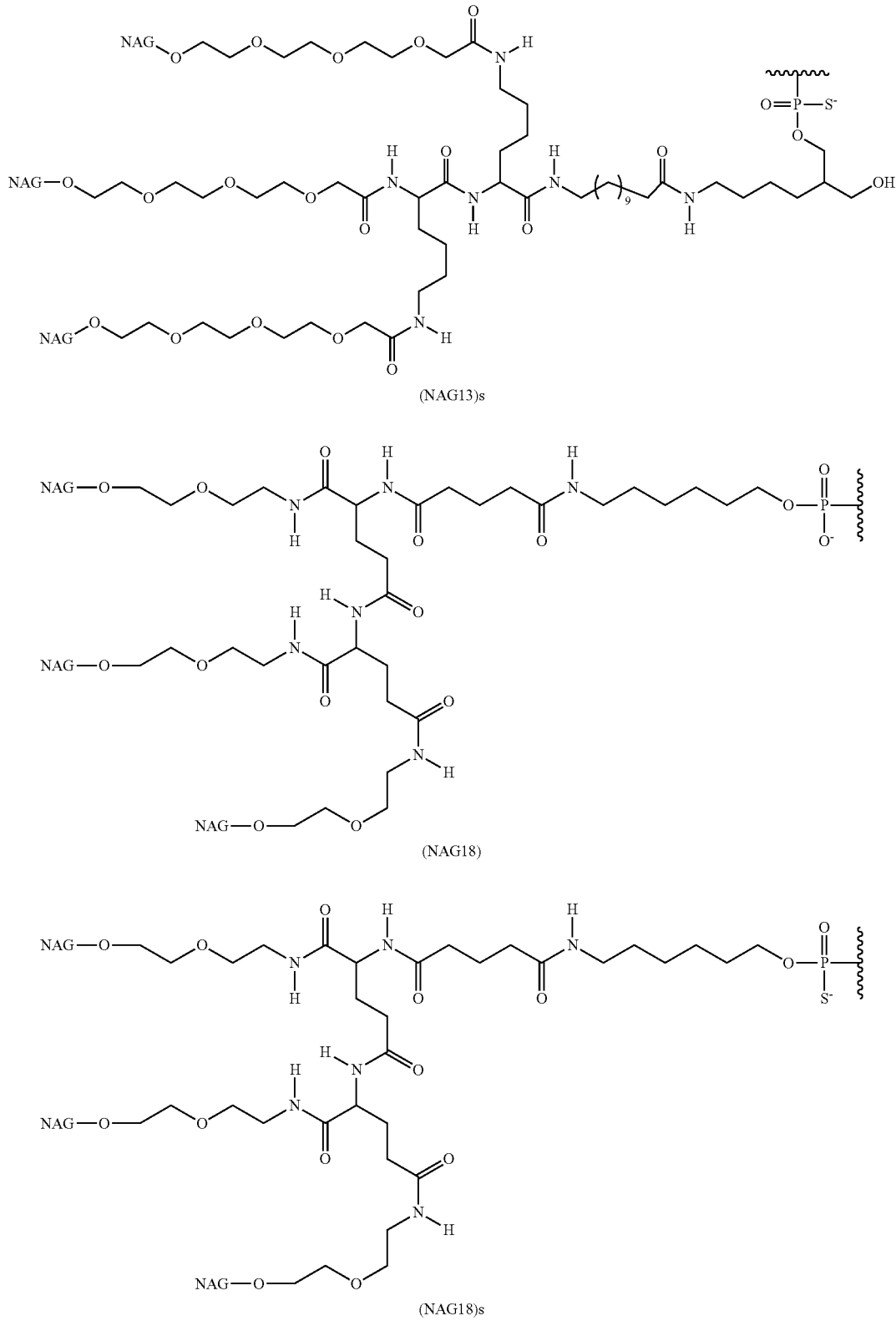
(NAG13)s
(NAG18)
(NAG18)s TABLE 7-continued
Structures Representing Various Modified Nucleotides, Targeting Groups, and Linking Groups
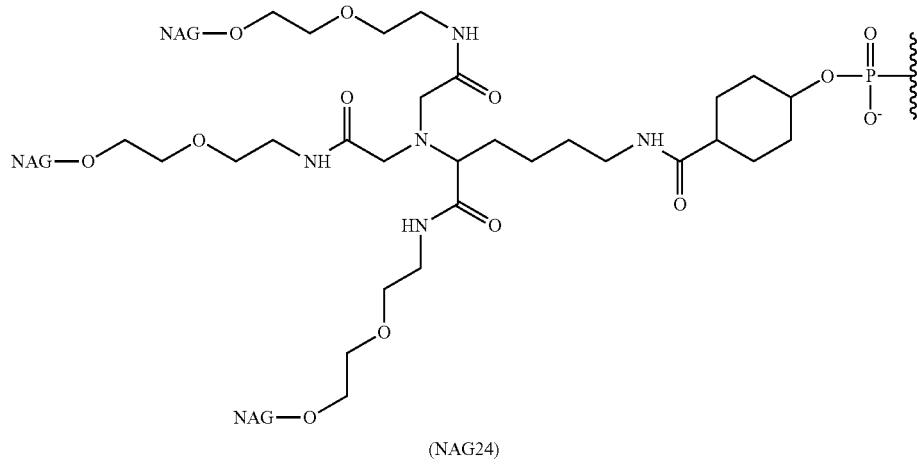
(NAG24)
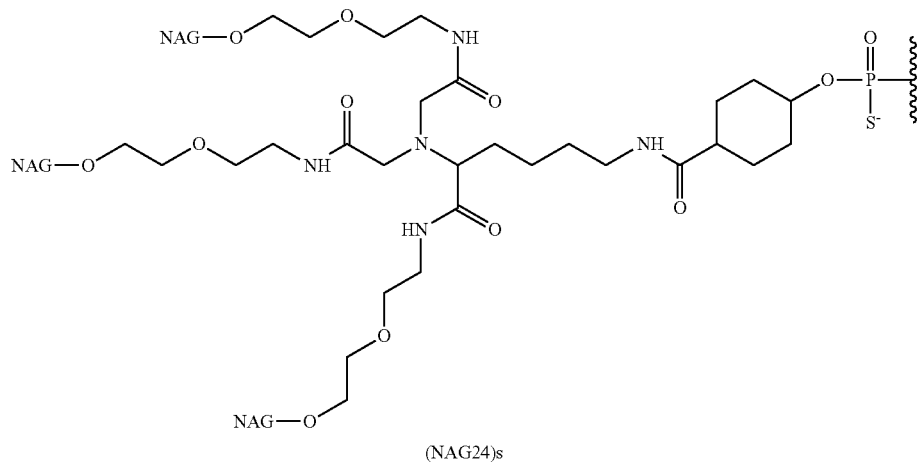
(NAG24)s
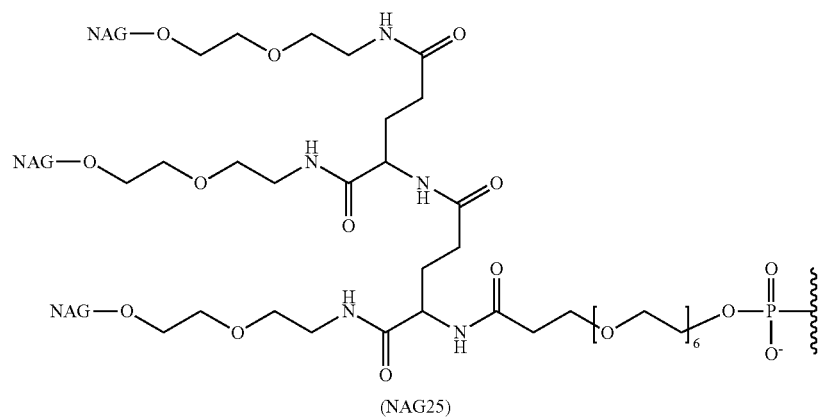
(NAG25)

TABLE 7-continued
Structures Representing Various Modified Nucleotides, Targeting Groups, and Linking Groups
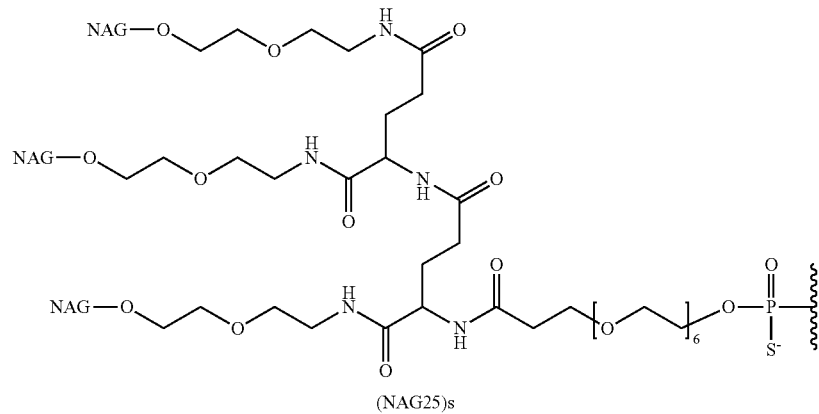
(NAG25)s
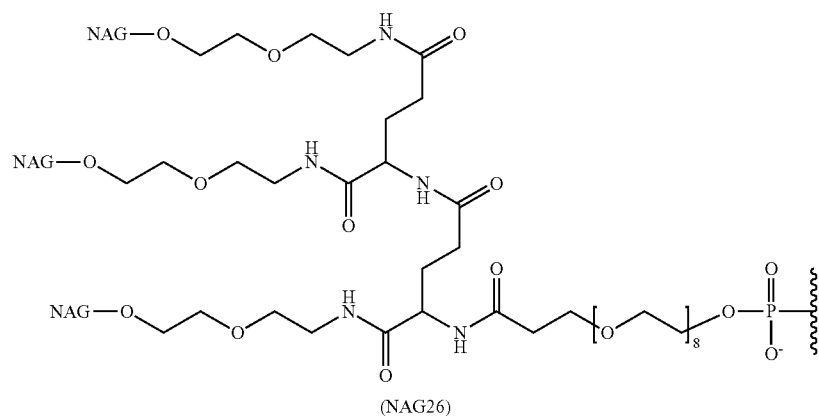
(NAG26)
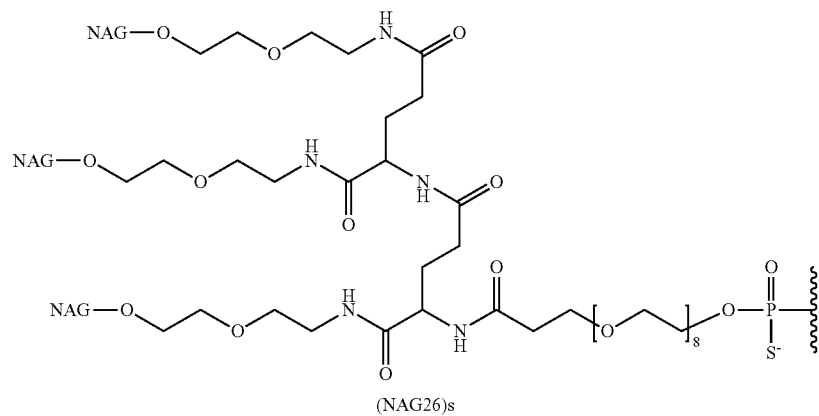
(NAG26)s TABLE 7-continued
Structures Representing Various Modified Nucleotides, Targeting Groups, and Linking Groups
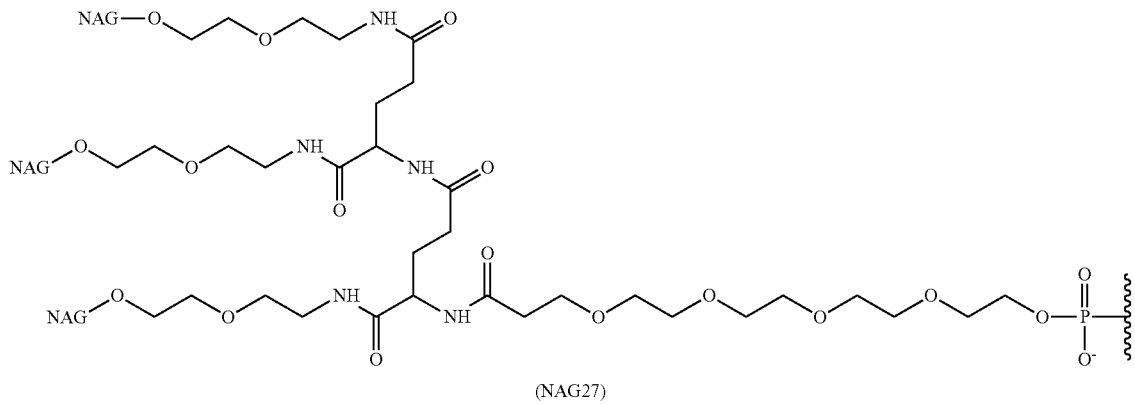
(NAG27)
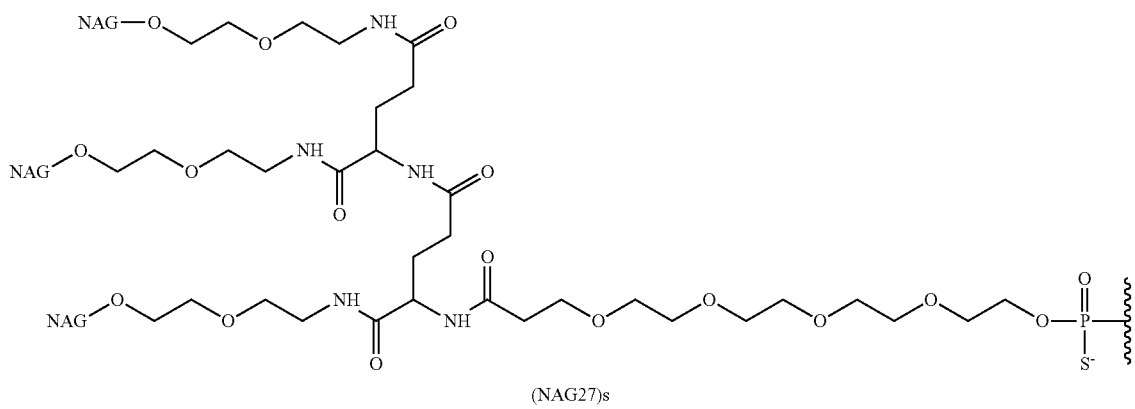
(NAG27)s
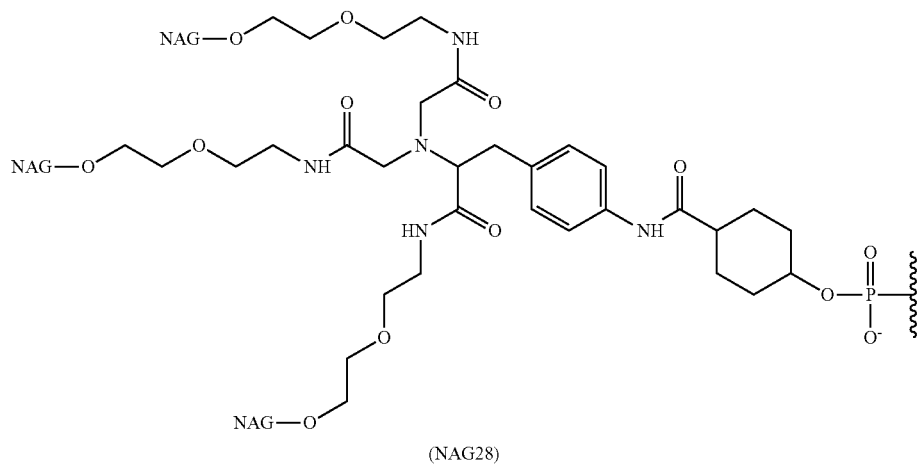
(NAG28)

TABLE 7-continued
Structures Representing Various Modified Nucleotides, Targeting Groups, and Linking Groups
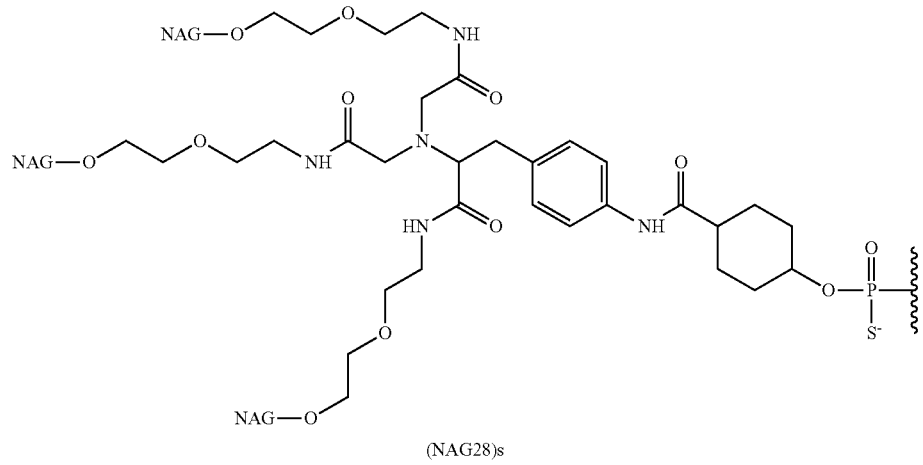
(NAG28)s
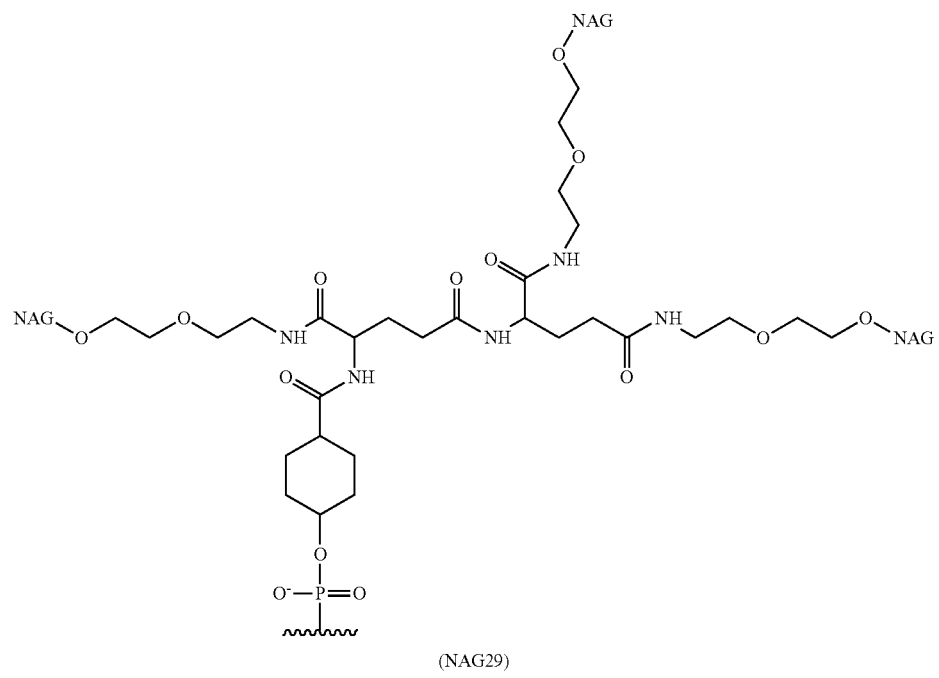
(NAG29)

TABLE 7-continued
Structures Representing Various Modified Nucleotides, Targeting Groups, and Linking Groups
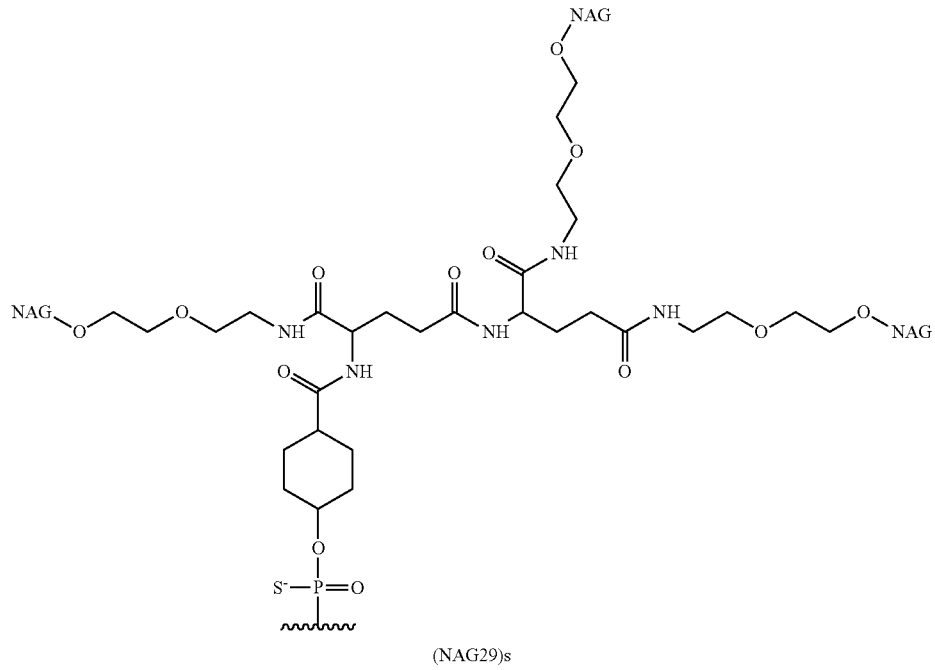
(NAG29)s
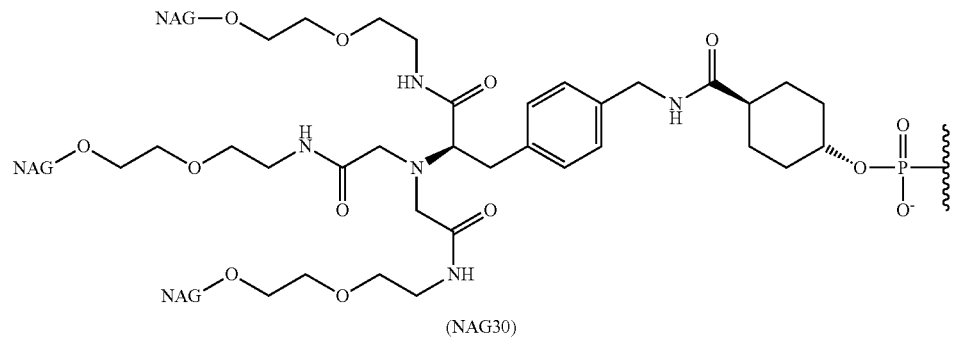
(NAG30)
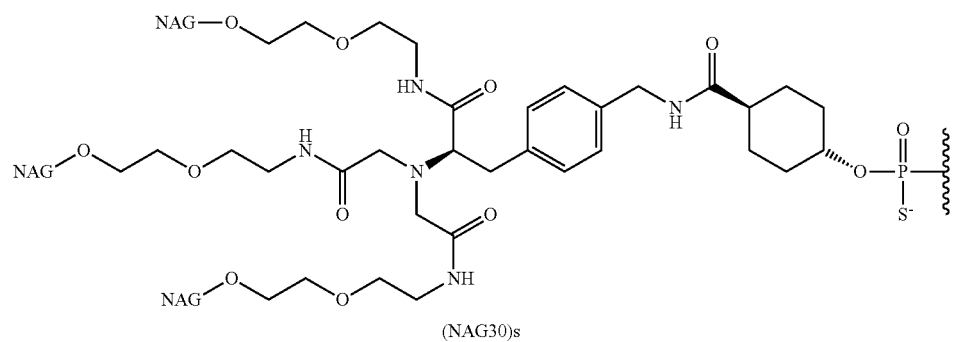
(NAG30)s TABLE 7-continued
Structures Representing Various Modified Nucleotides, Targeting Groups, and Linking Groups
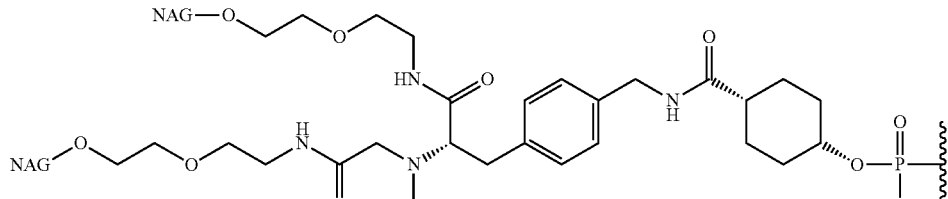
(NAG31)
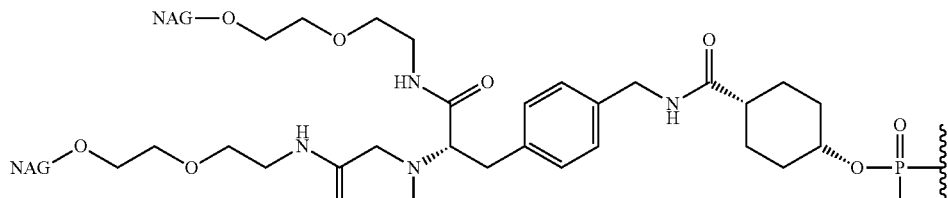
(NAG31)s
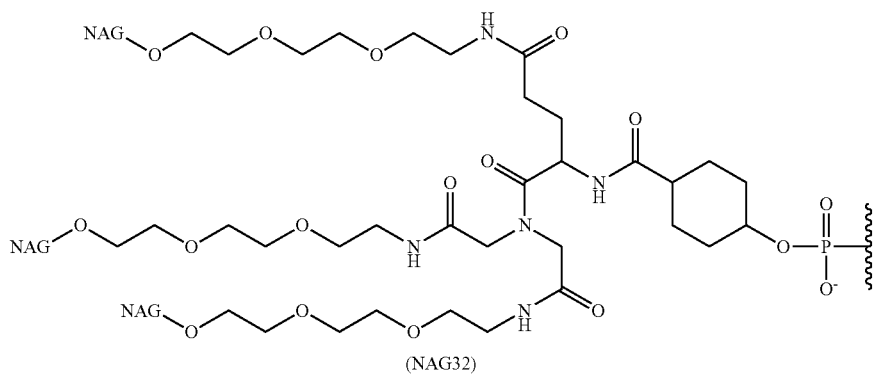
(NAG32)
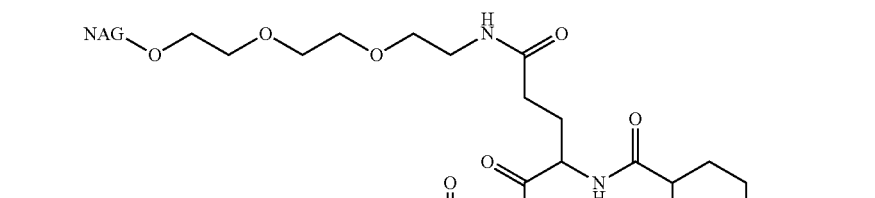
(NAG32)s TABLE 7-continued
Structures Representing Various Modified Nucleotides, Targeting Groups, and Linking Groups
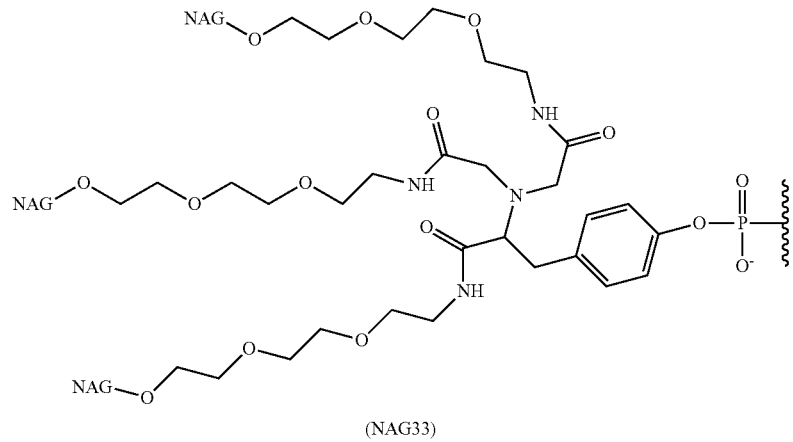
(NAG33)
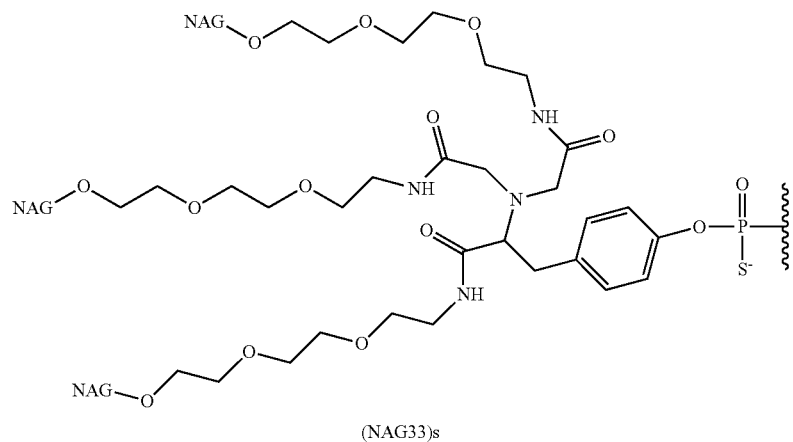
(NAG33)s
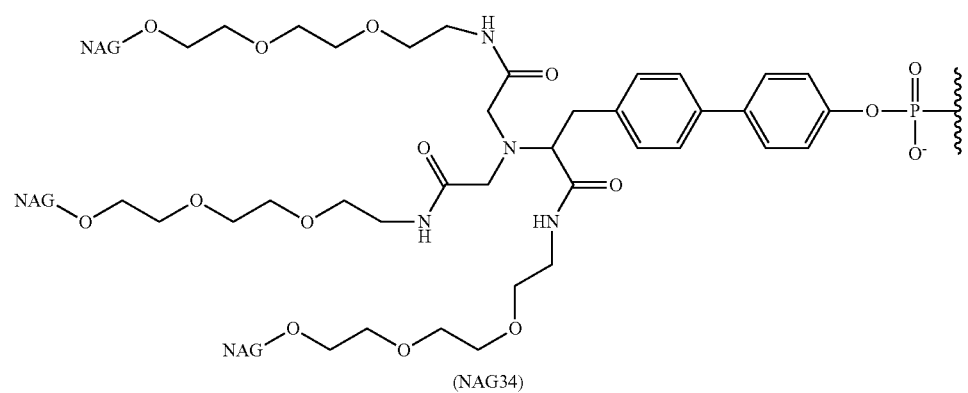
(NAG34)

TABLE 7-continued
Structures Representing Various Modified Nucleotides, Targeting Groups, and Linking Groups
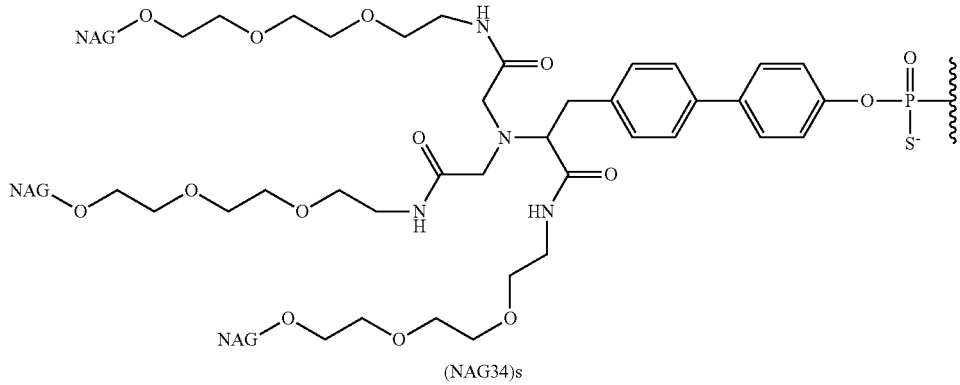
(NAG34)s
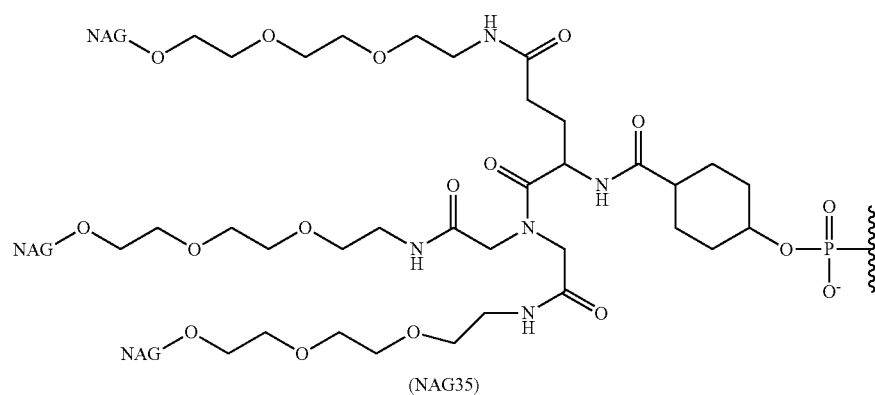
(NAG35)
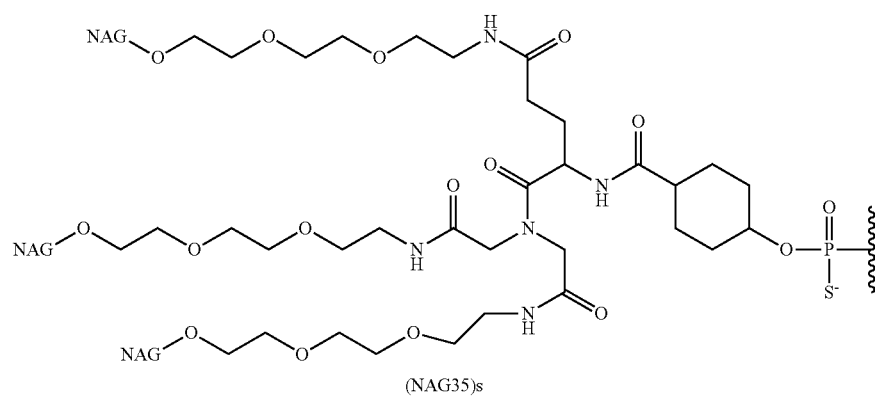
(NAG35)s TABLE 7-continued
Structures Representing Various Modified Nucleotides, Targeting Groups, and Linking Groups
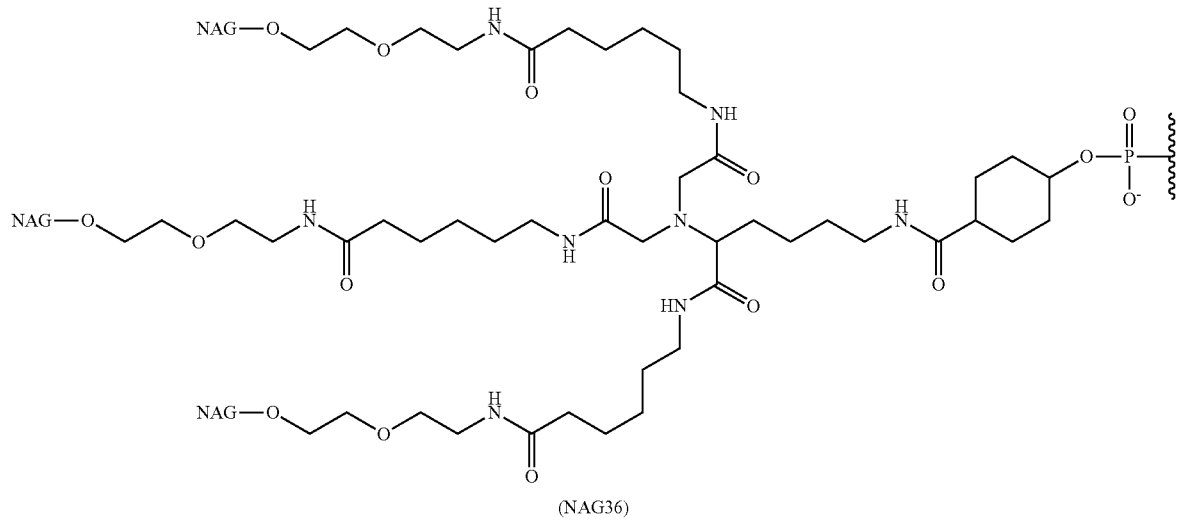
(NAG36)
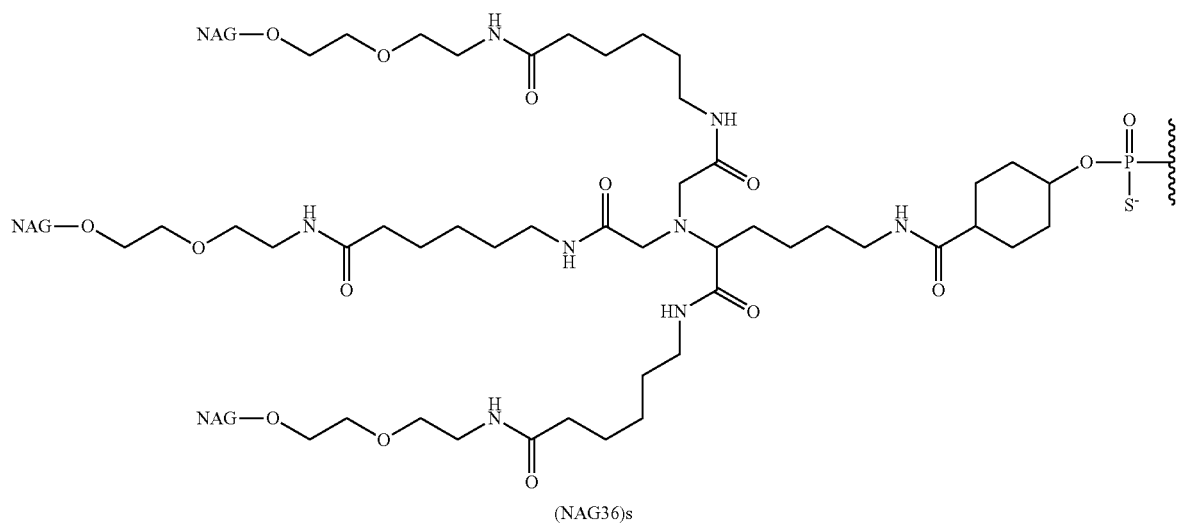
(NAG36)s
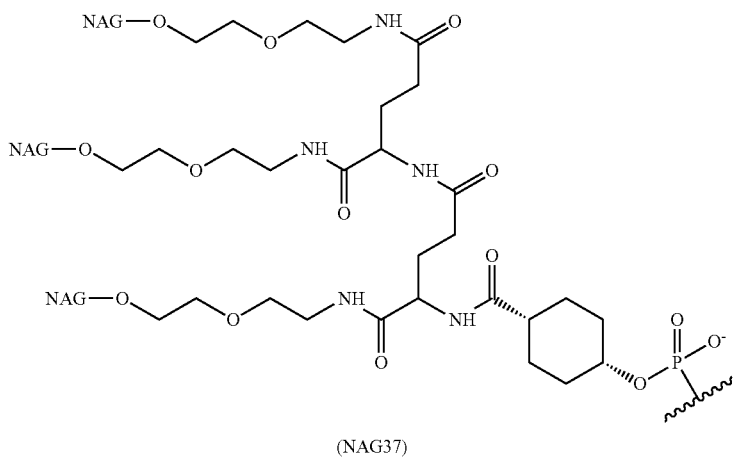
(NAG37)

TABLE 7-continued
Structures Representing Various Modified Nucleotides, Targeting Groups, and Linking Groups
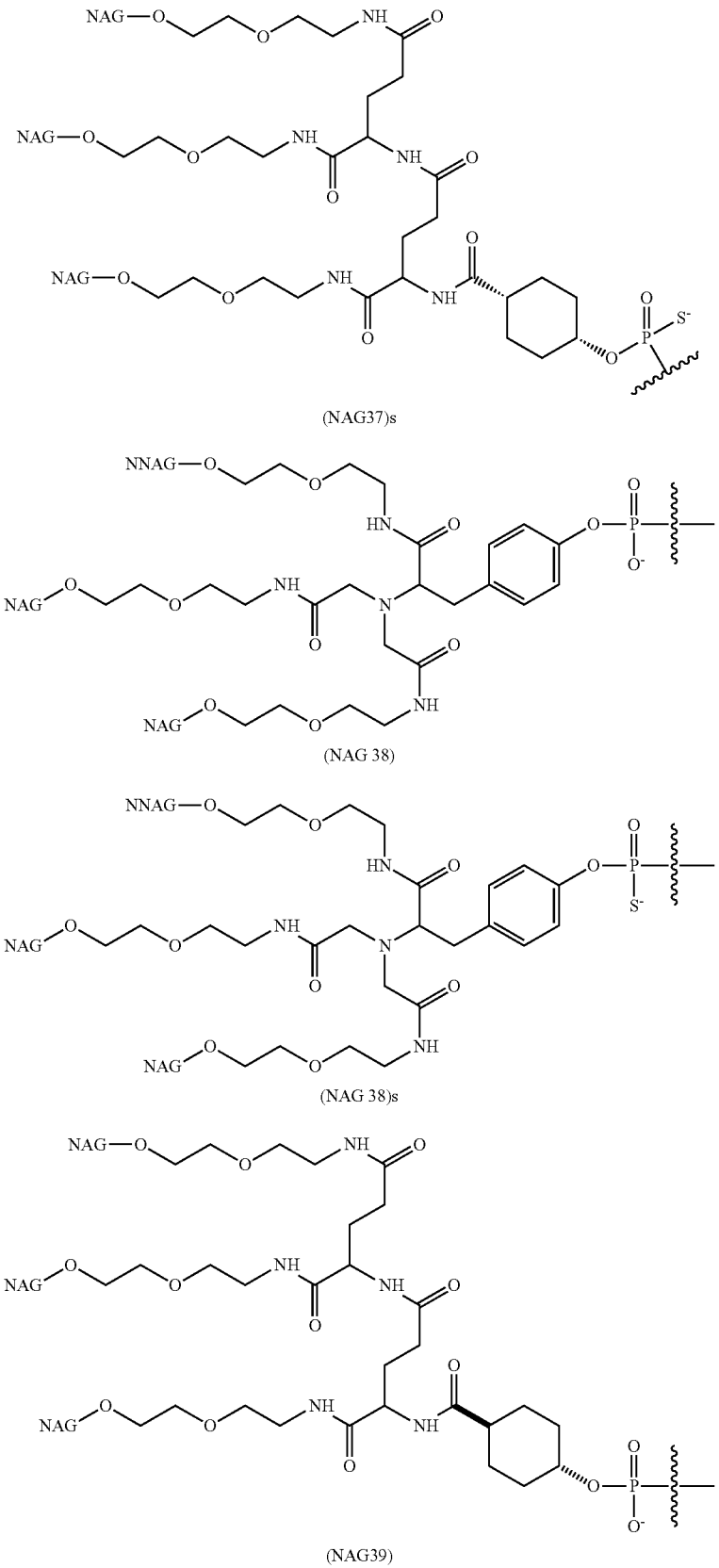
(NAG37)s
(NAG 38)
(NAG 38)s
(NAG39)

TABLE 7-continued

Structures Representing Various Modified Nucleotides, Targeting Groups, and Linking Groups

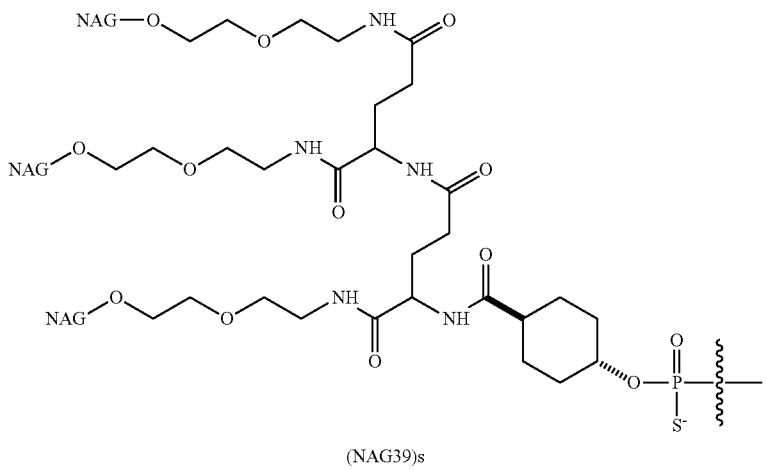

(NAG39)s

In each of the above structures in Table 7, NAG comprises an N-acetyl-galactosamine or another asialoglycoprotein receptor ligand, as would be understood by a person of ordinary skill in the art to be attached in view of the structures above and description provided herein. For example, in some embodiments, NAG in the structures provided in Table 7 is represented by the following structure:

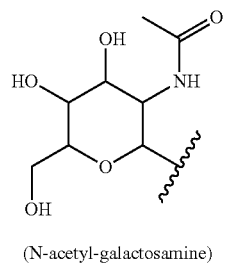

(N-acetyl-galactosamine)

Each (NAGx) can be attached to an AAT RNAi agent via a phosphate group (as in (NAG25), (NAG30), and (NAG31)), or a phosphorothioate group, (as is (NAG25)s, (NAG29)s, (NAG30)s, (NAG31)s, or (NAG37)s), or another linking group.

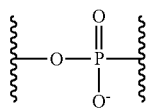   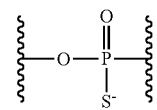

Phosphate group   Phosphorothioate group

Other linking groups known in the art may be used.

In some embodiments, a delivery vehicle can be used to deliver an RNAi agent to a cell or tissue. A delivery vehicle is a compound that improves delivery of the RNAi agent to a cell or tissue. A delivery vehicle can include, or consist of, but is not limited to: a polymer, such as an amphipathic polymer, a membrane active polymer, a peptide, a melittin peptide, a melittin-like peptide (MLP), a lipid, a reversibly modified polymer or peptide, or a reversibly modified membrane active polyamine. In some embodiments, the RNAi agents can be combined with lipids, nanoparticles, polymers, liposomes, micelles, DPCs or other delivery systems available in the art. The RNAi agents can also be chemically conjugated to targeting groups, lipids (including, but not limited to cholesterol and cholesteryl derivatives), nanoparticles, polymers, liposomes, micelles, DPCs (see, for example WO 2000/053722, WO 2008/0022309, WO 2011/104169, and WO 2012/083185, WO 2013/032829, WO 2013/158141, each of which is incorporated herein by reference), or other delivery systems available in the art.

Pharmaceutical Compositions and Formulations

The AAT RNAi agents disclosed herein can be prepared as pharmaceutical compositions or formulations. In some embodiments, pharmaceutical compositions include at least one AAT RNAi agent. These pharmaceutical compositions are particularly useful in the inhibition of the expression of the target mRNA in a target cell, a group of cells, a tissue, or an organism. The pharmaceutical compositions can be used to treat a subject having a disease or disorder that would benefit from reduction in the level of the target mRNA, or inhibition in expression of the target gene. The pharmaceutical compositions can be used to treat a subject at risk of developing a disease or disorder that would benefit from reduction of the level of the target mRNA or an inhibition in expression the target gene. In one embodiment, the method includes administering an AAT RNAi agent linked to a targeting ligand as described herein, to a subject to be treated. In some embodiments, one or more pharmaceutically acceptable excipients (including vehicles, carriers, diluents, and/or delivery polymers) are added to the pharmaceutical compositions including an AAT RNAi agent, thereby forming a pharmaceutical formulation suitable for in vivo delivery to a subject, including a human.

The pharmaceutical compositions that include an AAT RNAi agent and methods disclosed herein decrease the level of the target mRNA in a cell, group of cells, group of cells, tissue, or subject, including: administering to the subject a therapeutically effective amount of a herein described AAT RNAi agent, thereby inhibiting the expression of AAT mRNA in the subject.

In some embodiments, the described pharmaceutical compositions including an AAT RNAi agent are used for treating or managing clinical presentations in a subject with AATD, such as chronic hepatitis, cirrhosis, hepatocellular carcinoma, transaminitis, cholestasis, fibrosis, and even fulminant hepatic failure. In some embodiments, a therapeutically or prophylactically effective amount of one or more of pharmaceutical compositions is administered to a subject in need of such treatment. In some embodiments, administration of any of the disclosed AAT RNAi agents can be used to decrease the number, severity, and/or frequency of symptoms of a disease in a subject.

The described pharmaceutical compositions including an AAT RNAi agent can be used to treat at least one symptom in a subject having a disease or disorder that would benefit from reduction or inhibition in expression of AAT mRNA. In some embodiments, the subject is administered a therapeutically effective amount of one or more pharmaceutical compositions including an AAT RNAi agent thereby treating the symptom. In other embodiments, the subject is administered a prophylactically effective amount of one or more AAT RNAi agents, thereby preventing the at least one symptom.

The route of administration is the path by which an AAT RNAi agent is brought into contact with the body. In general, methods of administering drugs and nucleic acids for treatment of a mammal are well known in the art and can be applied to administration of the compositions described herein. The AAT RNAi agents disclosed herein can be administered via any suitable route in a preparation appropriately tailored to the particular route. Thus, herein described pharmaceutical compositions can be administered by injection, for example, intravenously, intramuscularly, intracutaneously, subcutaneously, intraarticularly, or intraperitoneally. In some embodiments, the herein described pharmaceutical compositions are administered via subcutaneous injection.

The pharmaceutical compositions including an AAT RNAi agent described herein can be delivered to a cell, group of cells, tissue, or subject using oligonucleotide delivery technologies known in the art. In general, any suitable method recognized in the art for delivering a nucleic acid molecule (in vitro or in vivo) can be adapted for use with the compositions described herein. For example, delivery can be by local administration, (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In certain embodiments, the compositions are administered by subcutaneous or intravenous infusion or injection.

Accordingly, in some embodiments, the pharmaceutical compositions described herein comprise one or more pharmaceutically acceptable excipients. The pharmaceutical compositions described herein are formulated for administration to a subject.

As used herein, a pharmaceutical composition or medicament includes a pharmacologically effective amount of at least one of the described AAT RNAi agents and one or more pharmaceutically acceptable excipients. Pharmaceutically acceptable excipients (excipients) are substances other than the Active Pharmaceutical Ingredient (API, therapeutic product, e.g., AAT RNAi agent) that are intentionally included in the drug delivery system. Excipients do not exert or are not intended to exert a therapeutic effect at the intended dosage. Excipients can act to a) aid in processing of the drug delivery system during manufacture, b) protect, support, or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor® EL™ (BASF, Parsippany, NJ) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle, which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

The AAT RNAi agents can be formulated in compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). It is also envisioned that cells, tissues, or isolated organs that express or comprise the herein defined RNAi agents may be used as "pharmaceutical compositions." As used herein, "pharmacologically effective amount," "therapeutically effective amount," or simply "effective amount" refers to that amount of an RNAi agent to produce a pharmacological, therapeutic or preventive result.

Generally, an effective amount of an active compound will be in the range of from about 0.1 to about 100 mg/kg of body weight/day, e.g., from about 1.0 to about 50 mg/kg of body weight/day. In some embodiments, an effective amount of an active compound will be in the range of from about 0.25 to about 5 mg/kg of body weight per dose. In some embodiments, an effective amount of an active ingredient will be in the range of from about 0.5 to about 4 mg/kg of body weight per dose. The amount administered will also likely depend on such variables as the overall health status of the patient, the relative biological efficacy of the compound delivered, the formulation of the drug, the presence and types of excipients in the formulation, and the route of administration. Also, it is to be understood that the initial dosage administered can, in some instances, be increased beyond the above upper level to rapidly achieve the desired blood-level or tissue level, or the initial dosage can, in some instances, be smaller than the optimum.

For treatment of disease or for formation of a medicament or composition for treatment of a disease, the pharmaceutical compositions described herein including an AAT RNAi agent can be combined with an excipient or with a second therapeutic agent or treatment including, but not limited to: a second or other RNAi agent, a small molecule drug, an antibody, an antibody fragment, peptide and/or aptamer.

The described AAT RNAi agents, when added to pharmaceutically acceptable excipients or adjuvants, can be packaged into kits, containers, packs, or dispensers. The pharmaceutical compositions described herein can be packaged in pre-filled syringes or vials.

Methods of Treatment and Inhibition of Expression

The AAT RNAi agents disclosed herein can be used to treat a subject (e.g., a human or other mammal) having a disease or disorder that would benefit from administration of the compound. In some embodiments, the RNAi agents disclosed herein can be used to treat a subject (e.g., a human) having AATD, or symptoms, diseases, or disorders that would benefit from reduction or inhibition in expression of AAT mRNA, such as AATD liver disease. The subject is administered a therapeutically effective amount of any one or more of the AAT RNAi agents described herein. The subject can be a human, patient, or human patient. The subject may be an adult, adolescent, child, or infant. The described pharmaceutical compositions including an AAT RNAi agent can be used to provide methods for the therapeutic treatment of diseases, such as AATD. Such methods include administration of a pharmaceutical composition described herein to a human being or animal.

In some embodiments, the AAT RNAi agents described herein are used to treat a subject with AATD, including symptoms, diseases or disorders related to AATD. AATD liver diseases or disorders include, but are not limited to, chronic hepatitis, cirrhosis, hepatocellular carcinoma, transaminitis, cholestasis, fibrosis, and fulminant hepatic failure. In some embodiments, the described AAT RNAi agents are used to treat at least one symptom in a subject having AATD. The subject is administered a therapeutically effective amount of any one or more of the described RNAi agents.

In certain embodiments, the present invention provides methods for treatment of AATD in a patient in need thereof, comprising administering to the patient any of the AAT RNAi agents described herein.

In some embodiments, the AAT RNAi agents are used to treat or manage a clinical presentation of a subject with an AATD liver disease or disorder. The subject is administered a therapeutically effective amount of one or more of the AAT RNAi agents or AAT RNAi agent-containing compositions described herein. In some embodiments, the method comprises administering a composition comprising an AAT RNAi agent described herein to a subject to be treated.

In some embodiments, the gene expression level and/or mRNA level of an AAT gene in a subject to whom a described AAT RNAi agent is administered is reduced by at least about 5%, 10%, 15%, 20%, 25%, 30%, 35%, 40%, 45%, 50%, 55%, 60%, 65%, 70%, 75%, 80%, 85%, 95%, 96%, 97%, 98%, 99%, or greater than 99% relative to the subject prior to being administered the AAT RNAi agent or to a subject not receiving the AAT RNAi agent. The gene expression level and/or mRNA level in the subject is reduced in a cell, group of cells, and/or tissue of the subject.

In some embodiments, the protein level of AAT in a subject to whom a described AAT RNAi agent has been administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the AAT RNAi agent or to a subject not receiving the AAT RNAi agent. The protein level in the subject is reduced in a cell, group of cells, tissue, blood, and/or other fluid of the subject.

In some embodiments, the Z-AAT polymer protein level in a subject having AATD to whom a described AAT RNAi agent has been administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the AAT RNAi agent or to a subject not receiving the AAT RNAi agent. In some embodiments, the Z-AAT polymer protein level in a subject to whom a described AAT RNAi agent has been administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the AAT RNAi agent or to a subject not receiving the AAT RNAi agent.

A reduction in AAT gene expression, AAT mRNA, or AAT protein levels can be assessed and quantified by general methods known in the art. The Examples disclosed herein set forth generally known methods for assessing inhibition of AAT gene expression and reduction in AAT protein levels. The reduction or decrease in AAT mRNA level and/or protein level (including Z-AAT polymer and/or monomer) are collectively referred to herein as a reduction or decrease in AAT or inhibiting or reducing the expression of AAT.

Cells and Tissues and Non-Human Organisms

Cells, tissues, and non-human organisms that include at least one of the AAT RNAi agents described herein is contemplated. The cell, tissue, or non-human organism is made by delivering the RNAi agent to the cell, tissue, or non-human organism.

The above provided embodiments and items are now illustrated with the following, non-limiting examples.

EXAMPLES

Example 1. Identification of RNAi Agent Sequences and Synthesis of RNAi Agents

A selection process for identifying lead sequences for inhibiting expression of the AAT gene began with in silico methods to identify conserved sequences across variants of an AAT gene (SEQ ID NO: 1). The AAT sequence was initially screened using bioinformatics for 19-nucleotide sequences having a complementary sequence in known variants of human AAT. Sequences known to have manufacturing challenges and those predicted to have poor RNAi activity based on known parameters were eliminated. Sequences were then subjected to cross-species reactivity analysis to select candidates that would cross-react with cynomolgus monkey AAT. The sequences were also evaluated for specificity to avoid off-target effects against the human and cynomolgus monkey genomes. One-hundred fifteen (115) sequence families of 19-mers were selected as candidates.

The duplexes in Table 6 herein were synthesized according to the following procedures:

Synthesis

The sense and antisense strands of the AAT RNAi agents were synthesized according to phosphoramidite technology on solid phase used in oligonucleotide synthesis. Depending on the scale, either a MerMade96E® (Bioautomation) or a MerMade12® (Bioautomation) was used. Syntheses were performed on a solid support made of controlled pore glass (CPG, 500 Å or 600 Å, obtained from Prime Synthesis, Aston, PA, USA). All RNA and 2'-modified RNA phosphoramidites were purchased from Thermo Fisher Scientific (Milwaukee, WI, USA). Specifically, the following 2'-O-methyl phosphoramidites were used: (5'-O-dimethoxytrityl-N6-(benzoyl)-2'-O-methyl-adenosine-3-O-(2-cyanoethyl-N, N-diisopropy-lamino) phosphoramidite, 5'-O-dimethoxytrityl-N4-(acetyl)-2'-O-methyl-cytidine-3'-O-(2-cyanoethyl-N,N-diisopropyl-amino) phosphoramidite, (5'-O-dimethoxytrityl-N2-(isobutyryl)-2'-O-methyl-guanosine-3'-O-(2-cyano-ethyl-N,N-diisopropylamino)phosphoramidite, and 5'-O-dimethoxy-trityl-2'-O-methyl-uridine-3'-O-(2-cyanoethyl-N,N-diisopropylamino)phosphoramidite. The 2'-deoxy-2'-fluoro-phosphoramidites carried the same protecting groups as the 2'-O-methyl RNA amidites. The following UNA phosphoramidites were used: 5'-(4,4'-Dimethoxytrityl)-N-benzoyl-2',3'-seco-adenosine, 2'-benzoyl-3'-[(2-cyanoethyl)-(N,N-diisopropyl)]-phosphor-amidite, 5'-(4,4'-Dimethoxytrityl)-N-acetyl-2',3'-seco-cytosine, 2'-benzoyl-3'-[(2-cyanoethyl)-(N,N-diiso-propyl)]-phosphoramidite, 5'-(4,4'-Dimethoxytrityl)-N-isobutyryl-2',3'-seco-guanosine, 2'-benzoyl-3'-[(2-cyanoethyl)-(N,N-diisopropyl)]-phosphoramidite, and 5'-(4,4'-Dimethoxy-trityl)-2',3'-seco-uridine, 2'-benzoyl-3'-[(2-cyanoethyl)-(N,N-diiso-propyl)]-phosphoramidite.

Targeting ligand-containing phosphoramidites were dissolved in anhydrous dichloromethane or anhydrous acetonitrile (50 mM), while all other amidites were dissolved in anhydrous acetonitrile (50 mM) and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 min (RNA), 15 min (targeting ligand), 90 sec (2'OMe), and 60 sec (2'F). In order to introduce phosphorothioate linkages, a 100 mM solution of 3-phenyl 1,2,4-dithiazoline-5-one (POS, obtained from PolyOrg, Inc., Leominster, MA, USA) in anhydrous Acetonitrile was employed.

Cleavage and Deprotection of Support Bound Oligomers.

After finalization of the solid phase synthesis, the dried solid support was treated with a 1:1 volume solution of 40 wt. % methylamine in water and 28% ammonium hydroxide solution (Aldrich) for two hours at 30° C. The solution was evaporated and the solid residue was reconstituted in water (see below).

Purification

Crude oligomers were purified by anionic exchange HPLC using a TKSgel SuperQ-5PW 13 u column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 16/40 column packed with Sephadex G-25 medium with a running buffer of 100 mM ammonium bicarbonate, pH 6.7 and 20% Acetonitrile.

Annealing

Complementary strands were mixed by combining equimolar RNA solutions (sense and antisense) in 0.2×PBS (Phosphate-Buffered Saline, 1×, Corning, Cellgro) to form the RNAi agents. This solution was placed into a thermomixer at 70° C., heated to 95° C., held at 95° C. for 5 min, and cooled to room temperature slowly. Some RNAi agents were lyophilized and stored at −15 to −25° C. Duplex concentration was determined by measuring the solution absorbance on a UV-Vis spectrometer in 0.2×PBS. The solution absorbance at 260 nm was then multiplied by a conversion factor and the dilution factor to determine the duplex concentration. Unless otherwise stated, all conversion factor was 0.037 mg/(mL·cm). For some experiments, a conversion factor was calculated from an experimentally determined extinction coefficient.

Example 2. In Vitro Testing of AAT RNAi Agents

Candidate sequence duplexes were tested in vitro. The antisense strand sequences and sense strand sequences were annealed to form duplexes of 21-mer strands (having 19 base pairs and a di-nucleotide UU overhang on each 3' end) for in vitro testing, as shown in the following Table 8:

TABLE 8

Sequences of AAT RNAi Agents in Example 2

| SEQ ID NO: | Antisense Sequence (5' → 3') | SEQ ID NO: | Sense Sequence (5' → 3') | Duplex ID No. |
|---|---|---|---|---|
| 1035 | AGAAGAUAUUGGUGCUGUUUU | 1150 | AACAGCACCAAUAUCUUCUUU | D1 |
| 1036 | AGGAACUUGGUGAUGAUAUUU | 1151 | AUAUCAUCACCAAGUUCCUUU | D2 |
| 1037 | UGUCUUCUGGGCAGCAUCUUU | 1152 | AGAUGCUGCCCAGAAGACAUU | D3 |
| 1038 | UGUUGGACUGGUGUGCCAGUU | 1153 | CUGGCACACCAGUCCAACAUU | D4 |
| 1039 | CUGUUGGACUGGUGUGCCAUU | 1154 | UGGCACACCAGUCCAACAGUU | D5 |
| 1040 | UGCUGUUGGACUGGUGUGCUU | 1155 | GCACACCAGUCCAACAGCAUU | D6 |
| 1041 | UAUUGGUGCUGUUGGACUGUU | 1156 | CAGUCCAACAGCACCAAUAUU | D7 |
| 1042 | AUAUUGGUGCUGUUGGACUUU | 1157 | AGUCCAACAGCACCAAUAUUU | D8 |
| 1043 | GAUAUUGGUGCUGUUGGACUU | 1158 | GUCCAACAGCACCAAUAUCUU | D9 |
| 1044 | AAGAUAUUGGUGCUGUUGGUU | 1159 | CCAACAGCACCAAUAUCUUUU | D10 |
| 1045 | GUAGCGAUGCUCACUGGGGUU | 1160 | CCCCAGUGAGCAUCGCUACUU | D11 |
| 1046 | AAAGGCUGUAGCGAUGCUCUU | 1161 | GAGCAUCGCUACAGCCUUUUU | D12 |
| 1047 | GCAAAGGCUGUAGCGAUGCUU | 1162 | GCAUCGCUACAGCCUUUGCUU | D13 |
| 1048 | UGCAAAGGCUGUAGCGAUGUU | 1163 | CAUCGCUACAGCCUUUGCAUU | D14 |
| 1049 | AUUGCAAAGGCUGUAGCGAUU | 1164 | UCGCUACAGCCUUUGCAAUUU | D15 |
| 1050 | AGCAUUGCAAAGGCUGUAGUU | 1165 | CUACAGCCUUUGCAAUGCUUU | D16 |
| 1051 | AGAGCAUUGCAAAGGCUGUUU | 1166 | ACAGCCUUUGCAAUGCUCUUU | D17 |
| 1052 | GGAGUUCCUGGAAGCCUUCUU | 1167 | GAAGGCUUCCAGGAACUCCUU | D18 |
| 1053 | UCCAAAAACUUAUCCACUAUU | 1168 | UAGUGGAUAAGUUUUUGGAUU | D19 |
| 1054 | AAGGCUUCUGAGUGGUACAUU | 1169 | UGUACCACUCAGAAGCCUUUU | D20 |
| 1055 | GAAGGCUUCUGAGUGGUACUU | 1170 | GUACCACUCAGAAGCCUUCUU | D21 |
| 1056 | UUCUUGGCCUCUUCGGUGUUU | 1171 | ACACCGAAGAGGCCAAGAAUU | D22 |
| 1057 | GUUUCUUGGCCUCUUCGGUUU | 1172 | ACCGAAGAGGCCAAGAAACUU | D23 |
| 1058 | UUGAUCUGUUUCUUGGCCUUU | 1173 | AGGCCAAGAAACAGAUCAAUU | D24 |
| 1059 | GUUGAUCUGUUUCUUGGCCUU | 1174 | GGCCAAGAAACAGAUCAACUU | D25 |
| 1060 | CGUUGAUCUGUUUCUUGGCUU | 1175 | GCCAAGAAACAGAUCAACGUU | D26 |
| 1061 | CACAAUUUCCCUUGAGUAUU | 1176 | UACUCAAGGGAAAUUGUGUUU | D27 |
| 1062 | UCCACAAUUUCCCUUGAGUUU | 1177 | CUCAAGGGAAAUUGUGGAUUU | D28 |
| 1063 | AUCCACAAUUUCCCUUGAUU | 1178 | UCAAGGGAAAUUGUGGAUUUU | D29 |
| 1064 | UGUCAAGCUCCUUGACCAAUU | 1179 | UUGGUCAAGGAGCUUGACAUU | D30 |
| 1065 | GUGUCUCUGUCAAGCUCCUUU | 1180 | AGGAGCUUGACAGAGACACUU | D31 |
| 1066 | ACUGUGUCUCUGUCAAGCUUU | 1181 | AGCUUGACAGAGACACAGUUU | D32 |
| 1067 | UGUAAUUCACCAGAGCAAAUU | 1182 | UUUGCUCUGGUGAAUUACAUU | D33 |
| 1068 | UUAAACAUGCCUAAACGCUUU | 1183 | AGCGUUUAGGCAUGUUUAAUU | D34 |
| 1069 | GUUAAACAUGCCUAAACGCUU | 1184 | GCGUUUAGGCAUGUUUAACUU | D35 |
| 1070 | UGUUAAACAUGCCUAAACGUU | 1185 | CGUUAGGCAUGUUUAACAUU | D36 |
| 1071 | GGAUGUUAAACAUGCCUAAUU | 1186 | UUAGGCAUGUUUAACAUCCUU | D37 |
| 1072 | AUUUCAUCAGCAGCACCCAUU | 1187 | UGGGUGCUGCUGAUGAAAUUU | D38 |

TABLE 8-continued

Sequences of AAT RNAi Agents in Example 2

| SEQ ID NO: | Antisense Sequence (5' → 3') | SEQ ID NO: | Sense Sequence (5' → 3') | Duplex ID No. |
|---|---|---|---|---|
| 1073 | GAAGAAGAUGGCGGUGGCAUU | 1188 | UGCCACCGCCAUCUUCUUCUU | D39 |
| 1074 | GGUGAGUUCAUUUUCCAGGUU | 1189 | CCUGGAAAAUGAACUCACCUU | D40 |
| 1075 | GAACUUGGUGAUGAUAUCGUU | 1190 | CGAUAUCAUCACCAAGUUCUU | D41 |
| 1076 | CAUUUUCCAGGAACUUGGUUU | 1191 | ACCAAGUUCCUGGAAAAUGUU | D42 |
| 1077 | CAUAGGUUCCAGUAAUGGAUU | 1192 | UCCAUUACUGGAACCUAUGUU | D43 |
| 1078 | UCAUAGGUUCCAGUAAUGGUU | 1193 | CCAUUACUGGAACCUAUGAUU | D44 |
| 1079 | UCAGAUCAUAGGUUCCAGUUU | 1194 | ACUGGAACCUAUGAUCUGAUU | D45 |
| 1080 | UCUUCAGAUCAUAGGUUCCUU | 1195 | GGAACCUAUGAUCUGAAGAUU | D46 |
| 1081 | CUCUUCAGAUCAUAGGUUCUU | 1196 | GAACCUAUGAUCUGAAGAGUU | D47 |
| 1082 | GAGGUCAGCCCCAUUGCUGUU | 1197 | CAGCAAUGGGGCUGACCUCUU | D48 |
| 1083 | GAGAGGUCAGCCCCAUUGCUU | 1198 | GCAAUGGGGCUGACCUCUCUU | D49 |
| 1084 | CUUCAGGGGUGCCUCCUCUUU | 1199 | AGAGGAGGCACCCCUGAAGUU | D50 |
| 1085 | GAGAGCUUCAGGGGUGCCUUU | 1200 | AGGCACCCCUGAAGCUCUCUU | D51 |
| 1086 | UUAUGCACGGCCUUGGAGAUU | 1201 | UCUCCAAGGCCGUGCAUAAUU | D52 |
| 1087 | CCUUAUGCACGGCCUUGGAUU | 1202 | UCCAAGGCCGUGCAUAAGGUU | D53 |
| 1088 | GCCUUAUGCACGGCCUUGGUU | 1203 | CCAAGGCCGUGCAUAAGGCUU | D54 |
| 1089 | AGCCUUAUGCACGGCCUUGUU | 1204 | CAAGGCCGUGCAUAAGGCUUU | D55 |
| 1090 | CGAUGGUCAGCACAGCCUUUU | 1205 | AAGGCUGUGCUGACCAUCGUU | D56 |
| 1091 | GUCGAUGGUCAGCACAGCCUU | 1206 | GGCUGUGCUGACCAUCGACUU | D57 |
| 1092 | AAAAACAUGGCCCCAGCAGUU | 1207 | CUGCUGGGGCCAUGUUUUUUU | D58 |
| 1093 | CUAAAAACAUGGCCCCAGCUU | 1208 | GCUGGGGCCAUGUUUUUAGUU | D59 |
| 1094 | UCUAAAAACAUGGCCCCAGUU | 1209 | CUGGGGCCAUGUUUUUAGAUU | D60 |
| 1095 | CCUCUAAAAACAUGGCCCCUU | 1210 | GGGGCCAUGUUUUUAGAGGUU | D61 |
| 1096 | GCCUCUAAAAACAUGGCCCUU | 1211 | GGGCCAUGUUUUUAGAGGCUU | D62 |
| 1097 | UAGACAUGGGUAUGGCCUCUU | 1212 | GAGGCCAUACCCAUGUCUAUU | D63 |
| 1098 | GAUAGACAUGGGUAUGGCCUU | 1213 | GGCCAUACCCAUGUCUAUCUU | D64 |
| 1099 | UGUUGAACUUGACCUCGGGUU | 1214 | CCCGAGGUCAAGUUCAACAUU | D65 |
| 1100 | GGUUUGUUGAACUUGACCUUU | 1215 | AGGUCAAGUUCAACAAACCUU | D66 |
| 1101 | AAAGGGUUUGUUGAACUUGUU | 1216 | CAAGUUCAACAAACCCUUUUU | D67 |
| 1102 | ACAAAGGGUUUGUUGAACUUU | 1217 | AGUUCAACAAACCCUUUGUUU | D68 |
| 1103 | GACAAAGGGUUUGUUGAACUU | 1218 | GUUCAACAAACCCUUUGUCUU | D69 |
| 1104 | AAGACAAAGGGUUUGUUGAUU | 1219 | UCAACAAACCCUUUGUCUUUU | D70 |
| 1105 | CAUUAAGAAGACAAAGGGUUU | 1220 | ACCCUUUGUCUUCUUAAUGUU | D71 |
| 1106 | AUCAUUAAGAAGACAAAGGUU | 1221 | CCUUUGUCUUCUUAAUGAUUU | D72 |
| 1107 | GAAGAGGGGAGACUUGGUAUU | 1222 | UACCAAGUCUCCCCUCUUCUU | D73 |
| 1108 | CCAUGAAGAGGGGAGACUUUU | 1223 | AAGUCUCCCCUCUUCAUGGUU | D74 |
| 1109 | CCCAUGAAGAGGGGAGACUUU | 1224 | AGUCUCCCCUCUUCAUGGGUU | D75 |

TABLE 8-continued

Sequences of AAT RNAi Agents in Example 2

| SEQ ID NO: | Antisense Sequence (5' → 3') | SEQ ID NO: | Sense Sequence (5' → 3') | Duplex ID No. |
|---|---|---|---|---|
| 1110 | UUCCCAUGAAGAGGGGAGAUU | 1225 | UCUCCCCUCUUCAUGGGAAUU | D76 |
| 1111 | UUUCCCAUGAAGAGGGGAGUU | 1226 | CUCCCCUCUUCAUGGGAAAUU | D77 |
| 1112 | AACCCUUCUUUAAUGUCAUUU | 1227 | AUGACAUUAAAGAAGGGUUUU | D78 |
| 1113 | UUGUUGGACUGGUGUGCCAUU | 1228 | UGGCACACCAGUCCAACAAUU | D79 |
| 1114 | UAUAUUGGUGCUGUUGGACUU | 1229 | GUCCAACAGCACCAAUAUAUU | D80 |
| 1115 | UUAGCGAUGCUCACUGGGGUU | 1230 | CCCCAGUGAGCAUCGCUAAUU | D81 |
| 1116 | UCAAAGGCUGUAGCGAUGCUU | 1231 | GCAUCGCUACAGCCUUUGAUU | D82 |
| 1117 | UGAGUUCCUGGAAGCCUUCUU | 1232 | GAAGGCUUCCAGGAACUCAUU | D83 |
| 1118 | UAAGGCUUCUGAGUGGUACUU | 1233 | GUACCACUCAGAAGCCUUAUU | D84 |
| 1119 | UUUUCUUGGCCUCUUCGGUUU | 1234 | ACCGAAGAGGCCAAGAAAAUU | D85 |
| 1120 | UUUGAUCUGUUUCUUGGCCUU | 1235 | GGCCAAGAAACAGAUCAAAUU | D86 |
| 1121 | UGUUGAUCUGUUUCUUGGCUU | 1236 | GCCAAGAAACAGAUCAACAUU | D87 |
| 1122 | UACAAUUUUCCCUUGAGUAUU | 1237 | UACUCAAGGGAAAAUUGUAUU | D88 |
| 1123 | UUGUCUCUGUCAAGCUCCUUU | 1238 | AGGAGCUUGACAGAGACAAUU | D89 |
| 1124 | UUUAAACAUGCCUAAACGCUU | 1239 | GCGUUUAGGCAUGUUUAAAUU | D90 |
| 1125 | UGAUGUUAAACAUGCCUAAUU | 1240 | UUAGGCAUGUUUAACAUCAUU | D91 |
| 1126 | UAAGAAGAUGGCGGUGGCAUU | 1241 | UGCCACCGCCAUCUUCUUAUU | D92 |
| 1127 | UGUGAGUUCAUUUUCCAGGUU | 1242 | CCUGGAAAAUGAACUCACAUU | D93 |
| 1128 | UAACUUGGUGAUGAUAUCGUU | 1243 | CGAUAUCAUCACCAAGUUAUU | D94 |
| 1129 | UAUUUUCCAGGAACUUGGUUU | 1244 | ACCAAGUUCCUGGAAAAUAUU | D95 |
| 1130 | UAUAGGUUCCAGUAAUGGAUU | 1245 | UCCAUUACUGGAACCUAUAUU | D96 |
| 1131 | UUCUUCAGAUCAUAGGUUCUU | 1246 | GAACCUAUGAUCUGAAGAAUU | D97 |
| 1132 | UAGGUCAGCCCCAUUGCUGUU | 1247 | CAGCAAUGGGGCUGACCUAUU | D98 |
| 1133 | UAGAGGUCAGCCCCAUUGCUU | 1248 | GCAAUGGGGCUGACCUCUAUU | D99 |
| 1134 | UUUCAGGGGUGCCUCCUCUUU | 1249 | AGAGGAGGCACCCCUGAAAUU | D100 |
| 1135 | UAGAGCUUCAGGGGUGCCUUU | 1250 | AGGCACCCCUGAAGCUCUAUU | D101 |
| 1136 | UCUUAUGCACGGCCUUGGAUU | 1251 | UCCAAGGCCGUGCAUAAGAUU | D102 |
| 1137 | UCCUUAUGCACGGCCUUGGUU | 1252 | CCAAGGCCGUGCAUAAGGAUU | D103 |
| 1138 | UGAUGGUCAGCACAGCCUUUU | 1253 | AAGGCUGUGCUGACCAUCAUU | D104 |
| 1139 | UUCGAUGGUCAGCACAGCCUU | 1254 | GGCUGUGCUGACCAUCGAAUU | D105 |
| 1140 | UUAAAAACAUGGCCCCAGCUU | 1255 | GCUGGGGCCAUGUUUUUAAUU | D106 |
| 1141 | UCUCUAAAAACAUGGCCCCUU | 1256 | GGGGCCAUGUUUUUAGAGAUU | D107 |
| 1142 | UCCUCUAAAAACAUGGCCCUU | 1257 | GGGCCAUGUUUUUAGAGGAUU | D108 |
| 1143 | UAUAGACAUGGGUAUGGCCUU | 1258 | GGCCAUACCCAUGUCUAUAUU | D109 |
| 1144 | UGUUUGUUGAACUUGACCUUU | 1259 | AGGUCAAGUUCAACAAACAUU | D110 |
| 1145 | UACAAAGGGUUUGUUGAACUU | 1260 | GUUCAACAAACCCUUUGUAUU | D111 |
| 1146 | UAUUAAGAAGACAAAGGGUUU | 1261 | ACCCUUUGUCUUCUUAAUAUU | D112 |
| 1147 | UAAGAGGGGAGACUUGGUAUU | 1262 | UACCAAGUCUCCCCUCUUAUU | D113 |

TABLE 8-continued

Sequences of AAT RNAi Agents in Example 2

| SEQ ID NO: | Antisense Sequence (5' → 3') | SEQ ID NO: | Sense Sequence (5' → 3') | Duplex ID No. |
|---|---|---|---|---|
| 1148 | UCAUGAAGAGGGGAGACUUUU | 1263 | AAGUCUCCCCUCUUCAUGAUU | D114 |
| 1149 | UCCAUGAAGAGGGGAGACUUU | 1264 | AGUCUCCCCUCUUCAUGGAUU | D115 |

AAT RNAi agents were evaluated by transfection of Hep3B cells, a human hepatocellular carcinoma line. Cells were plated at ~10,000 cells per well in 96-well format, and each of the 115 AAT RNAi agent duplexes was transfected at three concentrations (10 nM, 1 nM, and 0.1 nM), using LipoFectamine RNAiMax (Thermo Fisher) transfection reagent. Relative expression of each of the 115 AAT RNAi agents was determined by qRT-PCR by comparing the expression levels of AAT mRNA to an endogenous control, and normalized to untreated Hep3B cells ($\Delta\Delta C_T$ analysis), as shown in Table 9.

TABLE 9

In Vitro Data from Duplexes of Example 2

| Duplex ID No. (From Table 8) | Avg. Rel. Exp. 10 nM | Avg. Rel. Exp. 1 nM | Avg. Rel. Exp. 0.1 nM |
|---|---|---|---|
| D1 | 1.037 | 0.896 | 0.709 |
| D2 | 0.068 | 0.089 | 0.381 |
| D3 | 0.046 | 0.064 | 0.403 |
| D4 | 0.075 | 0.090 | 0.391 |
| D5 | 0.408 | 0.424 | 0.743 |
| D6 | 0.018 | 0.032 | 0.347 |
| D7 | 0.069 | 0.125 | 0.666 |
| D8 | 0.092 | 0.193 | 0.794 |
| D9 | 0.206 | 0.228 | 0.839 |
| D10 | 0.023 | 0.032 | 0.235 |
| D11 | 0.309 | 0.522 | 0.894 |
| D12 | 0.049 | 0.092 | 0.732 |
| D13 | 0.549 | 0.665 | 0.955 |
| D14 | 0.531 | 0.654 | 0.934 |
| D15 | 0.108 | 0.197 | 0.820 |
| D16 | 0.558 | 0.516 | 0.834 |
| D17 | 0.626 | 0.606 | 0.841 |
| D18 | 0.668 | 0.703 | 0.778 |
| D19 | 0.624 | 0.803 | 0.785 |
| D20 | 0.071 | 0.080 | 0.506 |
| D21 | 0.022 | 0.037 | 0.345 |
| D22 | 0.086 | 0.127 | 0.588 |
| D23 | 0.175 | 0.238 | 0.893 |
| D24 | 0.134 | 0.078 | 0.368 |
| D25 | 0.056 | 0.075 | 0.687 |
| D26 | 0.122 | 0.196 | 0.756 |
| D27 | 0.517 | 0.560 | 0.846 |
| D28 | 0.801 | 0.838 | 0.884 |
| D29 | 0.820 | 0.870 | 0.903 |
| D30 | 0.558 | 0.632 | 0.879 |
| D31 | 1.112 | 1.110 | 0.922 |
| D32 | 0.246 | 0.359 | 1.041 |
| D33 | 0.107 | 0.355 | 0.967 |
| D34 | 0.096 | 0.170 | 0.962 |
| D35 | 0.317 | 0.552 | 0.949 |
| D36 | 0.064 | 0.134 | 0.873 |
| D37 | 0.463 | 1.005 | 1.006 |
| D38 | 0.428 | 0.688 | 0.486 |
| D39 | 0.730 | 0.918 | 1.258 |
| D40 | 0.059 | 0.067 | 0.912 |
| D41 | 0.093 | 0.095 | 0.952 |
| D42 | 0.582 | 0.665 | 0.944 |
| D43 | 0.196 | 0.283 | 1.004 |
| D44 | 0.195 | 0.278 | 0.860 |
| D45 | 0.053 | 0.103 | 0.817 |
| D46 | 0.082 | 0.127 | 1.034 |
| D47 | 0.089 | 0.156 | 0.821 |
| D48 | 0.735 | 0.695 | 0.838 |
| D49 | 0.604 | 0.610 | 0.838 |
| D50 | 0.543 | 0.633 | 0.806 |
| D51 | 0.114 | 0.144 | 0.775 |
| D52 | 0.108 | 0.203 | 0.836 |
| D53 | 1.062 | 0.836 | 0.931 |
| D54 | 0.091 | 0.274 | 1.081 |
| D55 | 0.526 | 0.623 | 0.914 |
| D56 | 0.500 | 0.588 | 0.884 |
| D57 | 0.049 | 0.126 | 0.797 |
| D58 | 0.198 | 0.302 | 0.917 |
| D59 | 0.732 | 0.745 | 0.953 |
| D60 | 0.389 | 0.580 | 0.897 |
| D61 | 0.585 | 0.624 | 1.802 |
| D62 | 0.174 | 0.215 | 1.115 |
| D63 | 0.093 | 0.074 | 0.917 |
| D64 | 0.133 | 0.133 | 1.055 |
| D65 | 0.395 | 0.362 | 0.986 |
| D66 | 0.054 | 0.055 | 1.083 |
| D67 | 0.105 | 0.118 | 1.018 |
| D68 | 0.106 | 0.122 | 1.290 |
| D69 | 0.201 | 0.194 | 1.062 |
| D70 | 0.050 | 0.048 | 0.709 |
| D71 | 0.231 | 0.216 | 0.767 |
| D72 | 0.046 | 0.030 | 0.737 |
| D73 | 0.521 | 0.423 | 0.782 |
| D74 | 0.479 | 0.467 | 0.694 |
| D75 | 0.531 | 0.583 | 0.794 |
| D76 | 0.210 | 0.285 | 0.924 |
| D77 | 0.152 | 0.181 | 0.803 |
| D78 | 0.425 | 0.485 | 0.703 |
| D79 | 0.120 | 0.127 | 0.711 |
| D80 | 0.203 | 0.167 | 0.672 |
| D81 | 0.477 | 0.402 | 0.611 |
| D82 | 0.540 | 0.489 | 0.661 |
| D83 | 0.315 | 0.316 | 0.838 |
| D84 | 0.135 | 0.118 | 0.375 |
| D85 | 0.209 | 0.270 | 1.050 |
| D86 | 0.120 | 0.136 | 0.928 |
| D87 | 0.172 | 0.207 | 1.056 |
| D88 | 0.218 | 0.308 | 1.006 |
| D89 | 0.605 | 0.643 | 0.925 |
| D90 | 0.205 | 0.259 | 0.927 |
| D91 | 0.594 | 1.097 | 1.052 |
| D92 | 0.337 | 0.887 | 1.015 |
| D93 | 0.068 | 0.503 | 0.864 |
| D94 | 0.067 | 0.475 | 0.811 |
| D95 | 0.186 | 0.770 | 0.931 |
| D96 | 0.062 | 0.389 | 0.550 |
| D97 | 0.066 | 0.470 | 0.896 |
| D98 | 0.567 | 0.998 | 1.044 |
| D99 | 0.451 | 1.092 | 1.359 |
| D100 | 0.292 | 0.745 | 0.875 |
| D101 | 0.049 | 0.320 | 0.659 |
| D102 | 0.313 | 0.799 | 0.732 |
| D103 | 0.068 | 0.541 | 0.630 |
| D104 | 0.077 | 0.552 | 0.682 |
| D105 | 0.071 | 0.355 | 0.459 |
| D106 | 1.179 | 1.117 | 1.076 |

TABLE 9-continued

In Vitro Data from Duplexes of Example 2

| Duplex ID No. (From Table 8) | Avg. Rel. Exp. 10 nM | Avg. Rel. Exp. 1 nM | Avg. Rel. Exp. 0.1 nM |
|---|---|---|---|
| D107 | 0.328 | 0.597 | 0.876 |
| D108 | 0.125 | 0.467 | 0.573 |
| D109 | 0.141 | 0.545 | 0.753 |
| D110 | 0.076 | 0.497 | 0.778 |
| D111 | 0.132 | 0.511 | 0.634 |
| D112 | 0.216 | 0.586 | 0.784 |
| D113 | 0.462 | 0.687 | 1.021 |
| D114 | 0.507 | 0.792 | 1.170 |
| D115 | 0.259 | 0.797 | 1.027 |

Example 3. In Vivo Testing of NAG-Conjugated AAT RNAi Agents in PiZ Mice

A transgenic PiZ mouse model (PiZ mice) was used to evaluate AAT RNAi agents in vivo. PiZ mice harbor the human PiZ AAT mutant allele and model human AATD (Carlson et al., Journal of Clinical Investigation 1989).

NAG-conjugated AAT RNAi agents were prepared in a pharmaceutically acceptable saline buffer and administered to PiZ mice to evaluate knockdown of AAT gene expression. On day 1, each mouse received a single subcutaneous (SQ) dose into the loose skin on the back between the shoulders of 5.0 mg/kg (mpk) of either AD04446, AD04447, AD04448, AD04449, AD04450, AD04451, AD04454, AD04455, AD04456, AD04457, AD04458, or AD04459. (See Tables 4-7 for the modified AAT RNAi agents and NAG ligand structures). AAT RNAi agents AD04451 and AD04459 included a modified nucleotide antisense strand sequence designed to target an AAT gene (SEQ ID NO: 1) at position 1000; AAT RNAi agents AD04446 and AD04454 included a modified nucleotide antisense strand sequence designed to target an AAT gene (SEQ ID NO: 1) at position 1142; AAT RNAi agents AD04447 and AD04455 included a modified nucleotide antisense strand sequence designed to target an AAT gene (SEQ ID NO: 1) at position 1211; AAT RNAi agents AD04448 and AD04456 included a modified nucleotide antisense strand sequence designed to target an AAT gene (SEQ ID NO: 1) at position 1326; AAT RNAi agents AD04449 and AD04457 included a modified nucleotide antisense strand sequence designed to target an AAT gene (SEQ ID NO: 1) at position 1338; and AAT RNAi agents AD04450 and AD04458 included a modified nucleotide antisense strand sequence designed to target an AAT gene (SEQ ID NO: 1) at position 1427. (See also Tables 1 and 2). Three mice were dosed with each AAT RNAi agent (n=3).

Plasma samples were drawn and analyzed for AAT (Z-AAT) protein levels on day 1 (pre-dose), day 8, day 15, day 22, day 29, and day 36. AAT levels were normalized to day 1 (pre-dose) AAT plasma levels. Protein levels were measured by quantifying circulating human Z-AAT levels in plasma by a commercially available ELISA kit according to the manufacturer's recommendations. The average normalized AAT (Z-AAT) levels for each RNAi agent are reported in the following Table 10:

TABLE 10

Average Normalized AAT Protein (Normalized to Pre-Treatment) from Example 3

| Group ID | Day 8 Avg AAT | Day 8 Std Dev (+/−) | Day 15 Avg AAT | Day 15 Std Dev (+/−) | Day 22 Avg AAT | Day 22 Std Dev (+/−) | Day 29 Avg AAT | Day 29 Std Dev (+/−) | Day 36 Avg AAT | Day 36 Std Dev (+/−) |
|---|---|---|---|---|---|---|---|---|---|---|
| Group 1 (5.0 mg/kg AD04447) | 1.010 | 0.256 | 1.050 | 0.108 | 1.451 | 0.137 | 1.145 | 0.154 | 1.117 | 0.080 |
| Group 2 (5.0 mg/kg AD04448) | 0.884 | 0.262 | 0.866 | 0.276 | 1.306 | 0.112 | 1.147 | 0.119 | 1.076 | 0.172 |
| Group 3 (5.0 mg/kg AD04449) | 0.909 | 0.060 | 0.969 | 0.152 | 1.290 | 0.185 | 1.290 | 0.201 | 1.245 | 0.106 |
| Group 4 (5.0 mg/kg AD04450) | 0.595 | 0.083 | 0.799 | 0.131 | 1.099 | 0.256 | 1.090 | 0.346 | 1.229 | 0.444 |
| Group 5 (5.0 mg/kg AD04451) | 0.282 | 0.006 | 0.525 | 0.020 | 1.358 | 0.188 | 1.767 | 0.325 | 1.586 | 0.297 |
| Group 6 (5.0 mg/kg AD04455) | 0.656 | 0.126 | 0.639 | 0.039 | 0.741 | 0.089 | 0.738 | 0.235 | 0.819 | 0.156 |
| Group 7 (5.0 mg/kg AD04456) | 0.605 | 0.129 | 0.469 | 0.036 | 0.717 | 0.105 | 0.662 | 0.097 | 0.875 | 0.195 |
| Group 8 (5.0 mg/kg AD04457) | 0.501 | 0.108 | 0.663 | 0.091 | 1.031 | 0.324 | 1.176 | 0.368 | 1.603 | 0.597 |
| Group 9 (5.0 mg/kg AD04458) | 0.308 | 0.081 | 0.174 | 0.031 | 0.177 | 0.010 | 0.211 | 0.010 | 0.345 | 0.041 |
| Group 10 (5.0 mg/kg AD04459) | 0.256 | 0.021 | 0.134 | 0.045 | 0.174 | 0.084 | 0.234 | 0.174 | 0.315 | 0.336 |
| Group 11 (5.0 mg/kg AD04446) | 0.686 | 0.178 | 0.739 | 0.130 | 0.973 | 0.263 | 0.955 | 0.107 | 0.885 | 0.119 |
| Group 12 (5.0 mg/kg AD04454) | 0.338 | 0.014 | 0.361 | 0.105 | 0.602 | 0.252 | 0.729 | 0.266 | 0.970 | 0.245 |

As shown from the data in Table 10, above, while AAT RNAi agent AD04447 showed essentially no reduction in AAT protein, AAT RNAi agents AD04458 (which included a modified nucleotide sequence designed to target an AAT gene (SEQ ID NO: 1) at position 1427) and AD04459 (which included a modified nucleotide sequence designed to target an AAT gene (SEQ ID NO: 1) at position 1000) showed a substantial reduction in AAT protein across all timepoints. For example, AD04458 showed knockdown of approximately 69% at day 8 (0.308); approximately 83% at day 15 (0.174), and approximately 82% at day 22 (0.177). Additionally, for example, AD04459 showed a knockdown of approximately 74% at day 8 (0.256), approximately 87% at day 15 (0.134), and approximately 83% at day 22 (0.174).

Example 4. In Vivo Testing of NAG-Conjugated AAT RNAi Agents in Cynomolgus Monkeys NAG-conjugated AAT RNAi agents were made and combined in a pharmaceutically acceptable saline buffer as known in the art for subcutaneous (SC) injection. On day 1, cynomolgus macaque (*Macaca fascicularis*) primates (referred to herein as "cynos" or "monkeys") were injected subcutaneously with 3 mg/kg of either AD04824, AD04825, AD04826, or AD04827 (see Tables 4-7 for the modified AAT RNAi agents and NAG ligand structures). Each of these AAT RNAi agents included a modified nucleotide sequence designed to target an AAT gene (SEQ ID NO: 1) at position 1000, and was cross-reactive with cynos. Three monkeys in each group were tested (n=3).

Serum samples from treated cynomolgus monkeys were taken on day −7 and day 1 (pre-dose), and on days 8, 15, 22, and 29 to monitor knockdown. Day 36 was also measured for cynos that were injected with AD04825 and AD04826. At the indicated time points, blood samples were drawn and analyzed for cynomolgus monkey AAT (cAAT). Blood was collected from the femoral vein. cAAT levels were determined on a Cobas Integra 400 Plus (Roche Diagnostics) according to the manufacturer's recommendations. AAT levels for each animal at a respective time point was divided by the pre-treatment level (average of day −7 and day 1 (pre-dose)) of expression in that animal to determine the ratio of expression "normalized to pre-dose."

Normalized cynomolgus monkey AAT (cAAT) protein levels after treatment with each respective AAT RNAi agent are reported in the following Table 11:

TABLE 11

Normalized cAAT Protein (Normalized to Pre-Treatment) from Example 4 in Cynomolgus Monkeys.

| Group ID | Day 8 cAAT | Day 15 cAAT | Day 22 cAAT | Day 29 cAAT | Day 36 cAAT |
|---|---|---|---|---|---|
| Group 1, Cyno A (3.0 mg/kg AD04824) | 0.62 | 0.52 | 0.45 | 0.52 | |
| Group 1, Cyno B (3.0 mg/kg AD04824) | 0.60 | 0.36 | 0.32 | 0.32 | |
| Group 1, Cyno C (3.0 mg/kg AD04824) | 0.62 | 0.44 | 0.41 | 0.41 | |
| Group 2, Cyno A (3.0 mg/kg AD04825) | 0.58 | 0.33 | 0.24 | 0.24 | 0.22 |
| Group 2, Cyno B (3.0 mg/kg AD04825) | 0.58 | 0.38 | 0.27 | 0.25 | 0.27 |
| Group 2, Cyno C (3.0 mg/kg AD04825) | 0.79 | 0.58 | 0.43 | 0,43 | 0.44 |
| Group 3, Cyno A (3.0 mg/kg AD04826) | 0.75 | 0.59 | 0.44 | 0.42 | 0.38 |
| Group 3, Cyno B (3.0 mg/kg AD04826) | 0.66 | 0.43 | 0.30 | 0.26 | 0.24 |
| Group 3, Cyno C (3.0 mg/kg AD04826) | 0.62 | 0.36 | 0.27 | 0.25 | 0.25 |
| Group 4, Cyno A (3.0 mg/kg AD04827) | 0.57 | 0.38 | 0.26 | 0.26 | |
| Group 4, Cyno B (3.0 mg/kg AD04827) | 0.61 | 0.37 | 0.34 | 0.34 | |
| Group 4, Cyno C (3.0 mg/kg AD04827) | 0.66 | 0.43 | 0.41 | 0.39 | |

Figure 9:
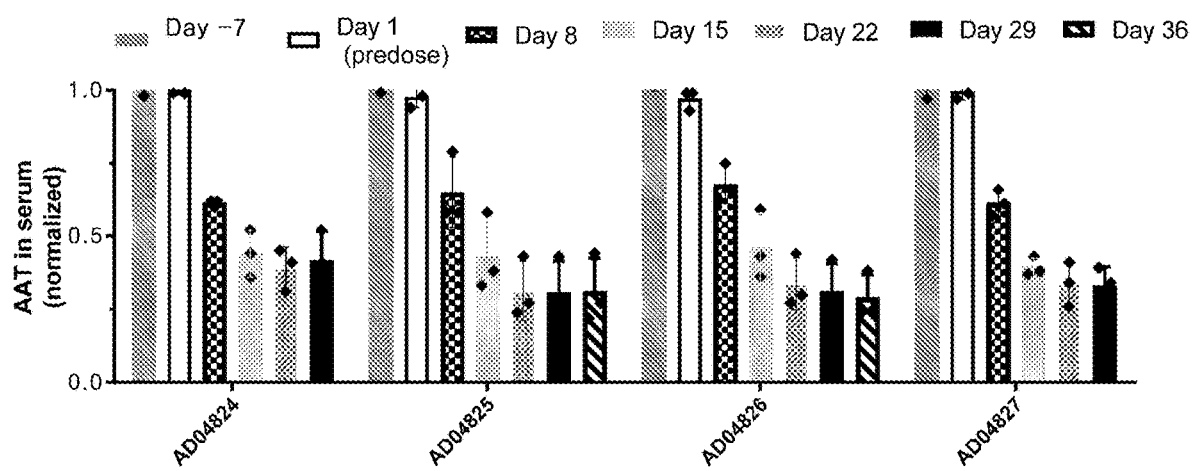
FIG. 9 is a bar graph showing average normalized cynomolgus monkey (cyno) AAT (cAAT) serum levels in cynos (n=3) following a single subcutaneous administration of 3 mg/kg of either AD04824, AD04825, AD04826, or AD04827, according to Example 4. AAT serum levels were normalized to average pre-treatment values. Experimental error is shown as standard deviation.

Average normalized cAAT levels for each of the respective treatment groups is shown in the bar graph of FIG. 9. As illustrated in Table 11, above, and in FIG. 9, each of the AAT RNAi agents tested showed substantial knockdown of cAAT in cynomolgus monkeys across all time points measured.

Example 5. In Vivo Testing of NAG-Conjugated AAT RNAi Agents in Cynomolgus Monkeys NAG-conjugated AAT RNAi agents were made and combined in a pharmaceutically acceptable saline buffer as known in the art for subcutaneous (SC) injection. On day 1, cynomolgus macaque (*Macaca fascicularis*) primates were injected subcutaneously with 3 mg/kg of either AD04828, AD04831, AD04836, or AD04837 (see Tables 4-7 for the modified AAT RNAi agents and NAG ligand structures). Each of these AAT RNAi agents included a modified nucleotide sequence designed to target an AAT gene (SEQ ID NO: 1) at position 1000, and was cross-reactive with cynos. Three monkeys in each group were tested (n=3) for AD04828 and AD04831, and two monkeys in each group were tested (n=2) for AD04836 and AD04837.

Serum samples from treated cynos were taken on day −35 and day 1 (pre-dose), and on days 8, 15, 21, and 29 to monitor knockdown. At the indicated time points, blood samples were drawn and analyzed for cAAT. Blood was collected from the femoral vein. cAAT levels were determined on a Cobas Integra 400 Plus (Roche Diagnostics) according to the manufacturer's recommendations. cAAT levels for each animal at a respective time point was divided by the pre-treatment level (average of day −35 and day 1 (pre-dose)) of expression in that animal to determine the ratio of expression "normalized to pre-treatment".

Normalized cynomolgus monkey AAT (cAAT) protein levels after treatment with each respective AAT RNAi agent are reported in the following Table 12:

TABLE 12

Normalized AAT Protein (Normalized to Pre-Treatment) from Example 5 in Cynomolgus Monkeys

| Group ID | Day 8 cAAT | Day 15 cAAT | Day 22 cAAT | Day 29 cAAT |
|---|---|---|---|---|
| Group 1, Cyno A (3,0 mg/kg AD04828) | 0.60 | 0.32 | 0.25 | 0.23 |
| Group 1, Cyno B (3,0 mg/kg AD04828) | 0.67 | 0.59 | 0.61 | 0.76 |
| Group 1, Cyno C (3.0 mg/kg AD04828) | 0.51 | 0.35 | 0.29 | 0.29 |
| Group 2, Cyno A (3.0 mg/kg AD04831) | 0.68 | 0.43 | 0.32 | 0.28 |

TABLE 12-continued

Normalized AAT Protein (Normalized to Pre-Treatment) from Example 5 in Cynomolgus Monkeys

| Group ID | Day 8 cAAT | Day 15 cAAT | Day 22 cAAT | Day 29 cAAT |
|---|---|---|---|---|
| Group 2, Cyno B (3.0 mg/kg AD04831) | 0.71 | 0.49 | 0.47 | 0.44 |
| Group 2, Cyno C (3.0 mg/kg AD04831) | 0.61 | 0.43 | 0.34 | 0.30 |
| Group 3, Cyno A (3.0 mg/kg AD04836) | 0.61 | 0.37 | 0.27 | 0.23 |
| Group 3, Cyno B (3.0 mg/kg AD04836) | 0.67 | 0.43 | 0.32 | 0.27 |
| Group 4, Cyno A (3.0 mg/kg AD04837) | 0.65 | 0.40 | 0.28 | 0.24 |
| Group 4, Cyno B (3.0 mg/kg AD04837) | 0.55 | 0.29 | 0.20 | 0.17 |

Figure 10:
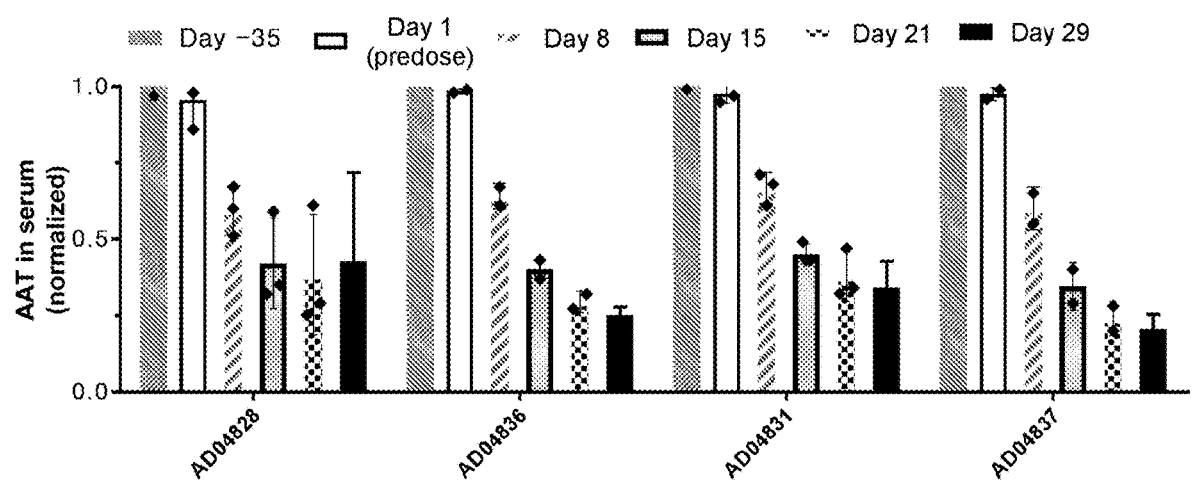
FIG. 10 is a bar graph showing average normalized cAAT serum levels in cynos (n=2 or n=3) following a single subcutaneous administration of 3 mg/kg of either AD04828, AD04836, AD04831, or AD04837, according to Example 5. AAT serum levels were normalized to average pre-treatment values. Experimental error is shown as standard deviation.

Average normalized cAAT levels for each of the respective treatment groups is shown in the bar graph of FIG. 10. As shown above in Table 12, as well as in the bar graph of FIG. 10, each of the AAT RNAi agents tested showed substantial knockdown of cAAT in cynomolgus monkeys across all time points measured.

Example 6. In Vivo Testing of NAG-Conjugated AAT RNAi Agents in PiZ Mice

The transgenic PiZ mouse model (PiZ mice) as set forth in Example 3 was used to evaluate AAT RNAi agents in vivo. NAG-conjugated AAT RNAi agents were prepared in a pharmaceutically acceptable saline buffer and administered to PiZ mice to evaluate knockdown of AAT gene expression. On day 1, each mouse received a single subcutaneous (SQ) dose into the loose skin on the back between the shoulders of 2.0 mg/kg (mpk) of either AD04824, AD04828, AD04829, AD04830, AD04831, AD04832, AD04833, AD04834, AD04836, AD04837, AD04838, AD04839, or AD04857. (See Tables 4-7 for the modified AAT RNAi agents and NAG ligand structures). Each of the AAT RNAi agents in this study included a modified nucleotide antisense strand sequence designed to target an AAT gene (SEQ ID NO: 1) at position 1000. (See also Tables 1 and 2). Three mice were dosed with each AAT RNAi agent (n=3).

Plasma samples were drawn and analyzed for AAT (Z-AAT) protein levels on days −2, day 1 (pre-dose), day 8, day 15, day 22, day 29, and day 36. AAT levels were normalized to day 1 (pre-dose) AAT plasma levels. Protein levels were measured by quantifying circulating human Z-AAT levels in plasma by a commercially available ELISA kit according to the manufacturer's recommendations. The average normalized AAT (Z-AAT) levels for each RNAi agent are reported in the following Table 13:

As shown from the data in Table 13, above, each of the AAT RNAi agent showed a substantial reduction in AAT protein through at least day 29. For example, at day 15, each of the AAT RNAi agents tested achieved at least approximately 70% knockdown of protein compared to pre-treatment levels, with multiple groups achieving 90% or better knockdown.

Example 7. In Vivo Testing of NAG-Conjugated AAT RNAi Agents in PiZ Mice

The transgenic PiZ mouse model described in Example 3 was used. Each mouse was 5 weeks old at the beginning of the study. NAG-conjugated AAT RNAi agents were prepared in a pharmaceutically acceptable saline buffer and administered to PiZ mice to evaluate knockdown of AAT gene expression. Starting on day 1, each mouse received a subcutaneous (SQ) dose q2w (i.e., one injection every two weeks, for a total of 4 injections) into the loose skin on the back between the shoulders of 4.0 mg/kg (mpk) of either: (1) saline vehicle; (2) AD04837 (see Tables 4-7 for the modified AAT RNAi agent and NAG ligand structures), which as noted previously included a modified nucleotide antisense strand sequence designed to target an AAT gene (SEQ ID NO: 1) at position 1000; or (3) a NAG-conjugated RNAi agent that included a nucleotide sequence targeting the HBV gene, to be used as a negative control. Single subcutaneous injections for the saline vehicle group, AAT RNAi agent group, and HBV RNAi agent group were performed on days 1, 15, 29, and 43. Seven (7) mice were dosed q2w with the saline vehicle (Group 1); nine (9) mice were dosed q2w with the AAT RNAi agent (Group 2); and six (6) mice were dosed with the HBV RNAi agent (Group 3). The mice in the three treatment groups were sacrificed on day 57 (13 weeks old). In addition to the treatment groups, seven (7) mice were sacrificed at week 1 of the study (i.e., 5-week old mice) to serve as a baseline control.

TABLE 13

Average Normalized AAT Protein (Normalized to Pre-Treatment) from Example 6

| Group ID | Day 8 Avg AAT | Day 8 Std Dev (+/−) | Day 15 Avg AAT | Day 15 Std Dev (+/−) | Day 22 Avg AAT | Day 22 Std Dev (+/−) | Day 29 Avg AAT | Day 29 Std Dev (+/−) | Day 36 Avg AAT | Day 36 Std Dev (+/−) |
|---|---|---|---|---|---|---|---|---|---|---|
| Group 1 (2.0 mg/kg AD04824) | 0.105 | 0.036 | 0.140 | 0.067 | 0.204 | 0.108 | 0.313 | 0.104 | 0.437 | 0.229 |
| Group 2 (2.0 mg/kg AD04828) | 0.141 | 0.055 | 0.236 | 0.111 | 0.304 | 0.138 | 0.624 | 0.289 | 0.814 | 0.139 |
| Group 3 (2.0 mg/kg AD04829) | 0.109 | 0.072 | 0.119 | 0.102 | 0.140 | 0.119 | 0.141 | 0.116 | 0.179 | 0.145 |
| Group 4 (2.0 mg/kg AD04830) | 0.147 | 0.095 | 0.190 | 0.148 | 0.307 | 0.192 | 0.521 | 0.424 | 0.547 | 0.202 |
| Group 5 (2.0 mg/kg AD04831) | 0.154 | 0.104 | 0.215 | 0.171 | 0.449 | 0.375 | 0.701 | 0.519 | 0.584 | 0.418 |
| Group 6 (2.0 mg/kg AD04832) | 0.088 | 0.032 | 0.089 | 0.048 | 0.090 | 0.046 | 0.117 | 0.071 | 0.193 | 0.131 |
| Group 7 (2.0 mg/kg AD04833) | 0.168 | 0.029 | 0.282 | 0.047 | 0.448 | 0.048 | 0.748 | 0.223 | 1.361 | 0.346 |
| Group 8 (2.0 mg/kg AD04834) | 0.159 | 0.037 | 0.255 | 0.159 | 0.470 | 0.315 | 0.662 | 0.346 | 0.728 | 0.141 |
| Group 9 (2.0 mg/kg AD04836) | 0.108 | 0.035 | 0.070 | 0.024 | 0.083 | 0.032 | 0.090 | 0.035 | 0.168 | 0.078 |
| Group 10 (2.0 mg/kg AD04837) | 0.157 | 0.071 | 0.209 | 0.104 | 0.242 | 0.097 | 0.417 | 0.198 | 0.550 | 0.193 |
| Group 11 (2.0 mg/kg AD04838) | 0.106 | 0.017 | 0.099 | 0.022 | 0.108 | 0.039 | 0.158 | 0.072 | 0.188 | 0.050 |
| Group 12 (2.0 mg/kg AD04839) | 0.096 | 0.026 | 0.069 | 0.019 | 0.089 | 0.036 | 0.120 | 0.038 | 0.186 | 0.083 |
| Group 12 (2.0 mg/kg AD04857) | 0.272 | 0.130 | 0.302 | 0.145 | 0.478 | 0.187 | 0.815 | 0.436 | 1.772 | 1.412 |

Plasma samples were drawn and analyzed for AAT (Z-AAT) protein levels on day 1 (pre-dose), day 8, day 15, day 22, day 29, and day 36 for all groups. Additional samples for the AAT RNAi agent group and the saline vehicle group were drawn on day 43, day 50, and day 57. AAT levels were normalized to day 1 (pre-dose) AAT plasma levels. Protein levels were measured by quantifying circulating human Z-AAT levels in plasma by a commercially available ELISA kit according to the manufacturer's recommendations. The average normalized AAT (Z-AAT) levels for the saline vehicle and each RNAi agent are reported in the following Table 14:

TABLE 14

Average Normalized AAT Protein (Normalized to Pre-Treatment) from Example 7

| Group ID | Day 8 | | Day 15 | | Day 22 | | Day 29 | |
|---|---|---|---|---|---|---|---|---|
| | Avg AAT | Std Dev (+/−) | Avg AAT | Std Dev (+/−) | Avg AAT | Std Dev (+/−) | Avg AAT | Std Dev (+/−) |
| Group 1 (saline vehicle) (n = 7) | 0.876 | 0.172 | 1.264 | 0.386 | 1.234 | 0.457 | 1.319 | 0.453 |
| Group 2 (AD04837) (n = 9) | 0.139 | 0.050 | 0.146 | 0.064 | 0.067 | 0.029 | 0.072 | 0.038 |
| Group 3 (HBV RNAi agent − negative control) (n = 6) | 1.212 | 0.360 | 1.019 | 0.201 | 1.540 | 0.155 | 1.585 | 0.640 |

| Group ID | Day 36 | | Day 43 | | Day 50 | | Day 57 | |
|---|---|---|---|---|---|---|---|---|
| | Avg AAT | Std Dev (+/−) | Avg AAT | Std Dev (+/−) | Avg AAT | Std Dev (+/−) | Avg AAT | Std Dev (+/−) |
| Group 1 (saline vehicle) (n = 7) | 1.267 | 0.491 | 1.441 | 0.416 | 1.172 | 0.340 | 1.058 | 0.299 |
| Group 2 (AD04837) (n = 9) | 0.040 | 0.011 | 0.051 | 0.020 | 0.034 | 0.007 | 0.038 | 0.009 |
| Group 3 (HBV RNAi agent − negative control) (n = 6) | 1.665 | 0.476 | 1.943 | 0.221 | 1.580 | 0.491 | 2.001 | 0.770 |

As shown from the data in Table 14, above, the HBV RNAi agent performed successfully as a negative control showing essentially no AAT inhibition. Further, the NAG-conjugated AAT RNAi agent (AD04837) achieved significant knockdown of expression compared to saline and the HBV RNAi agent negative control across all timepoints. In dosing q2w, the AAT RNAi agent in Example 7 showed a knockdown of approximately 96% of AAT protein at day 36 (0.040) and maintained a similar level of knockdown through day 57.

In addition to monitoring serum AAT levels, homogenized liver tissue from PiZ mice treated with NAG-conjugated AAT RNAi agent (AD04837) was further analyzed to determine if both soluble Z-AAT (which is expected to be predominantly monomeric protein), and insoluble polymers of Z-AAT (which is expected to be polymeric protein) were effectively reduced. A modified western blot protocol was used to separate the soluble and insoluble Z-AAT fractions under non-denaturing conditions as previously described and known in the art (see, e.g., Mueller et al., Molecular Therapy, March 2012, 20(3): 590-600).

Figure 11:
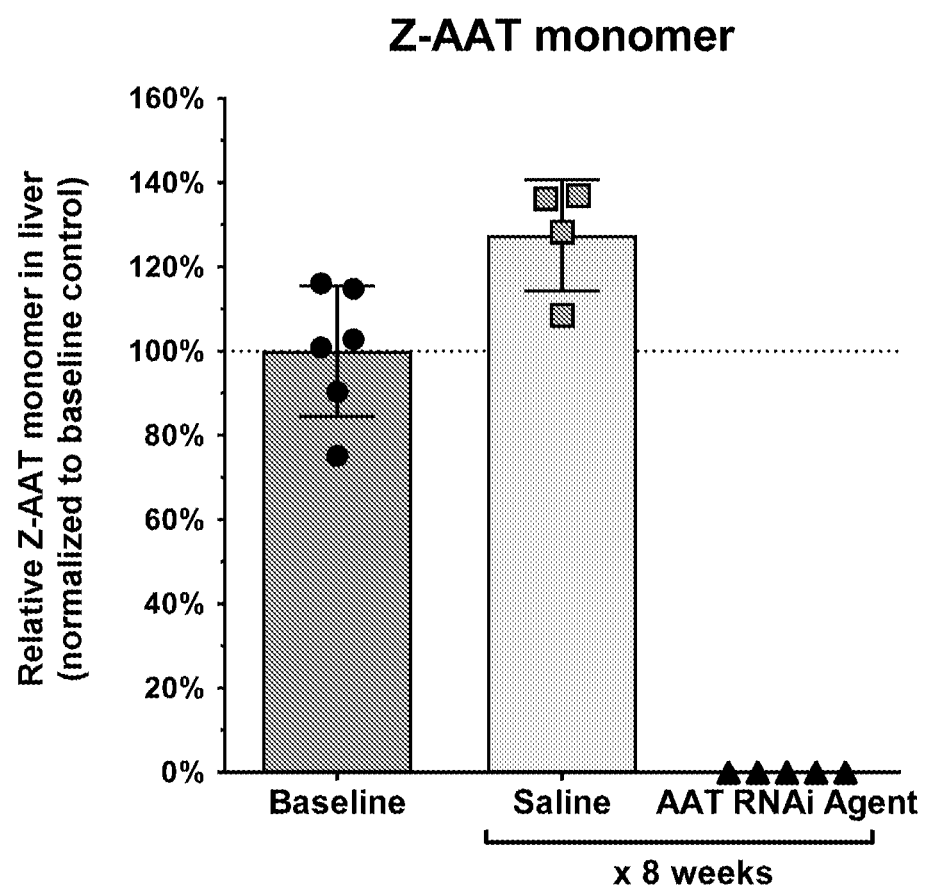
FIG. 11. is a bar graph showing the results of a western blot analysis of the soluble fractions (Z-AAT monomer) from livers of PiZ mice dosed with either saline or NAG-conjugated AAT RNAi agent having the duplex structure AD04837, dosed for 8 weeks q2w, normalized to baseline control, according to Example 7. Individual mouse measurements are shown grouped by treatment group, and experimental error is shown as standard deviation.
Figure 12:
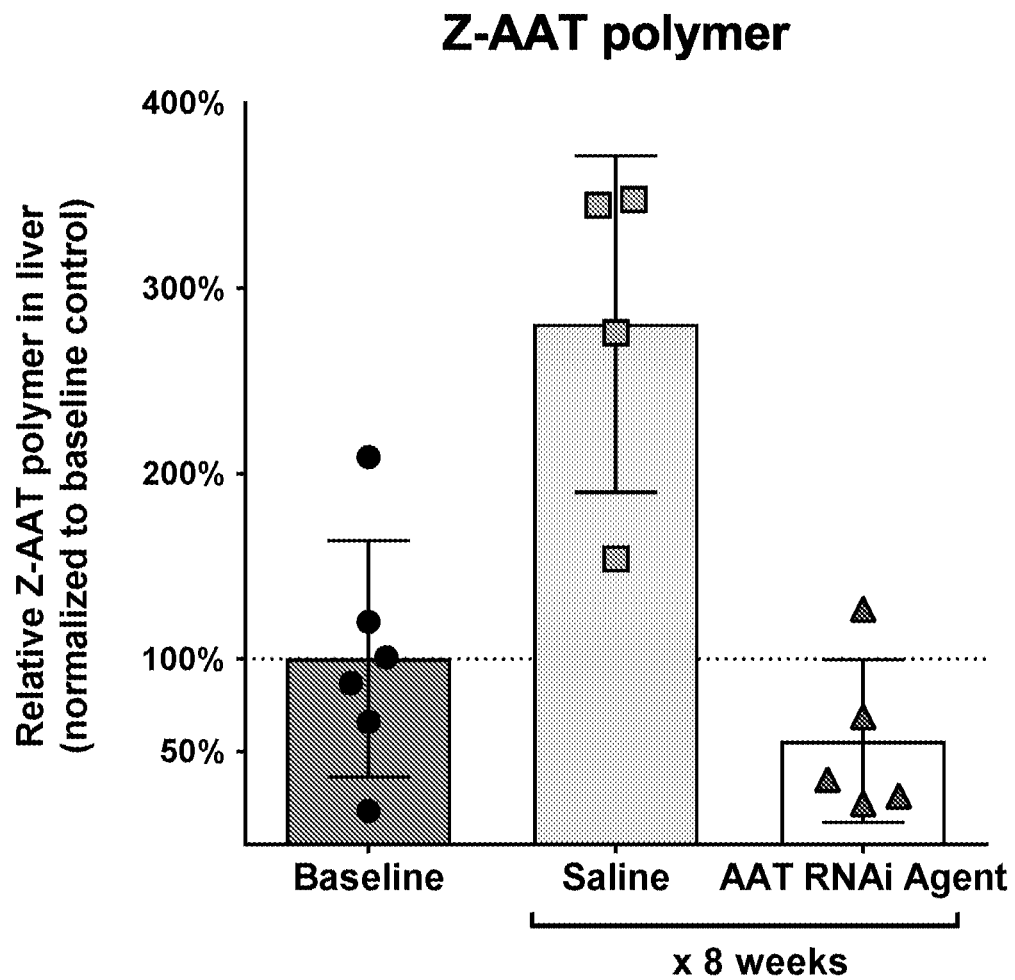
FIG. 12. is a bar graph showing the results of a western blot analysis of the insoluble fractions (Z-AAT polymer) from livers of PiZ mice dosed with either saline or NAG-conjugated AAT RNAi agent having the duplex structure AD04837, according to Example 7. Individual mouse measurements are shown grouped by treatment group, and experimental error is shown as standard deviation.

A western blot was prepared to examine certain livers of the sacrificed mice. Specifically, livers were examined of (i) 6 baseline mice; (ii) 5 AAT RNAi agent mice; and (iii) 4 saline mice. (The gels used for the western blot analysis included 15 wells). The samples for the animals used for this western blot were randomly selected from the various groups. FIGS. 11 and 12 show bar graphs reflecting the Z-AAT polymer and Z-AAT monomer levels quantified from the western blot analysis.

As seen from the bar graph in FIG. 11, which reports the monomeric protein levels, when compared to baseline each of the mice dosed with AAT RNAi agent shown a significant reduction in AAT monomeric protein across all time points, indicating significant inhibition of the gene. Further, as shown in FIG. 12, which reports the polymeric protein levels, the animals treated with the saline vehicle continued to have increased polymeric AAT burden after 8 weeks. Conversely, the animals treated with AAT RNAi agent showed a reduction in polymeric burden of approximately 50% over the course of 8 weeks as compared to the baseline (5-week-old) mice, indicating that the administration of NAG-conjugated AAT RNAi agent (AD04837) is capable of preventing and potentially reversing the production of polymeric AAT protein.

Example 8. In Vivo Testing of NAG-Conjugated AAT RNAi Agents in PiZ Mice

The transgenic PiZ mouse model described in Example 3 was used to evaluate RNAi agents in vivo. Each mouse received a single subcutaneous (SQ) dose on day 1 into the loose skin on the back between the shoulders of either: (1) saline; (2) 1.0 mg/kg of the NAG-conjugated AAT RNAi agent of AD04837 (which includes a modified nucleotide antisense strand sequence designed to target an AAT gene (SEQ ID NO: 1) at position 1000); (3) 2.0 mg/kg of AD04837; (4) 4.0 mg/kg of AD04837; or (5) 8.0 mg/kg of AD04837. Four animals were dosed in group 1 (saline), and all four were sacrificed on day 43. Fifteen (15) animals were dosed in each of groups 2, 3, 4, and 5, and 3 animals from each group were sacrificed on day 8, day 15, day 22, day 29, and day 43, respectively.

Plasma samples were drawn and analyzed for AAT (Z-AAT) protein levels on day 1 (pre-dose), day 8, day 15, day 22, day 29, day 36, and day 43 for all groups. For the sacrificed mice, cardiac sticks were performed for serum isolation for Z-AAT protein level assessment (200 µl plasma). AAT levels were normalized to day 1 (pre-dose) AAT plasma levels. Protein levels were measured by quantifying circulating human Z-AAT levels in plasma by a commercially available ELISA kit according to the manufacturer's recommendations. The average normalized AAT (Z-AAT) levels for the saline vehicle and each RNAi agent dosing group are reported in the following Table 15:

TABLE 15

Average Normalized Plasma AAT Protein (Normalized to Pre-Treatment) from Example 8.

| Group ID | Day 8 | | Day 15 | | Day 22 | | Day 29 | |
|---|---|---|---|---|---|---|---|---|
| | Avg AAT | Std Dev (+/−) | Avg AAT | Std Dev (+/−) | Avg AAT | Std Dev (+/−) | Avg AAT | Std Dev (+/−) |
| Group 1 (saline vehicle) | 1.240 | 0.633 | 1.037 | 0.256 | 0.884 | 0.229 | 0.857 | 0.286 |
| Group 2 (1.0 mg/kg AD04837) | 0.266 | 0.100 | 0.250 | 0.107 | 0.259 | 0.060 | 0.412 | 0.191 |
| Group 3 (2.0 mg/kg AD04837) | 0.170 | 0.102 | 0.162 | 0.132 | 0.199 | 0.161 | 0.511 | 0.514 |
| Group 4 (4.0 mg/kg AD04837) | 0.051 | 0.015 | 0.038 | 0.010 | 0.051 | 0.021 | 0.110 | 0.045 |
| Group 5 (8.0 mg/kg AD04837) | 0.030 | 0.011 | 0.025 | 0.010 | 0.040 | 0.024 | 0.063 | 0.030 |

| | Day 36 | | Day 43 | |
|---|---|---|---|---|
| Group 1 (saline vehicle) | 1.485 | 0.431 | 0.932 | 0.243 |
| Group 2 (1.0 mg/kg AD04837) | 0.791 | 0.207 | 0.560 | 0.111 |
| Group 3 (2.0 mg/kg AD04837) | 0.600 | 0.140 | 0.595 | 0.217 |
| Group 4 (4.0 mg/kg AD04837) | 0.156 | 0.008 | 0.148 | 0.022 |
| Group 5 (8.0 mg/kg AD04837) | 0.239 | 0.183 | 0.202 | 0.119 |

As shown from the data in Table 15, above, the NAG-conjugated AAT RNAi agent achieved significant knockdown of expression compared to saline across all timepoints measured at all dosing levels tested.

In addition, AAT mRNA levels were also assessed for the sacrificed mice at each respective timepoint. As described above, for Groups 2 through 5 (i.e., the RNAi agent groups), 3 mice were sacrificed on each of days 8, 15, 22, 29 and 43; and for Group 1, all 4 mice were sacrificed on day 43. Half of the left lateral liver lobe was collected and snap-frozen in liquid nitrogen for RNA isolation.

TABLE 16

Relative AAT mRNA Levels in PiZ Mice Following Administration of a Single SQ Injection of Saline or AAT RNAi Agent

| Treatment Group | Day | Animals | Average Relative mRNA Expression | Low Variance | High Variance |
|---|---|---|---|---|---|
| Group 1 (saline vehicle) | 43 | n = 4 | 1.000 | 0.071 | 0.076 |
| Group 2 (1.0 mg/kg AD04837) | 8 | n = 3 | 0.412 | 0.080 | 0.099 |
| | 15 | n = 3 | 0.419 | 0.037 | 0.040 |
| | 22 | n = 3 | 0.483 | 0.066 | 0.076 |
| | 29 | n = 3 | 0.696 | 0.069 | 0.076 |
| | 43 | n = 3 | 0.813 | 0.103 | 0.118 |
| Group 3 (2.0 mg/kg AD04837) | 8 | n = 3 | 0.272 | 0.101 | 0.160 |
| | 15 | n = 3 | 0.235 | 0.039 | 0.046 |
| | 22 | n = 3 | 0.327 | 0.099 | 0.141 |
| | 29 | n = 3 | 0.587 | 0.155 | 0.210 |
| | 43 | n = 3 | 0.845 | 0.123 | 0.145 |
| Group 4 (4.0 mg/kg AD04837) | 8 | n = 3 | 0.129 | 0.025 | 0.031 |
| | 15 | n = 3 | 0.161 | 0.017 | 0.020 |
| | 22 | n = 3 | 0.222 | 0.048 | 0.061 |
| | 29 | n = 3 | 0.247 | 0.067 | 0.093 |
| | 43 | n = 3 | 0.454 | 0.051 | 0.057 |
| Group 5 (8.0 mg/kg AD04837) | 8 | n = 3 | 0.078 | 0.013 | 0.015 |
| | 15 | n = 3 | 0.055 | 0.014 | 0.019 |
| | 22 | n = 3 | 0.077 | 0.009 | 0.010 |
| | 29 | n = 3 | 0.116 | 0.038 | 0.056 |
| | 43 | n = 3 | 0.332 | 0.122 | 0.193 |

As shown in Table 16, above, relative AAT mRNA expression levels were significantly reduced across all time-points measured compared to saline vehicle. For example, on day 15, Group 2 (1.0 mg/kg AAT RNAi agent) showed approximately 58% reduction of AAT mRNA levels (0.419); Group 3 (2.0 mg/kg AAT RNAi agent) showed approximately 67% reduction of AAT mRNA levels (0.327); Group 4 (4.0 mg/kg AAT RNAi agent) showed approximately 84% reduction of AAT mRNA levels (0.161); and Group 5 (8.0 mg/kg AAT RNAi agent) showed approximately 94% reduction of Z-AAT mRNA levels (0.055) upon a single SQ dose at day 1.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An RNAi agent for inhibiting the expression of an alpha-1 antitrypsin (AAT) gene comprising a sense strand and an antisense strand,
wherein nucleotides 2-18 of the antisense strand comprise nucleotides 2-18 of

NGUUAAACAUGCCUAAACN, (SEQ ID NO: 83)

wherein the sense strand is at least substantially complementary to the antisense strand; and
wherein the antisense strand comprises (i) 2 or 3 phosphorothioate linkages at its 5' end,
(ii) at least 8 nucleotides selected from 2'-fluoro adenosine, 2'-fluoro cytidine, 2'-fluoro guanosine, and 2'-fluoro uridine, (iii) at least 11 nucleotides selected from 2'-O-methyl adenosine, 2'-O-methyl cytidine, 2'-O-methyl guanosine, and 2'-O-methyl uridine, or (iv) any combination thereof.

2. The RNAi agent of claim 1, wherein the antisense strand comprises a nucleotide sequence selected from (5'→3'):

(i)
UGUUAAACAUGCCUAAACGUU; (SEQ ID NO: 794)

(ii)
UGUUAAACAUGCCUAAACGCUU; (SEQ ID NO: 839)

(iii)
UGUUAAACAUGCCUAAACGCG; (SEQ ID NO: 800)
and (iv)
UGUUAAACAUGCCUAAACGCU. (SEQ ID NO: 801)

3. The RNAi agent of claim 1, wherein the sense strand comprises a nucleotide sequence selected from (5'→3'):

(i)
AGCGUUUAGGCAUGUUUAACA; (SEQ ID NO: 866)

(ii)
CGUUUAGGCAUGUUUAACAUU; (SEQ ID NO: 857)

(iii)
GCGUUUAGGCAUGUUUAACAUU; (SEQ ID NO: 885)
and, (iv)
CGCGUUUAGGCAUGUUUAACA. (SEQ ID NO: 864)

4. The RNAi agent of claim 1, wherein the RNAi agent comprises a targeting group.

5. The RNAi agent of claim 4, wherein the targeting group is conjugated to the 5'-terminal end of the sense strand.

6. The RNAi agent of claim 4, wherein the targeting group comprises an asialoglycoprotein receptor ligand.

7. The RNAi agent of claim 6, wherein the asialoglycoprotein receptor ligand comprises an N-acetylgalactosamine trimer.

8. The RNAi agent of claim 1, wherein the RNAi agent further comprises one or more targeting groups, wherein the targeting group comprises a structure of: (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), or (NAG39)s.

9. The RNAi agent of claim 8, wherein the targeting group is (NAG37)s, and (NAG37)s has the following chemical structure:

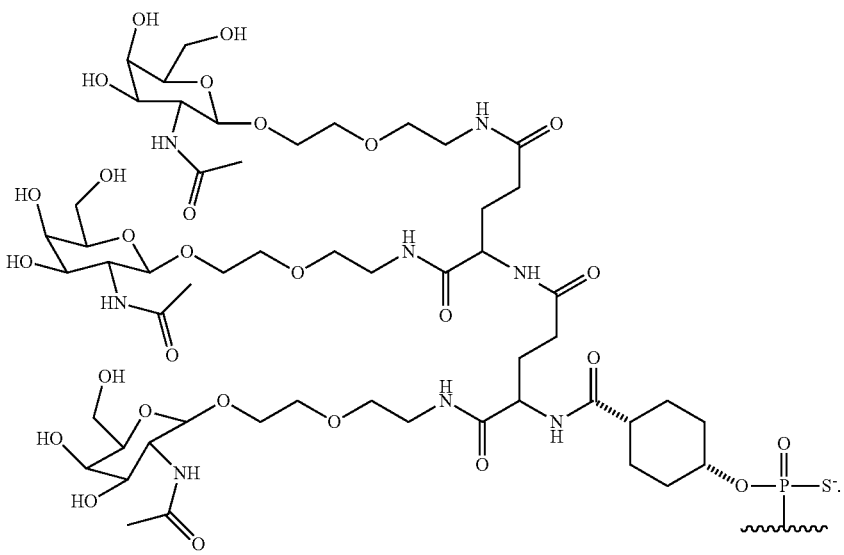

10. The RNAi agent of claim 1, wherein the antisense strand comprises the nucleotide sequence (5'→3') usGfsuUfaAfacaugCfcUfaAfaCfgCfsu (SEQ ID NO: 960), wherein:
  a, c, g, and u are 2'-O-methyl adenosine, 2'-O-methyl cytidine, 2'-O-methyl guanosine, and 2'-O-methyl uridine, respectively;
  Af, Cf, Gf, and Uf are 2'-fluoro adenosine, 2'-fluoro cytidine, 2'-fluoro guanosine, and 2'-fluoro uridine, respectively; and
  s is a phosphorothioate linkage.

11. The RNAi agent of claim 10, wherein the sense strand comprises the sequence (5'→3') agcguuuaGfGfCfauguuuaaca (SEQ ID NO: 1279), wherein:
  a, c, g, and u are 2'-O-methyl adenosine, 2'-O-methyl cytidine, 2'-O-methyl guanosine, and 2'-O-methyl uridine, respectively;
  Af, Cf, Gf, and Uf are 2'-fluoro adenosine, 2'-fluoro cytidine, 2'-fluoro guanosine, and 2'-fluoro uridine, respectively; and
  s is a phosphorothioate linkage;
  wherein optionally present on the sense strand is one or two inverted abasic deoxyribose residues (invAb) and/or one, two, three, or four phosphorothioate internucleoside linkages; and
  wherein optionally linked to the 5' terminal end of the sense strand is a targeting ligand that comprises N-acetyl-galactosamine.

12. The RNAi agent of claim 1, wherein the antisense strand of the RNAi agent comprises the sequence (5'→3') usGfsusUfaAfaCfaUfgCfcUfaAfaCfgusu (SEQ ID NO: 913), wherein:
  a, c, g, and u are 2'-O-methyl adenosine, 2'-O-methyl cytidine, 2'-O-methyl guanosine, and 2'-O-methyl uridine, respectively;
  Af, Cf, Gf, and Uf are 2'-fluoro adenosine, 2'-fluoro cytidine, 2'-fluoro guanosine, and 2'-fluoro uridine, respectively; and
  s is a phosphorothioate linkage.

13. The RNAi agent of claim 12, wherein the sense strand comprises the sequence (5'→3') cguuuaGfGfCfauguuuaacausu (SEQ ID NO: 1276), wherein:
  a, c, g, and u are 2'-O-methyl adenosine, 2'-O-methyl cytidine, 2'-O-methyl guanosine, and 2'-O-methyl uridine, respectively;
  Af, Cf, Gf, and Uf are 2'-fluoro adenosine, 2'-fluoro cytidine, 2'-fluoro guanosine, and 2'-fluoro uridine, respectively; and
  s is a phosphorothioate linkage;
  wherein optionally present on the sense strand is one or two inverted abasic deoxyribose residues (invAb) and/or one, two, three, or four phosphorothioate internucleoside linkages; and
  wherein optionally linked to the 5' terminal end of the sense strand is a targeting ligand that comprises N-acetyl-galactosamine.

14. The RNAi agent of claim 1, wherein the antisense strand of the RNAi agent comprises the sequence (5'→3') usGfsusUfaAfaCfaUfgCfcUfaAfaCfgcusu (SEQ ID NO: 958), wherein:
  a, c, g, and u are 2'-O-methyl adenosine, 2'-O-methyl cytidine, 2'-O-methyl guanosine, and 2'-O-methyl uridine, respectively;
  Af, Cf, Gf, and Uf are 2'-fluoro adenosine, 2'-fluoro cytidine, 2'-fluoro guanosine, and 2'-fluoro uridine, respectively; and
  s is a phosphorothioate linkage.

15. The RNAi agent of claim 14, wherein the sense strand comprises the sequence (5'→3') gcguuuaGfGfCfauguuuaacausu (SEQ ID NO: 1277), wherein:
  a, c, g, and u are 2'-O-methyl adenosine, 2'-O-methyl cytidine, 2'-O-methyl guanosine, and 2'-O-methyl uridine, respectively;
  Af, Cf, Gf, and Uf are 2'-fluoro adenosine, 2'-fluoro cytidine, 2'-fluoro guanosine, and 2'-fluoro uridine, respectively; and
  s is a phosphorothioate linkage;
  wherein optionally present on the sense strand is one or two inverted abasic deoxyribose residues (invAb) and/or one, two, three, or four phosphorothioate internucleoside linkages; and
  wherein optionally linked to the 5' terminal end of the sense strand is a targeting ligand that comprises N-acetyl-galactosamine.

16. The RNAi agent of claim 1, wherein the antisense strand of the RNAi agent comprises the sequence (5'→3') usGfsuUfaAfaCfaUfgCfcUfaAfaCfgsCfsg (SEQ ID NO: 959), wherein:
  a, c, g, and u are 2'-O-methyl adenosine, 2'-O-methyl cytidine, 2'-O-methyl guanosine, and 2'-O-methyl uridine, respectively;
  Af, Cf, Gf, and Uf are 2'-fluoro adenosine, 2'-fluoro cytidine, 2'-fluoro guanosine, and 2'-fluoro uridine, respectively; and
  s is a phosphorothioate linkage.

17. The RNAi agent of claim 16, wherein the sense strand comprises the sequence (5'→3') cgcguuuaGfGfCfauguuuaaca (SEQ ID NO: 1278), wherein:
  a, c, g, and u are 2'-O-methyl adenosine, 2'-O-methyl cytidine, 2'-O-methyl guanosine, or 2'-O-methyl uridine, respectively;
  Af, Cf, Gf, and Uf are 2'-fluoro adenosine, 2'-fluoro cytidine, 2'-fluoro guanosine, and 2'-fluoro uridine, respectively; and
  s is a phosphorothioate linkage;
  wherein optionally present on the sense strand is one or two inverted abasic deoxyribose residues (invAb) and/or one, two, three, or four phosphorothioate internucleoside linkages; and
  wherein optionally linked to the 5' terminal end of the sense strand is a targeting ligand that comprises N-acetyl-galactosamine.

18. The RNAi agent of claim 1, wherein the antisense strand is 21 or 22 nucleotides in length.

19. The RNAi agent of claim 1, wherein each nucleotide of the antisense strand is a modified nucleotide.

20. A composition comprising the RNAi agent of claim 1 and at least one pharmaceutically acceptable excipient.

21. The composition of claim 20, wherein the composition is formulated for administration by subcutaneous injection.

* * * * *